US012642862B2

(12) United States Patent
Ren et al.

(10) Patent No.: US 12,642,862 B2
(45) **Date of Patent: *Jun. 2, 2026**

(54) ANTI-CD79B ANTIBODY-DRUG CONJUGATE, AND PREPARATION METHOD THEREFOR AND PHARMACEUTICAL USE THEREOF

(71) Applicant: TUOJIE BIOTECH (SHANGHAI) CO., LTD., Shanghai (CN)

(72) Inventors: Wenming Ren, Shanghai (CN); Jindong Liang, Shanghai (CN); Jianyan Xu, Shanghai (CN); Jian Huang, Shanghai (CN); Changyong Yang, Shanghai (CN); Cheng Liao, Shanghai (CN)

(73) Assignee: TUOJIE BIOTECH (SHANGHAI) CO., LTD., Shanghai (CN)

( * ) Notice: Subject to any disclaimer, the term of this patent is extended or adjusted under 35 U.S.C. 154(b) by 643 days.

This patent is subject to a terminal disclaimer.

(21) Appl. No.: 18/018,241

(22) PCT Filed: Jul. 27, 2021

(86) PCT No.: PCT/CN2021/108666

§ 371 (c)(1),
(2) Date: Jan. 26, 2023

(87) PCT Pub. No.: WO2022/022508

PCT Pub. Date: Feb. 3, 2022

(65) Prior Publication Data

US 2023/0405138 A1 Dec. 21, 2023

(30) Foreign Application Priority Data

Jul. 27, 2020 (CN) ......................... 202010730899.8
Jul. 28, 2020 (CN) ......................... 202010735910.X

(51) Int. Cl.

| | |
|---|---|
| ***A61K 47/68*** | (2017.01) |
| ***A61P 35/00*** | (2006.01) |
| ***C07K 16/28*** | (2006.01) |

(52) U.S. Cl.

CPC .... *A61K 47/6849* (2017.08); *A61K 47/68031* (2023.08); *A61P 35/00* (2018.01); *C07K 16/2803* (2013.01); *C07K 2317/24* (2013.01); *C07K 2317/33* (2013.01); *C07K 2317/92* (2013.01)

(58) Field of Classification Search

None

See application file for complete search history.

(56) References Cited

U.S. PATENT DOCUMENTS

| | | | | |
|---|---|---|---|---|
| 6,884,869 | B2 | 4/2005 | Senter et al. | |
| 7,098,308 | B2 | 8/2006 | Senter et al. | |
| 2016/0159906 | A1 * | 6/2016 | Sun | A61K 47/68031 424/139.1 |
| 2022/0162304 | A1 | 5/2022 | Yang et al. | |

FOREIGN PATENT DOCUMENTS

| | | | | |
|---|---|---|---|---|
| AU | 2019202880 | A1 | 5/2019 | |
| WO | 2009099728 | A1 | 8/2009 | |
| WO | 2014177615 | A2 | 11/2014 | |
| WO | 2016090210 | A1 | 6/2016 | |
| WO | 2019200322 | A1 | 10/2019 | |
| WO | 2020063673 | A1 | 4/2020 | |
| WO | 2020063676 | A | 4/2020 | |
| WO | 2020088587 | A1 | 5/2020 | |
| WO | 2020156439 | A | 8/2020 | |
| WO | WO-2020156439 | A1 * | 8/2020 | A61P 35/02 |

OTHER PUBLICATIONS

Singh et al (Drug Metab. Dispos., 2017, 45:1120-1132).*

* cited by examiner

*Primary Examiner* — Laura B Goddard

(74) *Attorney, Agent, or Firm* — Morgan, Lewis & Bockius LLP

(57) ABSTRACT

Provided are an anti-CD79B antibody-drug conjugate, and a preparation method therefor and pharmaceutical use thereof. In particular, provided are an antibody-drug conjugate (ADC) which comprises an anti-CD79B antibody conjugated with an MMAE or a derivative thereof, exatecan or a derivative thereof, or Eribulin or a derivative thereof, a pharmaceutical composition containing the ADC, and use thereof in preparation of a drug for treatment of a CD79B-mediated disease or disorder, especially use thereof in preparation of an anti-cancer drug.

20 Claims, 14 Drawing Sheets

Specification includes a Sequence Listing.

SEQUENCE LISTING

```
<160> NUMBER OF SEQ ID NOS: 33

<210> SEQ ID NO 1
<211> LENGTH: 433
<212> TYPE: PRT
<213> ORGANISM: Artificial Sequence
<220> FEATURE:
<223> OTHER INFORMATION: Human CD79B ECD-hFc

<400> SEQUENCE: 1

Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp
        35                  40                  45
```

```
Leu Trp Lys Gln Glu Met Asp Glu Asn Pro Gln Gln Leu Lys Leu Glu
    50                  55                  60

Lys Gly Arg Met Glu Glu Ser Gln Asn Glu Ser Leu Ala Thr Leu Thr
65                  70                  75                  80

Ile Gln Gly Ile Arg Phe Glu Asp Asn Gly Ile Tyr Phe Cys Gln Gln
                85                  90                  95

Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp Gly Ile Ile Met Ile Gln Thr Leu Leu Ile Ile Leu Phe
    130                 135                 140

Ile Ile Val Pro Ile Phe Leu Leu Leu Asp Lys Asp Asp Ser Lys Ala
145                 150                 155                 160

Gly Met Glu Glu Asp His Thr Tyr Glu Gly Leu Asp Ile Asp Gln Thr
                165                 170                 175

Ala Thr Tyr Glu Asp Ile Val Thr Leu Arg Thr Gly Glu Val Lys Trp
            180                 185                 190

Ser Val Gly Glu His Pro Gly Gln Glu Glu Pro Lys Ser Cys Asp Lys
        195                 200                 205

Thr His Thr Cys Pro Pro Cys Pro Ala Pro Glu Leu Leu Gly Gly Pro
    210                 215                 220

Ser Val Phe Leu Phe Pro Pro Lys Pro Lys Asp Thr Leu Met Ile Ser
225                 230                 235                 240

Arg Thr Pro Glu Val Thr Cys Val Val Val Asp Val Ser His Glu Asp
                245                 250                 255

Pro Glu Val Lys Phe Asn Trp Tyr Val Asp Gly Val Glu Val His Asn
            260                 265                 270

Ala Lys Thr Lys Pro Arg Glu Glu Gln Tyr Asn Ser Thr Tyr Arg Val
        275                 280                 285

Val Ser Val Leu Thr Val Leu His Gln Asp Trp Leu Asn Gly Lys Glu
    290                 295                 300

Tyr Lys Cys Lys Val Ser Asn Lys Ala Leu Pro Ala Pro Ile Glu Lys
305                 310                 315                 320

Thr Ile Ser Lys Ala Lys Gly Gln Pro Arg Glu Pro Gln Val Tyr Thr
                325                 330                 335

Leu Pro Pro Ser Arg Glu Glu Met Thr Lys Asn Gln Val Ser Leu Thr
            340                 345                 350

Cys Leu Val Lys Gly Phe Tyr Pro Ser Asp Ile Ala Val Glu Trp Glu
        355                 360                 365

Ser Asn Gly Gln Pro Glu Asn Asn Tyr Lys Thr Thr Pro Pro Val Leu
    370                 375                 380

Asp Ser Asp Gly Ser Phe Phe Leu Tyr Ser Lys Leu Thr Val Asp Lys
385                 390                 395                 400

Ser Arg Trp Gln Gln Gly Asn Val Phe Ser Cys Ser Val Met His Glu
                405                 410                 415

Ala Leu His Asn His Tyr Thr Gln Lys Ser Leu Ser Leu Ser Pro Gly
            420                 425                 430

Lys
```

<210> SEQ ID NO 2
<211> LENGTH: 207
<212> TYPE: PRT

<213> ORGANISM: Artificial Sequence
<220> FEATURE:
<223> OTHER INFORMATION: Human CD79B ECD-His

<400> SEQUENCE: 2

```
Ala Arg Ser Glu Asp Arg Tyr Arg Asn Pro Lys Gly Ser Ala Cys Ser
1               5                   10                  15

Arg Ile Trp Gln Ser Pro Arg Phe Ile Ala Arg Lys Arg Gly Phe Thr
            20                  25                  30

Val Lys Met His Cys Tyr Met Asn Ser Ala Ser Gly Asn Val Ser Trp
        35                  40                  45

Leu Trp Lys Gln Glu Met Asp Glu Asn Pro Gln Gln Leu Lys Leu Glu
    50                  55                  60

Lys Gly Arg Met Glu Glu Ser Gln Asn Glu Ser Leu Ala Thr Leu Thr
65                  70                  75                  80

Ile Gln Gly Ile Arg Phe Glu Asp Asn Gly Ile Tyr Phe Cys Gln Gln
                85                  90                  95

Lys Cys Asn Asn Thr Ser Glu Val Tyr Gln Gly Cys Gly Thr Glu Leu
            100                 105                 110

Arg Val Met Gly Phe Ser Thr Leu Ala Gln Leu Lys Gln Arg Asn Thr
        115                 120                 125

Leu Lys Asp Gly Ile Ile Met Ile Gln Thr Leu Leu Ile Ile Leu Phe
    130                 135                 140

Ile Ile Val Pro Ile Phe Leu Leu Leu Asp Lys Asp Asp Ser Lys Ala
145                 150                 155                 160

Gly Met Glu Glu Asp His Thr Tyr Glu Gly Leu Asp Ile Asp Gln Thr
                165                 170                 175

Ala Thr Tyr Glu Asp Ile Val Thr Leu Arg Thr Gly Glu Val Lys Trp
            180                 185                 190

Ser Val Gly Glu His Pro Gly Gln Glu His His His His His His
        195                 200                 205
```

<210> SEQ ID NO 3
<211> LENGTH: 117
<212> TYPE: PRT
<213> ORGANISM: Mus musculus

<400> SEQUENCE: 3

```
Gln Val Gln Leu Gln Gln Ser Gly Ala Glu Leu Ala Arg Pro Gly Ala
1               5                   10                  15

Ser Val Lys Leu Ser Cys Lys Ala Ser Gly Ser Ser Phe Thr Ser Tyr
            20                  25                  30

Gly Ile Asn Trp Val Lys Gln Arg Thr Gly Gln Gly Leu Glu Trp Ile
        35                  40                  45

Gly Glu Ile Phe Pro Arg Ser Gly Asn Thr Tyr Tyr Asn Glu Lys Phe
    50                  55                  60

Glu Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Lys Gly Asp Leu Gly Asp Phe Asp Tyr Trp Gly Gln Gly Thr Thr
            100                 105                 110

Leu Thr Val Ser Ser
        115
```

<210> SEQ ID NO 4

```
<211> LENGTH: 112
<212> TYPE: PRT
<213> ORGANISM: Mus musculus

<400> SEQUENCE: 4

Asp Phe Leu Met Thr Gln Thr Pro Leu Ser Leu Pro Val Arg Leu Gly
1               5                   10                  15

Asp Gln Ala Ser Ile Ser Cys Arg Ser Ser Gln Ser Ile Val His Ser
            20                  25                  30

Asp Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110


<210> SEQ ID NO 5
<211> LENGTH: 119
<212> TYPE: PRT
<213> ORGANISM: Mus musculus

<400> SEQUENCE: 5

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Thr Tyr
            20                  25                  30

Gly Ile Asn Trp Val Lys Gln Arg Thr Gly Gln Gly Leu Glu Trp Ile
        35                  40                  45

Gly Glu Ile Tyr Pro Arg Ser Gly Asn Ile Tyr Tyr Asn Glu Lys Phe
    50                  55                  60

Lys Gly Lys Ala Thr Leu Thr Ala Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Ser Asp Tyr Asp Gly Asp Phe Ala Tyr Trp Gly Gln Gly
            100                 105                 110

Thr Leu Val Thr Val Ser Ala
        115


<210> SEQ ID NO 6
<211> LENGTH: 112
<212> TYPE: PRT
<213> ORGANISM: Mus musculus

<400> SEQUENCE: 6

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His His
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Gln Leu Glu Ile Lys
            100                 105                 110


<210> SEQ ID NO 7
<211> LENGTH: 7
<212> TYPE: PRT
<213> ORGANISM: Mus musculus

<400> SEQUENCE: 7

Gly Ser Ser Phe Thr Ser Tyr
1               5


<210> SEQ ID NO 8
<211> LENGTH: 6
<212> TYPE: PRT
<213> ORGANISM: Mus musculus

<400> SEQUENCE: 8

Phe Pro Arg Ser Gly Asn
1               5


<210> SEQ ID NO 9
<211> LENGTH: 8
<212> TYPE: PRT
<213> ORGANISM: Mus musculus

<400> SEQUENCE: 9

Gly Asp Leu Gly Asp Phe Asp Tyr
1               5


<210> SEQ ID NO 10
<211> LENGTH: 16
<212> TYPE: PRT
<213> ORGANISM: Mus musculus

<400> SEQUENCE: 10

Arg Ser Ser Gln Ser Ile Val His Ser Asp Gly Asn Thr Tyr Phe Glu
1               5                   10                  15


<210> SEQ ID NO 11
<211> LENGTH: 7
<212> TYPE: PRT
<213> ORGANISM: Mus musculus

<400> SEQUENCE: 11

Lys Val Ser Asn Arg Phe Ser
1               5


<210> SEQ ID NO 12
<211> LENGTH: 9
<212> TYPE: PRT
<213> ORGANISM: Mus musculus

<400> SEQUENCE: 12

Phe Gln Gly Ser His Val Pro Trp Thr
1               5


<210> SEQ ID NO 13
<211> LENGTH: 7
<212> TYPE: PRT
```

<213> ORGANISM: Mus musculus

<400> SEQUENCE: 13

Gly Tyr Thr Phe Thr Thr Tyr
1 5

<210> SEQ ID NO 14
<211> LENGTH: 6
<212> TYPE: PRT
<213> ORGANISM: Mus musculus

<400> SEQUENCE: 14

Tyr Pro Arg Ser Gly Asn
1 5

<210> SEQ ID NO 15
<211> LENGTH: 10
<212> TYPE: PRT
<213> ORGANISM: Mus musculus

<400> SEQUENCE: 15

Gly Ser Asp Tyr Asp Gly Asp Phe Ala Tyr
1 5 10

<210> SEQ ID NO 16
<211> LENGTH: 16
<212> TYPE: PRT
<213> ORGANISM: Mus musculus

<400> SEQUENCE: 16

Arg Ser Ser Gln Ser Ile Val His His Asp Gly Asn Thr Tyr Leu Glu
1 5 10 15

<210> SEQ ID NO 17
<211> LENGTH: 7
<212> TYPE: PRT
<213> ORGANISM: Mus musculus

<400> SEQUENCE: 17

Lys Val Ser Asn Arg Phe Ser
1 5

<210> SEQ ID NO 18
<211> LENGTH: 9
<212> TYPE: PRT
<213> ORGANISM: Mus musculus

<400> SEQUENCE: 18

Phe Gln Gly Ser His Val Pro Trp Thr
1 5

<210> SEQ ID NO 19
<211> LENGTH: 117
<212> TYPE: PRT
<213> ORGANISM: Artificial Sequence
<220> FEATURE:
<223> OTHER INFORMATION: Heavy chain variable region of hAb015-10
humanized antibody

<400> SEQUENCE: 19

Glu Val Gln Leu Val Gln Ser Gly Ala Glu Val Lys Lys Pro Gly Ser
1 5 10 15

Ser Val Lys Val Ser Cys Lys Ala Ser Gly Ser Ser Phe Ser Ser Tyr
20 25 30

```
Gly Ile Asn Trp Val Lys Gln Ala Pro Gly Gln Gly Leu Glu Trp Ile
        35                  40                  45

Gly Glu Ile Phe Pro Arg Ser Gly Asn Thr Tyr Tyr Asn Glu Lys Phe
    50                  55                  60

Glu Gly Arg Ala Thr Leu Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Lys Gly Asp Leu Gly Asp Phe Asp Tyr Trp Gly Gln Gly Thr Thr
            100                 105                 110

Val Thr Val Ser Ser
        115


<210> SEQ ID NO 20
<211> LENGTH: 112
<212> TYPE: PRT
<213> ORGANISM: Artificial Sequence
<220> FEATURE:
<223> OTHER INFORMATION: Light chain variable region of hAb015-10
      humanized antibody

<400> SEQUENCE: 20

Asp Phe Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asp Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110


<210> SEQ ID NO 21
<211> LENGTH: 119
<212> TYPE: PRT
<213> ORGANISM: Artificial Sequence
<220> FEATURE:
<223> OTHER INFORMATION: Heavy chain variable region of hAb017-10
      humanized antibody

<400> SEQUENCE: 21

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Asn Trp Val Lys Gln Ala Pro Gly Gln Gly Leu Glu Trp Ile
        35                  40                  45

Gly Glu Ile Tyr Pro Arg Ser Gly Asn Ile Tyr Tyr Asn Glu Lys Phe
    50                  55                  60

Lys Gly Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95
```

```
Ala Arg Gly Ser Asp Tyr Asp Gly Asp Phe Ala Tyr Trp Gly Gln Gly
            100                 105                 110

Thr Leu Val Thr Val Ser Ser
        115


<210> SEQ ID NO 22
<211> LENGTH: 112
<212> TYPE: PRT
<213> ORGANISM: Artificial Sequence
<220> FEATURE:
<223> OTHER INFORMATION: Light chain variable region of hAb017-10
      humanized antibody

<400> SEQUENCE: 22

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His His
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110


<210> SEQ ID NO 23
<211> LENGTH: 7
<212> TYPE: PRT
<213> ORGANISM: Artificial Sequence
<220> FEATURE:
<223> OTHER INFORMATION: Mutated HCDR2

<400> SEQUENCE: 23

Gly Ser Ser Phe Ser Ser Tyr
1               5


<210> SEQ ID NO 24
<211> LENGTH: 7
<212> TYPE: PRT
<213> ORGANISM: Artificial Sequence
<220> FEATURE:
<223> OTHER INFORMATION: General formula of HCDR1
<220> FEATURE:
<221> NAME/KEY: VARIANT
<222> LOCATION: (2)..(2)
<223> OTHER INFORMATION: Xaa is S or Y
<220> FEATURE:
<221> NAME/KEY: VARIANT
<222> LOCATION: (3)..(3)
<223> OTHER INFORMATION: Xaa is S or T
<220> FEATURE:
<221> NAME/KEY: VARIANT
<222> LOCATION: (5)..(5)
<223> OTHER INFORMATION: Xaa is T or S
<220> FEATURE:
<221> NAME/KEY: VARIANT
<222> LOCATION: (6)..(6)
<223> OTHER INFORMATION: Xaa is S or T

<400> SEQUENCE: 24

Gly Xaa Xaa Phe Xaa Xaa Tyr
1               5
```

```
<210> SEQ ID NO 25
<211> LENGTH: 6
<212> TYPE: PRT
<213> ORGANISM: Artificial Sequence
<220> FEATURE:
<223> OTHER INFORMATION: General formula of HCDR2
<220> FEATURE:
<221> NAME/KEY: VARIANT
<222> LOCATION: (1)..(1)
<223> OTHER INFORMATION: Xaa is F or Y

<400> SEQUENCE: 25

Xaa Pro Arg Ser Gly Asn
1               5


<210> SEQ ID NO 26
<211> LENGTH: 10
<212> TYPE: PRT
<213> ORGANISM: Artificial Sequence
<220> FEATURE:
<223> OTHER INFORMATION: General formula of HCDR3
<220> FEATURE:
<221> NAME/KEY: VARIANT
<222> LOCATION: (1)..(1)
<223> OTHER INFORMATION: Xaa is absent or G
<220> FEATURE:
<221> NAME/KEY: VARIANT
<222> LOCATION: (2)..(2)
<223> OTHER INFORMATION: Xaa is absent or S
<220> FEATURE:
<221> NAME/KEY: VARIANT
<222> LOCATION: (3)..(3)
<223> OTHER INFORMATION: Xaa is G or D
<220> FEATURE:
<221> NAME/KEY: VARIANT
<222> LOCATION: (4)..(4)
<223> OTHER INFORMATION: Xaa is D or Y
<220> FEATURE:
<221> NAME/KEY: VARIANT
<222> LOCATION: (5)..(5)
<223> OTHER INFORMATION: Xaa is L or D
<220> FEATURE:
<221> NAME/KEY: VARIANT
<222> LOCATION: (9)..(9)
<223> OTHER INFORMATION: Xaa is D or A

<400> SEQUENCE: 26

Xaa Xaa Xaa Xaa Xaa Gly Asp Phe Xaa Tyr
1               5                   10


<210> SEQ ID NO 27
<211> LENGTH: 15
<212> TYPE: PRT
<213> ORGANISM: Artificial Sequence
<220> FEATURE:
<223> OTHER INFORMATION: General formula of LCDR1
<220> FEATURE:
<221> NAME/KEY: VARIANT
<222> LOCATION: (9)..(9)
<223> OTHER INFORMATION: Xaa is S or H
<220> FEATURE:
<221> NAME/KEY: VARIANT
<222> LOCATION: (14)..(14)
<223> OTHER INFORMATION: Xaa is F or L

<400> SEQUENCE: 27

Arg Ser Ser Gln Ser Ile Val His Xaa Gly Asn Thr Tyr Xaa Glu
1               5                   10                  15


<210> SEQ ID NO 28
<211> LENGTH: 447
```

<212> TYPE: PRT
<213> ORGANISM: Artificial Sequence
<220> FEATURE:
<223> OTHER INFORMATION: Heavy chain of hAb015-10 humanized antibody

<400> SEQUENCE: 28

```
Glu Val Gln Leu Val Gln Ser Gly Ala Glu Val Lys Lys Pro Gly Ser
1               5                   10                  15

Ser Val Lys Val Ser Cys Lys Ala Ser Gly Ser Ser Phe Ser Ser Tyr
            20                  25                  30

Gly Ile Asn Trp Val Lys Gln Ala Pro Gly Gln Gly Leu Glu Trp Ile
        35                  40                  45

Gly Glu Ile Phe Pro Arg Ser Gly Asn Thr Tyr Tyr Asn Glu Lys Phe
    50                  55                  60

Glu Gly Arg Ala Thr Leu Thr Ala Asp Lys Ser Thr Ser Thr Ala Tyr
65                  70                  75                  80

Met Glu Leu Arg Ser Leu Arg Ser Glu Asp Thr Ala Val Tyr Tyr Cys
                85                  90                  95

Ala Lys Gly Asp Leu Gly Asp Phe Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380
```

```
Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 29
<211> LENGTH: 219
<212> TYPE: PRT
<213> ORGANISM: Artificial Sequence
<220> FEATURE:
<223> OTHER INFORMATION: Light chain of hAb015-10 humanized antibody

<400> SEQUENCE: 29

Asp Phe Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asp Gly Asn Thr Tyr Phe Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215


<210> SEQ ID NO 30
<211> LENGTH: 449
<212> TYPE: PRT
<213> ORGANISM: Artificial Sequence
<220> FEATURE:
<223> OTHER INFORMATION: Heavy chain of hAb017-10 humanized antibody

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30
```

-continued

```
Gly Ile Asn Trp Val Lys Gln Ala Pro Gly Gln Gly Leu Glu Trp Ile
        35                  40                  45

Gly Glu Ile Tyr Pro Arg Ser Gly Asn Ile Tyr Tyr Asn Glu Lys Phe
    50                  55                  60

Lys Gly Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Ser Asp Tyr Asp Gly Asp Phe Ala Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

Lys

<210> SEQ ID NO 31
<211> LENGTH: 219
<212> TYPE: PRT
<213> ORGANISM: Artificial Sequence
<220> FEATURE:
<223> OTHER INFORMATION: Light chain of hAb017-10 humanized antibody

<400> SEQUENCE: 31

```
Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His His
            20                  25                  30

Asp Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Trp Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 32
<211> LENGTH: 447
<212> TYPE: PRT
<213> ORGANISM: Artificial Sequence
<220> FEATURE:
<223> OTHER INFORMATION: Heavy chain of SN8

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Ser Ser Tyr
            20                  25                  30

Trp Ile Glu Trp Val Arg Gln Ala Pro Gly Lys Gly Leu Glu Trp Ile
        35                  40                  45

Gly Glu Ile Leu Pro Gly Gly Gly Asp Thr Asn Tyr Asn Glu Ile Phe
    50                  55                  60

Lys Gly Arg Ala Thr Phe Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                85                  90                  95

Thr Arg Arg Val Pro Ile Arg Leu Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

-continued

```
His Asn His Tyr Thr Gln Lys Ser Leu Ser Leu Ser Pro Gly Lys
        435                 440                 445


<210> SEQ ID NO 33
<211> LENGTH: 218
<212> TYPE: PRT
<213> ORGANISM: Artificial Sequence
<220> FEATURE:
<223> OTHER INFORMATION: Light chain of SN8

<400> SEQUENCE: 33

Asp Ile Gln Leu Thr Gln Ser Pro Ser Ser Leu Ser Ala Ser Val Gly
1               5                   10                  15

Asp Arg Val Thr Ile Thr Cys Lys Ala Ser Gln Ser Val Asp Tyr Glu
            20                  25                  30

Gly Asp Ser Phe Leu Asn Trp Tyr Gln Gln Lys Pro Gly Lys Ala Pro
        35                  40                  45

Lys Leu Leu Ile Tyr Ala Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Asn
                85                  90                  95

Glu Asp Pro Leu Thr Phe Gly Gln Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

ANTI-CD79B ANTIBODY-DRUG CONJUGATE, AND PREPARATION METHOD THEREFOR AND PHARMACEUTICAL USE THEREOF

CROSS-REFERENCE TO RELATED APPLICATIONS

The present application is a national stage application of International Patent Application No. PCT/CN2021/108666, filed Jul. 27, 2021, which claims the benefit of and priority to Chinese Patent Application No. 202010730899.8 filed on Jul. 27, 2020, and Chinese Application No. 202010735910.X filed on Jul. 28, 2020, each of which is incorporated herein by reference in their entirety.

SEQUENCE LISTING

The instant application contains a Sequence Listing which has been submitted electronically in ASCII format and is hereby incorporated by reference in its entirety. Said ASCII copy, created on Jan. 25, 2023, and is named "721085CPUS_126268-5048-US_Sequence_Listing.txt" and is approximately 36 kilobytes in size.

TECHNICAL FIELD

The present application relates to an anti-CD79B antibody and an antigen-binding fragment, a chimeric antibody or a humanized antibody comprising CDR regions of the anti-CD79B antibody, and a pharmaceutical composition comprising the human anti-CD79B antibody or the antigen-binding fragment thereof, and use thereof as an anti-cancer medicament.

BACKGROUND

Malignant tumors (cancers) are the second leading cause of death worldwide, and only ranked after heart disease. Among them, lymphoma is a malignant tumor originating from the lymphohematopoietic system and is the most common hematological tumor worldwide. Lymphomas are divided into two classes: non-Hodgkin's lymphoma (NHL) and Hodgkin's Lymphoma (HL). Non-Hodgkin's lymphoma is a general term for a group of abnormal proliferative lymphocytic diseases with relatively strong heterogeneity, and its incidence rate is much higher than that of Hodgkin's lymphoma, accounting for about 80% or more of lymphomas. Diffuse large B-cell lymphoma (DLBCL) is the most common type of lymphoma in adults, accounting for about 32.5% of all non-Hodgkin's lymphomas. In the Asian population, the percentage is higher, approaching 40%. It is more common in elderly patients, with a median age of onset of 60-64 years old, and with slightly more male patients than female patients.

The current first-line standard regimen for diffuse large B-cell lymphoma (DLBCL) is rituximab in combination with CHOP chemotherapy (R-CHOP). Prior to the marketing of rituximab, the anthracycline-based CHOP (cyclophosphamide, doxorubicin, vincristine, and prednisone) regimen was the first-line standard treatment regimen for DLBCL. The R-CHOP treatment regimen has resulted in a significant improvement in the long-term survival of DLBCL patients. Clinical trial results show that compared with the traditional CHOP regimen, the R-CHOP regimen for DLBCL can significantly prolong the median overall survival by 4.9 years, allow the median disease-free survival to exceed 6.6 years, and increase the 5-year progression-free survival rate from 30% to 54% in patients. However, there are still 10% to 15% of refractory patients who have no response and 20% to 30% of patients who experience relapse. Furthermore, not all DLBCL patients are candidates for the R-CHOP regimen, such as elderly patients over 80 years old, who are unable to undergo standard R-CHOP treatment in their physical abilities. The R-CHOP regimen may not be effective in more aggressive lymphoma types, as well as in relapsed lymphomas.

DLBCL is classified as B-cell lymphoma according to the origin of the lymphocytes. B cell antigen receptor (BCR) complex is the most prominent molecule on the surface of B cells. The BCR complex consists of a membrane immunoglobulin (mIg) that recognizes and binds to antigens and a heterodimer of Igα (CD79a) and Igβ (CD79B) that delivers antigen-stimulating signals. Igα and Igβ are glycoproteins of about 47 kDa and about 37 kDa, respectively, and are members of the immunoglobulin superfamily. The genes encoding Igα and Igβ are referred to as mb-1 and B29, respectively. Both Igα and Igβ have an Ig-like domain at the amino terminus in the extracellular region. Both Igα and Igβ can be used as substrates of protein tyrosine kinases and are involved in BCR signal transduction.

BCR is widely expressed on B-cell lymphomas as well as on normal B cells. Given the clinical success and reliable safety of rituximab targeting CD20, development of BCR-targeting therapies should also have good efficacy and safety. Therapeutic antibodies directed against the CD79B antigen are beneficial in that they produce minimal or no antigenicity when administered to patients (especially for long-term treatment). There is an urgent need in the art to develop an effective CD79B antibody and an antibody-drug conjugate thereof for use in cancer therapy or delaying cancer progression. WO2020156439A discloses an anti-CD79B antibody and use thereof in treating tumors, the content of which is incorporated herein in its entirety.

SUMMARY

The present disclosure relates to an anti-CD69B antibody or an antigen-binding fragment, an antibody-drug conjugate (ADC), and pharmaceutical use thereof, wherein an ADC drug comprising the anti-CD69B antibody or the antigen-binding fragment conjugated with a cytotoxic substance (MMAE or a derivative thereof, exatecan or a derivative thereof, and eribulin or a derivative thereof) is provided.

Anti-CD79B Antibody and Antigen-Binding Fragment Thereof

WO2020156439A discloses an anti-CD79B antibody and use thereof in treating tumors, the content of which is incorporated herein in its entirety.

The present disclosure provides an anti-CD79B antibody and an antigen-binding fragment thereof, which comprise:

- a heavy chain HCDR1 comprising a sequence set forth in $GX_1X_2FX_3X_4Y$ (SEQ ID NO: 24), wherein $X_1$ is S or Y, $X_2$ is S or T, $X_3$ is T or S, and $X_4$ is S or T;
- a heavy chain HCDR2 comprising a sequence set forth in $X_5PRSGN$ (SEQ ID NO: 25), wherein $X_5$ is F or Y;
- a heavy chain HCDR3 comprising $X_6X_7X_8X_9X_{10}GDFX_{11}Y$ (SEQ ID NO: 26), wherein $X_6$ is absent or G, $X_7$ is absent or S, $X_8$ is G or D, $X_9$ is D or Y, $X_{10}$ is L or D, and $X_{11}$ is D or A;
- a light chain LCDR1 comprising $RSSQSIVHX_{12}GNTYX_{13}E$ (SEQ ID NO: 27), wherein $X_{12}$ is S or H, and $X_{13}$ is F or L;

a light chain LCDR2 comprising a sequence set forth in SEQ ID NO: 11 or 17; and a light chain LCDR3 comprising a sequence set forth in SEQ ID NO: 12 or 18.

In some embodiments, the anti-CD79B antibody or the antigen-binding fragment thereof described above comprises:

an antibody heavy chain variable region comprising at least 1 HCDR set forth in a sequence selected from the group consisting of the following: SEQ ID NO: 23, SEQ ID NO: 7, SEQ ID NO: 8, SEQ ID NO: 9, SEQ ID NO: 13, SEQ ID NO: 14 and SEQ ID NO: 15; and/or an antibody light chain variable region comprising at least 1 LCDR set forth in a sequence selected from the group consisting of the following: SEQ ID NO: 10, SEQ ID NO: 11, SEQ ID NO: 12, SEQ ID NO: 16, SEQ ID NO: 17 and SEQ ID NO: 18.

In some embodiments, provided is an anti-CD79B antibody or an antigen-binding fragment thereof, which comprises:

(a) an HCDR1, an HCDR2 and an HCDR3 set forth in SEQ ID NOs: 23, 8 and 9, respectively, and an LCDR1, an LCDR2 and an LCDR3 set forth in SEQ ID NOs: 10, 11 and 12, respectively;

(b) an HCDR1, an HCDR2 and an HCDR3 set forth in SEQ ID NOs: 7, 8 and 9, respectively, and an LCDR1, an LCDR2 and an LCDR3 set forth in SEQ ID NOs: 10, 11 and 12, respectively; or (c) an HCDR1, an HCDR2 and an HCDR3 set forth in SEQ ID NOs: 13, 14 and 15, respectively, and an LCDR1, an LCDR2 and an LCDR3 set forth in SEQ ID NOs: 16, 17 and 18, respectively.

In some specific embodiments, in the above scheme (a) (specifically, provided is an anti-CD79B antibody or an antigen-binding fragment thereof, which comprises an HCDR1, an HCDR2 and HCDR3 set forth in SEQ ID NOs: 23, 8 and 9, respectively, and an LCDR1, an LCDR2 and an LCDR3 set forth in SEQ ID NOs: 10, 11 and 12, respectively), an anti-CD79B antibody or an antigen-binding fragment thereof comprising a VH set forth in SEQ ID NO: 19 and VL set forth in SEQ ID NO: 20, or an anti-CD79B antibody or an antigen-binding fragment thereof comprising a full-length heavy chain set forth in SEQ ID NO: 28 and a full-length light chain set forth in SEQ ID NO: 29 is not included.

In some embodiments, the anti-CD79B antibody or the antigen-binding fragment thereof described above is a murine antibody, a chimeric antibody, a humanized antibody or a human antibody, or a fragment thereof, e.g., a humanized antibody or a fragment thereof.

In some embodiments, provided is an anti-CD79B antibody or an antigen-binding fragment thereof, which comprises a heavy chain variable region (VH) and a light chain variable region (VL), wherein:

the heavy chain variable region (VH) comprises:

a sequence set forth in SEQ ID NO: 3 or 5 or having at least 80%, 85%, 90%, 95%, 96%, 97%, 98% or 99% identity to SEQ ID NO: 3 or 5;

and/or the light chain variable region (VL) comprises:

a sequence set forth in SEQ ID NO: 4 or 6 or having at least 80%, 85%, 90%, 95%, 96%, 97%, 98% or 99% identity to SEQ ID NO: 4 or 6.

In some specific embodiments, the anti-CD79B antibody or the antigen-binding fragment comprises a VH comprising a sequence set forth in SEQ ID NO: 3 and a VL comprising a sequence set forth in SEQ ID NO: 4; or a VH comprising a sequence set forth in SEQ ID NO: 5 and a VL comprising a sequence set forth in SEQ ID NO: 6.

In some other embodiments, provided is an anti-CD79B antibody or an antigen-binding fragment thereof, which comprises:

a VH comprising:

a sequence set forth in SEQ ID NO: 19 or 21 or having at least 80%, 85%, 90%, 95%, 96%, 97%, 98% or 99% identity to SEQ ID NO: 19 or 21;

and/or a VL comprising:

a sequence set forth in SEQ ID NO: 20 or 22 or having at least 80%, 85%, 90%, 95%, 96%, 97%, 98% or 99% identity to SEQ ID NO: 20 or 22.

In some specific embodiments, the anti-CD79B antibody or the antigen-binding fragment comprises a VH comprising a sequence set forth in SEQ ID NO: 19 and a VL comprising a sequence set forth in SEQ ID NO: 20; or a VH comprising a sequence set forth in SEQ ID NO: 21 and a VL comprising a sequence set forth in SEQ ID NO: 22.

In some embodiments, the anti-CD79B antibody or the antigen-binding fragment thereof described above comprises and a light chain constant region, wherein preferably, the heavy chain constant region is selected from the group consisting of constant regions of human IgG1, IgG2, IgG3 and IgG4 and conventional variants thereof and the light chain constant region is selected from the group consisting of constant regions of human antibody κ and λ chains and conventional variants thereof.

In some specific embodiments, the heavy chain constant region is human IgG1 or IgG2.

In some embodiments, provided is an anti-CD79B antibody or a fragment thereof, which comprises:

a heavy chain set forth in SEQ ID NO: 28 or a variant sequence thereof, wherein the variant sequence comprises 0 to 10 amino acid changes in the heavy chain; and a light chain set forth in SEQ ID NO: 29 or a variant sequence thereof, wherein the variant sequences comprise 0 to 10 amino acid changes in the light chain.

In some embodiments, provided is an anti-CD79B antibody or a fragment thereof, which comprises:

a heavy chain set forth in SEQ ID NO: 30 or a variant sequence thereof, wherein the variant sequence comprises 0 to 10 amino acid changes in the heavy chain; and a light chain set forth in SEQ ID NO: 31 or a variant sequence thereof, wherein the variant sequence comprises 0 to 10 amino acid changes in the light chain.

In some specific embodiments, the anti-CD79B antibody or the fragment thereof described above may be a variant having 0 to 10 (1, 2, 3, 4, 5, 6, 7, 8, 9 or 10) amino acid changes in VL and/or 0 to 10 (1, 2, 3, 4, 5, 6, 7, 8, 9 or 10) amino acid changes in VH.

In some specific embodiments, the variant described above has identical or similar biological function or effect to the original anti-CD79B antibody or the fragment thereof.

In some embodiments, the antigen-binding fragment of the anti-CD79B antibody described above includes a Fab, an Fv, an sFv, a Fab', an $F(ab')_2$, a linear antibody, a single-chain antibody, an scFv, an sdAb, an sdFv, a nanobody, a peptibody, a domain antibody, and a multispecific antibody (bispecific antibody, diabody, triabody, and tetrabody, tandem di-scFv, tandem tri-scFv).

In some embodiments, provided is a polynucleotide encoding the anti-CD79B antibody or the antigen-binding fragment thereof described above, e.g., DNA or RNA.

In some embodiments, provided is an expression vector comprising the polynucleotide described above, e.g., a eukaryotic expression vector, a prokaryotic expression vector or a viral vector.

In some embodiments, provided is a host cell, e.g., a eukaryotic cell or a prokaryotic cell, transformed with the expression vectors described above. In some specific embodiments, the host cell is bacteria (e.g., *Escherichia coli*), yeast (*Pichia pastoris*), or a mammalian cell (a Chinese hamster ovary (CHO) cell or a human embryonic kidney (HEK) 293 cell).

the ligand is an anti-CD79B antibody or an antigen-binding fragment thereof, wherein the anti-CD79B antibody or the antigen-binding fragment thereof is any one of the anti-CD79B antibodies or the antigen-binding fragments thereof described above of the present disclosure.

Ligand-Drug (Exatecan or Derivative Thereof) Conjugate

The present disclosure provides a ligand-exatecan (or a derivative thereof) conjugate or a pharmaceutically acceptable salt or solvate thereof, which is a ligand-exatecan (or a derivative thereof) conjugate of formula (I) or a pharmaceutically acceptable salt or solvate thereof:

formula (I)

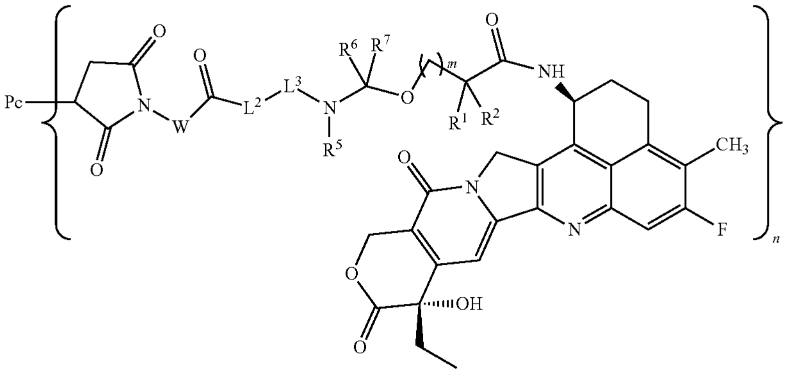

(Pc-$L_a$-Y-Dr)

In some embodiments, provided is a method for preparing the anti-CD79B antibody or the antigen-binding fragment thereof described above, which comprises: expressing the antibody or the antigen-binding fragment thereof in the host cell described above, and isolating the antibody or the antigen-binding fragment thereof from the host cell.

In some embodiments, provided is a method for treating or preventing a proliferative disease or delaying the progression of the proliferative disease, which comprises:

administering to a subject the anti-human CD79B antibody or the antigen-binding fragment thereof, the encoding polynucleotide thereof, or the pharmaceutical composition described above in an effective amount for treating or delaying the disease, wherein the proliferative disease is a cancer or a tumor.

In some specific embodiments, the cancer or tumor is lymphoma or leukemia;

the lymphoma is selected from the group consisting of: diffuse large B-cell lymphoma, non-Hodgkin's lymphoma, small lymphocytic lymphoma, and mantle cell lymphoma; the non-Hodgkin's lymphoma is selected from the group consisting of: aggressive NHL, relapsed and aggressive NHL, relapsed and indolent NHL, refractory NHL, and refractory and indolent NHL; and the leukemia is selected from the group consisting of: chronic lymphocytic leukemia, hairy cell leukemia, and acute lymphocytic leukemia.

Ligand-Drug Conjugate

The present disclosure provides a ligand-drug conjugate or a pharmaceutically acceptable salt or solvate thereof, wherein:

the drug is selected from the group consisting of MMAE or a derivative thereof, exatecan or a derivative thereof, and eribulin or a derivative thereof; and wherein:

W is selected from the group consisting of $C_{1-8}$ alkyl, $C_{1-8}$ alkyl-cycloalkyl and linear heteroalkyl of 1 to 8 atoms, the heteroalkyl comprising 1 to 3 heteroatoms selected from the group consisting of N, O and S, wherein the $C_{1-8}$ alkyl, cycloalkyl and linear heteroalkyl are each independently and optionally further substituted with one or more substituents selected from the group consisting of halogen, hydroxy, cyano, amino, alkyl, chloroalkyl, deuterated alkyl, alkoxy and cycloalkyl;

$L^2$ is selected from the group consisting of —$NR^4(CH_2CH_2O)p^1CH_2CH_2C(O)$—, —$NR^4(CH_2CH_2O)p^1CH_2C(O)$—, —$S(CH_2)p^1C(O)$— and a chemical bond, wherein $p^1$ is an integer from 1 to 20;

$L^3$ is a peptide residue consisting of 2 to 7 amino acids, wherein the amino acids are optionally further substituted with one or more substituents selected from the group consisting of halogen, hydroxy, cyano, amino, alkyl, chloroalkyl, deuterated alkyl, alkoxy and cycloalkyl;

$R^1$ is selected from the group consisting of hydrogen, halogen, cycloalkylalkyl, deuterated alkyl, cycloalkyl, heterocyclyl, aryl and heteroaryl; and $R^2$ is selected from the group consisting of hydrogen, halogen, haloalkyl, deuterated alkyl, cycloalkyl, heterocyclyl, aryl and heteroaryl;

or, $R^1$ and $R^2$, together with the carbon atom to which they are attached, form cycloalkyl or heterocyclyl;

$R^4$ and $R^5$ are identical or different and are each independently selected from the group consisting of hydrogen, alkyl, haloalkyl, deuterated alkyl and hydroxyalkyl;

$R^6$ and $R^7$ are identical or different and are each independently selected from the group consisting of hydrogen, halogen, alkyl, haloalkyl, deuterated alkyl and hydroxyalkyl;

m is an integer from 0 to 4;

n is 1 to 10 and can be an integer or a decimal; and

Pc is the anti-CD79B antibody or the antigen-binding fragment thereof provided herein.

In some embodiments, the present disclosure provides a ligand-exatecan (or a derivative thereof) conjugate or a pharmaceutically acceptable salt or solvate thereof of formula (II):

formula (II)

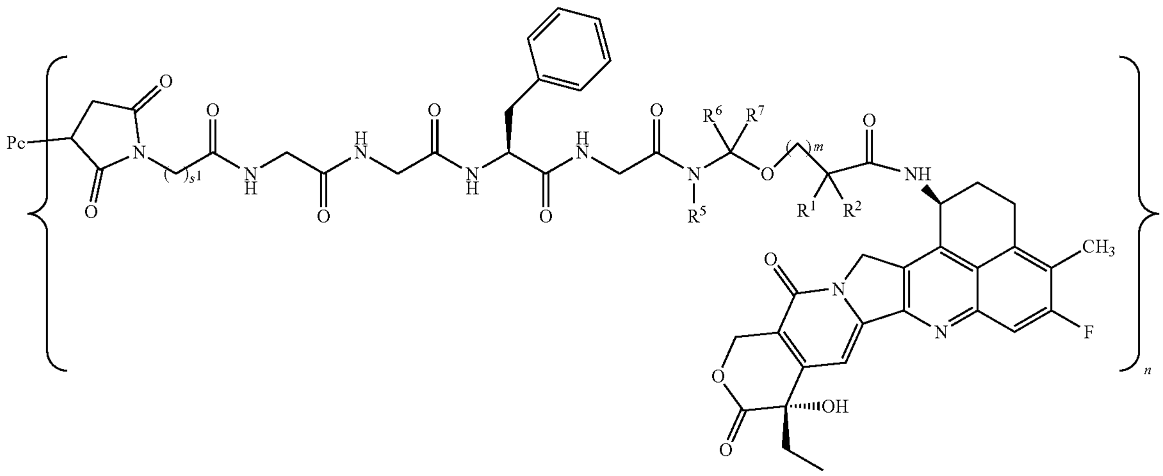

(Pc-$L_b$-Y-Dr)

wherein:

$s^1$ is an integer from 2 to 8, preferably 5; and

Pc, $R^1$, $R^2$, $R^5$-$R^7$, m and n are as defined in formula (I).

In some embodiments, the ligand-exatecan (or the derivative thereof) conjugate of the present disclosure comprises a linker unit -L-Y—, including but not limited to:

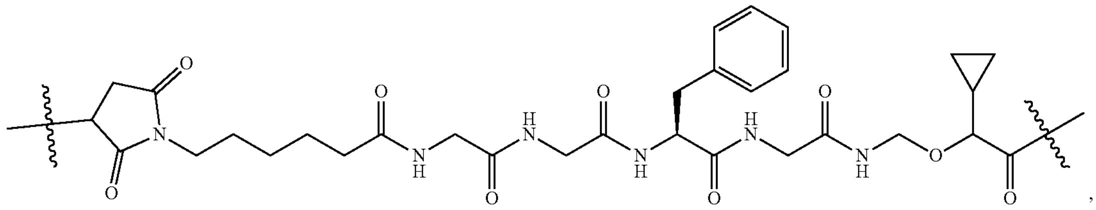

,

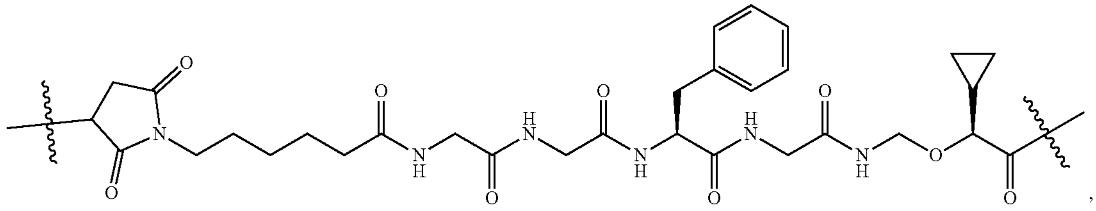

,

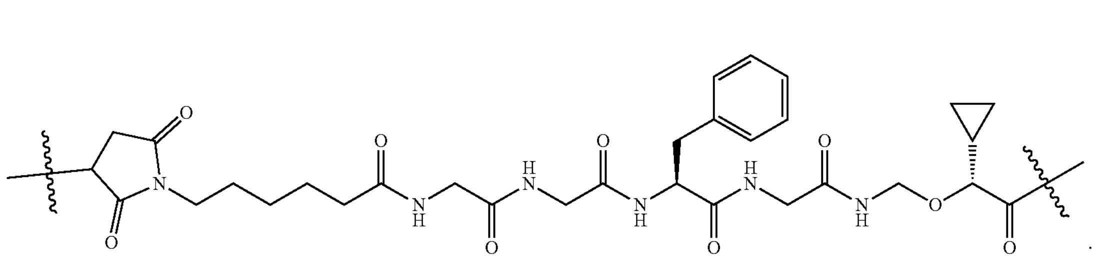

.

In some embodiments, the present disclosure provides a ligand-exatecan (or a derivative thereof) conjugate, or a pharmaceutically acceptable salt or a solvate thereof, which includes, but is not limited to:
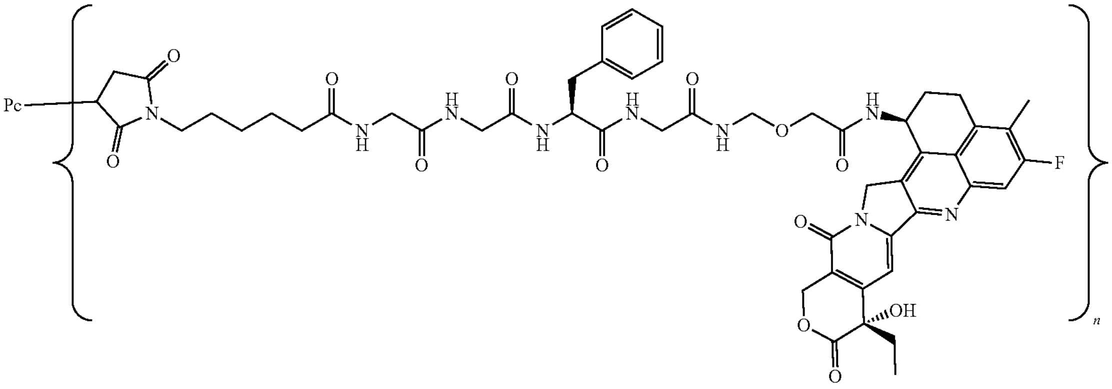
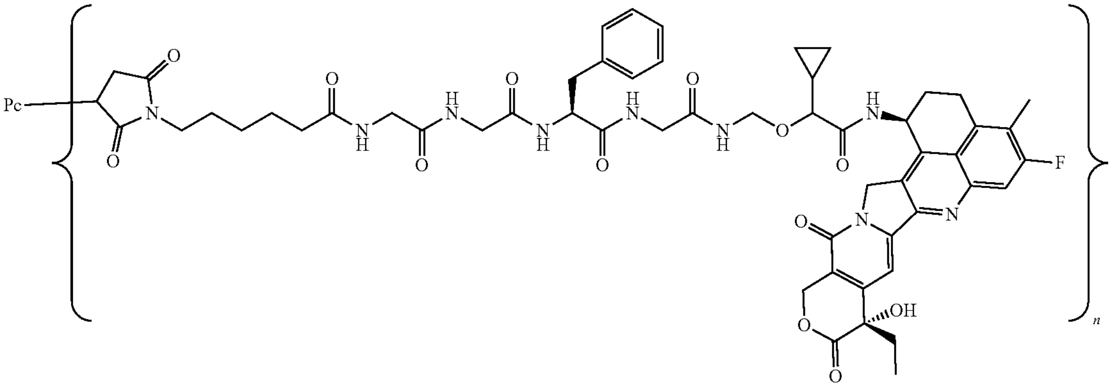
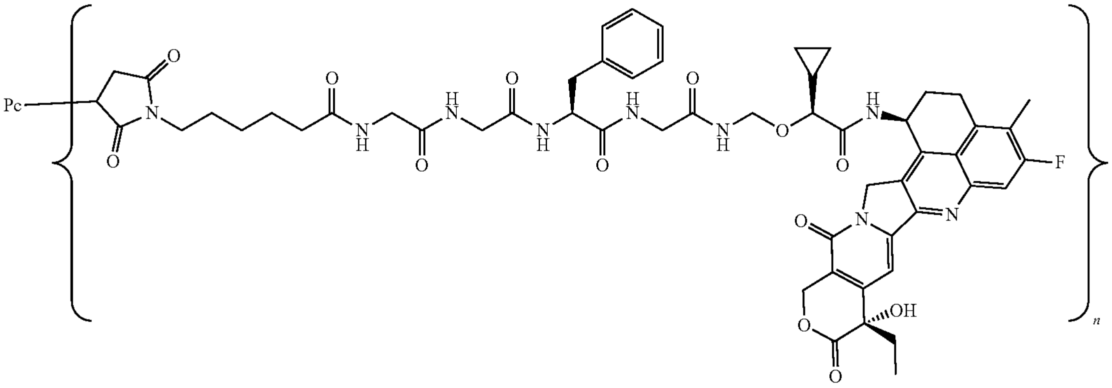
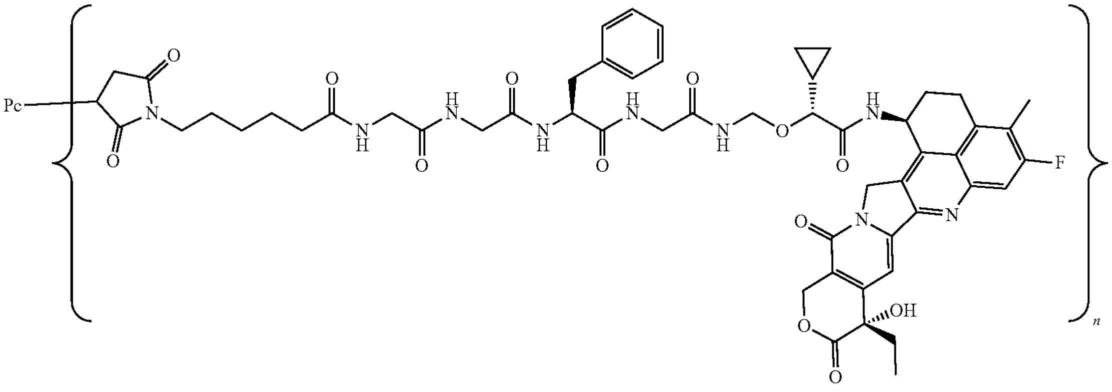

wherein:

n is 1 to 10 and can be an integer or a decimal; and

Pc is the anti-CD79B antibody or the antigen-binding fragment thereof described above of the present disclosure.

In some embodiments, provided is a method for preparing a ligand-exatecan (or a derivative thereof) conjugate of general formula (Pc-$L_a$-Y-D) or a pharmaceutically acceptable salt or solvate thereof, which comprises the following step:

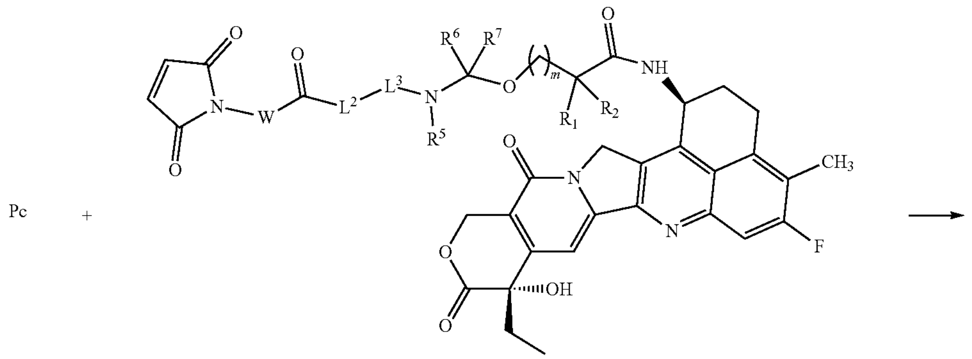

($L_a$-Y-D)

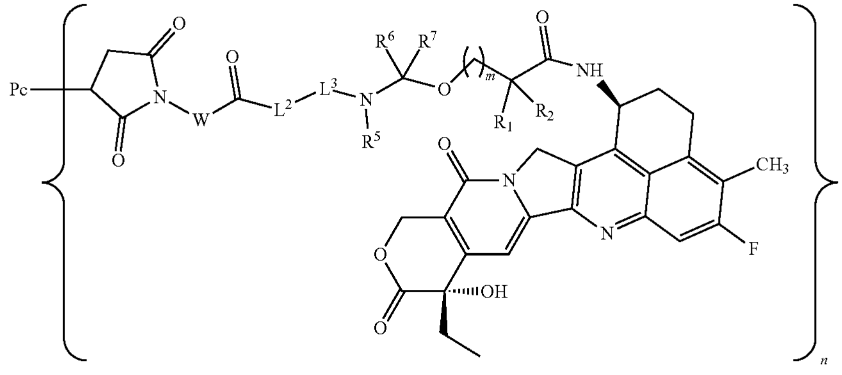

(Pc-$L_a$-Y-D)

subjecting reduced Pc to a coupling reaction with general formula ($L_a$-Y-D) to obtain the compound of general formula (Pc-$L_a$-Y-D);

wherein Pc is the anti-CD79B antibody or the antigen-binding fragment thereof of the present disclosure; and W, $L^2$, $L^3$, $R^1$, $R^2$, $R^5$-$R^7$, m and n are as defined in formula (I).

In the above embodiments, Pc is any one of the anti-CD79B antibodies or the antigen-binding fragments thereof of the present disclosure; preferably an antibody comprising a heavy chain set forth in SEQ ID NO: 28 and a light chain set forth in SEQ ID NO: 29, or an antibody comprising a heavy chain set forth in SEQ ID NO: 30 and a light chain set forth in SEQ ID NO: 31.

In some specific embodiments, the ligand-exatecan (or the derivative thereof) conjugate of the present disclosure includes a tautomer, mesomer, racemate, enantiomer, diastereomer or deuteride thereof or a mixture thereof.

The compound and the preparation method therefor described in WO2020063673 are incorporated herein in their entirety.

Ligand-Drug (Eribulin or Derivative Thereof) Conjugate

The present disclosure provides a ligand-eribulin (or a derivative thereof) conjugate of formula Pc-(L-D)$_k$ or a pharmaceutically acceptable salt or solvate thereof:

wherein the ligand is Pc, and the Pc is any one of the anti-CD79B antibodies or the antigen-binding fragments thereof of the present disclosure;

L is a linker covalently attaching Pc to D, and k is 1 to 20 (including 1, 2, 3, 4, 5, 6, 7, 8, 9, 10, 11, 12, 13, 14, 15, 16, 17, 18, 19, 20 or any value between any two of the values); and D is as shown in formula (III) below:

formula (III)

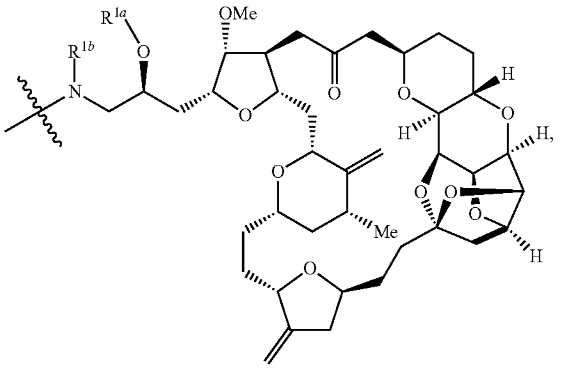

wherein R is selected from the group consisting of hydrogen, alkyl (e.g., $C_{1-6}$ alkyl including but not limited to methyl, ethyl and isopropyl), cycloalkyl (e.g., $C_{3-8}$ cycloalkyl including but not limited to cyclopropyl, cyclopentyl or cyclohexyl), aryl and heteroaryl, wherein the alkyl, cycloalkyl, aryl and heteroaryl are each independently and optionally substituted with one or more substituents selected from the group consisting of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl, heterocyclyl, aryl and heteroaryl; preferably, $R^{1a}$ is methyl; $R^{1b}$ is selected from the group consisting of hydrogen, alkyl (e.g., $C_{1-6}$ alkyl including but not limited to methyl, ethyl and isopropyl), alkoxy, cycloalkyl (e.g., $C_{3-8}$ cycloalkyl including but not limited to cyclopropyl, cyclopentyl or cyclohexyl), aryl and heteroaryl, wherein the alkyl, cycloalkyl, aryl and heteroaryl are each independently and optionally substituted with one or more substituents selected from the group consisting of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl, heterocyclyl, aryl and heteroaryl; preferably, $R^{1b}$ is hydrogen; or $R^{1a}$ and $R^{1b}$, together with the atom to which they are attached, form $C_{5-8}$ heterocycloalkyl, wherein the heterocycloalkyl is optionally substituted with one or more substituents of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl (e.g., $C_{3-8}$ cycloalkyl including but not limited to cyclopropyl, cyclopentyl or cyclohexyl), heterocyclyl, aryl and heteroaryl; and $R^{1a}$ and $R^{1b}$ are not both hydrogen.

In some embodiments, in the ligand-eribulin (or the derivative thereof) conjugate, $R^{1a}$ in D is methyl.

In some embodiments, in the ligand-eribulin (or the derivative thereof) conjugate, D is as shown in the formula below:

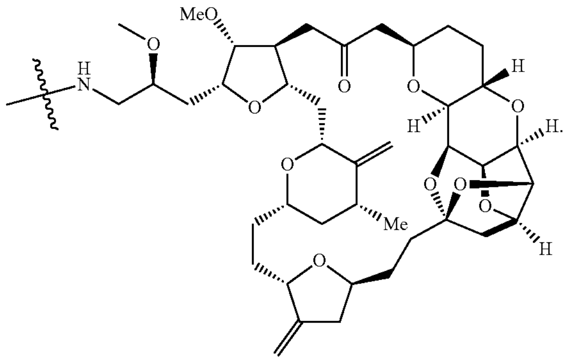

In some embodiments, in the ligand-eribulin (or the derivative thereof) conjugate of Pc-(L-D)$_k$, k is selected from the group consisting of 1 to 10 and can be an integer or a decimal.

In some embodiments, the linker is stable extracellularly, such that the ligand-eribulin (or the derivative thereof) conjugate remains intact in the extracellular environment, but is cleavable e.g., upon internalization into a cancer cell.

In some embodiments, when the ligand-drug conjugate enters an antigen-expressing cell, the drug moiety in the conjugate is cleaved from the ligand moiety, and the drug (e.g., eribulin or a derivative thereof) is released by the cleavage.

In some embodiments, the linker comprises a cleavable moiety; wherein the cleavable moiety is positioned such that there is no linker and Pc remaining in the drug (e.g., eribulin derivative) after cleavage.

In some embodiments, the cleavable moiety in the linker is a cleavable peptide moiety.

In some embodiments, the ligand-drug conjugate comprising the cleavable peptide moiety shows a lower aggregation level, an improved antibody-to-drug ratio, increased targeted killing of cancer cells, reduced off-target killing of non-cancer cells, and/or a higher drug loading (p).

In some embodiments, the addition of a cleavable moiety increases cytotoxicity and/or potency relative to a non-cleavable linker. In some embodiments, potency and/or cytotoxicity is increased in cancers that express moderate levels of antigen (e.g., CD79B). In some embodiments, the cleavable peptide moiety is cleavable by an enzyme, and the linker is one that is cleavable by an enzyme. In some embodiments, the linker is one that is cleavable by a cathepsin. In certain embodiments, the linker that is cleavable by an enzyme (e.g., the linker that is cleavable by a cathepsin) shows one or more of the improved properties described above.

In some embodiments, the linker comprises an amino acid unit (i.e., a peptide residue consisting of 2 to 7 amino acids), wherein preferably, the amino acids are selected from the group consisting of phenylalanine, glycine, valine, lysine, citrulline, serine, glutamic acid and aspartic acid, and more preferably valine-citrulline (Val-Cit), alanine-alanine-asparagine (Ala-Ala-Asn), glycine-glycine-lysine (Gly-Gly-lys), valine-lysine (Val-lys), valine-alanine (Val-Ala), valine-phenylalanine (Val-Phe) and glycine-glycine-phenylalanine-glycine (Gly-Gly-Phe-Gly).

In some embodiments, the linker in the conjugate of the present disclosure is selected from the group consisting of:

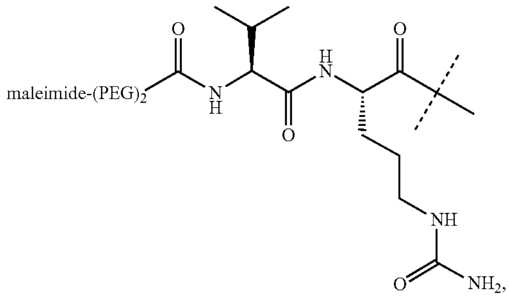

,

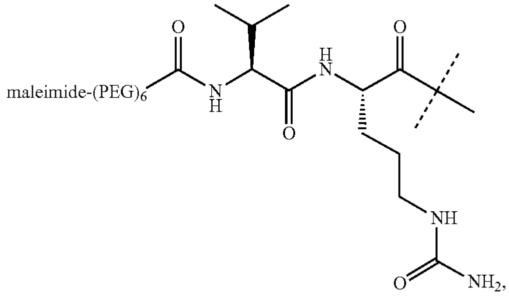

,

-continued

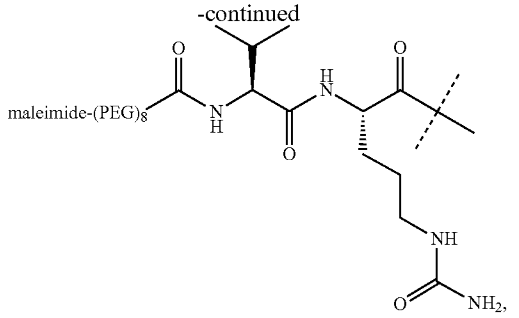

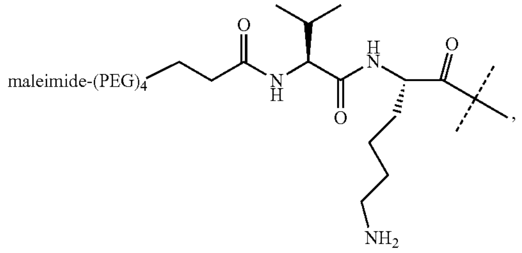

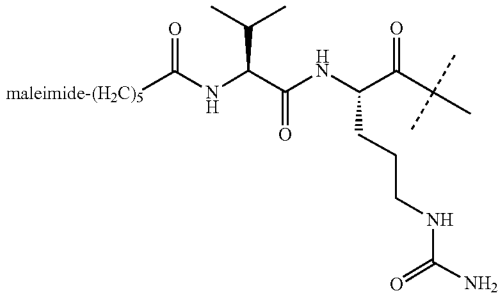

and

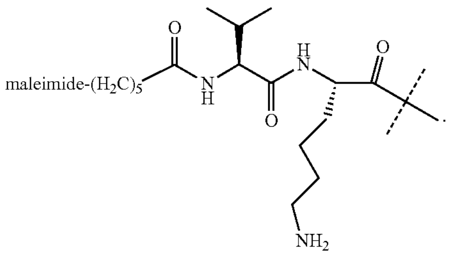

In some embodiments, the amino acid unit comprises valine-citrulline (Val-Cit).

In some embodiments, the ADC comprising Val-Cit shows increased stability, reduced off-target cell killing, increased targeted cell killing, a lower aggregation level, and/or a higher drug loading.

In another aspect, a linker provided by some embodiments comprises a cleavable sulfonamide moiety, and the linker is cleavable under reduced conditions.

In some embodiments, the linker comprises a cleavable disulfide moiety, and the linker cleavable under reduced conditions.

In another aspect, the linker of the present disclosure comprises at least one spacer unit that attaches D (e.g., an eribulin derivative) to a cleavable moiety.

In some embodiments, the spacer unit comprises p-aminobenzyloxycarbonyl (PAB) and

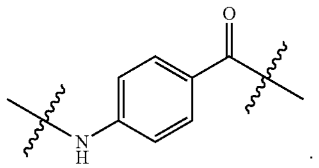 [SMILES: *Nc1ccc(C(*)=O)cc1]

In another aspect, a conjugate provided by some embodiments is as shown in the formula below:

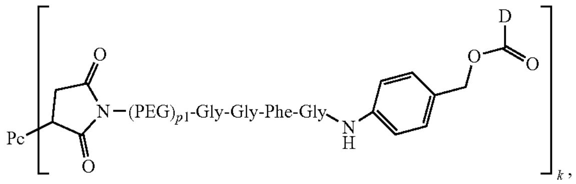

wherein k is selected from the group consisting of 1 to 10, and can be an integer or a decimal; and p1 is selected from the group consisting of 2, 4, 6 and 8;

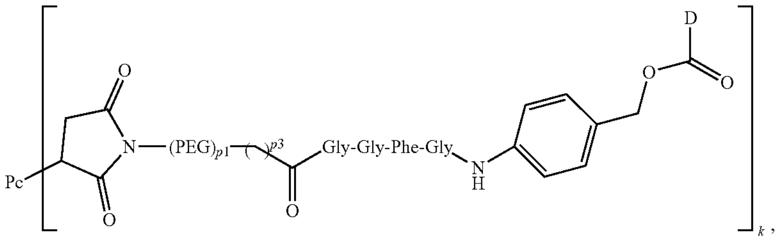

wherein k is selected from the group consisting of 1 to 10, and can be an integer or a decimal; p1 is selected from the group consisting of 2, 4, 6 and 8; and P3 is selected from the group consisting of 0, 1 and 2;

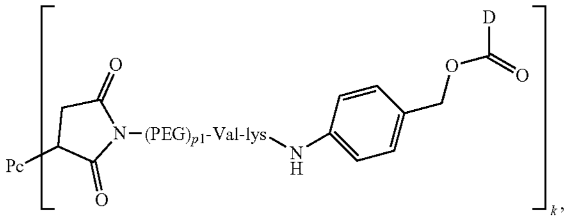

wherein k is selected from the group consisting of 1 to 10, and can be an integer or a decimal; and p1 is selected from the group consisting of 2, 4, 6 and 8;

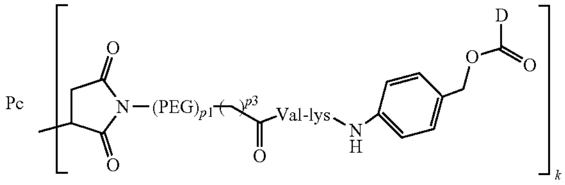

, wherein k is selected from the group consisting of 1 to 10, and can be an integer or a decimal; p1 is selected from the group consisting of 2, 4, 6 and 8; and P3 is selected from the group consisting of 0, 1 and 2;

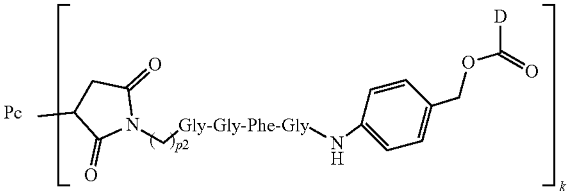

, wherein k is selected from the group consisting of 1 to 10, and can be an integer or a decimal; and p2 is selected from the group consisting of 2, 4, 6 and 8;

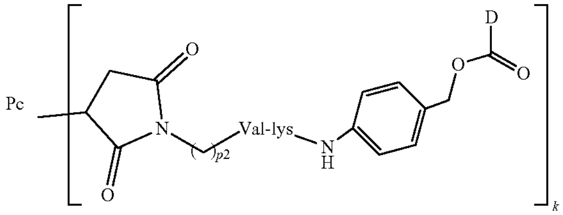

, wherein k is selected from the group consisting of 1 to 10, and can be an integer or a decimal; and p2 is selected from the group consisting of 2, 4, 6 and 8;

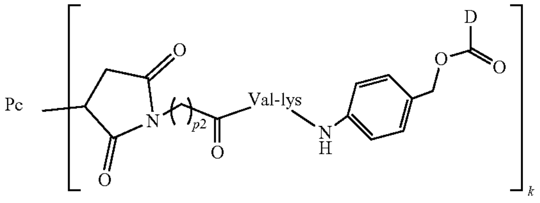

, wherein k is selected from the group consisting of 1 to 10, and can be an integer or a decimal; and p2 is selected from the group consisting of 2, 4, 6 and 8;

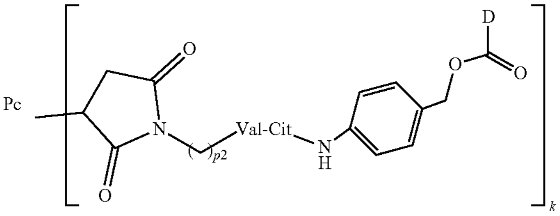

, wherein k is selected from the group consisting of 1 to 10, and can be an integer or a decimal; and p2 is selected from the group consisting of 2, 4, 6 and 8;

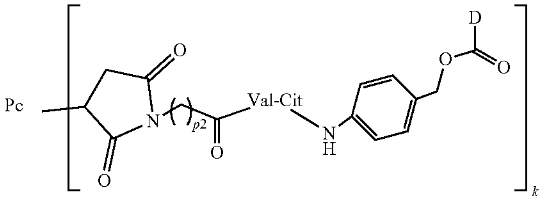

, wherein k is selected from the group consisting of 1 to 10, and can be an integer or a decimal; and p2 is selected from the group consisting of 2, 4, 6 and 8;

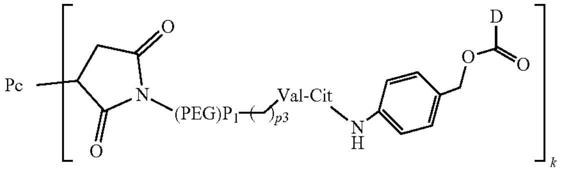

, wherein k is selected from the group consisting of 1 to 10, and can be an integer or a decimal; P1 is selected from the group consisting of 2, 4, 6 and 8; and P3 is selected from the group consisting of 0, 1 and 2;

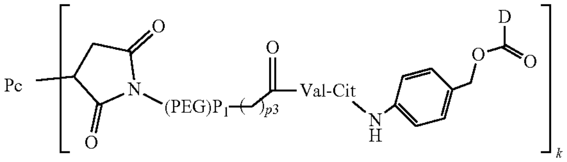

, wherein k is selected from the group consisting of 1 to 10, and can be an integer or a decimal; P1 is selected from the group consisting of 2, 4, 6 and 8; and P3 is selected from the group consisting of 0, 1 and 2.

In some embodiments, the conjugate is as shown in the following formulas:

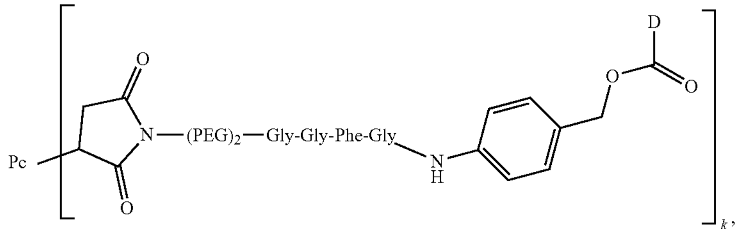

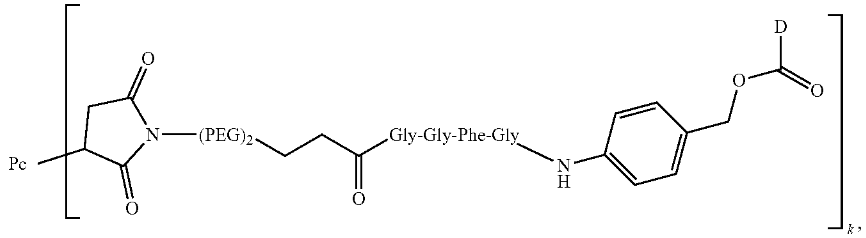

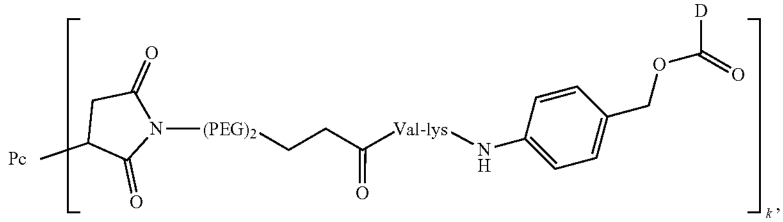

and

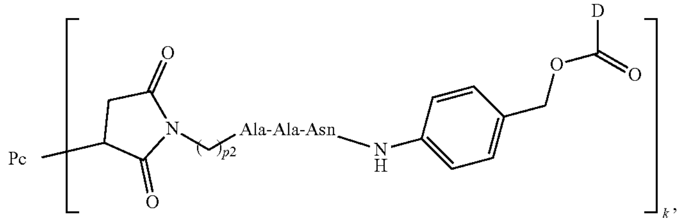

wherein k is selected from the group consisting of 1 to 10, and can be an integer or a decimal; further, $R^{1a}$ in D is preferably selected from methyl, and $R^{1b}$ in D is preferably selected from hydrogen.

The present disclosure also provides a compound of formula D (eribulin),

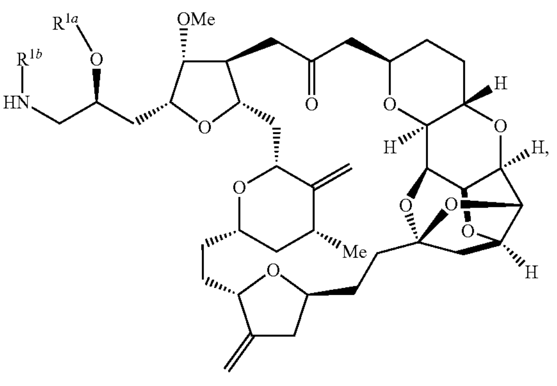

D(Eribulin)

or a pharmaceutically acceptable salt thereof, wherein, $R^{1a}$ is selected from the group consisting of hydrogen, alkyl (e.g., $C_{1-6}$ alkyl including but not limited to methyl, ethyl and isopropyl), cycloalkyl (e.g., $C_{3-8}$ cycloalkyl including but not limited to cyclopropyl, cyclopentyl or cyclohexyl), aryl and heteroaryl, wherein the alkyl, cycloalkyl, aryl and heteroaryl are each independently and optionally substituted with one or more substituents selected from the group consisting of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl, heterocyclyl, aryl and heteroaryl; preferably, $R^{1a}$ is methyl;

$R^{1b}$ is selected from the group consisting of hydrogen, alkyl (e.g., $C_{1-6}$ alkyl including but not limited to methyl, ethyl and isopropyl), alkoxy, cycloalkyl (e.g., $C_{3-8}$ cycloalkyl including but not limited to cyclopropyl, cyclopentyl or cyclohexyl), aryl and heteroaryl, wherein the alkyl, cycloalkyl, aryl and heteroaryl are each independently and optionally substituted with one or more substituents selected from the group consisting of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl, heterocyclyl, aryl and heteroaryl; preferably, $R^{1b}$ is hydrogen or methyl; or $R^{1a}$ and $R^{1b}$, together with the carbon atom to which they are attached, form $C_{5-8}$ heterocycloalkyl, wherein the heterocycloalkyl is optionally substituted with one or more substituents of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl (e.g., $C_{3-8}$ cycloalkyl including but not limited to cyclopropyl, cyclopentyl or cyclohexyl), heterocyclyl, aryl and heteroaryl; and $R^{1a}$ and $R^{1b}$ are not both hydrogen.

In some embodiments, in the compound of formula D (eribulin), Ria and $R^{1b}$ are each independently selected from $C_{1-6}$ alkyl, including but not limited to methyl, ethyl and isopropyl.

In some embodiments, in the compound of formula D (eribulin), $R^{1a}$ is selected from $C_{1-6}$ alkyl, including but not limited to methyl, ethyl and isopropyl; and $R^{1b}$ is selected from hydrogen.

In some embodiments, in the compound of formula D (eribulin), Ria and $R^{1b}$, together with the carbon atom to which they are attached, form $C_{6-8}$ heterocycloalkyl.

In some embodiments, the compound of formula D (eribulin) is:

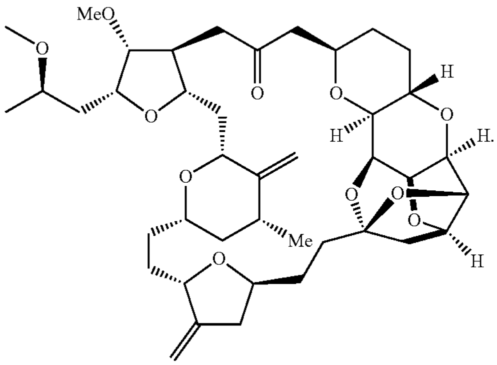

D(Eribulin)-1

In some embodiments, the compound of formula D (eribulin) is:

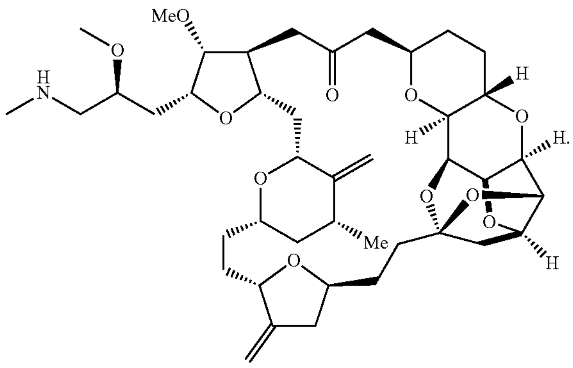

D(Eribulin)-2

In some embodiments, the compound of formula D (eribulin) is.

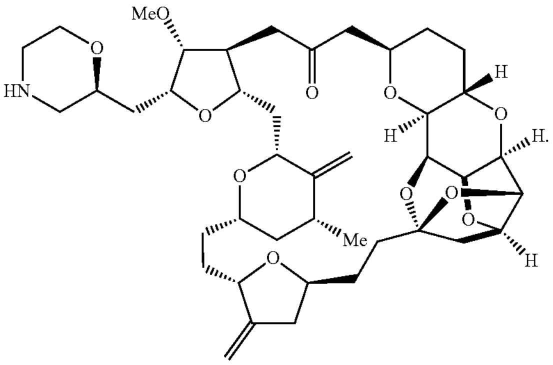

D(Eribulin)-3

The present disclosure also provides a compound of formula DZ (eribulin),

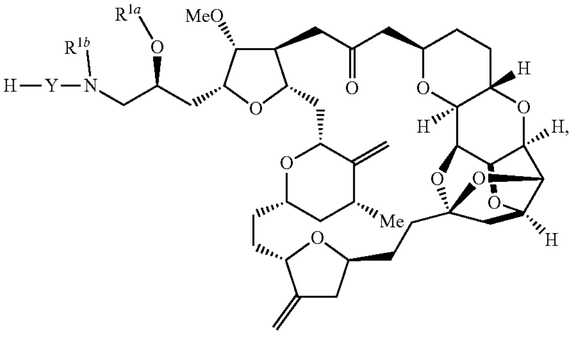

DZ(Eribulin)

or a pharmaceutically acceptable salt thereof, wherein $R^{1a}$ is selected from the group consisting of hydrogen, alkyl (e.g., $C_{1-6}$ alkyl including but not limited to methyl, ethyl and isopropyl), cycloalkyl (e.g., $C_{3-8}$ cycloalkyl including but not limited to cyclopropyl, cyclopentyl or cyclohexyl), aryl and heteroaryl, wherein the alkyl, cycloalkyl, aryl and heteroaryl are each independently and optionally substituted with one or more substituents selected from the group consisting of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl, heterocyclyl, aryl and heteroaryl; preferably, $R^{1a}$ is methyl;

$R^{1b}$ is selected from the group consisting of hydrogen, alkyl (e.g., $C_{1-6}$ alkyl including but not limited to methyl, ethyl and isopropyl), cycloalkyl (e.g., $C_{3-8}$ cycloalkyl including but not limited to cyclopropyl, cyclopentyl or cyclohexyl), alkoxy, aryl and heteroaryl, wherein the alkyl, cycloalkyl, aryl and heteroaryl are each independently and optionally substituted with one or more substituents selected from the group consisting of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl, heterocyclyl, aryl and heteroaryl; preferably, $R^{1b}$ is hydrogen;

or $R^{1a}$ and $R^{1b}$, together with the carbon atom to which they are attached, form $C_{5-8}$ heterocycloalkyl, wherein the heterocycloalkyl is optionally substituted with one or more substituents of alkyl (e.g., $C_{1-6}$ alkyl including but not limited to methyl, ethyl and isopropyl), alkoxy (e.g., $C_{1-6}$ alkoxy including but not limited to methoxy, ethoxy, propoxy and isopropoxy), halogen (e.g., fluoro, chloro and bromo), deuterium, amino, cyano, nitro, hydroxy, hydroxyalkyl, cycloalkyl (e.g., $C_{3-8}$ cycloalkyl including but not limited to cyclopropyl, cyclopentyl or cyclohexyl), heterocyclyl, aryl and heteroaryl; and $R^{1a}$ and $R^{1b}$ are not both hydrogen; and Y is selected from the group consisting of $—O(CR^aR^b)_{m2}—CR^8R^9—C(O)—$, $—NH—(CR^aR^b)_1$, $—CR^8R^9—C(O)—$, $—O—CR^8R^9(CR^aR^b)_{m2}—$, $—OCR^8R^9—C(O)—$, $—O(CR^aR^b)_{m2}C(O)—$ and $—S—(CR^aR^b)_{m2}—CR^8R^9—C(O)—$, wherein Ra and $R^b$ are identical or different and are each independently selected from the group consisting of hydrogen, deuterium, halogen and alkyl; $R^8$ is selected from the group consisting of hydrogen, $C_{3-6}$ cycloalkylalkyl and $C_{3-6}$ cycloalkyl; $R^9$ is selected from the group consisting of hydrogen, haloalkyl and $C_{3-6}$ cycloalkyl, preferably hydrogen; or $R^8$ and $R^9$, together with the carbon atom to which they are attached, form $C_{3-6}$ cycloalkyl; and m2 is selected from the group consisting of 0, 1, 2 and 3.

In some embodiments, in the compound of formula DZ (eribulin), Ria and $R^{1b}$ are each independently selected from $C_{1-6}$ alkyl, including but not limited to methyl, ethyl and isopropyl.

In some embodiments, in the compound of formula DZ (eribulin), Ria is selected from $C_{1-6}$ alkyl, including but not limited to methyl, ethyl and isopropyl; and $R^{1b}$ is selected from hydrogen.

In some embodiments, in the compound of formula DZ (eribulin), $R^{1a}$ and $R^{1b}$, together with the carbon atom to which they are attached, form $C_{6-8}$ heterocycloalkyl.

In some embodiments, the compound of formula DZ (eribulin) is:

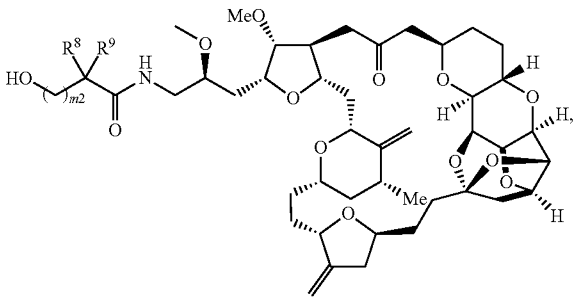

DZ(Eribulin)-1 or a pharmaceutically acceptable salt thereof, wherein: $R^8$ is selected from the group consisting of hydrogen, $C_{3-6}$ cycloalkylalkyl and $C_{3-6}$ cycloalkyl; $R^9$ is selected from the group consisting of hydrogen, haloalkyl and $C_{3-6}$ cycloalkyl, preferably hydrogen; or $R^8$ and $R^9$, together with the carbon atom to which they are connected, form $C_{3-6}$ cycloalkyl; and m2 is selected from the group consisting of 0, 1, 2 and 3.

In some embodiments, the compound of formula DZ (eribulin) is selected from the group consisting of:

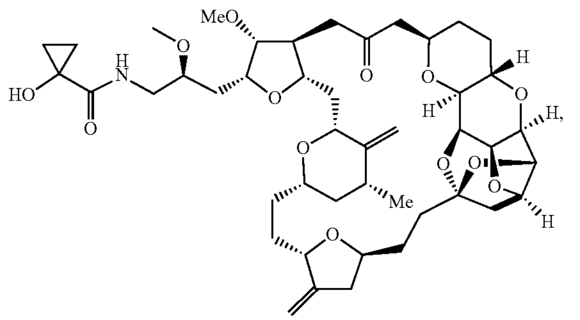

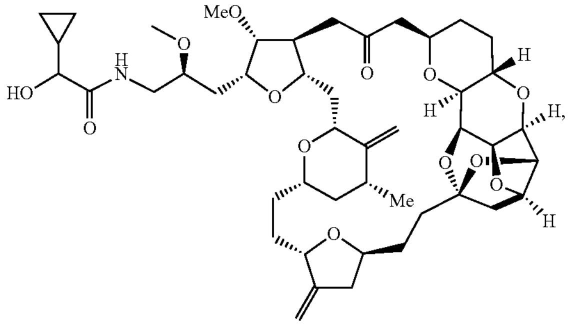

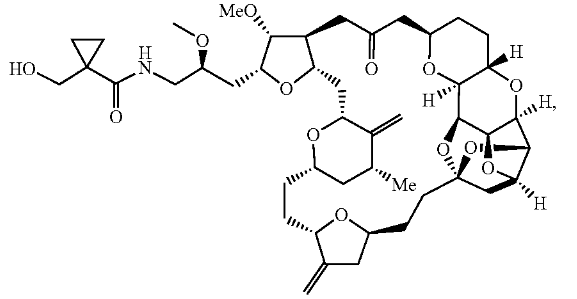

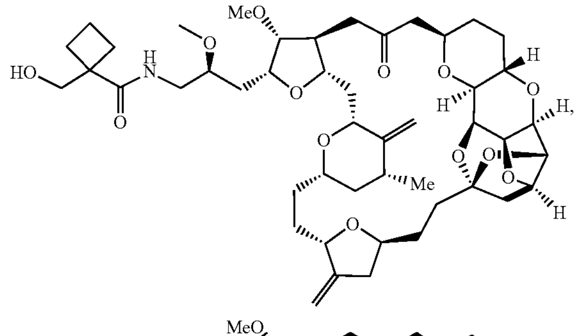

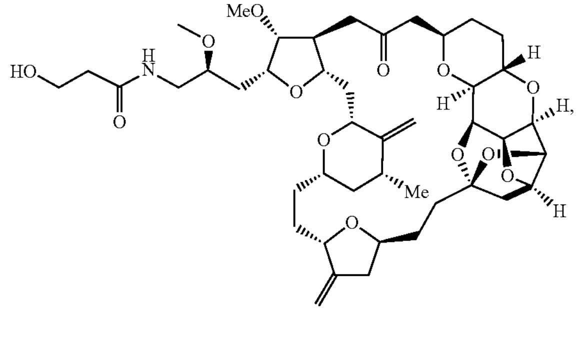

-continued

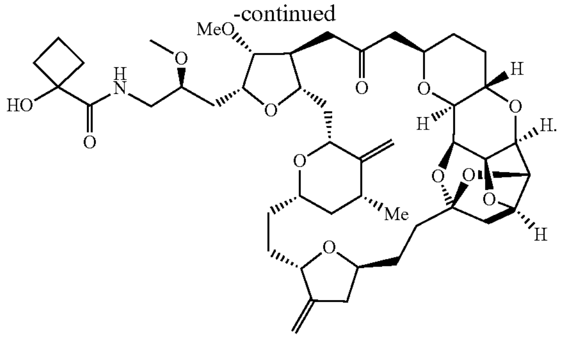

In another aspect, a compound of formula DZ (eribulin) provided by some embodiments may contain one or more asymmetric centers, for example,

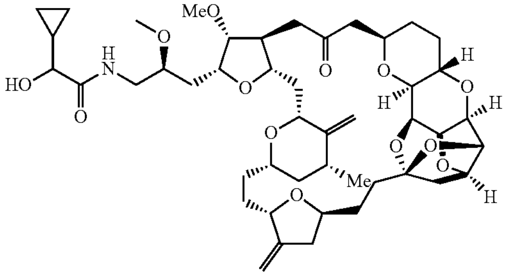

may be

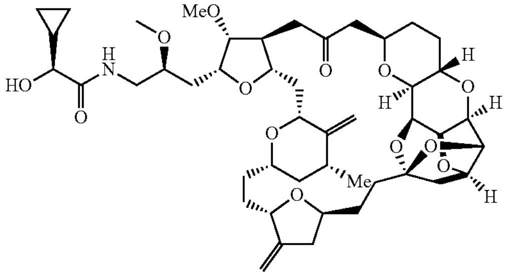

or

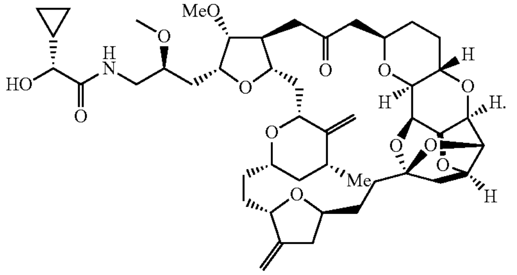

In the above embodiments, Pc is any one of the anti-CD79B antibodies or the antigen-binding fragments thereof of the present disclosure; preferably an antibody comprising a heavy chain set forth in SEQ ID NO: 28 and a light chain set forth in SEQ ID NO: 29, or an antibody comprising a heavy chain set forth in SEQ ID NO: 30 and a light chain set forth in SEQ ID NO: 31.

In some specific embodiments, the conjugate of the present disclosure includes a tautomer, mesomer, racemate, enantiomer, diastereomer or deuteride thereof or a mixture thereof.

The compound and the preparation method therefor described in CN202010073671.6 are incorporated herein in their entirety.

Ligand-Drug (MMAE or Derivative Thereof) Conjugate

The present disclosure provides an MMAE analog/derivative, which is a compound of general formula (D(MMAE)):

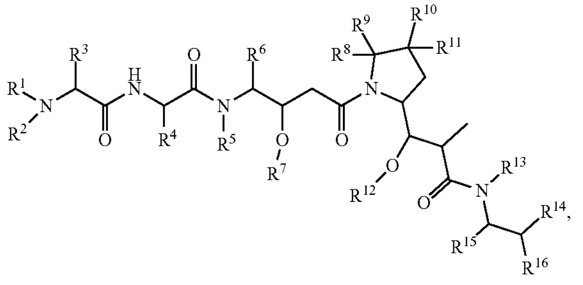

(D(MMAE))

or a pharmaceutically acceptable salt thereof, wherein:

$R^1$-$R^6$ are selected from the group consisting of hydrogen, halogen, hydroxy, cyano, alkyl, alkoxy and cycloalkyl;

$R^7$ is selected from the group consisting of hydrogen, alkyl, alkoxy and cycloalkyl; any two of $R^8$-$R^{11}$ form cycloalkyl, and the remaining two groups are selected from the group consisting of hydrogen, alkyl and cycloalkyl;

$R^{12}$ is selected from the group consisting of hydrogen and alkyl;

$R^{13}$-$R^{15}$ are selected from the group consisting of hydrogen, hydroxy, alkyl, alkoxy and halogen; and $R^{16}$ is selected from the group consisting of aryl and heteroaryl, wherein the aryl and heteroaryl are optionally further substituted with a substituent selected from the group consisting of hydrogen, halogen, hydroxy, alkyl, alkoxy and cycloalkyl.

In some embodiments of the present disclosure, provided is the compound of general formula (D(MMAE)), which is a compound of general formula $(D(MMAE)_1)$:

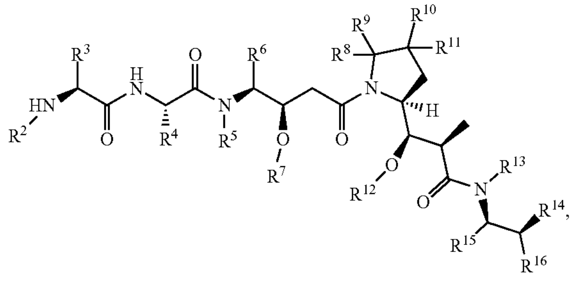

$(D(MMAE)_1)$ or a pharmaceutically acceptable salt thereof, wherein $R^9$ and $R^{10}$ form cycloalkyl; and $R^2$-$R^8$ and $R^{11}$-$R^{16}$ are as defined in general formula (D).

In some embodiments of the present disclosure, provided is the compound of general formula (D(MMAE)), which is:

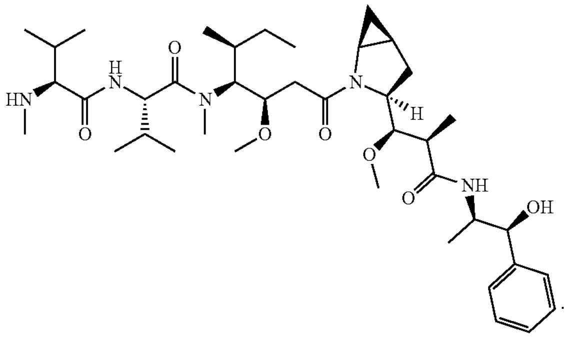

(1(MMAE))

Another aspect of the present disclosure relates to a ligand-drug conjugate or a pharmaceutically acceptable salt or solvate thereof, wherein the ligand-drug conjugate comprises a structure of formula (-D(MMAE)):

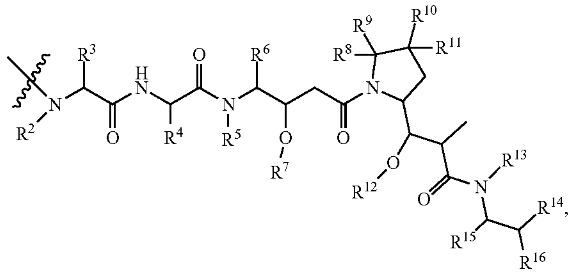

(-D(MMAE))

or a pharmaceutically acceptable salt thereof, wherein:

$R^2$-$R^6$ are selected from the group consisting of hydrogen, halogen, hydroxy, cyano, alkyl, alkoxy and cycloalkyl;

$R^7$ is selected from the group consisting of hydrogen, alkyl, alkoxy and cycloalkyl; any two of $R^8$-$R^{11}$ form cycloalkyl, and the remaining two groups are selected from the group consisting of hydrogen, alkyl and cycloalkyl;

$R^{12}$ is selected from the group consisting of hydrogen and alkyl;

$R^{13}$-$R^{15}$ are selected from the group consisting of hydrogen, hydroxy, alkyl, alkoxy and halogen;

$R^{16}$ is selected from the group consisting of aryl and heteroaryl, wherein the aryl and heteroaryl are optionally further substituted with a substituent selected from the group consisting of hydrogen, halogen, hydroxy, alkyl, alkoxy and cycloalkyl; and the wavy line indicates hydrogen or covalent attaching to a linker or to an antibody.

In some embodiments of the present disclosure, provided is the ligand-MMAE (or the derivative thereof) conjugate or the pharmaceutically acceptable salt or solvate thereof, which comprises a structure of formula (-D(MMAE)$_1$):

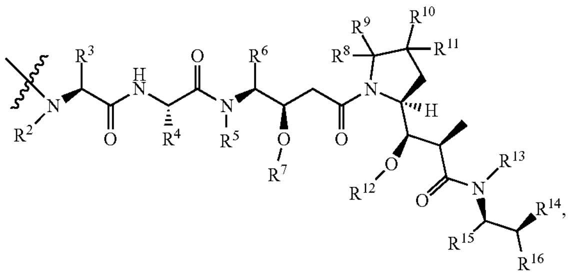

(-D(MMAE)$_1$)

wherein:

$R^9$ and $R^{10}$ form cycloalkyl; and the wavy line, $R^2$-$R^8$, and $R^{11}$-$R^{16}$ are as defined in general formula (D(MMAE)).

In some embodiments of the present disclosure, provided is the ligand-MMAE (or the derivative thereof) conjugate or the pharmaceutically acceptable salt or solvate thereof, wherein the ligand-MMAE (or the derivative thereof) conjugate comprises a structure of the following formula:

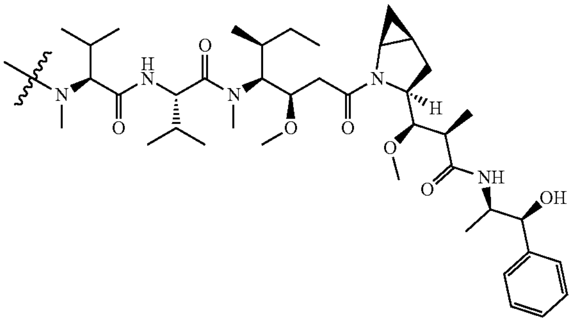 [SMILES: *N(C)[C@H](C(=O)N[C@H](C(=O)N(C)[C@@H]([C@@H](C)CC)[C@@H](CC(=O)N1[C@H]2C[C@H]2C[C@H]1[C@H](OC)[C@@H](C)C(=O)N[C@H](C)[C@@H](O)c1ccccc1)OC)C(C)C)C(C)C]

wherein the wavy line indicates hydrogen or covalent attaching to a linker or to an antibody.

In some embodiments of the present disclosure, provided is the ligand-MMAE (or the derivative thereof) conjugate or the pharmaceutically acceptable salt or solvate thereof, which is as shown in general formula (IV):

formula (IV)

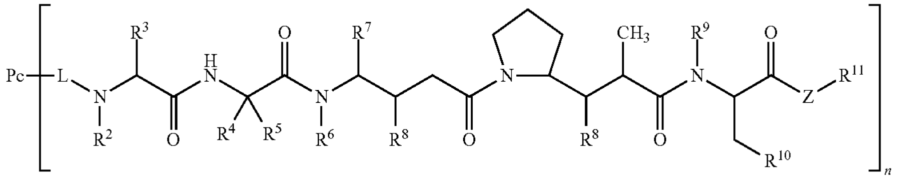

wherein, $R^2$ is $C_1$-$C_8$ alkyl;
$R^3$ is $C_1$-$C_8$ alkyl;
$R^4$ is $C_1$-$C_8$ alkyl;
$R^5$ is H;
$R^6$ is $C_1$-$C_8$ alkyl;
$R^7$ is $C_1$-$C_8$ alkyl;
$R^8$ are each independently O—($C_1$-$C_8$ alkyl);
$R^9$ is H;
$R^{10}$ is phenyl;
Z is O or NH;
$R^{11}$ is selected from the group consisting of H, $C_1$-$C_{20}$ alkyl and —($R^{13}$O)m-$R^{14}$;
m is 3;
$R^{13}$ is $C_2$-$C_8$ alkyl;
$R^{14}$ is $C_1$-$C_8$ alkyl;
Pc is the anti-CD79B antibody or the antigen-binding fragment thereof of the present disclosure; L is a linker; and n is 1 to 10 and can be an integer or a decimal.

In some specific embodiments, provided is the ligand-MMAE (or the derivative thereof) conjugate or the pharmaceutically acceptable salt or solvate thereof, which comprises a structure as shown below:

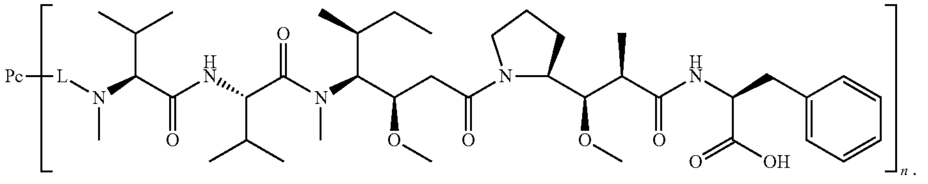

In some embodiments of the present disclosure, provided is the ligand-MMAE (or the derivative thereof) conjugate or the pharmaceutically acceptable salt or solvate thereof, which is as shown in general formula (Pc-L-D(MMAE)):

formula (V)

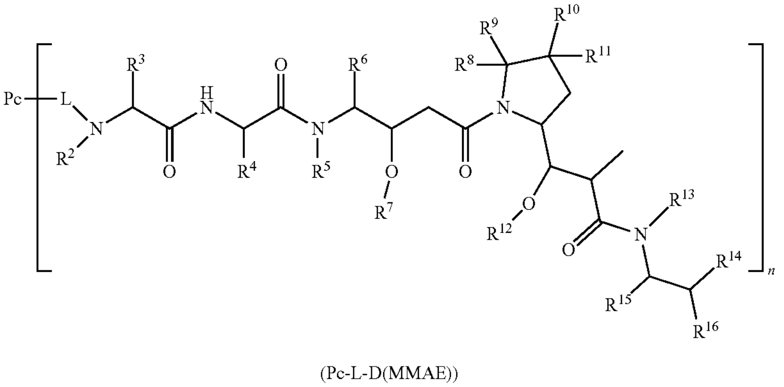

(Pc-L-D(MMAE))

wherein:
$R^2$-$R^{16}$ are as defined in general formula (D(MMAE));
n is 1 to 10 and can be an integer or a decimal;
Pc is the anti-CD79B antibody or the antigen-binding fragment thereof of the present disclosure; and L is a linker.

In some embodiments of the present disclosure, provided is the ligand-MMAE (or the derivative thereof) conjugate or the pharmaceutically acceptable salt or solvate thereof, which is a ligand-MMAE (or a derivative thereof) conjugate of general formula (Pc-L-D1) or a pharmaceutically acceptable salt or solvate thereof:

formula (VI)

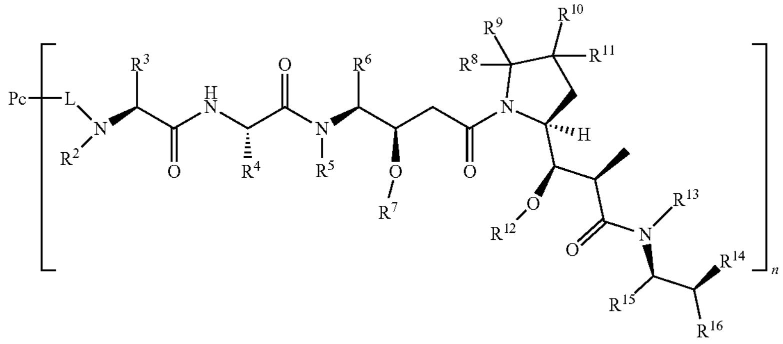

(Pc-L-D(MMAE)$_1$)

wherein:

$R^2$-$R^{16}$ are as defined in general formula (-D(MMAE)); and

Pc, L and n are as defined in general formula (Pc-L-D (MMAE)).

In some embodiments of the present disclosure, provided is the ligand-MMAE (or the derivative thereof) conjugate or the pharmaceutically acceptable salt or solvate thereof, which is as shown in the general formula below:

formula (VII)

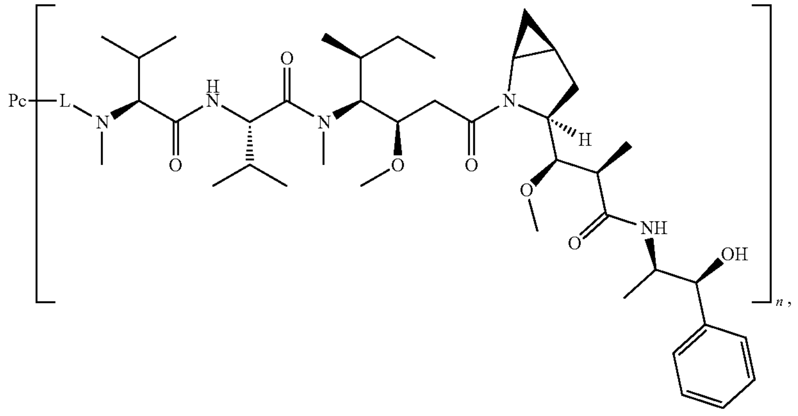

wherein Pc, L and n are as defined in general formula (Pc-L-D(MMAE)).

In some embodiments of the present disclosure, provided is the ligand-MMAE (or the derivative thereof) conjugate or the pharmaceutically acceptable salt or solvate thereof, wherein n is 1 to 8, and can be an integer or decimal; preferably n is 1 to 6, and can be an integer or a decimal.

In some embodiments of the present disclosure, provided is the ligand-MMAE (or the derivative thereof) conjugate or the pharmaceutically acceptable salt or solvate thereof, wherein the linker is —Y-$L^1$-$L^2$-$L^3$-$L^4$, wherein: Y is a stretcher unit selected from the group consisting of

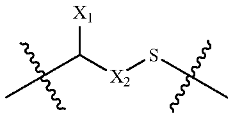

and a chemical bond, wherein $X_1$ is selected from the group consisting of hydrogen, alkyl, alkoxy, aryl and halogen, and $X_2$ is selected from alkylene, the alkylene being optionally further substituted with one or more substituents selected from the group consisting of halogen, hydroxy, cyano, amino, alkyl, chloroalkyl, deuterated alkyl, alkoxy and cycloalkyl; $L^1$ is a stretcher unit selected from the group consisting of -(succinimid-3-yl-N)—W—C(O)—, —$CH_2$—C(O)—$NR^{17}$—W—C(O)— and —C(O)—W—C(O)—, wherein W is selected from the group consisting of $C_{1-8}$ alkyl, $C_{1-8}$ alkyl-cycloalkyl and linear heteroalkyl of 1 to 8 atoms, the heteroalkyl comprising 1 to 3 heteroatoms selected from the group consisting of N, O and S, wherein the $C_{1-8}$ alkyl, cycloalkyl and linear heteroalkyl are each independently and optionally further substituted with one or more substituents selected from the group consisting of halogen, hydroxy, cyano, amino, alkyl, chloroalkyl, deuterated alkyl, alkoxy and cycloalkyl;

$L^2$ is selected from the group consisting of —$NR^{18}$($CH_2CH_2O$)$p^1$$CH_2CH_2C$(O)—, —$NR^{18}$($CH_2CH_2O$)$p^1$$CH_2C$(O)—, —S($CH_2$)$p^1$C(O)— and a chemical bond, wherein p1 is an integer from 1 to 20; preferably, a chemical bond;

$L^3$ is a peptide residue consisting of 2 to 7 amino acids preferably selected from the group consisting of valine, citrulline and methyl valine; wherein the amino acids are optionally further substituted with one or more substituents selected from the group consisting of halogen, hydroxy, cyano, amino, alkyl, chloroalkyl, deuterated alkyl, alkoxy and cycloalkyl;

$R^{17}$ and $R^{18}$ are identical or different and are each independently selected from the group consisting of hydrogen, alkyl, haloalkyl, deuterated alkyl and hydroxyalkyl; and $L^4$ is an extension unit, preferably PAB.

In some embodiments of the present disclosure, provided is the ligand-MMAE (or the derivative thereof) conjugate or the pharmaceutically acceptable salt or solvate thereof, wherein Y is selected from

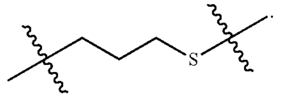 [SMILES: *CCCS*]

In some embodiments of the present disclosure, provided is the ligand-MMAE (or the derivative thereof) conjugate or the pharmaceutically acceptable salt or solvate thereof, wherein $L^1$ is selected from -(succinimid-3-yl-N)—$(CH_2)s^1$-C(O)—, wherein $s^1$ is an integer from 2 to 8; preferably

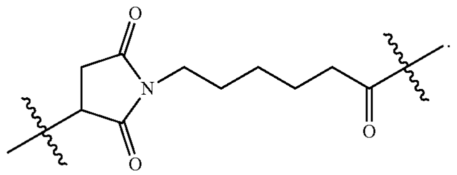 [SMILES: *C(=O)CCCCCN1C(=O)CC(*)C1=O]

In some embodiments of the present disclosure, provided is the ligand-MMAE (or the derivative thereof) conjugate or the pharmaceutically acceptable salt or solvate thereof, wherein $L^3$ is a dipeptide amino acid unit, preferably selected from valine-citrulline.

In some embodiments of the present disclosure, provided is the ligand-MMAE (or the derivative thereof) or the pharmaceutically acceptable salt or solvate thereof, wherein the linker is selected from the group consisting of:

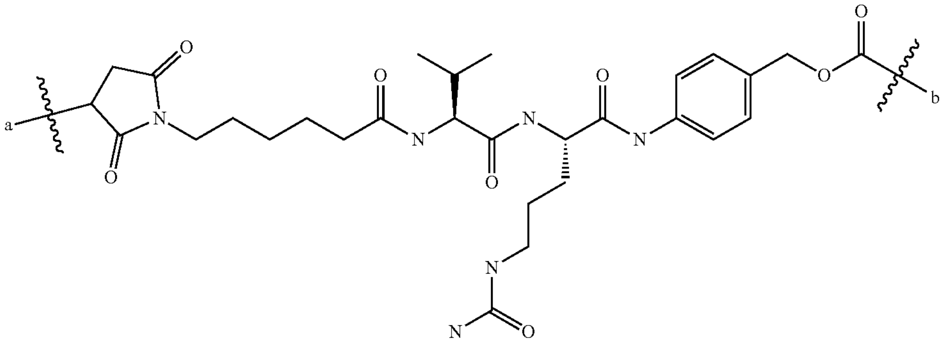

and

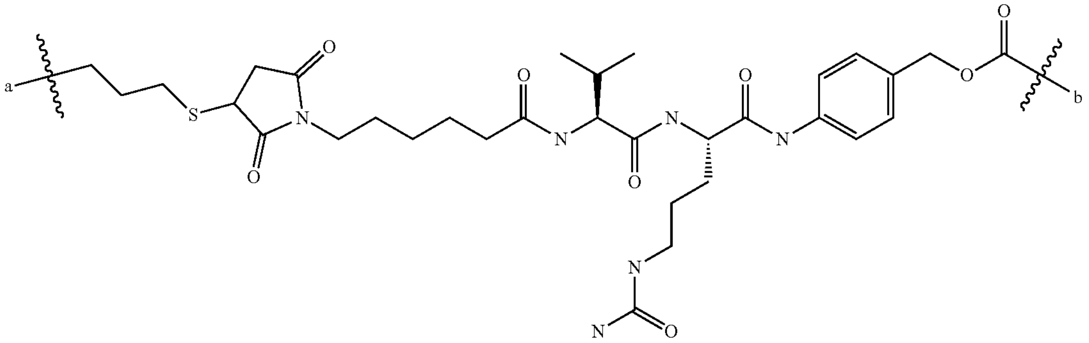

wherein the end a is linked to a ligand, and the end b is linked to a drug.

In some embodiments of the present disclosure, provided is the ligand-MMAE (or the derivative thereof) conjugate or the pharmaceutically acceptable salt or solvate thereof, which selected from the group consisting of the following formulas:

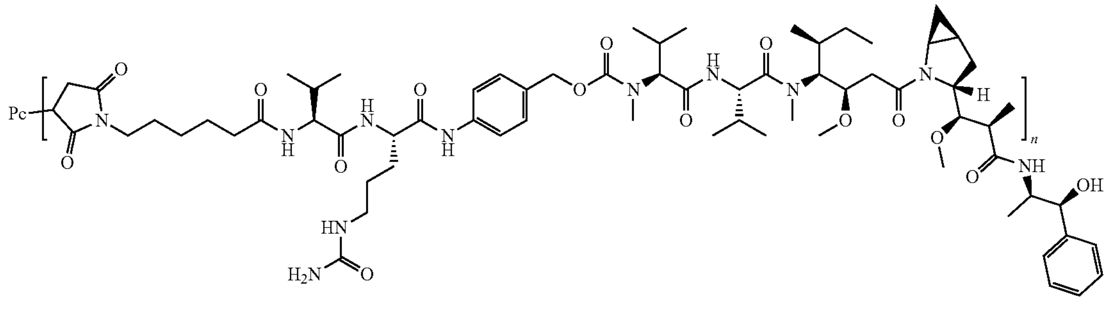

and

-continued

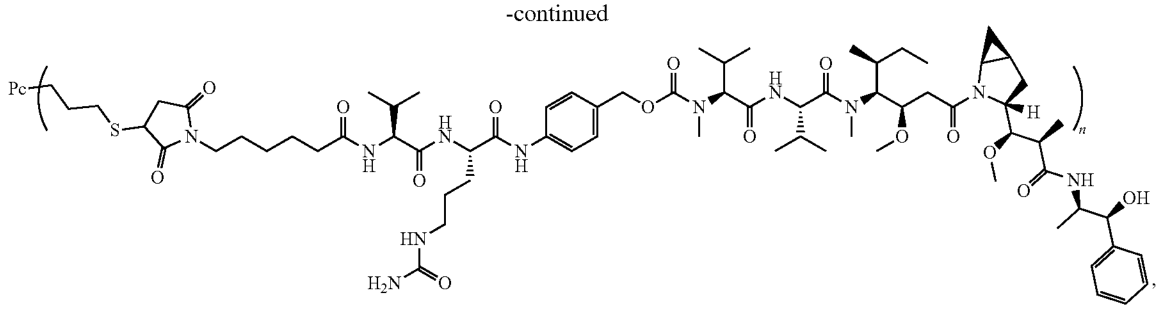

wherein:

n is 1 to 10 and can be an integer or a decimal; and

Pc is the anti-CD79B antibody or the antigen-binding fragment thereof of the present disclosure; preferably an antibody comprising a heavy chain set forth in SEQ ID NO: 28 and a light chain set forth in SEQ ID NO: 29, or an antibody comprising a heavy chain set forth in SEQ ID NO: 30 and a light chain set forth in SEQ ID NO: 31.

Another aspect of the present disclosure relates to a method for preparing a compound of general formula (D(MMAE)) or a pharmaceutically acceptable salt thereof, which comprises the following step:

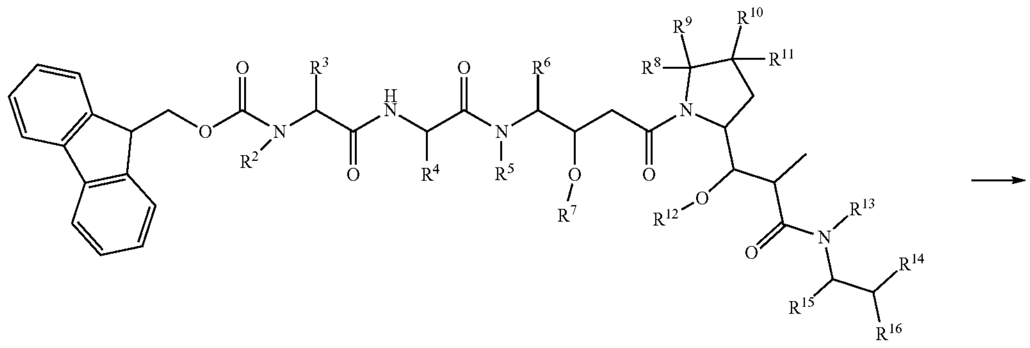

(-DA(MMAE))

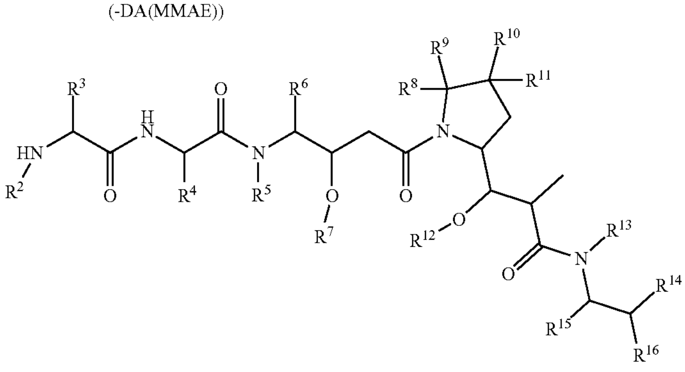

(-D(MMAE))

subjecting the general formula (-DA(MMAE)) to a deprotection reaction to obtain a compound of general formula (-D(MMAE)), wherein: $R^2$-$R^{16}$ are as defined in general formula (D).

Another aspect of the present disclosure relates to a compound as shown below:

(2(MMAE))
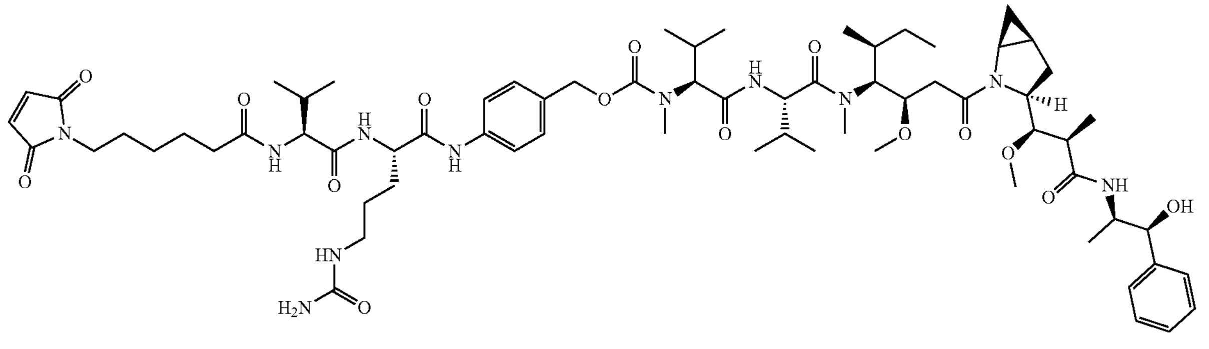
or a pharmaceutically acceptable salt thereof, which may be used as an intermediate in the preparation of the ligand-drug conjugate of the present disclosure.
Another aspect of the present disclosure relates to a method for preparing compound 2(MMAE) or a pharmaceutically acceptable salt thereof, which comprises the following step:
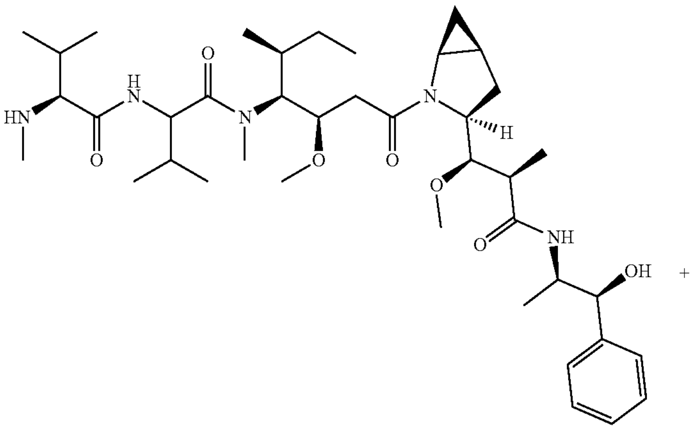
(1(MMAE))
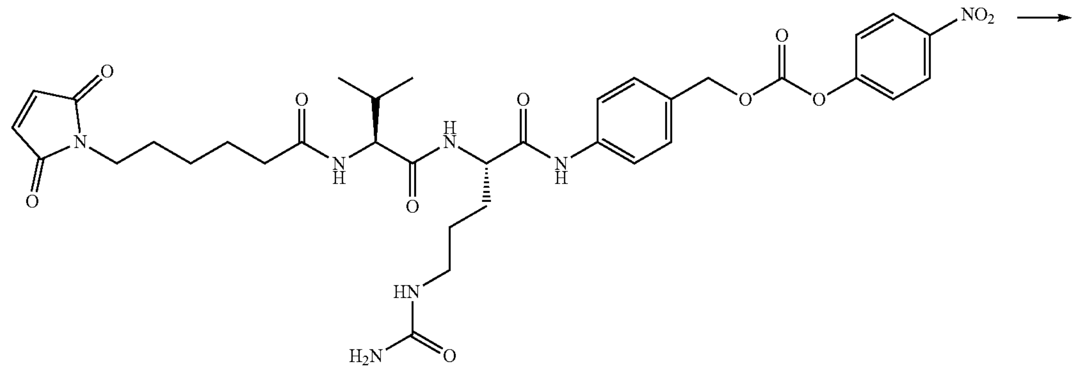
(2a(MMAE))

-continued

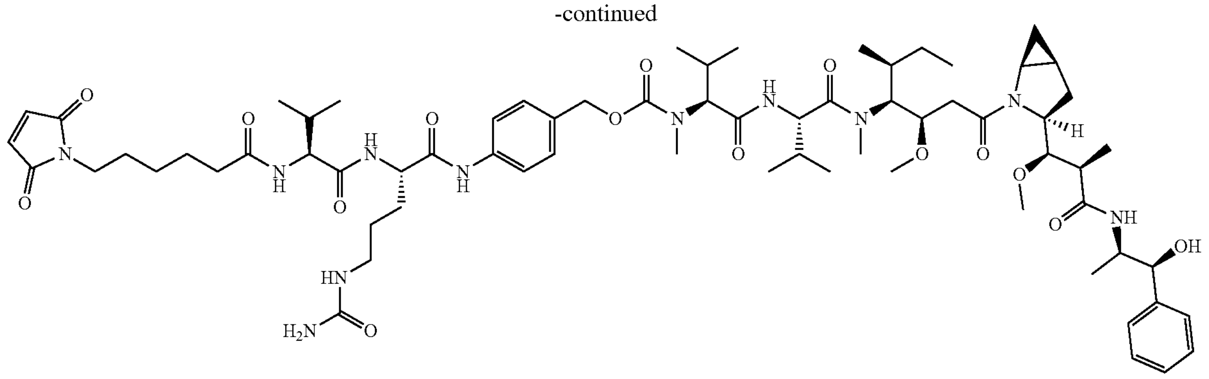

(2(MMAE))

subjecting compound 1(MMAE) to a condensation reaction with compound 2a(MMAE) to obtain compound 2(MMAE).

Another aspect of the present disclosure relates to a method for preparing a ligand-drug conjugate of general formula (Pc-L-D(MMAE)) or a pharmaceutically acceptable salt or solvate thereof, which comprises the following step:

Pc +

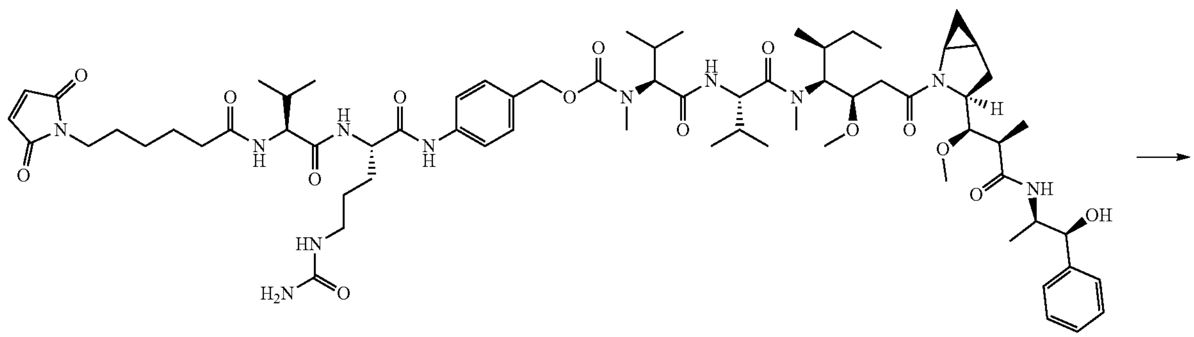

(2(MMAE))

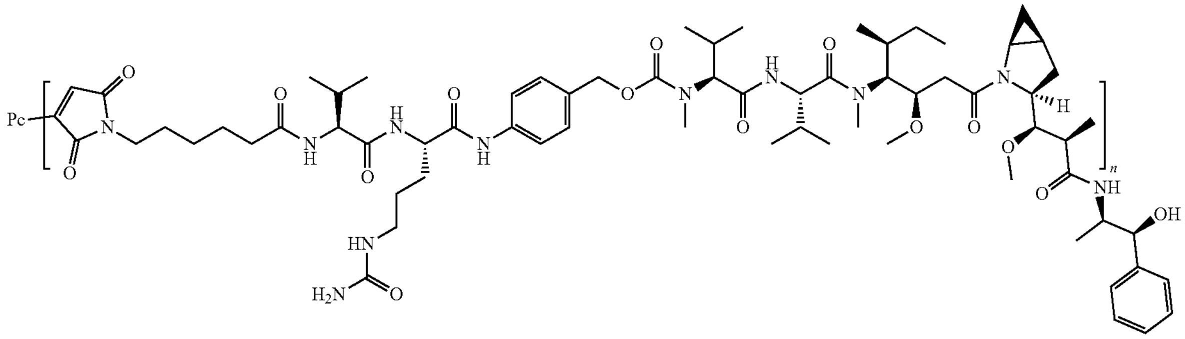

(ADC(MMAE)-1)

subjecting reduced Pc to a coupling reaction with compound 2(MMAE) to obtain a compound of general formula (ADC(MMAE)-1);

wherein Pc and n are as defined in general formula (Pc-L-D(MMAE)).

In order to achieve the purpose of the synthesis of the MMAE and the derivative thereof of the present disclosure, the following synthesis technical schemes are adopted in the present disclosure:

Scheme 1:

Provided is a method for preparing the compound of general formula (D(MMAE)) or the pharmaceutically acceptable salt thereof of the present disclosure, which comprises the following step:

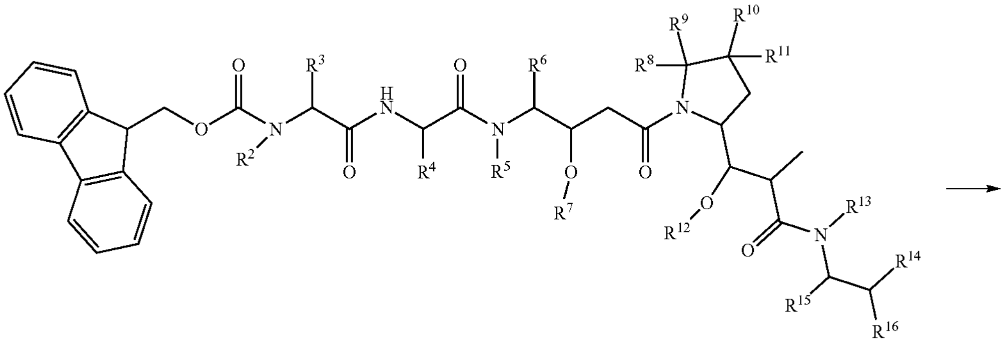

(DA(MMAE))

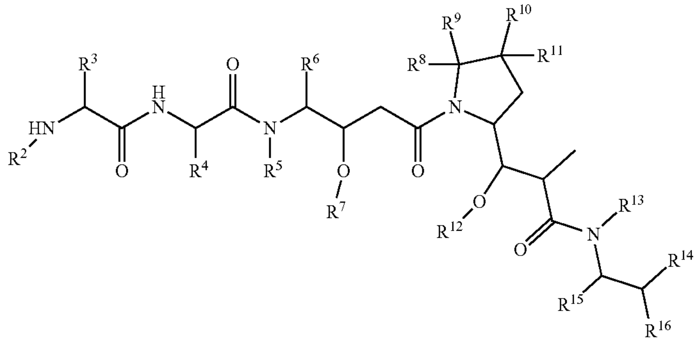

(D(MMAE))

subjecting general formula (DA(MMAE)) to a deprotection reaction under an alkaline condition to obtain the compound of general formula (D(MMAE)), wherein: $R^2$-$R^{16}$ are as defined in general formula (D(MMAE)).

The reagents that provides the alkaline condition include organic and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide or potassium tert-butoxide, and the inorganic bases include, but are not limited to, sodium hydride, potassium phosphate, sodium carbonate, potassium carbonate, cesium carbonate, sodium hydroxide, and lithium hydroxide, preferably diethylamine.

Scheme 2:

Provided is a method for preparing the compound 2(MMAE) or the pharmaceutically acceptable salt or solvate thereof of the present disclosure, which comprises:

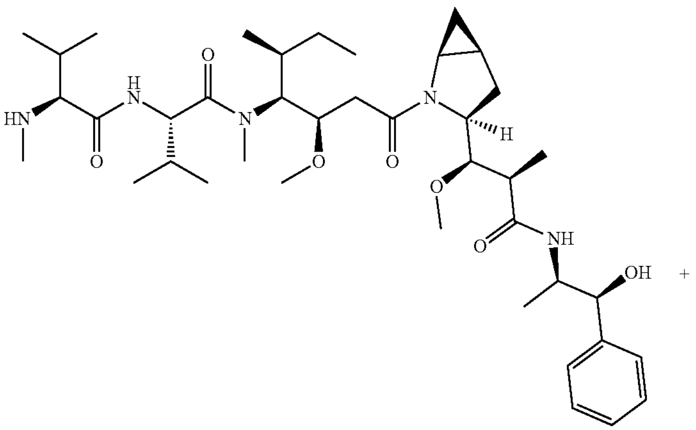

(1(MMAE))

-continued

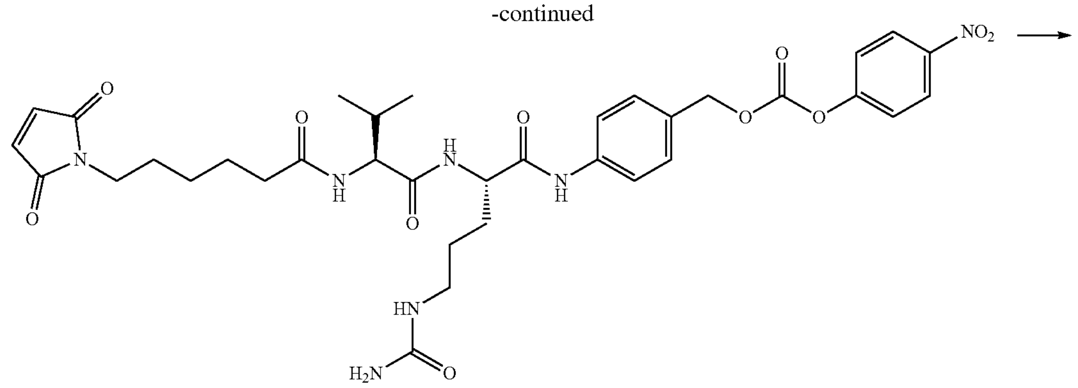

(2a(MMAE))

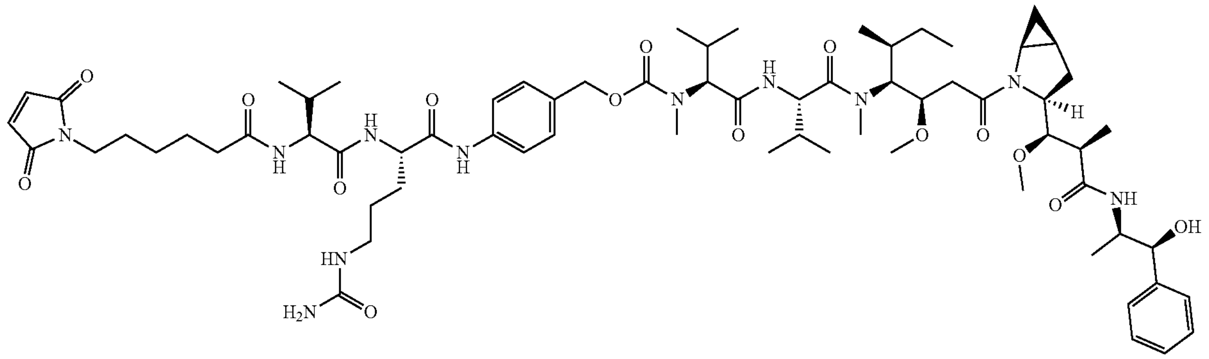

(2(MMAE))

subjecting a compound (1(MMAE)) to a condensation reaction with a compound (2a(MMAE)) by adding a condensing agent under an alkaline condition to obtain compound 2.

The reagents that provides the alkaline condition include organic and inorganic bases, wherein the organic bases include, but are not limited to, triethylamine, diethylamine, N-methylmorpholine, pyridine, piperidine, N,N-diisopropylethylamine, n-butyllithium, lithium diisopropylamide, potassium acetate, sodium tert-butoxide or potassium tert-butoxide, and the inorganic bases include, but are not limited to, sodium hydride, potassium phosphate, sodium carbonate, potassium carbonate, cesium carbonate, sodium hydroxide, and lithium hydroxide, preferably N,N-diisopropylethylamine.

The condensing agent is selected from the group consisting of 4-(4,6-dimethoxy-1,3,5-triazin-2-yl)-4-methylmorpholinium chloride, 1-hydroxybenzotriazole, 1-(3-dimethylaminopropyl)-3-ethylcarbodiimide hydrochloride, N,N-dicyclohexylcarbodiimide, N,N-diisopropylcarbodiimide, 0-benzotriazole-N,N,N,N-tetramethyluronium tetrafluoroborate, 1-hydroxybenzotriazole, 1-hydroxy-7-azobenzotriazole, 0-benzotriazole-N,N,N,N-tetramethyluronium hexafluorophosphate, 2-(7-azobenzotriazole)-N,N,N,N-tetramethyluronium hexafluorophosphate, benzotriazol-1-yloxytris(dimethylamino)phosphonium hexafluorophosphate and benzotriazol-1-yl-oxytripyrrolidinophosphonium hexafluorophosphate, preferably 4-(4,6-dimethoxy-1,3,5-triazin-2-yl)-4-methylmorpholinium chloride or 1-hydroxy benzotriazole or 1-(3-dimethylaminopropyl)-3-ethylcarbodiimide hydrochloride, preferably 1-hydroxybenzotriazole.

Scheme 3:

Provided is a method for preparing the ligand-drug conjugate of general formula (Pc-L-D) or the pharmaceutically acceptable salt or solvate thereof of the present disclosure, which comprises the following step:

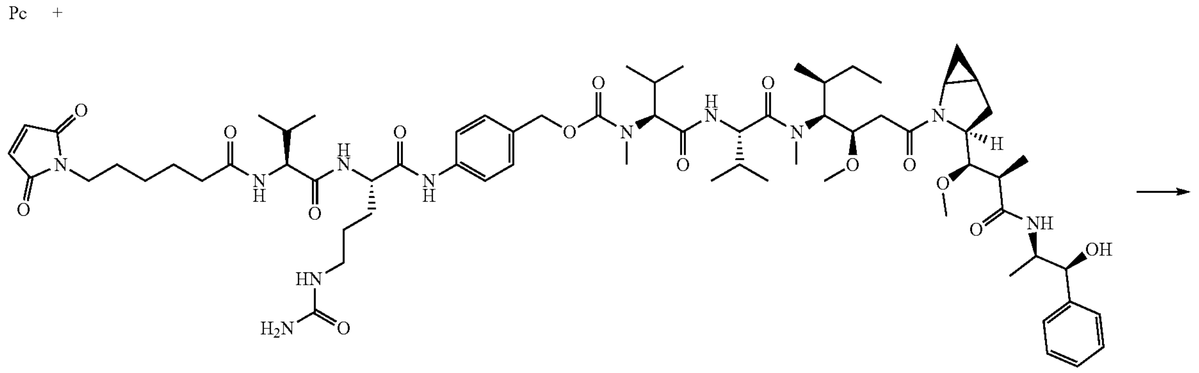

(2(MMAE))

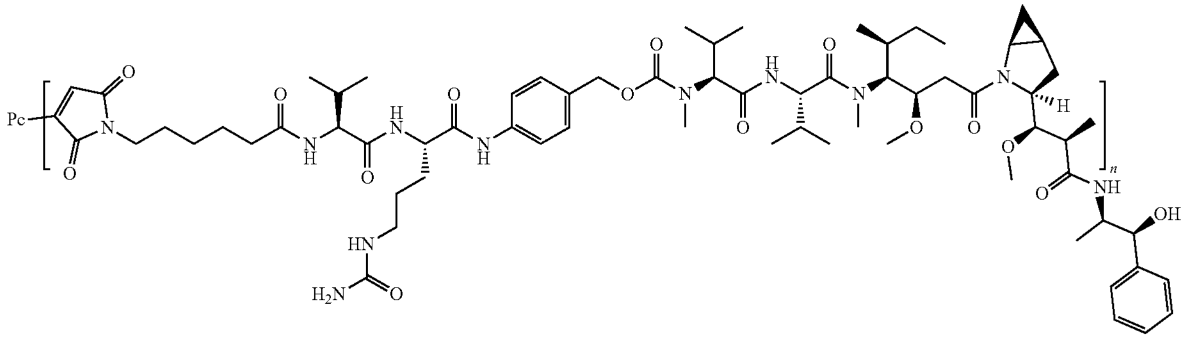

(ADC(MMAE)-1)

subjecting reduced Pc to a coupling reaction with compound 2(MMAE) to obtain a compound of general formula (ADC(MMAE)-1); wherein the reductant is preferably TCEP, particularly, disulfide bonds on the antibody are preferably reduced; wherein Pc and n are as defined in general formula (Pc-L-D(MMAE)).

Compounds of Examples

The present disclosure provides a ligand-drug conjugate or a pharmaceutically acceptable salt or solvate thereof, which is selected from the group consisting of:

ADC-2

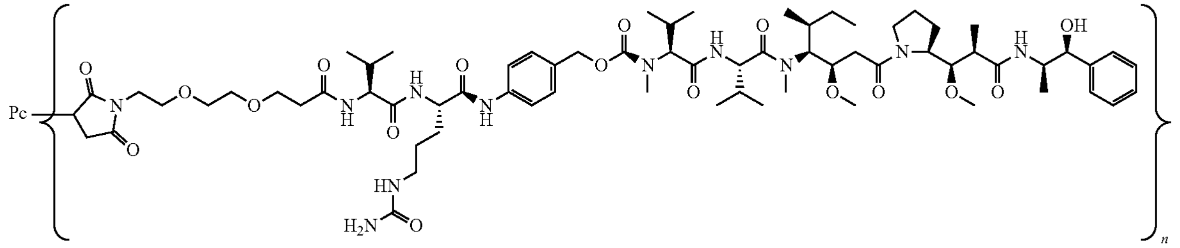

-continued

ADC-1

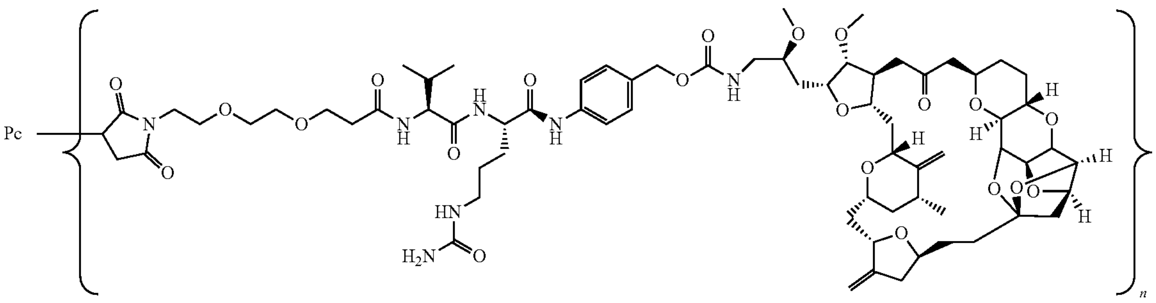

ADC-3

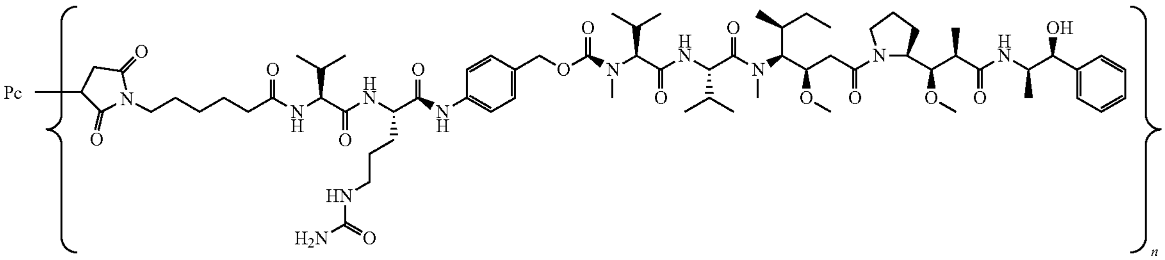

ADC-4

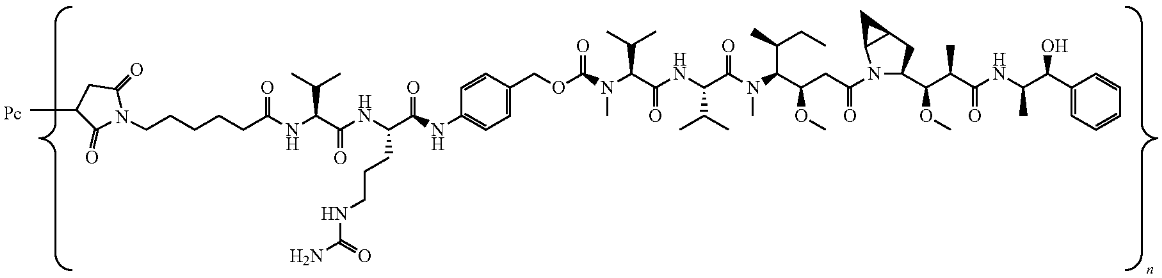

ADC-5

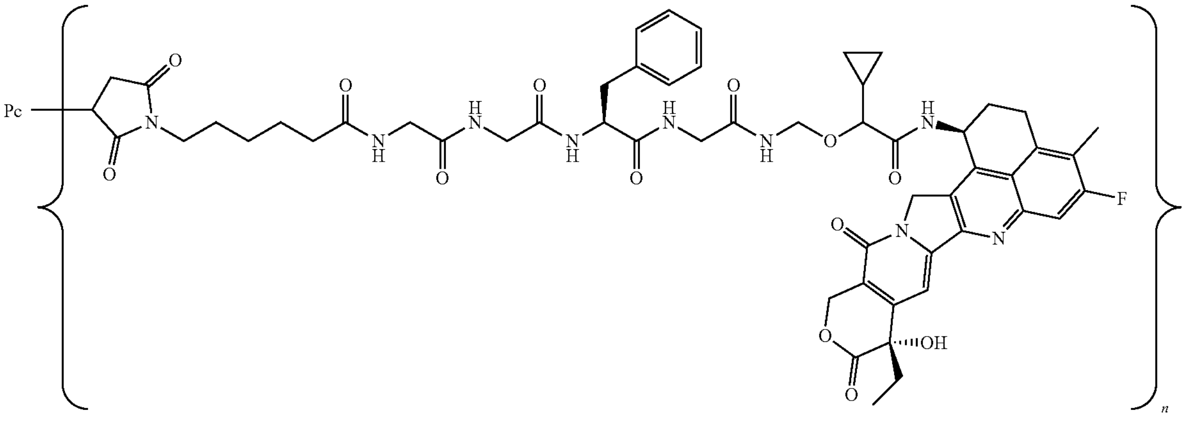

wherein Pc is any one of the anti-CD79B antibodies or the antigen-binding fragments thereof of the present disclosure, and n is 1 to 10 and can be an integer or a decimal.

In some specific embodiments, Pc is the anti-CD79B antibody or the antigen-binding fragment thereof of the present disclosure; e.g., an antibody comprising a heavy chain set forth in SEQ ID NO: 28 and a light chain set forth in SEQ ID NO: 29, or an antibody comprising a heavy chain set forth in SEQ ID NO: 30 and a light chain set forth in SEQ ID NO: 31; and n is an integer or a decimal from 1 to 6.

In some specific embodiments, the antibody-drug conjugate of the present disclosure has a mean DAR value, which may be any value between 1-10, e.g., 2-8, or 2-6, or 1-6, or 4-6.

Although all of the above structural formulas are represented as specific isomeric forms for the sake of simplicity, the present disclosure may include all isomers, such as tautomers, rotamers, geometric isomers, diastereomers, racemates and enantiomers.

Tautomers are structural isomers that readily interconvert by a chemical reaction referred to as tautomerization. Such a reaction often results in the migration of hydrogen atoms or protons accompanied by the conversion of a single bond to an adjacent double bond. Some common tautomeric pairs include: keto-enol and lactam-lactim. An example of the lactam-lactim equilibrium is present between A and B as shown below.

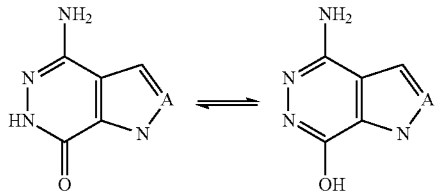

A B

All compounds of the present disclosure can be represented as form A or form B. All tautomeric forms are within the scope of the present disclosure. The nomenclature of the compounds does not exclude any tautomers.

Pharmaceutical Composition

The present disclosure further provides a pharmaceutical composition comprising the conjugate as described above, and a pharmaceutically acceptable excipient, diluent or carrier.

Use

The present disclosure further provides use of any one or a combination selected from the group of the followings in the preparation of a medicament: the anti-CD79B antibody or the antigen-binding fragment thereof according to the present disclosure, the conjugate according to the present disclosure, and the pharmaceutical composition according to the present disclosure; wherein the antibody or the antigen-binding fragment thereof or the drug-conjugate thereof is used for treating a proliferative disease or delaying progression of the proliferative disease; the proliferative disorder may be a cancer or tumor; the cancer or tumor is selected from the group consisting of lymphoma, diffuse large B-cell lymphoma, non-Hodgkin's lymphoma (NHL), aggressive NHL, relapsed and aggressive NHL, relapsed and indolent NHL, refractory NHL, refractory and indolent NHL, chronic lymphocytic leukemia (CLL), small lymphocytic lymphoma, leukemia, hairy cell leukemia (HCL), acute lymphocytic leukemia (ALL), and/or mantle cell lymphoma.

Treatment Method

The present disclosure provides a method for treating or preventing a proliferative disease or delaying progression of the proliferative disease, which comprises administering to a subject the anti-CD79B antibody or the antigen-binding fragment thereof according to the present disclosure, or the pharmaceutical composition according to the present disclosure, or the antibody-drug conjugate according to the present disclosure in an effective amount for treating or delaying the disease; wherein the proliferative disorder is a cancer or tumor.

The present disclosure provides a method for treating a B-cell proliferative disorder or an autoimmune disorder or delaying progression of the B-cell proliferative disorder or the autoimmune disorder in a subject in need thereof. In some embodiments, the B-cell proliferative disorder is a cancer or a tumor.

The present disclosure provides a method for enhancing immune function in a subject having a cell proliferative disorder or an autoimmune disorder. In some embodiments, the cell proliferative disorder is a cancer or a tumor.

The cancer or tumor in the above schemes may be selected from the group consisting of lymphoma, diffuse large B-cell lymphoma, non-Hodgkin's lymphoma (NHL), aggressive NHL, relapsed and aggressive NHL, relapsed and indolent NHL, refractory NHL, refractory and indolent NHL, chronic lymphocytic leukemia (CLL), small lymphocytic lymphoma, leukemia, hairy cell leukemia (HCL), acute lymphocytic leukemia (ALL), and/or mantle cell lymphoma.

BRIEF DESCRIPTION OF THE DRAWINGS

FIG. 12A shows assay results of the binding of monkey peripheral blood mononuclear cells to a blank control by FACS; FIG. 12B shows assay results of the binding of monkey peripheral blood mononuclear cells to a negative control antibody by FACS; FIG. 12C shows assay results of the binding of a positive control antibody to monkey peripheral blood mononuclear cells by FACS; FIG. 12D shows assay results of the anti-CD79B antibody mAb018 to monkey peripheral blood mononuclear cells by FACS; FIG. 12E shows assay results of the anti-CD79B antibody mAb019 to monkey peripheral blood mononuclear cells by FACS; FIG. 12F shows assay results of the anti-CD79B antibody mAb020 to monkey peripheral blood mononuclear cells by FACS; and FIG. 12G shows assay results of the anti-CD79B antibody mAb021 to monkey peripheral blood mononuclear cells by FACS. The positive control used is SN8 from Genentech.

DETAILED DESCRIPTION

Terms

Figure 1:
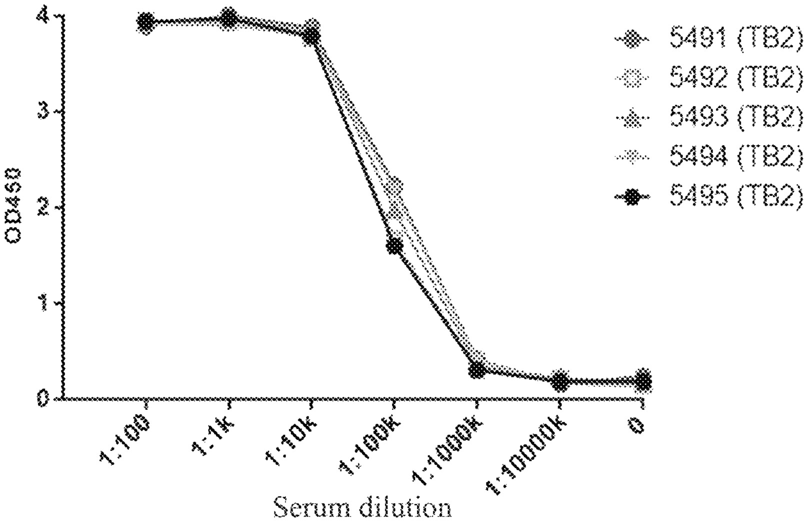
FIG. 1: assay results of serum titers of Balb/c mice immunized by human CD79B ECD-hFc proteins by ELISA.

In order to facilitate the understanding of the present disclosure, some technical and scientific terms are specifically defined below. Unless otherwise specifically defined herein, all other technical and scientific terms used herein have the meanings generally understood by those of ordinary skill in the art to which the present disclosure belongs.

The three-letter and single-letter codes for amino acids used in the present disclosure are described as in *J. Biol. Chem,* 243, p 3558 (1968).

"Antibody" is used in the broadest sense and encompasses a variety of antibody structures, including but not limited to monoclonal antibodies, polyclonal antibodies; monospecific antibodies, multispecific antibodies (e.g., bispecific antibodies); and full-length antibodies, and antibody fragments (or antigen-binding fragments, or antigen-binding portions) so long as they exhibit the desired antigen-binding activity. An antibody may refer to an immunoglobulin, which is of a tetrapeptide chain structure formed by two heavy chains and two light chains linked by interchain disulfide bonds. The heavy chain constant regions of an immunoglobulin differ in their amino acid composition and arrangement. Accordingly, immunoglobulins can be divided into five classes, or isotypes of immunoglobulins, namely IgM, IgD, IgG, IgA and IgE, with their corresponding heavy chains being μ chain, δ chain, γ chain, α chain and ε chain, respectively. Ig of the same class can be further divided into different subclasses according to differences in the amino acid composition of the hinge regions and the number and positions of disulfide bonds of the heavy chains; for example, IgG may be divided into IgG1, IgG2, IgG3 and IgG4 subtypes. Light chains are classified into κ or λ chains according to differences in the constant regions. Each class of Ig may have a κ chain or λ chain.

In the heavy and light chains of antibody, the sequences of about 110 amino acids near the N-terminus vary considerably and thus are referred to as variable regions (V regions); the remaining amino acid sequences near the C-terminus are relatively stable and thus are referred to as constant regions (C regions). The variable regions comprise 3 hypervariable regions (CDRs) and 4 framework regions (FRs) with relatively conservative sequences. The 3 hypervariable regions determine the specificity of the antibody and thus are also known as complementarity determining regions (CDRs). Each of the light chain variable regions (VLs) and the heavy chain variable regions (VHs) consists of 3 CDR regions and 4 FR regions arranged from the amino terminus to the carboxyl terminus in the following order: FR1, CDR1, FR2, CDR2, FR3, CDR3, and FR4. The 3 CDR regions of the light chain refer to LCDR1, LCDR2, and LCDR3; and the 3 CDR regions of the heavy chain refer to HCDR1, HCDR2, and HCDR3.

In the present application, the antibody light chain variable region described herein may further comprise a light chain constant region comprising human or murine κ and λ chains or variants thereof.

In the present application, the antibody heavy chain variable region described herein may further comprise a heavy chain constant region comprising human or murine IgG1, IgG2, IgG3 and IgG4 or variants thereof.

The term "murine antibody" in the present application refers to a monoclonal antibody against human CD79B or an epitope thereof prepared according to the knowledge and skill in the art. During the preparation, a test subject is injected with a CD79B antigen, and then hybridoma of antibodies expressing the desired sequence or functional properties is isolated. In a specific embodiment of the present disclosure, the murine anti-human CD79B antibody or the antigen-binding fragment thereof may further comprise a light chain constant region of a murine κ or λ chain or a variant thereof, or further comprise a heavy chain constant region of a murine IgG1, IgG2, IgG3 or IgG4 or a variant thereof.

The term "fully human antibody" includes antibodies having variable and constant regions derived from human germline immunoglobulin sequences. The fully human antibody of the present disclosure may include amino acid residues not encoded by human germline immunoglobulin sequences (e.g., mutations introduced by random or site-specific mutagenesis in vitro or by somatic mutations in vivo). However, the term "fully human antibody" does not include humanized antibodies.

The term "humanized antibody", also known as a CDR-grafted antibody, refers to an antibody produced by grafting non-human CDR sequences into the framework of variable regions of a human antibody. Such antibody can overcome the strong immune response induced by the chimeric antibody because of carrying a large amount of non-human protein components. To avoid the decrease in activity caused by the decrease in immunogenicity, the variable regions of a fully human antibody can be subjected to minimum reverse mutation to maintain activity.

The term "chimeric antibody" refers to an antibody obtained by fusing a variable region of an antibody of a first species to a constant region of an antibody of a second species, which can reduce an immune response induced by the antibody of the first species. As an example, the chimeric antibody is established by firstly establishing rabbits secreting a rabbit specific monoclonal antibody, isolating the antibody, then cloning a constant region gene of fully human antibody as required, linking the rabbit variable region gene and the human constant region gene into a chimeric gene, inserting the chimeric gene into a human vector, and finally expressing chimeric antibody molecules in a eukaryotic industrial system or prokaryotic industrial system. The constant region of the fully human antibody may be selected from the group consisting of the heavy chain constant regions of human IgG1, IgG2, IgG3 and IgG4 or variants thereof, preferably comprising human IgG1 or IgG4 heavy chain constant regions, or IgG1 mutated at amino acids without ADCC (antibody-dependent cell-mediated cytotoxicity) toxicity.

The term "antigen-binding fragment" includes a single chain antibody (i.e., full-length heavy and light chains); a Fab, a modified Fab, a Fab', a modified Fab', an $F(ab')_2$, an Fv, a Fab-Fv, a Fab-dsFv, a single domain antibody (e.g., VH or VL or VHH), an scFv, a bivalent or trivalent or tetravalent antibody, a Bis-scFv, a diabody, a tribody, a triabody, a tetrabody and an epitope-binding fragment of any of the above (see, e.g., Holliger and Hudson, 2005, Nature Biotech. 23 (9): 1126-1136; Adair and Lawson, 2005, Drug Design Reviews-Online 2 (3), 209-217).

Methods for producing and preparing such antibody fragments are well known in the art (see, e.g., Verma et al., 1998, *Journal of Immunological Methods,* 216, 165-181). Fab-Fv was first disclosed in WO2009/040562, and its disulfide-stabilized form Fab-dsFv was first disclosed in WO2010/035012. The antigen-binding fragment of the present disclosure also include Fab and Fab' fragments described in WO2005/003169, WO2005/003170 and WO2005/003171. Multivalent antibodies may comprise multiple specificities (e.g., bispecificites) or may be monospecific (see, e.g., WO92/22583 and WO05/113605), and an example of the latter is Tri-Fab (or TFM) described in WO92/22583.

The term "single chain antibody", "single chain Fv" or "scFv" refers to a molecule comprising an antibody heavy chain variable domain (or region; VH) and an antibody light chain variable domain (or region; VL) linked by a linker. Such scFv molecules may have a general structure: $NH_2$-VL-linker-VH—COOH or $NH_2$—VH-linker-VL-COOH. Suitable linkers in the prior art consist of repeated GGGGS amino acid sequences or variants thereof, for example, 1-4 repeated variants (Holliger et al. (1993), *Proc. Natl. Acad. Sci. USA* 90: 6444-6448). Other linkers that can be used in the present disclosure are described in Alfthan et al. (1995), *Protein Eng.* 8:725-731; Choi et al. (2001), *Eur. J. Immunol.* 31:94-106; Hu et al. (1996), *Cancer Res.* 56:3055-3061, Kipriyanov et al. (1999), *J. Mol. Biol.* 293:41-56; and Roovers et al. (2001), *Cancer Immunol.*

The term "CDR" refers to one of the 6 hypervariable regions within the variable domain of an antibody which primarily contribute to antigen binding. In general, there are three CDRs (HCDR1, HCDR2 and HCDR3) in each heavy chain variable region and three CDRs (LCDR1, LCDR2 and LCDR3) in each light chain variable region. One of the most common definitions for the 6 CDRs is provided in Kabat E. A. et al., (1991) *Sequences of proteins of immunological interest*. NIH Publication 91-3242. As used herein, the Kabat definition of CDRs applies only to the CDR1, CDR2 and CDR3 of the light chain variable domain, and to the CDR2 and CDR3 of the heavy chain variable domain.

The amino acid sequence boundaries of the CDRs can be determined using any one of a variety of well-known schemes, including "Kabat" numbering scheme (see Kabat et al. (1991), "*Sequences of Proteins of Immunological Interest*", 5th edition, Public Health Service, National Institutes of Health, Bethesda, MD), "Chothia" numbering scheme (see Al-Lazikani et al. (1997) JMB 273: 927-948) and ImMunoGenTics (IMGT) numbering scheme (see Lefranc M. P., Immunologist, 7, 132-136 (1999); Lefranc, M. P. et al., Dev. Comp. Immunol., 27, 55-77 (2003)), and the like. For example, for the classical format, according to the Kabat scheme, the CDR amino acid residues in the heavy chain variable domain (VH) are numbered 31-35 (HCDR1), 50-65 (HCDR2) and 95-102 (HCDR3); the CDR amino acid residues in the light chain variable domain (VL) are numbered 24-34 (LCDR1), 50-56 (LCDR2) and 89-97 (LCDR3). According to the Chothia scheme, the CDR amino acids in VH are numbered 26-32 (HCDR1), 52-56 (HCDR2) and 95-102 (HCDR3); and amino acid residues in VL are numbered 26-32 (LCDR1), 50-52 (LCDR2) and 91-96 (LCDR3). According to the CDR definitions by combining both the Kabat scheme and the Chothia scheme, the CDR consists of amino acid residues 26-35 (HCDR1), 50-65 (HCDR2) and 95-102 (HCDR3) in the human VH and amino acid residues 24-34 (LCDR1), 50-56 (LCDR2) and 89-97 (LCDR3) in the human VL. According to the IMGT scheme, the CDR amino acid residues in VH are roughly numbered 26-35 (CDR1), 51-57 (CDR2) and 93-102 (CDR3), and the CDR amino acid residues in VL are roughly numbered 27-32 (CDR1), 50-52 (CDR2) and 89-97 (CDR3). According to the IMGT scheme, the CDRs of the antibody can be determined by using the program IMGT/DomainGap Align.

The term "antibody framework" refers to a portion of a variable domain VL or VH, which serves as a framework for the antigen-binding loops (CDRs) of the variable domain. It is essentially a variable domain without CDRs.

The term "binding to CD79B" herein refers to the ability to interact with CD79B or an epitope thereof, wherein the CD79B or the epitope thereof may be derived from human.

The term "antigen" refers to a molecule used for immunization of an immunocompetent molecule derived from vertebrate to produce an antibody that recognizes the antigen or to screen an expression library (e.g., particularly phage, yeast or ribosome display library). Herein, the antigen is determined more broadly and generally includes target molecules that are specifically recognized by the antibody, and thus includes a portion or a mimic of the molecule used in an immunization process for producing the antibody or in library screening for selecting the antibody. The human CD79B of the present disclosure and truncated and other variants of human CD79B are referred to as antigens.

The term "epitope" refers to a site on an antigen to which an immunoglobulin or an antibody binds. An epitope may be formed from contiguous amino acids, or non-contiguous amino acids juxtaposed by tertiary folding of the protein. An epitope formed from contiguous amino acids are generally retained after exposure to a denaturing solvent, while an epitope formed by tertiary folding are generally lost after a denaturing solvent treatment. An epitope generally comprise, for example, at least 3-15 amino acids in a unique spatial conformation. Methods for determining what epitope is bound by a given antibody are well known in the art and include an immunoblotting assay, an immunoprecipitation assay, and the like. Methods for determining the spatial conformation of an epitope include techniques in the art and techniques described herein, such as X-ray crystallography and two-dimensional nuclear magnetic resonance.

The term "specific binding" or "selective binding" refers to binding of an antibody to an epitope on a predetermined antigen. In general, an antibody binds to a predetermined antigen or an epitope thereof with an equilibrium dissociation constant (KD) of about less than $10^{-7}$ M or even less and with an affinity that is at least twice as high as its affinity for binding to a non-specific antigen (e.g., BSA, etc.) other than the predetermined antigen (or the epitope thereof) or a closely related antigen, when determined by surface plasmon resonance (SPR) techniques in an instrument using recombinant human CD79B or an epitope thereof as the analyte and an antibody as the ligand. The term "antigen-recognizing antibody" is used interchangeably herein with the term "specifically bound antibody".

The term "nucleic acid molecule" refers to a DNA molecule and an RNA molecule. The nucleic acid molecule may be single-stranded or double-stranded, and is preferably double-stranded DNA.

The term "vector" refers to a nucleic acid molecule capable of transporting another nucleic acid to which it has been linked. In one embodiment, the vector is a "plasmid" that refers to a circular double-stranded DNA loop into which additional DNA segments can be ligated. In another embodiment, the vector is a viral vector. The vectors disclosed herein are capable of autonomously replicating in a host cell (e.g., bacterial vectors having a bacterial origin of replication and episomal mammalian vectors) or capable of integrating into the genome of a host cell and thus replicating with the host genome (e.g., non-episomal mammalian vectors).

The term "host cell" refers to a cell into which an expression vector has been introduced. Host cells may include bacterial, microbial, plant or animal cells. Bacteria susceptible to transformation include members of the species enterobacteria, such as strains of *Escherichia coli* or *Salmonella; Bacillaceae* such as *Bacillus subtilis; Pneumococcus; Streptococcus* and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

The engineered antibody or the antigen-binding fragment of the present disclosure can be prepared and purified by conventional methods. For example, cDNA sequences encoding the heavy and light chains can be cloned and recombined into a GS expression vector. Recombinant immunoglobulin expression vectors can be stably transfected into CHO cells. As a more recommended prior art, mammalian expression systems will result in glycosylation of the antibody. Positive clones are expanded in a serum-free medium of a bioreactor to produce antibodies. The culture with the secreted antibody can be purified by conventional techniques, for example, using an A or G Sepharose FF column. Non-specifically bound fractions are washed away. The bound antibody is eluted using pH gradient method, and the antibody fragments are detected by SDS-PAGE and collected. The antibody can be filtered and concentrated by conventional methods. Soluble mixtures and polymers can also be removed by conventional methods, such as molecular sieves and ion exchange. The resulting product needs to be immediately frozen, e.g., at −70° C., or lyophilized.

The amino acid sequence "identity" refers to the percentage of amino acid residues in a first sequence that are identical to those in a second sequence, wherein in aligning the amino acid sequences and when necessary, gaps are introduced to achieve maximum percent sequence identity (and no conservative substitution is considered as part of the sequence identity). In order to determine percent amino acid sequence identity, alignments can be achieved in a variety of ways that are within the skill in the art, for example, using computer software such as BLAST, BLAST-2, ALIGN, ALIGN-2 or Megalign (DNASTAR) software. Those skilled in the art can determine parameters suitable for measuring alignment, including any algorithms required to achieve maximum alignment of the full length of the aligned sequences.

The term "cross-reactivity" refers to the ability of the antibody of the present application to bind to CD79B from different species. For example, the antibody of the present application that binds to human CD79B may also bind to CD79B from another species. Cross-reactivity is determined by detecting specific reactivity with purified antigen in binding assays (e.g., SPR and ELISA) or binding or functional interactions with cells expressing CD79B. Methods for determining cross-reactivity include standard binding assays as described herein, for example, surface plasmon resonance analysis or flow cytometry.

The terms "inhibition" and "blocking" are used interchangeably and encompass both partial and complete inhibition/blocking. Inhibition/blocking of CD79B preferably reduces or alters the normal level or type of activity that occurs when CD79B binding occurs without inhibition or blocking. Inhibition and blocking are also intended to include any measurable decrease in CD79B binding affinity when in contact with an anti-CD79B antibody as compared to CD79B not in contact with an anti-CD79B antibody.

The term "inhibition of growth" (e.g., involving cells) is intended to include any measurable reduction in cell growth.

The terms "inducing immune response" and "enhancing immune response" are used interchangeably and refer to an immune response to stimulation (i.e., passive or adaptive) by a specific antigen.

"ADCC", i.e., antibody-dependent cell-mediated cytotoxicity, described herein means that the Fc receptor-expressing cells directly kill antibody-coated target cells by recognition of the Fc segment of the antibody. The ADCC effector function of the antibody may be reduced or eliminated by modification of the Fc segment of the IgG. The modification refers to a mutation in the heavy chain constant region of the antibody, such as a mutation selected from the group consisting of N297A, L234A and L235A of IgG1; IgG2/4 chimera, F235E of IgG4, and L234A/E235A mutation.

Methods for producing and purifying antibodies and antigen-binding fragments are well known in the prior art and can be found in, for example, "Antibodies: A Laboratory Manual", Cold Spring Harbor Press (chapters 5-8 and 15). For example, animals can be immunized with human CD79B or a fragment thereof, and the resulting antibodies can be renatured and purified, and amino acid sequencing can be performed by using conventional methods. Likewise, antigen-binding fragments can be prepared by conventional methods. The antibody or the antigen-binding fragment is genetically engineered to contain one or more additional human FRs in the non-human-derived CDRs. Human FR germline sequences can be obtained from ImMunoGeneTics (IMGT) or from the Immunoglobulin Journal, 20011SBN012441351.

The term "drug" refers to a cytotoxic drug or an immunomodulator. The cytotoxic drug may have a chemical molecule within the cell that is strong enough to disrupt its normal growth. The cytotoxic drug can kill cells in principle at a sufficiently high concentration; however, due to lack of specificity, the cytotoxic drug can cause apoptosis of normal cells while killing tumor cells, resulting in serious side effects. This term includes toxins (such as small molecule toxins or enzymatically active toxins of bacterial, fungal, plant or animal origin), radioisotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic drugs, antibiotics and nucleolytic enzymes. The immunomodulator is an inhibitor of immune checkpoint molecules.

The term "linker" refers to a fragment or a bond, which is linked to a ligand at one end and linked to a drug at the other end, and also may be linked to other linkers and then linked to the drug.

The linker may comprise one or more linker components. Exemplary linker components include 6-maleimidocaproyl ("MC"), maleimidopropionyl ("MP"), valine-citrulline ("val-cit" or "vc"), alanine-phenylalanine ("ala-phe"), p-aminobenzyloxycarbonyl ("PAB"), and those derived from coupling to a linker reagent: N-succinimidyl 4-(2-pyridylthio)pentanoate ("SPP"), N-succinimidyl 4-(N-maleimidomethyl)cyclohexane-1 carboxylate ("SMCC", also referred to herein as "MCC"), and N-succinimidyl(4-iodo-acetyl)aminobenzoate ("SIAB"). The linker may include a stretcher unit, a spacer unit, an amino acid unit and an extension unit, and may be synthesized by methods known in the art, such as those described in US2005-0238649A1. The linker may be a "cleavable linker" favoring the release of drugs in cells. For example, acid-labile linkers (e.g., hydrazones), protease-sensitive (e.g., peptidase-sensitive) linkers, photolabile linkers, dimethyl linkers or disulfide-containing linkers can be used (Chari et al., *Cancer Research* 52: 127-131(1992); U.S. Pat. No. 5,208,020).

The term "amino acid unit" refers to an amino acid that can attach a carbonyl group in the following structural formula $Y_R$ to an extension unit in the presence of the extension unit, or directly attaching $Y_R$ to a drug in the absence of the extension unit. In embodiments of the present disclosure, the amino acid unit is represented as —$K_k$—:

$Y_R$

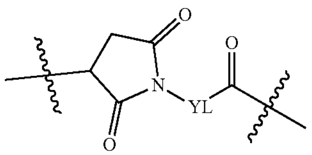

—$K_k$— is a dipeptide, tripeptide, tetrapeptide, pentapeptide, hexapeptide, heptapeptide, octapeptide, nonapeptide or decapeptide-, wherein each —K— unit independently has the following structural formula $K_a$ or $K_b$, and k is an integer between 0 and 10:

$K_a$

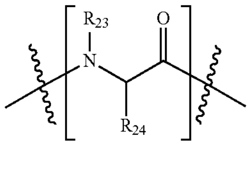

or $K_b$

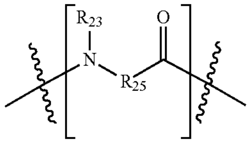

wherein:

$R^{23}$ in the above amino acid unit is —H or methyl;

$R^{24}$ is H, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl-, cyclohexyl,

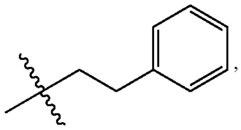,

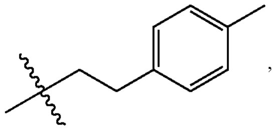,

-continued

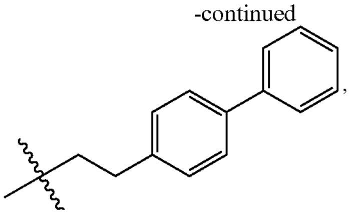,

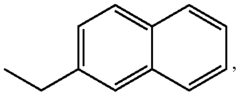,

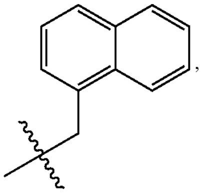,

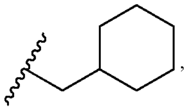,

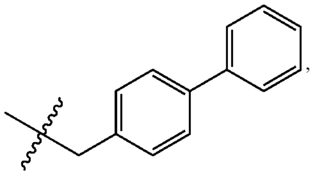,

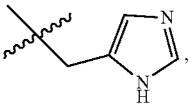,

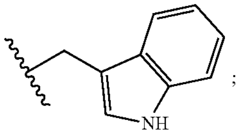;

$R^{25}$ is -aryl-, -alkyl-aryl-, -cycloalkyl-, -alkyl-cycloalkyl-, -cycloalkyl-alkyl-, -alkyl-cycloalkyl-alkyl-, -heterocyclyl-, -alkyl-heterocyclyl-, -heterocyclyl-alkyl-, -alkyl-heterocyclyl-alkyl-, -aryl-, -alkyl-aryl-, -aryl-alkyl-, -alkyl-aryl-alkyl-, -heteroaryl-, -alkyl-heteroaryl-, -heteroaryl-alkyl-, or -alkyl-heteroaryl-alkyl-.

In one embodiment, —$K_k$— is a dipeptide, preferably -valine-citrulline-, -phenylalanine-lysine- or —N-methylvaline-citrulline-, further preferably -valine-citrulline-.

The term "stretcher unit" refers to a chemical structure segment that is covalently linked to a ligand through a carbon atom at one end and to a drug (directly or indirectly) through a sulfur atom at the other end.

The term "spacer unit" is a bifunctional compound structural fragment that can be used to couple linker to a drug to finally form a ligand-drug conjugate, in such a way that the drug may be selectively linked to the linker.

The term "amino acid" refers to an organic compound that contains amino and carboxyl in the molecular structure and in which both amino and carboxyl are directly linked to a —CH— structure. The general formula is $H_2NCHRCOOH$. Amino acids are classified as α, β, γ, δ, ε . . . -amino acids according to the position of the carbon atom to which the amino is linked in the carboxylic acid. In the biological world, the amino acids that make up the natural proteins have their specific structural characteristics, that is, their amino groups are directly linked to the α-carbon atom, i.e., form α-amino acids.

The term "extension unit" refers to a chemical structure that can couple an amino acid unit to a drug in the presence of the amino acid unit or to a drug via the carbonyl group on YR in the absence of the amino acid unit.

In the present disclosure, the extension unit is PAB with a structure of 4-iminobenzylcarbamoyl fragment shown as the following formula, and is linked to D,

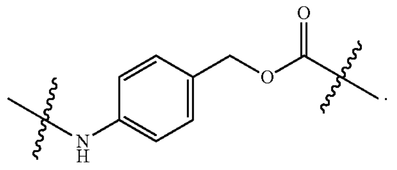 [SMILES: *Nc1ccc(COC(*)=O)cc1]

Abbreviations

Linker components include, but are not limited to:

MC=6-maleimidocaproyl, with a structure shown as follows:

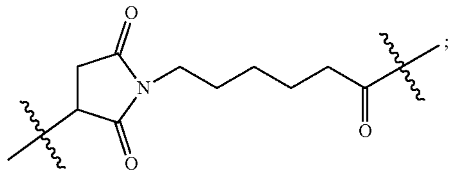 [SMILES: *C(=O)CCCCCN1C(=O)CC(*)C1=O]

Val-Cit or "vC"=valine-citrulline (an exemplary dipeptide in a protease cleavable linker);

citrulline=2-amino-5-ureidopentanoic acid;

PAB=p-aminobenzyloxycarbonyl (an example of "self-immolative" linker components);

Me-Val-Cit=N-methyl-valine-citrulline (wherein the linker peptide bond has been modified to prevent it from being cleaved by cathepsin B);

MC(PEG)6-OH=maleimidocaproyl-polyethylene glycol (attachable to antibody cysteine);

SPP=N-succinimidyl 4-(2-pyridylthio)valerate;

SPDP=N-succinimidyl 3-(2-pyridyldithio)propionate;

SMCC=succinimidyl 4-(N-maleimidomethyl)cyclohexane-1-carboxylate;

IT=iminothiolane; and

PBS=phosphate-buffered saline.

The term "antibody-drug conjugate" (ADC) means that an antibody is linked to a drug via a linker (or a linker unit). In the present disclosure, "antibody-drug conjugate" means that a monoclonal antibody (or an antigen-binding fragment) is linked to a toxic drug via a linker unit.

The term "drug-to-antibody ratio" (DAR) refers to the average number of drugs conjugated to each antibody in a population of antibody-drug conjugates, and can also be expressed as a ratio of the number of drugs to the number of antibodies. The drug loading may range from 1 to 20, preferably from 1 to 10 cytotoxic drugs (D) linked to each antibody (Ab). In embodiments of the present disclosure, the drug loading is represented as k or n, and may illustratively be 1, 2, 3, 4, 5, 6, 7, 8, 9, 10, 11, 12, 13, 14, 15, 16, 17, 18, 19, 20, or an average of any two values; preferably an average of 1 to 10, and more preferably an average of 1 to 8, or 2 to 8, or 2 to 7, or 3 to 8, or 3 to 7, or 3 to 6, or 4 to 7, or 4 to 6, or 4 to 5. The drug loading can be determined by conventional methods such as UV/visible spectroscopy, mass spectrometry, ELISA assays, monoclonal antibody molecule size variant assay (CE-SDS) and HPLC characterization.

The monoclonal antibody molecular size variant assay (CE-SDS) of the present disclosure may be used for quantitatively determining the purity of a recombinant monoclonal antibody product by adopting capillary electrophoresis-sodium dodecyl sulfate (CE-SDS) ultraviolet assay based on the molecular weight under reduced and non-reduced conditions and according to a capillary electrophoresis method (*Chinese Pharmacopoeia* 0542, 2015 Edition).

In one embodiment of the present disclosure, the drug is coupled to the N-terminal amino of the ligand and/or F-amino of the lysine residue through a linker unit, and generally, the number of drug molecules that can be coupled to the antibody in the coupling reaction will be less than the theoretical maximum.

The loading of the antibody-drug conjugate can be controlled by the following non-limiting methods, including:

(1) controlling a molar ratio of a linking reagent to a monoclonal antibody, (2) controlling reaction time and temperature, and (3) selecting different reaction reagents.

Although the drug-to-antibody ratio has an exact value (e.g. n in formula (I)) for a specific conjugate molecule, it will be understood that when used to describe a sample containing many molecules, the value will often be an average value, which attributed to a certain degree of non-uniformity typically associated with the conjugation step. The mean drug loading of conjugate is referred to herein as the drug-to-antibody ratio or "DAR". In some embodiments, the DAR is between about 1 and about 6, and typically about 1, 1.5, 2, 2.5, 3, 3.5, 4, 4.5, 5, 5.5, 6, 6.5, 7.0, 7.5 or 8.0. In some embodiments, at least 50% by weight of the sample is a compound with mean DAR±2, and preferably at least 50% of the sample is a conjugate containing mean DAR±1. Embodiments include those with a DAR of about 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.4, 5.4, 5.5, 5.6, 5.7, 5.8, 5.9, 6.0, 6.1, 6.2, 6.3, 6.4, 6.5, 6.6, 6.7, 6.8, 6.9 or 7.0. In some embodiments, a DAR of 'about x' means that the measurement value of the DAR is within 20% of x.

The DAR was determined for example by extrapolating DAR values from LC-MS data of reduced and deglycosylated samples. LC/MS allows for quantification of the average number of payload (drug moiety) molecules linked to the antibody in the ADC. HPLC separates the antibody into light and heavy chains, and also separates the heavy (HC) and light (LC) chains according to the number of linker-payload groups in each chain. Mass spectrometry data enables identification of the types of components in a mixture, e.g., LC+1, LC+2, HC+1, HC+2, etc. From the average loading of the LC and HC chains, mean DAR for the ADC can be calculated. The DAR for a given immunoconjugate sample represents the average number of drug (payload) molecules linked to a tetrameric antibody containing two light chains and two heavy chains. An example is the determination method for DAR described in WO2018142322.

The term "alkyl" refers to a saturated aliphatic hydrocarbon group that is a linear or branched group containing 1 to 20 carbon atoms, preferably alkyl containing 1 to 12 (e.g., 1, 2, 3, 4, 5, 6, 7, 8, 9, 10, 11 and 12) carbon atoms, more preferably alkyl containing 1 to 10 carbon atoms, and most preferably alkyl containing 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and various side-chain isomers thereof, and the like. More preferably, the alkyl is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl and the like. The alkyl may be substituted or unsubstituted. When it is substituted, the substitution with a substituent may be performed at any accessible connection site, wherein the substituent is preferably one or more of the groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "heteroalkyl" refers to alkyl containing one or more heteroatoms selected from the group consisting of N, O and S, wherein the alkyl is as defined above.

The term "alkylene" refers to a saturated linear or branched aliphatic hydrocarbon group, which has a residue derived by removal of two hydrogen atoms from the same carbon atom or two different carbon atoms of the parent alkane. It is a linear or branched group containing 1 to 20 carbon atoms, preferably alkylene containing 1 to 12 (e.g., 1, 2, 3, 4, 5, 6, 7, 8, 9, 10, 11 and 12) carbon atoms, and more preferably alkylene containing 1 to 6 carbon atoms. Non-limiting examples of alkylene include, but are not limited to, methylene ($—CH_2—$), 1,1-ethylidene ($—CH(CH_3)—$), 1,2-ethylidene ($—CH_2CH_2)—$, 1,1-propylidene ($—CH(CH_2CH_3)—$), 1,2-propylidene ($—CH_2CH(CH_3)—$), 1,3-propylidene ($—CH_2CH_2CH_2—$), 1,4-butylidene ($—CH_2CH_2CH_2CH_2—$), 1,5-butylidene ($—CH_2CH_2CH_2CH_2CH_2—$), and the like. The alkylene may be substituted or unsubstituted, and when it is substituted, the substitution with a substituent may be performed at any accessible connection site, wherein the substituent is preferably independently and optionally selected from the group consisting of alkyl, alkenyl, alkynyl, alkoxy, alkylthio, alkylamino, halogen, mercapto, hydroxy, nitro, cyano, cycloalkyl, heterocyclyl, aryl, heteroaryl, cycloalkoxy, heterocycloalkoxy, cycloalkylthio, heterocycloalkylthio and oxo.

The term "alkoxy" refers to —O-(alkyl) and —O-(cycloalkyl), wherein the alkyl or cycloalkyl is as defined above. Non-limiting examples of alkoxy include: methoxy, ethoxy, propoxy, butoxy, cyclopropyloxy, cyclobutoxy, cyclopentyloxy and cyclohexyloxy. The alkoxy may be optionally substituted or unsubstituted, and when it is substituted, the substituent is preferably one or more of the groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "cycloalkyl" refers to a saturated or partially unsaturated monocyclic or polycyclic hydrocarbon substituent. The cycloalkyl ring contains 3 to 20 carbon atoms, preferably 3 to 12 carbon atoms, more preferably 3 to 10 carbon atoms, and most preferably 3 to 8 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes spiro cycloalkyl, fused cycloalkyl, or bridged cycloalkyl.

The term "heterocyclyl" refers to a saturated or partially unsaturated monocyclic or polycyclic hydrocarbon substituent containing 3 to 20 ring atoms, wherein one or more of the ring atoms are heteroatoms selected from the group consisting of nitrogen, oxygen and $S(O)_m$ (where m is an integer from 0 to 2), excluding a cyclic portion of —O—O—, —O—S— or —S—S—, and the remaining ring atoms are carbon atoms. The heterocycloalkyl preferably contains 3 to 12 ring atoms, of which 1 to 4 are heteroatoms; and more preferably contains 3 to 10 ring atoms. Non-limiting examples of monocyclic heterocyclyl include pyrrolidinyl, piperidinyl, piperazinyl, morpholinyl, thiomorpholinyl, homopiperazinyl, and the like. Polycyclic heterocyclyl includes spiro heterocyclyl, fused heterocyclyl, or bridged heterocyclyl.

The term "spiro heterocyclyl" refers to a 5- to 20-membered polycyclic heterocyclyl group in which rings share one atom (referred to as the spiro atom), wherein one or more ring atoms are heteroatoms selected from the group consisting of nitrogen, oxygen and $S(O)_m$ (where m is an integer from 0 to 2), and the remaining ring atoms are carbon atoms. Those rings may contain one or more double bonds, but none of them has a fully conjugated 2-electron system. For example, the spiro heterocyclyl is 6- to 14-membered, and for another example, 7- to 10-membered. According to the number of spiro atoms shared among the rings, the spiro heterocyclyl may be monospiro heterocyclyl, bispiro heterocyclyl or polyspiro heterocyclyl, preferably monospiro heterocyclyl or bispiro heterocyclyl, for example, 4-membered/4-membered, 4-membered/5-membered, 4-membered/6-membered, 5-membered/5-membered or 5-membered/6-membered monospiro heterocyclyl. Non-limiting examples of spiro heterocyclyl include:

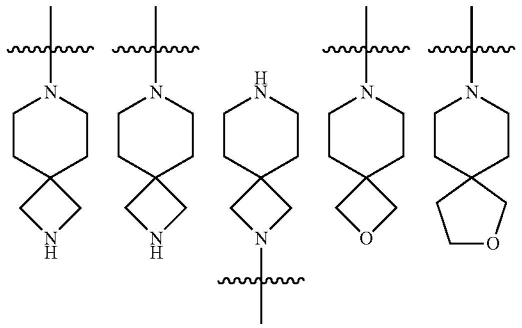

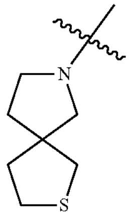

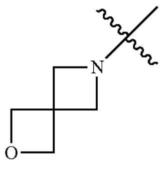

and

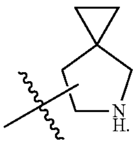

The term “fused heterocyclyl” refers to a 5- to 20-membered polycyclic heterocyclyl group in which each ring shares a pair of adjacent atoms with the other rings in the system, wherein one or more of the rings may contain one or more double bonds, but none of them has a fully conjugated 7r-electron system, wherein one or more of the ring atoms are heteroatoms selected from the group consisting of nitrogen, oxygen and $S(O)_m$ (where m is an integer from 0 to 2), and the remaining ring atoms are carbon atoms. For example, the spiro heterocyclyl is 6- to 14-membered, and for another example, 7- to 10-membered. According to the number of the formed rings, the fused heterocyclyl may be bicyclic, tricyclic, tetracyclic or polycyclic fused heterocyclyl, for example, bicyclic or tricyclic fused heterocyclyl, and for another example, 5-membered/5-membered or 5-membered/6-membered bicyclic fused heterocyclyl. Non-limiting examples of fused heterocyclyl include:

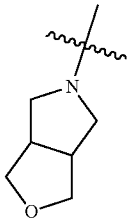
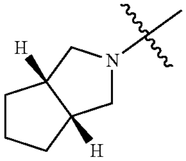
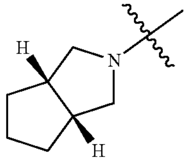
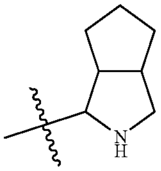
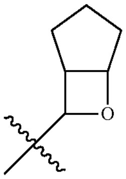
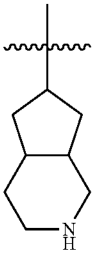
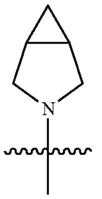
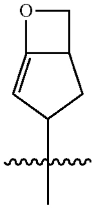
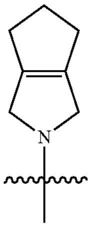
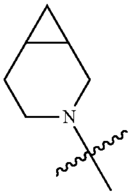
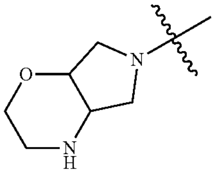
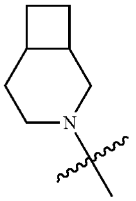
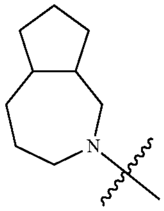
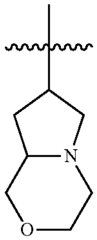
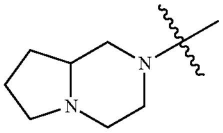

and

-continued

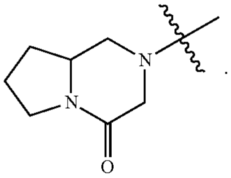

The term “bridged heterocyclyl” refers to a 5- to 14-membered polycyclic heterocyclyl group in which any two rings share two atoms that are not directly linked to each other, wherein those rings may contain one or more double bonds, but none of them has a fully conjugated 7r-electron system, wherein one or more of the ring atoms are heteroatoms selected from the group consisting of nitrogen, oxygen and $S(O)_m$ (where m is an integer from 0 to 2), and the remaining ring atoms are carbon atoms. For example, the spiro heterocyclyl is 6- to 14-membered, and for another example, 7- to 10-membered. According to the number of the formed rings, the bridged heterocyclyl may be bicyclic, tricyclic, tetracyclic or polycyclic, for example, bicyclic, tricyclic or tetracyclic, and more preferably bicyclic or tricyclic. Non-limiting examples of bridged heterocyclyl include:

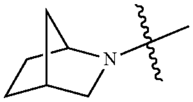
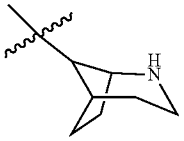
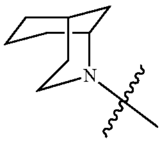
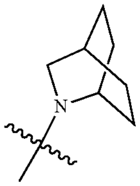
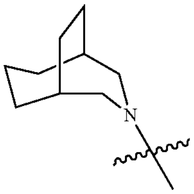
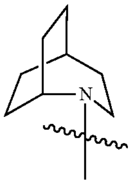
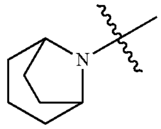

and

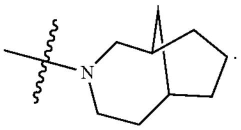

The heterocyclyl ring may be fused to an aryl, heteroaryl or cycloalkyl ring, wherein the ring attached to the parent structure is heterocyclyl; non-limiting examples include, but are not limited to:

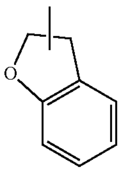
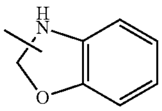
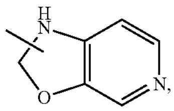
,

-continued

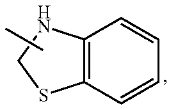

etc.

The heterocyclyl may be optionally substituted or unsubstituted, and when it is substituted, the substituent is preferably one or more of the groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio, heterocycloalkylthio and oxo.

The term "aryl" refers to a 6- to 14-membered, for example, 6- to 10-membered, carbon monocyclic or fused polycyclic (i.e., rings sharing a pair of adjacent carbon atoms) group having a conjugated 2-electron system, such as phenyl and naphthyl, specifically phenyl. The aryl ring may be fused to a heteroaryl, heterocyclyl or cycloalkyl ring, wherein the ring attached to the parent structure is the aryl ring; non-limiting examples include, but are not limited to:

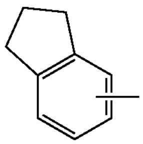 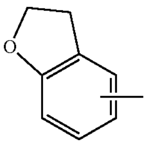 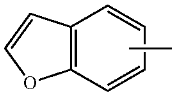

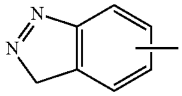 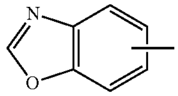

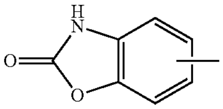 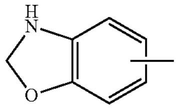

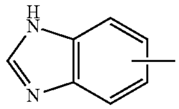 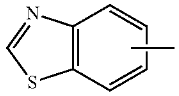

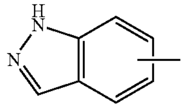 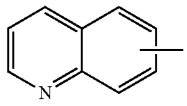

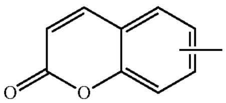 and 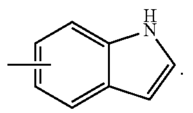.

The aryl may be substituted or unsubstituted, and when it is substituted, the substituent is preferably one or more of the groups independently selected from the group consisting of: alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "heteroaryl" refers to a heteroaromatic system containing 1 to 4 heteroatoms and 5 to 14 ring atoms, wherein the heteroatoms are selected from the group consisting of oxygen, sulfur and nitrogen. The heteroaryl is preferably 5- to 10-membered, more preferably 5- or 6-membered, such as furanyl, thienyl, pyridyl, pyrrolyl, N-alkylpyrrolyl, pyrimidinyl, pyrazinyl, imidazolyl and tetrazolyl. The heteroaryl ring may be fused to an aryl, heterocyclyl or cycloalkyl ring, wherein the ring attached to the parent structure is heteroaryl; non-limiting examples include, but are not limited to:

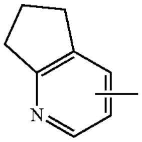 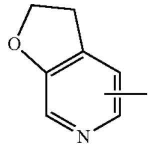 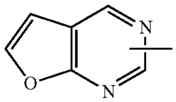

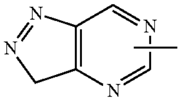 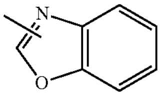 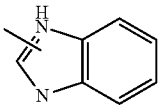

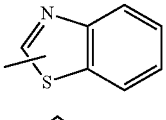 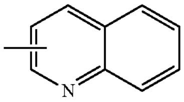

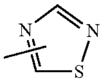 and 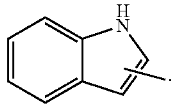.

The heteroaryl may be optionally substituted or unsubstituted, and when it is substituted, the substituent is preferably one or more of the groups independently selected from the group consisting of alkyl, alkenyl, alkynyl, alkoxy, alkylthio, alkylamino, halogen, mercapto, hydroxy, nitro, cyano, cycloalkyl, heterocycloalkyl, aryl, heteroaryl, cycloalkoxy, heterocycloalkoxy, cycloalkylthio and heterocycloalkylthio.

The term "cycloalkylalkyl" refers to alkyl in which the hydrogen is substituted with one or more cycloalkyl groups, preferably one cycloalkyl group, wherein the alkyl is as defined above, and the cycloalkyl is as defined above.

The term "haloalkyl" refers to alkyl in which the hydrogen is substituted with one or more halogens, wherein the alkyl is as defined above. The term "deuterated alkyl" refers to alkyl in which the hydrogen is substituted with one or more deuterium atoms, wherein the alkyl is as defined above.

The term "hydroxy" refers to —OH group.

The term "halogen" refers to fluorine, chlorine, bromine or iodine.

The term "amino" refers to $—NH_2$.

The term "nitro" refers to $—NO_2$.

In the chemical formula, the abbreviation "Me" refers to methyl.

The term "optionally" or "optional" means that the event or circumstance subsequently described may, but not necessarily, occur, and that the description includes instances where the event or circumstance occurs or does not occur. For example, "$C_1$-$C_6$ alkyl optionally substituted with halogen or cyano" means that halogen or cyano may, but not necessarily, be present, and the description includes the instance where alkyl is substituted with halogen or cyano and the instance where alkyl is not substituted with halogen and cyano.

The compound of the present disclosure may contain one or more asymmetric centers and thus enantiomers and diastereomers may be generated. The enantiomers and diastereomers may be defined in terms of absolute stereochemistry as (R)- or (S)-, or other stereoisomeric forms of (D)- or (L)- for amino acids. The present disclosure includes all possible isomers as well as racemic and optically pure forms thereof. Optically active (+) and (−), (R)- and (S)-, or (D)- and (L)-isomers may be prepared by using chiral synthons or chiral reagents, or may be prepared by using conventional methods such as chromatography and fractional crystallization. Conventional methods for the preparation/separation of enantiomers include chiral synthesis from suitable optically pure precursors or resolution of the racemate (or the racemate of a salt or derivative) by using, for example, chiral high performance liquid chromatography (HPLC). When a compound described herein contains an olefinic double bond or other geometric asymmetric centers, it is meant that the compound includes both E and Z geometric isomers, unless otherwise specified. Moreover, all tautomeric forms are also intended to be included.

In the chemical structure of the compound described herein, when no configuration is specified, a “/” bond may be “ ” or “ ”, or includes both “ ” and “ ” configurations. In the chemical structure of the compound described herein, when no configuration is specified, a “ ” bond may be in a Z configuration or an E configuration, or includes both configurations. For example,

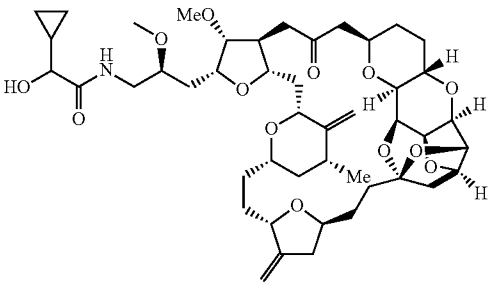

may be

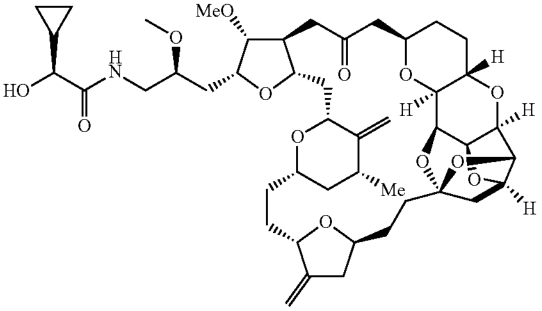

or

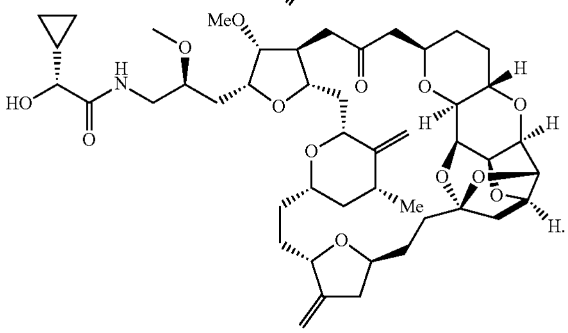

The term “stereoisomer” refers to compounds composed of identical atoms bonded by the same bonds but with different three-dimensional structures, which are not interchangeable. The present disclosure contemplates various stereoisomers and mixtures thereof, including “enantiomers” that refer to a pair of stereoisomers that are non-superimposable mirror images of one another.

Any isotopically-labeled derivative of the compound or the pharmaceutically acceptable salt or the isomer thereof described herein is encompassed by the present disclosure. Atoms that can be isotopically labeled include, but are not limited to, hydrogen, carbon, nitrogen, oxygen, phosphorus, fluorine, chlorine, iodine, etc. They can be separately replaced by the isotopes $^{2}H$ (D), $^{3}H$, $^{11}C$, $^{13}C$, $^{14}C$, $^{15}N$, $^{18}F$, $^{31}P$, $^{32}P$, $^{35}S$, $^{36}Cl$ and $^{125}I$, etc. Unless otherwise stated, when a position is specifically designated as deuterium (D), that position shall be understood to be deuterium having an abundance that is at least 3000 times greater than the natural abundance of deuterium (which is 0.015%) (i.e., incorporating at least 45% deuterium).

The term “substituted” means that one or more, preferably up to 5, more preferably 1 to 3 hydrogen atoms in the group are independently substituted with a substituent. A substituent is only in its possible chemical position, and those skilled in the art will be able to determine (experimentally or theoretically) possible or impossible substitution without undue efforts. For example, it may be unstable when amino or hydroxy having a free hydrogen is bound to a carbon atom having an unsaturated (e.g., olefinic) bond.

The term “pharmaceutical composition” refers to a mixture containing one or more of the compounds or the physiologically/pharmaceutically acceptable salts or prodrugs thereof described herein, and other chemical components, for example, physiologically/pharmaceutically acceptable carriers and excipients. The pharmaceutical composition is intended to promote the administration to an organism, so as to facilitate the absorption of the active ingredient, thereby exerting biological activities.

The term “pharmaceutically acceptable salt” refers to a salt of the ligand-drug conjugate of the present disclosure, or a salt of the compound described in the present disclosure. Such salts are safe and effective when used in a subject and possess the required biological activity. The antibody-drug conjugate of the present disclosure at least comprises one amino group and thus may form a salt with an acid. Non-limiting examples of the pharmaceutically acceptable salts include: hydrochloride, hydrobromide, hydriodate, sulphate, bisulfate, citrate, acetate, succinate, ascorbate, oxalate, nitrate, sorbate, hydrophosphate, dihydrophosphate, salicylate, hydrocitrate, tartrate, maleate, fumarate, formate, benzoate, mesylate, ethanesulfonate, benzenesulphonate and p-toluenesulfonate.

The term “solvate” refers to a pharmaceutically acceptable solvate formed by the ligand-drug conjugate of the present disclosure and one or more solvent molecules. Non-limiting examples of the solvent molecules include water, ethanol, acetonitrile, isopropanol, DMSO and ethyl acetate.

The present disclosure relates to a cleavable linker arm with a specific structure, an active substance with a specific structure, and an antibody-drug conjugate (ADC) consisting of the linker arm, the active substance and an antibody. Such an ADC is a complex formed by linking a toxic substance to an antibody via a spacer unit. The ADC is degraded in vivo to release active molecules, thereby playing an anti-tumor role.

The term “carrier”, when used for the pharmaceutical composition of the present disclosure, refers to a system that can alter the manner in which the drug gets into a subject and the distribution of the drug in the body, control the release rate of the drug, and deliver the drug to a target. The drug carrier release and targeted system can reduce drug degradation and loss, reduce side effects and improve bioavailability. For example, polymeric surfactants that can be used as carriers can self-assemble due to their unique amphiphilic structures to form various forms of aggregates, such as micelles, microemulsions, gels, liquid crystals and vesicles, as preferred examples. The aggregates have the capability of encapsulating drug molecules and have good permeability for membranes, and therefore can be used as excellent drug carriers.

The term "excipient" is an addition, besides the active ingredient, to a pharmaceutical formulation. It may also be referred to as an auxiliary material. For example, binders, fillers, disintegrants, lubricants in tablets; the matrix part in semisolid ointment and cream preparations; preservatives, antioxidants, corrigents, fragrances, cosolvents, emulsifiers, solubilizers, tonicity adjusting agents, colorants and the like in liquid formulations can all be referred to as excipients.

The term "diluent", also referred to as a filler, is used primarily to increase the weight and volume of the tablet. The addition of the diluent not only ensures a certain volume, but also reduces the dose deviation of the main ingredients, and improves the drug's compression moldability and the like. When the drug in the tablet form contains oily components, an absorbent is necessarily added to absorb the oily components so as to maintain a "dry" state and thus to facilitate the preparation of the tablet. Examples include starch, lactose, inorganic salts of calcium, microcrystalline cellulose and the like.

"Giving", "administering" and "treating", when applied to animals, humans, experimental subjects, cells, tissues, organs or biological fluid, refer to contact of an exogenous drug, a therapeutic agent, a diagnostic agent or a composition with the animals, humans, subjects, cells, tissues, organs or biological fluid. "Giving", "administering" and "treating" can refer to, for example, therapeutic, pharmacokinetic, diagnostic, research, and experimental methods. The treatment of the cells comprises making the reagent in contact with the cells and making the reagent in contact with fluid, where the fluid is in contact with the cells. "Giving", "administering" and "treating" also refer to treating, e.g., a cell, by a reagent, diagnosis, a binding composition, or by another cell in vitro and ex vivo. "Treating", when applied to humans, veterinary or research subjects, refers to therapeutic treatment, preventive or prophylactic measures, and research and diagnostic applications.

"Treatment" refers to administering a therapeutic agent, such as a composition comprising any of the antibodies or the antigen-binding fragments thereof or the conjugates thereof of the present application, either internally or externally to a subject who has had, is suspected of having, or is predisposed to having one or more diseases or symptoms thereof on which the therapeutic agent is known to have a therapeutic effect. In general, the therapeutic agent is administered in an effective amount for alleviating one or more symptoms of the disease in the subject or population being treated, whether by inducing regression of such symptoms or inhibiting the development of such symptoms into any clinically measurable degree. The amount of therapeutic agent effective to alleviate any particular symptom of the disease (also referred to as the "therapeutically effective amount") may vary depending on factors such as the disease state, age and weight of the subject, and the ability of the drug to produce a desired therapeutic effect in the subject. Whether a symptom of a disease has been alleviated can be evaluated by any clinical testing methods commonly used by doctors or other health care professionals to evaluate the severity or progression of the symptom. Although embodiments of the present application (e.g., treatment methods or articles of manufacture) may be ineffective in alleviating symptoms of a disease of interest in a certain subject, they alleviate the symptoms of the disease of interest in a statistically significant number of subjects as determined by any statistical test method known in the art, such as the Student's t-test, Chi-square test, U-test by Mann and Whitney, Kruskal-Wallis test (H-test), Jonckheere-Terpstra test and Wilcoxon test.

EXAMPLES

The present disclosure is further described below with reference to examples, which, however, are not intended to limit the scope of the present disclosure.

Experimental procedures without specific conditions indicated in the examples or test examples are generally conducted according to conventional conditions, or according to conditions recommended by the manufacturers of the starting materials or commercial products, see Sambrook et al., *Molecular Cloning: A Laboratory Manual*, Cold Spring Harbor Laboratory Press; *Current Protocols in Molecular Biology*, Ausubel et al., Greene Publishing Association, Wiley Interscience, NY. Reagents without specific origins indicated are commercially available conventional reagents.

1. Preparation of Antibodies

Example 1-1. Cloning and Expression of Protein Antigens

Antibodies (comprising light and heavy chains) and antigens were constructed by overlap extension PCR known in the art, and DNA fragments obtained by overlap extension PCR were inserted into expression vector pEE6.4 (Lonza Biologics) through HindIII/BstBI enzymatic digestion site, and expressed in 293F cells (Invitrogen, Cat #R790-07) to obtain recombinant proteins. The obtained recombinant proteins were used for immunization or screening. The amino acid sequence of human CD79B was derived from NCBI (NP_000617.1), and the extracellular region (ECD) of human CD79B comprises 159 amino acids (Met1-Asp159).

The amino acid sequence of a fusion protein of human CD79B extracellular domain (ECD) and human Fc region (human CD79B ECD-hFc) is shown in SEQ ID NO: 1:

SEQ ID NO: 1

ARSEDRYRNPKGSACSRIWQSPRFIARKRGFTVKMHCYMNSASGNVSWL

WKQEMDENPQQLKLEKGRMEESQNESLATLTIQGIRFEDNGIYFCQQKC

NNTSEVYQGCGTELRVMGFSTLAQLKQRNTLKDGIIMIQTLLIILFIIV

PIFLLLDKDDSKAGMEEDHTYEGLDIDQTATYEDIVTLRTGEVKWSVGE

HPGQEEPKSCDKTHTCPPCPAPELLGGPSVFLFPPKPKDTLMISRTPEV

TCVVVDVSHEDPEVKFNWYVDGVEVHNAKTKPREEQYNSTYRVVSVLTV

LHQDWLNGKEYKCKVSNKALPAPIEKTISKAKGQPREPQVYTLPPSREE

MTKNQVSLTCLVKGFYPSDIAVEWESNGQPENNYKTTPPVLDSDGSFFL

YSKLTVDKSRWQQGNVFSCSVMHEALHNHYTQKSLSLSPGK.

The amino acid sequence of a fusion protein of human CD79B extracellular domain (ECD) and His tag (human CD79B ECD-His) is shown in SEQ ID NO: 2:

SEQ ID NO: 2
ARSEDRYRNPKGSACSRIWQSPRFIARKRGFTVKMHCYMNSASGNVSWL

WKQEMDENPQQLKLEKGRMEESQNESLATLTIQGIRFEDNGIYFCQQKC

NNTSEVYQGCGTELRVMGFSTLAQLKQRNTLKDGIIMIQTLLIILFIIV

PIFLLLDKDDSKAGMEEDHTYEGLDIDQTATYEDIVTLRTGEVKWSVGE

HPGQEHHHHHH.

Example 1-2. Preparation of Mouse Monoclonal Antibody

1. Mouse Immunization and Serum Titer Determination

The fusion protein of human CD79B extracellular domain (ECD) and human Fc region (human CD79B ECD-hFc) and the fusion protein of human CD79B extracellular domain (ECD) and His tag (human CD79B ECD-His) were taken as immunogens and used to immunize and Balb/c and SJL mice by intraperitoneal injection, respectively, so as to stimulate the mice to produce antibodies against the human CD79B extracellular domain (ECD). In addition, the fusion protein of cynomolgus monkey CD79B extracellular domain (ECD) and His tag (cyno CD79B ECD-His) was taken as an immunogen to immunize SJL mice by intraperitoneal injection, so as to stimulate the mice to produce antibodies against the monkey CD79B extracellular domain (ECD). Experimental Procedures:

1) Intraperitoneal injection immunization The amount of antigen required for this immunization was calculated according to the immunization program. The protein antigen was diluted to the corresponding concentration with PBS as required, and subsequently emulsified. A mixture of the emulsified antigen and adjuvant was transferred to a 2.0 mL sterile syringe and injected into the right side of abdomen of mice.

2) Mouse serum collection The serum tube corresponding to each mouse was marked; about 100 μL of whole blood was collected through the submaxillary vein of the mouse, and the collected whole blood sample was left to stand at room temperature for about 2 h and then centrifuged to collect serum. The serum was stored in a refrigerator at 4° C. for antibody titer determination and the like.

3) Serum titer determination of immunized mice by ELISA A 96-well plate was coated with 1 μg/mL antigen at 50 μL/well and incubated in a refrigerator at 4° C. overnight. The next day, the coated plate was washed once (washing solution: 1×PBST). After washing, the plate was blocked with 1% BSA blocking solution prepared in 1×PBST at 37° C. for 1 h. After washing the plate 3 times with 1×PBST, the test serum samples at different dilution concentrations were added to the plate, and the plate was incubated in an incubator at 37° C. for 1 h. After washing the plate 3 times with 1×PBST, 100 μL of goat anti-mouse secondary antibody diluted in a 1:5000 ratio was added, and the plate was incubated in an incubator at 37° C. for 0.5 h. After washing the plate, TMB color development solutions A and B were mixed in a 1:1 ratio for color development. 15 min later, the color development reaction was stopped with 1 N hydrochloric acid. Fluorescence value was read at 450 nm on a Spectra Max M5 microplate reader.

4) Serum titer determination of immunized mice by FACS The suspension of DoHH2 cells or monkey peripheral blood mononuclear cells was centrifuged, resuspended in PBS containing 0.1% BSA, and counted. The test serum of each group of immunized mice was added, and the cells were incubated at room temperature for 60 min and washed three times. Then Anti-Mouse IgG (Fc specific)-FITC secondary antibody was added, and the cells were incubated at room temperature for 30 min away from the light, washed three times, gently resuspended in PBS containing 0.1% BSA, and loaded on the machine for assay.

The assay results of serum titers of all groups of mice by ELISA and FACS are shown in FIGS. 1 to 7.

Figure 2:
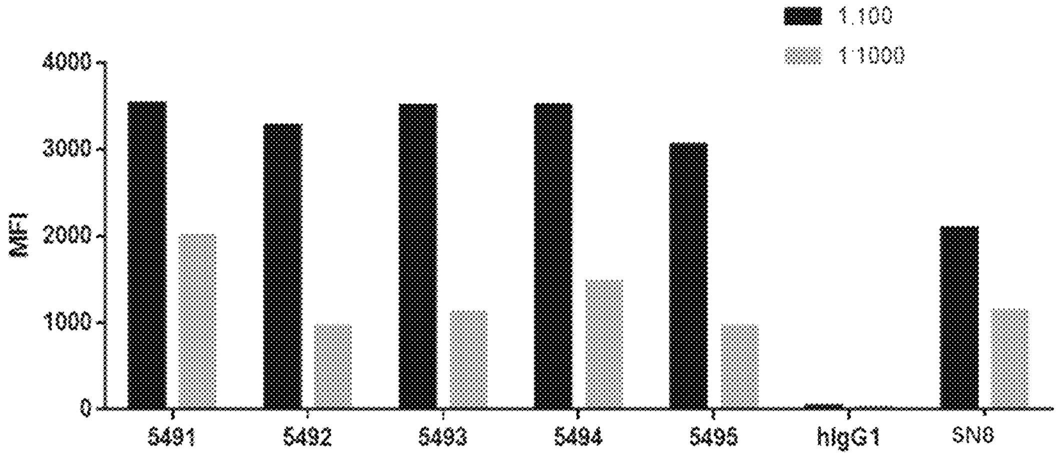
FIG. 2: assay results of serum titers of Balb/c mice immunized by human CD79B ECD-hFc proteins by FACS.

A total of 5 Balb/c mice were immunized with the human CD79B ECD-hFc protein, and numbered 5491, 5492, 5493, 5494 and 5495, respectively. The assay results of serum titers by ELISA are shown in FIG. 1. The results show that the serum titers of mice after immunization reach more than 1:100 K. The assay results of serum titers of mice by FACS are shown in FIG. 2. It can be seen that the antibodies produced in mouse serum can specifically recognize CD79B protein on the surface of DoHH2 cells.

Figure 3:
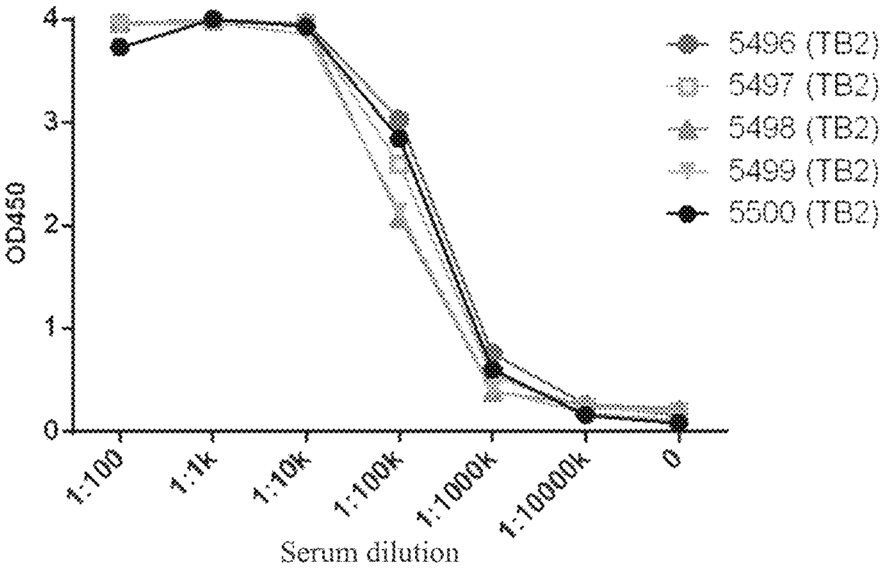
FIG. 3: assay results of serum titers of SJL mice immunized by human CD79B ECD-hFc proteins by ELISA.
Figure 4:
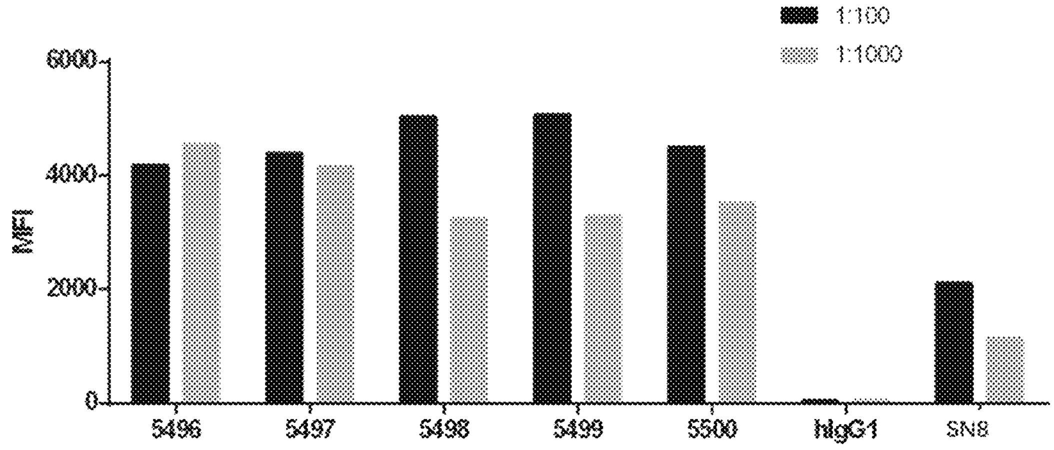
FIG. 4: assay results of serum titers of SJL mice immunized by human CD79B ECD-hFc proteins by FACS.

A total of 5 SJL mice were immunized with the human CD79B ECD-hFc protein, and numbered 5496, 5497, 5498, 5499 and 5500, respectively. The assay results of serum titers by ELISA are shown in FIG. 3. The results show that the serum titers of mice after immunization reach more than 1:100 K. The assay results of serum titers of mice by FACS are shown in FIG. 4. It can be seen that the antibodies produced in mouse serum can specifically recognize CD79B protein on the surface of DoHH2 cells.

Figure 5:
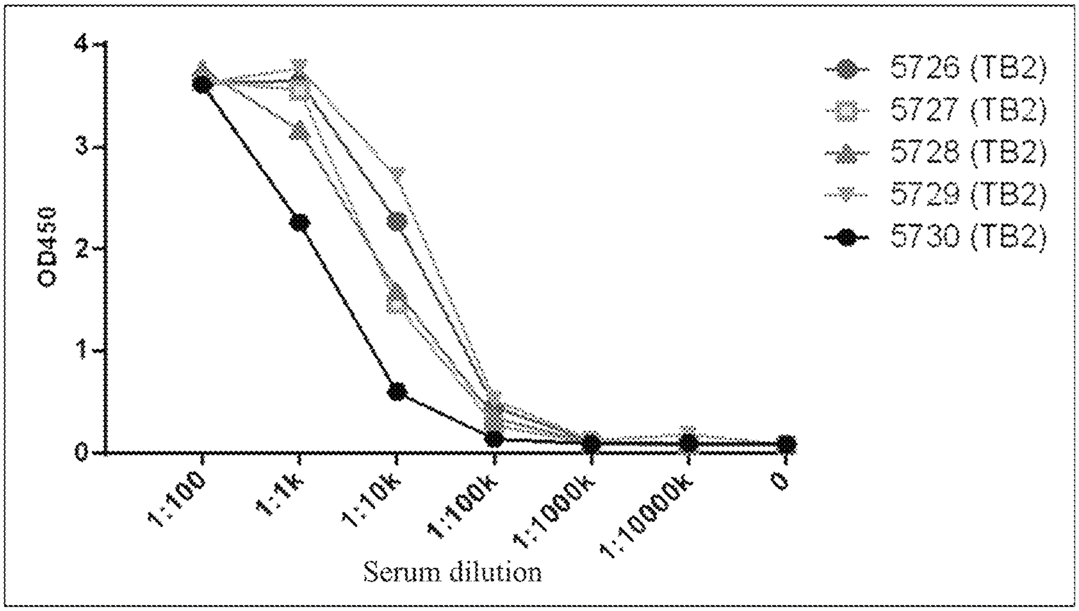
FIG. 5: assay results of serum titers of SJL mice immunized by human CD79B ECD-his proteins by ELISA.
Figure 6:
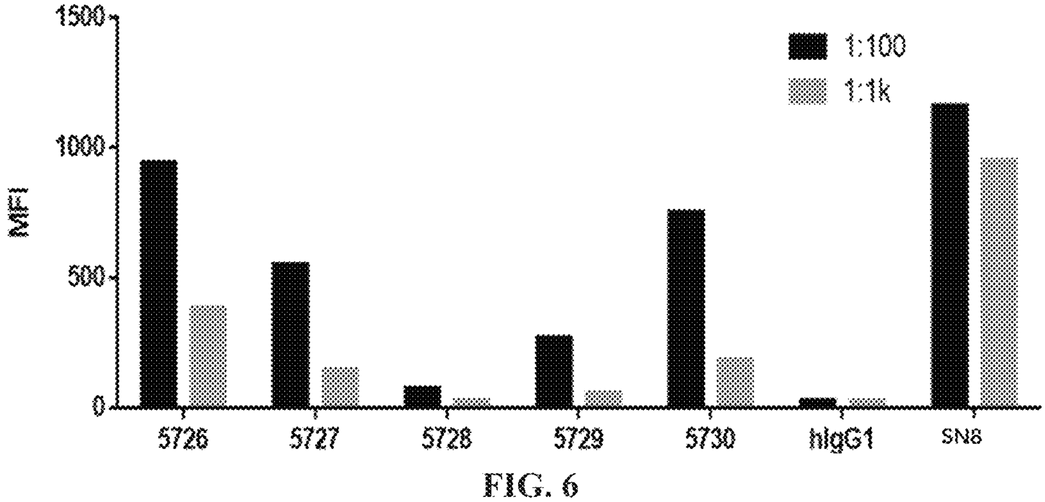
FIG. 6: assay results of serum titers of SJL mice immunized by human CD79B ECD-his proteins by FACS.

A total of 5 SJL mice were immunized with the human CD79B ECD-his protein, and numbered 5726, 5727, 5728, 5729 and 5730, respectively. The assay results of serum titers by ELISA are shown in FIG. 5. The results show that the serum titers of mice after immunization reach more than 1:10 K. The assay results of serum titers of mice by FACS are shown in FIG. 6. It can be seen that the antibodies produced in mouse serum can specifically recognize CD79B protein on the surface of DoHH2 cells.

Figure 7:
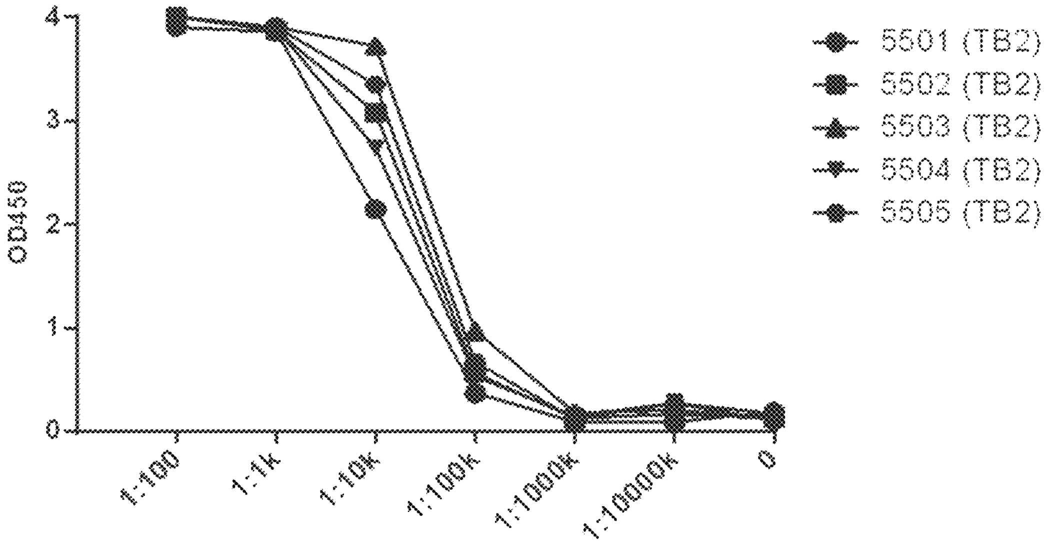
FIG. 7: assay results of serum titers of SJL mice immunized by monkey CD79B ECD-his proteins by ELISA.

A total of 5 SJL mice were immunized with the monkey CD79B ECD-his protein, and numbered 5501, 5502, 5503, 5504 and 5505, respectively. The assay results of serum titers by ELISA are shown in FIG. 7. The results show that the serum titers of mice after immunization reach more than 1:10 K.

From the above results, it can be seen that specific antibodies against CD79B are produced in the immunized mice. The above mice can be used for cell fusion to produce hybridoma cell lines capable of secreting specific antibodies against CD79B.

2. Hybridoma Preparation and Antibody Screening

Lymphocytes and myeloma cells SP2/0 (ATCC, CCL-121™) of immunized mice were fused by electrofusion for subsequent antibody screening.

1) Electrofusion experiment SP2/0 cells were expanded in 10% DMEM medium one week before fusion. Spleens and lymph nodes of mice were harvested, rinsed and ground to collect lymphocytes. SP2/0 and lymphocytes were mixed in proportion, and fused using an electrofusion apparatus. After fusion, the cells were plated in a 96-well plate and cultured in an incubator at 37° C. with 5% $CO_2$; the cell state was observed every day, and the cell fusion rate was calculated 5 days after fusion. The fused hybridoma cells were screened 9-14 days after fusion, and the cells in positive wells were picked for amplification culture in a 24-well plate.

2) Subcloning by limiting dilution method The cell strains to be subcloned were resuspended in the wells of the 24-well culture plate and counted. The cell concentration of each cell strain was diluted to 5-10 cells/mL, the diluted cell suspension was added to a 96-well culture plate at 0.2 mL/1-2 cells/well. The 96-well plate was incubated in an incubator at 37° C. with 5% $CO_2$. 7-10 days later, positive clones were picked and added to a 24-well plate for further confirmation.

3) ELISA screening A 96-well plate was coated with 1 μg/mL antigen at 50 μL/well and incubated in a refrigerator at 4° C. overnight. The next day, the coated antigen plate was washed once (washing solution: 1×PBST). After washing, the plate was blocked with 1% BSA blocking solution prepared in 1×PBST at 37° C. for 1 h. After washing the plate 3 times with 1×PBST, 50 μL of the test cell supernatant was added, and the plate was incubated in an incubator at 37° C. for 1 h. After washing the plate 3 times with 1×PBST, 100 μL of goat anti-mouse secondary antibody diluted in a 1:5000 ratio was added, and the plate was incubated in an incubator at 37° C. for 0.5 h. After washing the plate, TMB color development solutions A and B were mixed in a 1:1 ratio for color development. 15 min later, the color development reaction was stopped with 1 N hydrochloric acid. Fluorescence value was read at 450 nm on a Spectra Max M5 microplate reader.

4) FACS screening The suspension of DoHH2 cells was centrifuged, resuspended in PBS containing 0.1% BSA, and counted. The test serum was added, and the cells were incubated at room temperature for 60 min and washed. Then Anti-Mouse IgG (Fc specific)-FITC secondary antibody was added, and the cells were incubated at room temperature for 30 min away from the light, washed three times, gently resuspended in PBS containing 0.1% BSA, and loaded on the machine for assay.

5) Identification of hybridoma positive clones A plurality of specific antibodies against human CD79B antigen were obtained; and 17 strains of hybridomas having strongest binding force to ELISA and FACS in assays were taken for production and purification of antibodies. Assay results of anti-human CD79B hybridoma positive clones by ELISA are shown in Table 1. Assay results of anti-human CD79B hybridoma positive clones by FACS are shown in Table 2. Specific antibodies against monkey CD79B antigen were also obtained; and 4 strains of hybridomas having strongest binding force to ELISA and FACS in assays were taken for production and purification of antibodies. Assay results of anti-monkey CD79B hybridoma positive clone cells by ELISA are shown in Table 3. Assay results of anti-monkey CD79B hybridoma positive clone cells by FACS are shown in Table 4. mIgG was used as negative control in the both assays.

TABLE 1

Assay results of anti-human CD79B hybridoma positive clones by ELISA

| Antibody No. | Clone No. | Results (OD450) |
|---|---|---|
| Negative control | mIgG | 0.05 |
| mAb001 | 12A11-1G1 | 3.26 |
| mAb002 | 19F10-1D7 | 3.69 |
| mAb003 | 51E5G6 | 3.02 |
| mAb004 | 67B10C1 | 3.41 |
| mAb005 | 78A9F4 | 3.73 |
| mAb006 | 48F11D6 | 3.34 |
| mAb007 | 61A11F1 | 3.40 |

TABLE 1-continued

Assay results of anti-human CD79B hybridoma positive clones by ELISA

| Antibody No. | Clone No. | Results (OD450) |
|---|---|---|
| mAb008 | 63G2A2 | 3.56 |
| mAb009 | 75F1E2 | 3.57 |
| mAb010 | 66G3E7 | 3.83 |
| mAb011 | 66E12H3 | 3.41 |
| mAb012 | 73A8F3 | 3.45 |
| mAb013 | 74C4F3 | 3.31 |
| mAb014 | 70B8B3 | 3.10 |
| mAb015 | 83B2G2 | 3.41 |
| mAb016 | 83C2D4 | 3.46 |
| mAb017 | 86F11F6 | 3.80 |

TABLE 2

Assay results of anti-human CD79B hybridoma positive clones by FACS

| Antibody No. | Clone No. | Mean fluorescence value |
|---|---|---|
| Negative control | mIgG | 58 |
| mAb001 | 12A11-1G1 | 13032 |
| mAb002 | 19F10-1D7 | 5943 |
| mAb003 | 51E5G6 | 33918 |
| mAb004 | 67B10C1 | 26000 |
| mAb005 | 78A9F4 | 24454 |
| mAb006 | 48F11D6 | 20120 |
| mAb007 | 61A11F1 | 18039 |
| mAb008 | 63G2A2 | 16453 |
| mAb009 | 75F1E2 | 16001 |
| mAb010 | 66G3E7 | 15897 |
| mAb011 | 66E12H3 | 14688 |
| mAb012 | 73A8F3 | 14073 |
| mAb013 | 74C4F3 | 12894 |
| mAb014 | 70B8B3 | 8776 |
| mAb015 | 83B2G2 | 10036 |
| mAb016 | 83C2D4 | 9990 |
| mAb017 | 86F11F6 | 8132 |

TABLE 3

Assay results of anti-monkey CD79B hybridoma positive clones by ELISA

| Antibody No. | Clone No. | Results (OD450) |
|---|---|---|
| Negative control | mIgG | 0.08 |
| mAb018 | 121H1E9 | 2.36 |
| mAb019 | 152E5F6 | 2.80 |
| mAb020 | 159E3E5 | 2.71 |
| mAb021 | 134H2F5 | 2.95 |

TABLE 4

Assay results of anti-monkey CD79B hybridoma positive clones by FACS

| Antibody No. | Clone No. | Mean fluorescence value |
|---|---|---|
| Negative control | mIgG | 35 |
| mAb018 | 121H1E9 | 1973 |

TABLE 4-continued

| Assay results of anti-monkey CD79B hybridoma positive clones by FACS | | |
|---|---|---|
| Antibody No. | Clone No. | Mean fluorescence value |
| mAb019 | 152E5F6 | 1708 |
| mAb020 | 159E3E5 | 1488 |
| mAb021 | 134H2F5 | 1225 |

3. Production, Purification and Identification of Mouse Monoclonal Antibodies

1) Production and purification of mouse monoclonal antibodies The hybridoma cells required for antibody production were observed under a microscope. When the cells grew to ≥70% or more and had good cell state, the cells were collected and counted using a Countstar IC1000-type cell counter. The cell concentration was adjusted to $1\times10^5$ to $5\times10^5$ cells/mL and transferred to a Roller Bottle. The Roller Bottle was placed in an incubator for culturing at 37° C. for 10-15 days, and the growth condition of cells were observed every day. The cells were taken out for purification when the culture solution turned orange and transparent. The cell supernatant was subjected to antibody purification using a Protein A column according to a conventional method.

Figure 8:
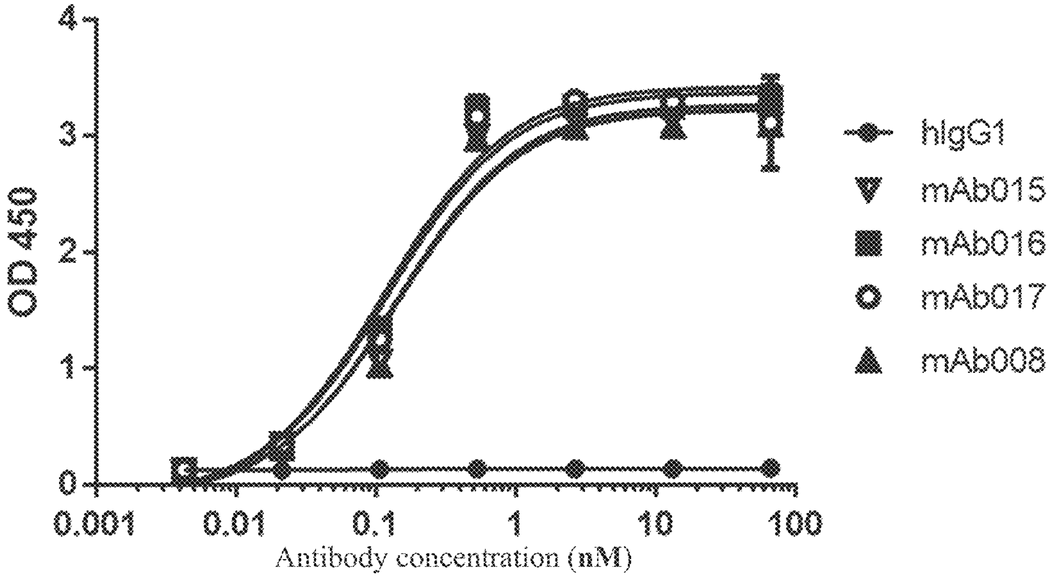
FIG. 8: assay results of anti-human CD79B mouse monoclonal antibodies by ELISA.

2) Assay on anti-human CD79B mouse monoclonal antibodies by ELISA A 96-well plate was coated with 1 μg/mL antigen at 50 μL/well and incubated in a refrigerator at 4° C. overnight. The next day, the coated antigen plate was washed once (washing solution: 1×PBST). After washing, the plate was blocked with 1% BSA blocking solution prepared in 1×PBST at 37° C. for 1 h. After washing the plate 3 times with 1×PBST, 50 μL of antibody diluted in a 1:10 ratio from 100 nM was added, and the plate was incubated in an incubator at 37° C. for 1 h. After washing the plate 3 times with 1×PBST, 100 μL of goat anti-mouse secondary antibody diluted in a 1:5000 ratio was added, and the plate was incubated in an incubator at 37° C. for 0.5 h. After washing the plate, TMB color development solutions A and B were mixed in a 1:1 ratio for color development. 15 min later, the color development reaction was stopped with 1 N hydrochloric acid. Fluorescence value was read at 450 nm on a Spectra Max M5 microplate reader. Four of those anti-human CD79B mouse monoclonal antibodies showed the strongest ELISA binding force (mAb008, mAb015, mAb016 and mAb017). The specific data are shown in FIG. 8.

Figure 9A:
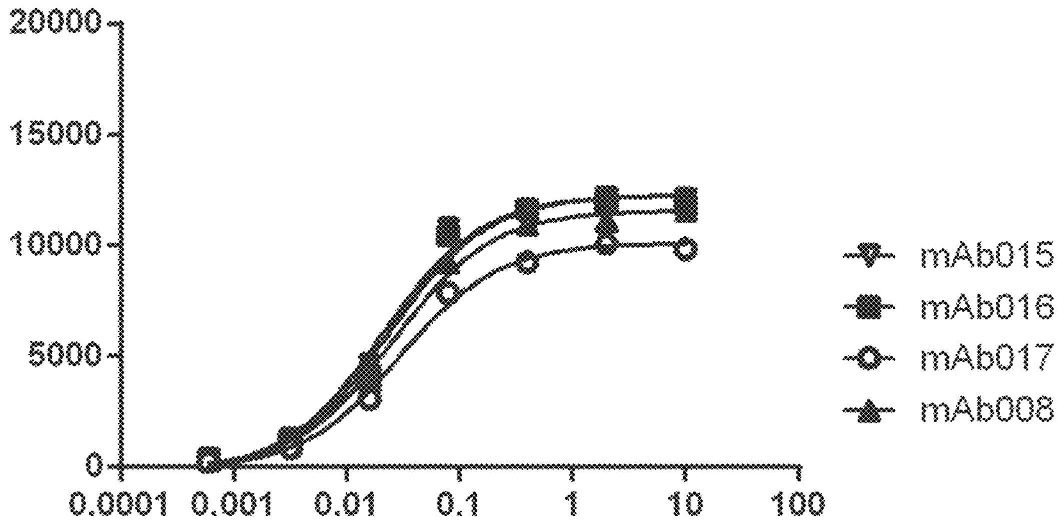
FIG. 9A shows assay results of anti-human CD79B mouse monoclonal antibodies by FACS.
Figure 9B:
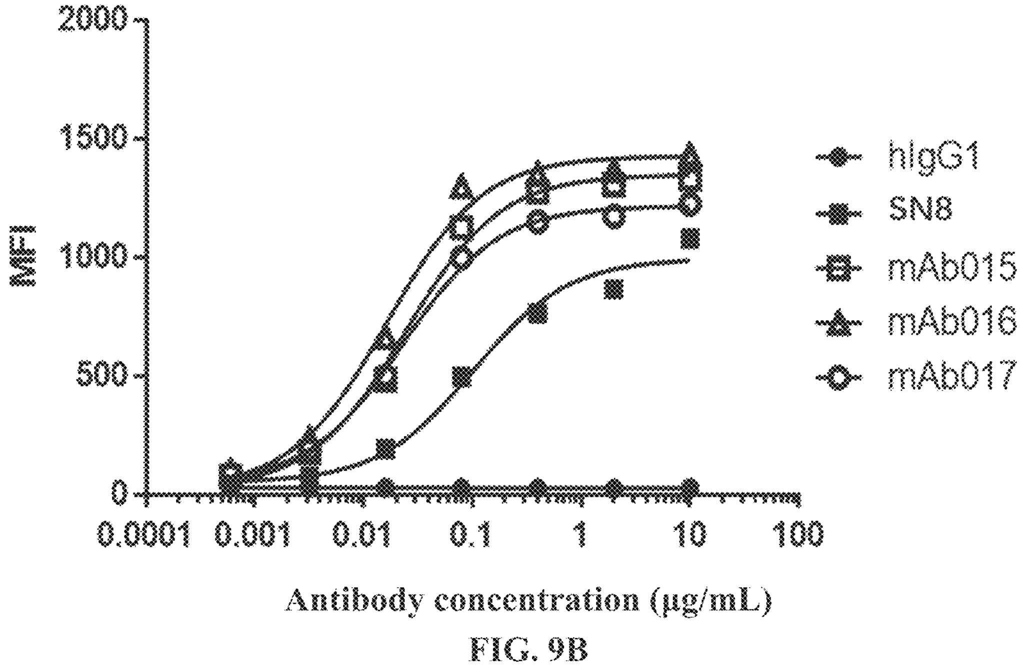
FIG. 9B shows assay results of anti-human CD79B mouse monoclonal antibodies by FACS, in which hIgG1 is a negative control antibody and SN8 is a positive control antibody.

3) Assay on anti-human CD79B mouse monoclonal antibodies by FACS The cell suspension of DoHH2 cells was centrifuged, resuspended in PBS containing 0.1% BSA, and counted. 100 μL of antibody diluted in a 1:10 ratio from 100 nM was added, and the cells were incubated at room temperature for 1 h and washed three times. Then Anti-Mouse IgG (Fc specific)-FITC secondary antibody was added, and the cells were incubated at room temperature for 30 min away from the light, washed three times, gently resuspended in PBS containing 0.1% BSA, and loaded on the machine for assay. Four of those anti-human CD79B mouse monoclonal antibodies showed the strongest FACS binding force (mAb008, mAb015, mAb016 and mAb017). The specific data are shown in FIGS. 9A and 9B, in which hIgG1 is a negative control antibody and SN8 is a positive control antibody. SN8 is an antibody (reference sequence source: US20170362318A) used in the antibody-drug conjugate polatuzumab vedotin developed by Roche pharmaceutical. Polatuzumab vedotin has been approved by the FDA for marketing. From the results, it can be seen that the three preferred anti-human CD79B mouse monoclonal antibodies mAb015, mAb016 and mAb017 of the present disclosure all have superior binding force to SN8 in the FACS assay.

Figure 10:
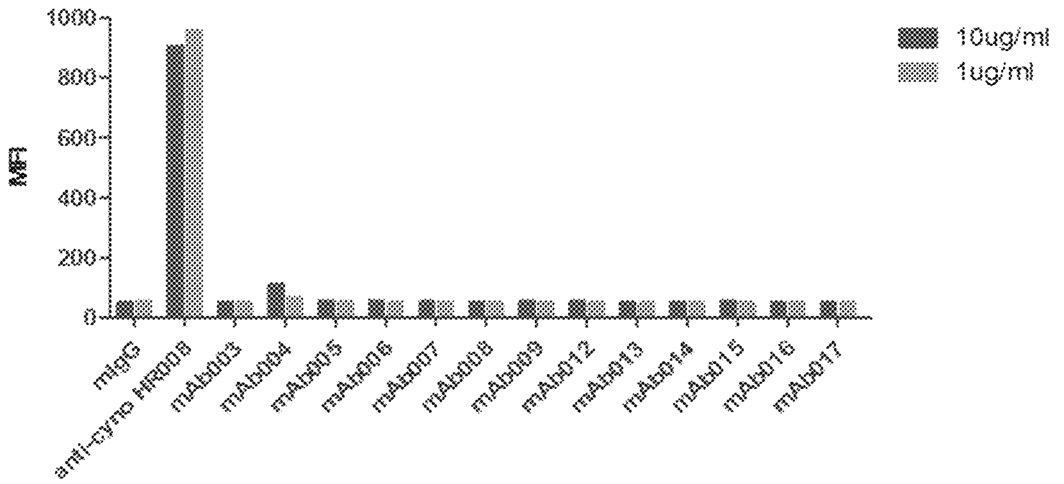
FIG. 10: assay results of cross-reactivity of anti-human CD79B mouse monoclonal antibodies by FACS.

4) Assay on cross-reactivity of anti-human CD79B mouse monoclonal antibodies by FACS 293F-cynoCD79B cells were obtained by transient transfection, and the cell suspension was centrifuged, resuspended in PBS containing 0.1% BSA, and counted. Antibodies at concentrations of 10 μg/mL and 1 μg/mL were separately added, each at 100 μL. The cells were incubated at room temperature for 1 h and washed three times. Then Anti-Mouse IgG (Fc specific)-FITC secondary antibody was added, and the cells were incubated at room temperature for 30 min away from the light, washed three times, gently resuspended in PBS containing 0.1% BSA, and loaded on the machine for assay. The assay results of cross-reactivity of anti-human CD79B mouse monoclonal antibodies by FACS are shown in FIG. 10.

Figure 11:
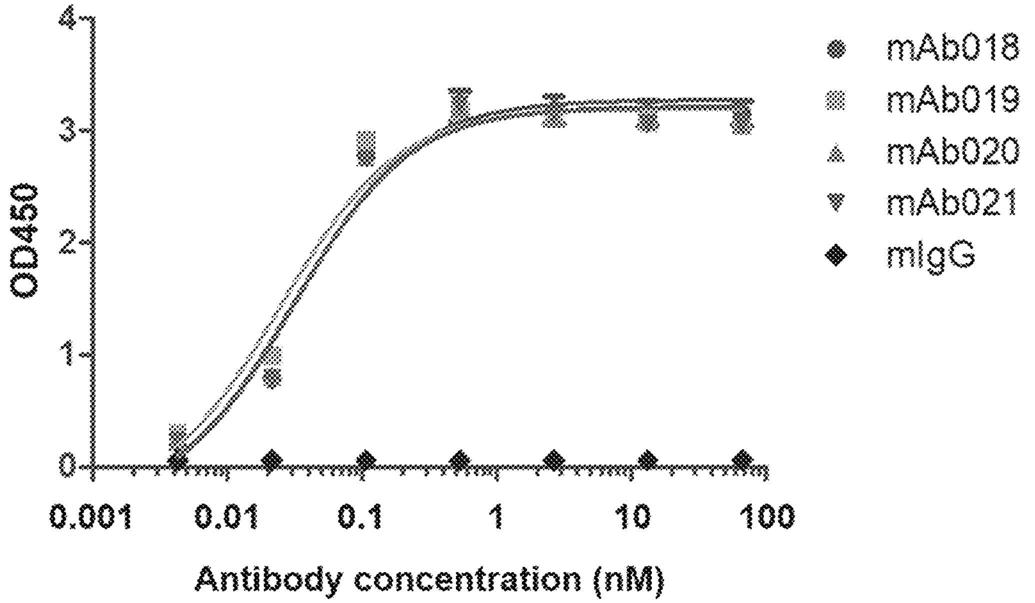
FIG. 11: assay results of anti-monkey CD79B mouse monoclonal antibodies by ELISA.
Figure 12A:
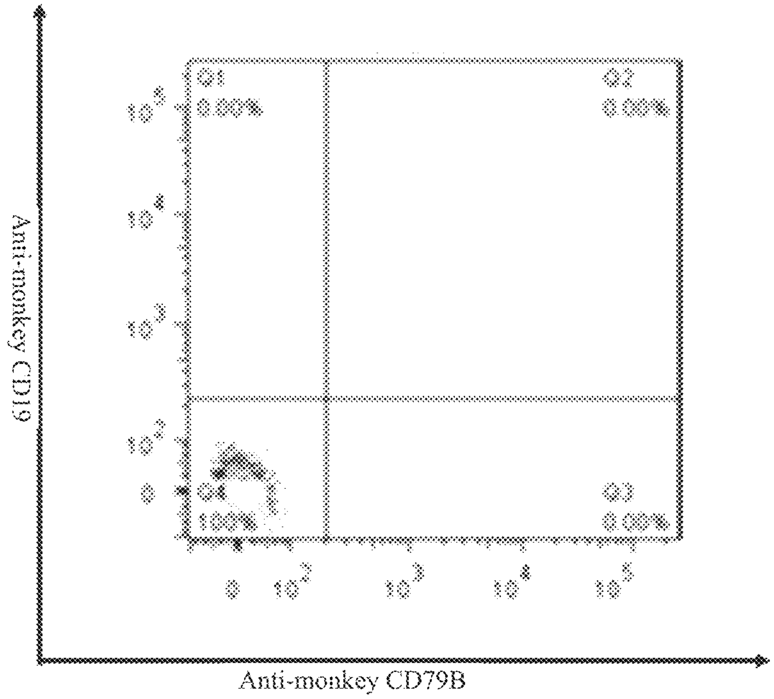
FIGS. 12A-12G: assay on the binding of anti-monkey CD79B mouse monoclonal antibodies to monkey peripheral blood mononuclear cells by FACS.
Figure 12B:
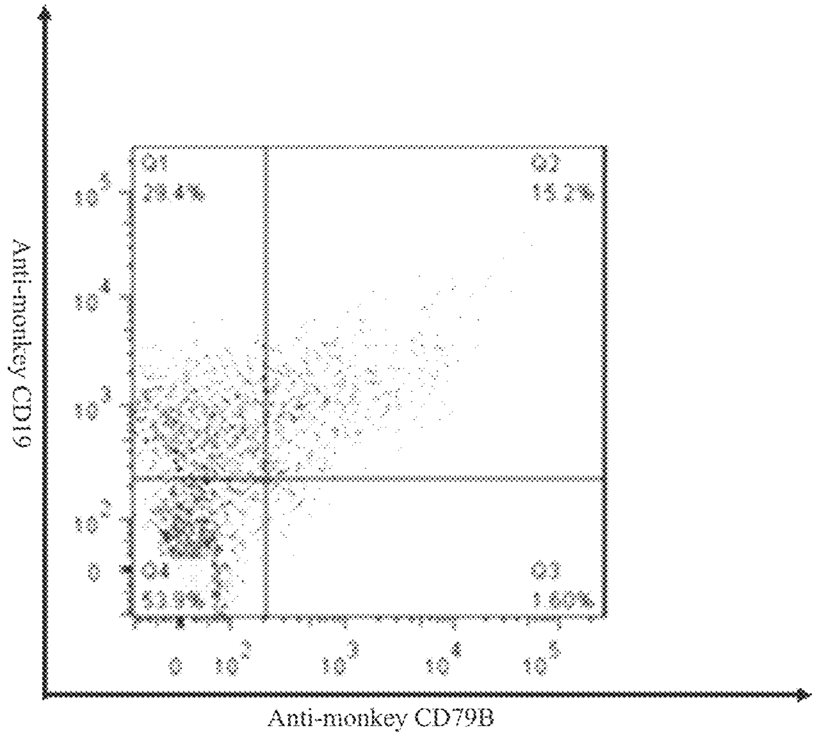
Figure 12C:
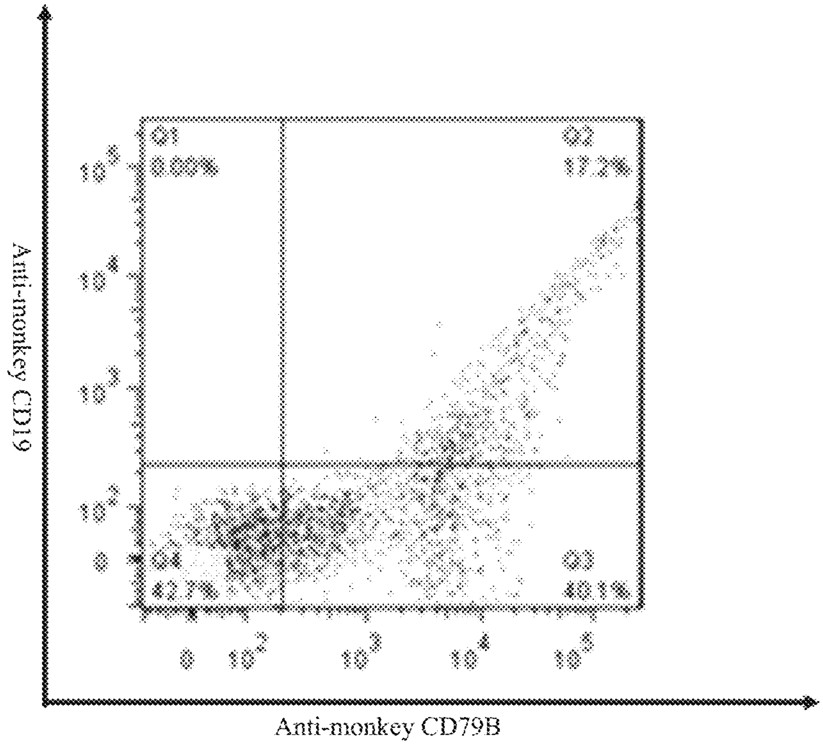
Figure 12D:
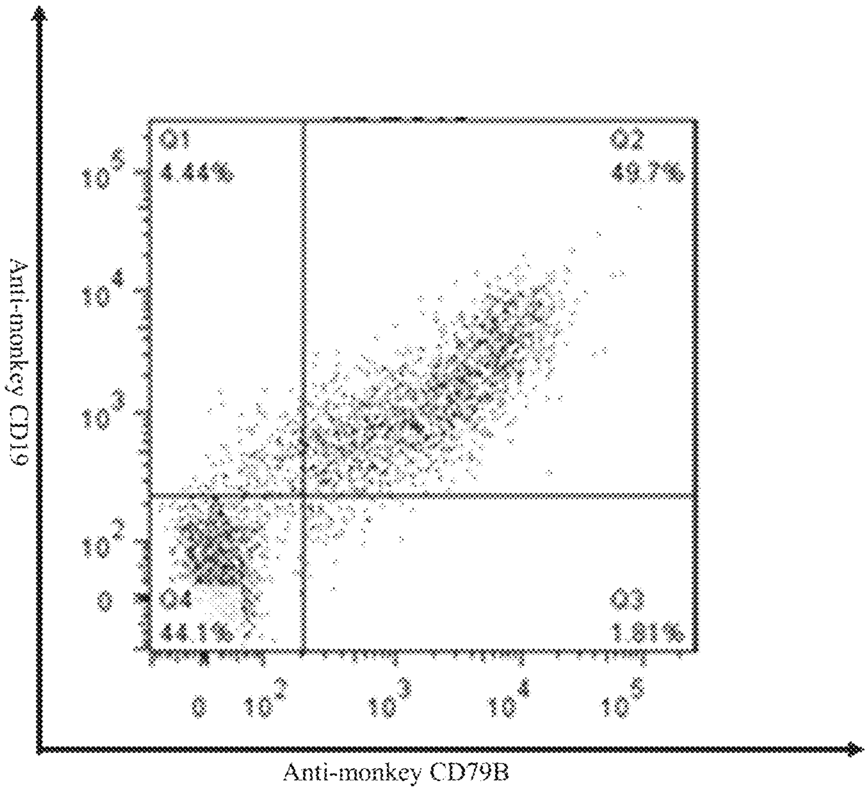
Figure 12E:
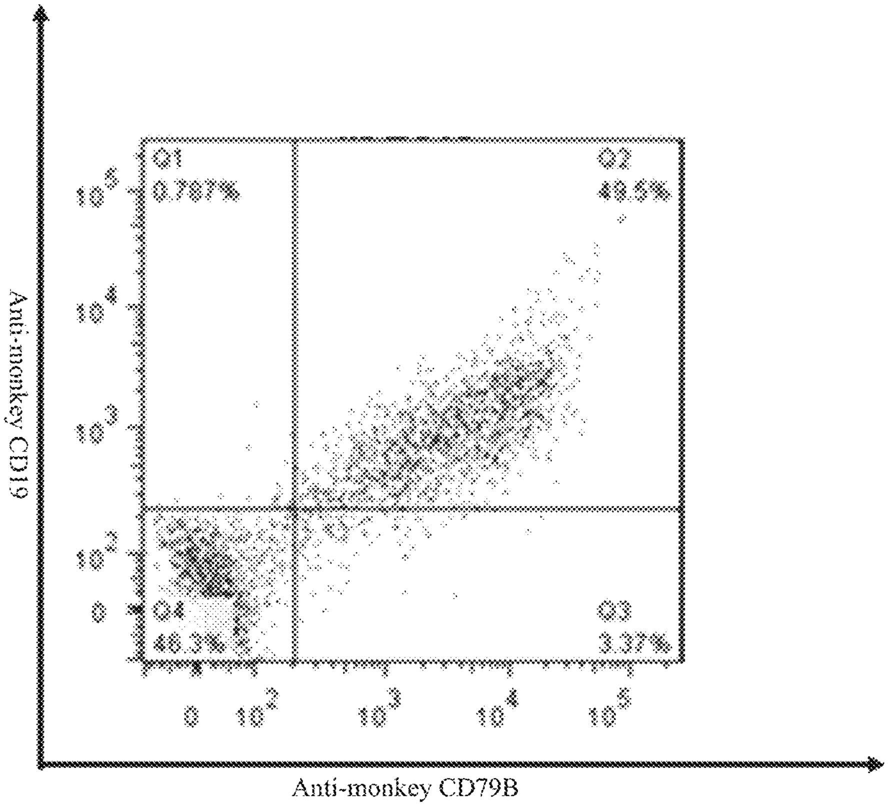
Figure 12F:
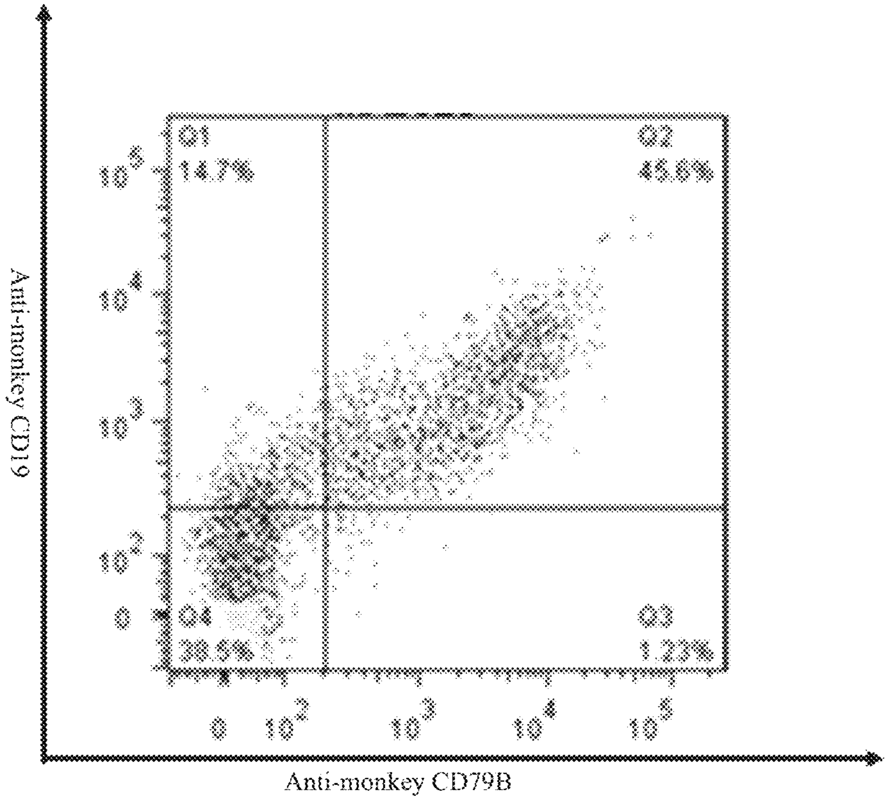
Figure 12G:
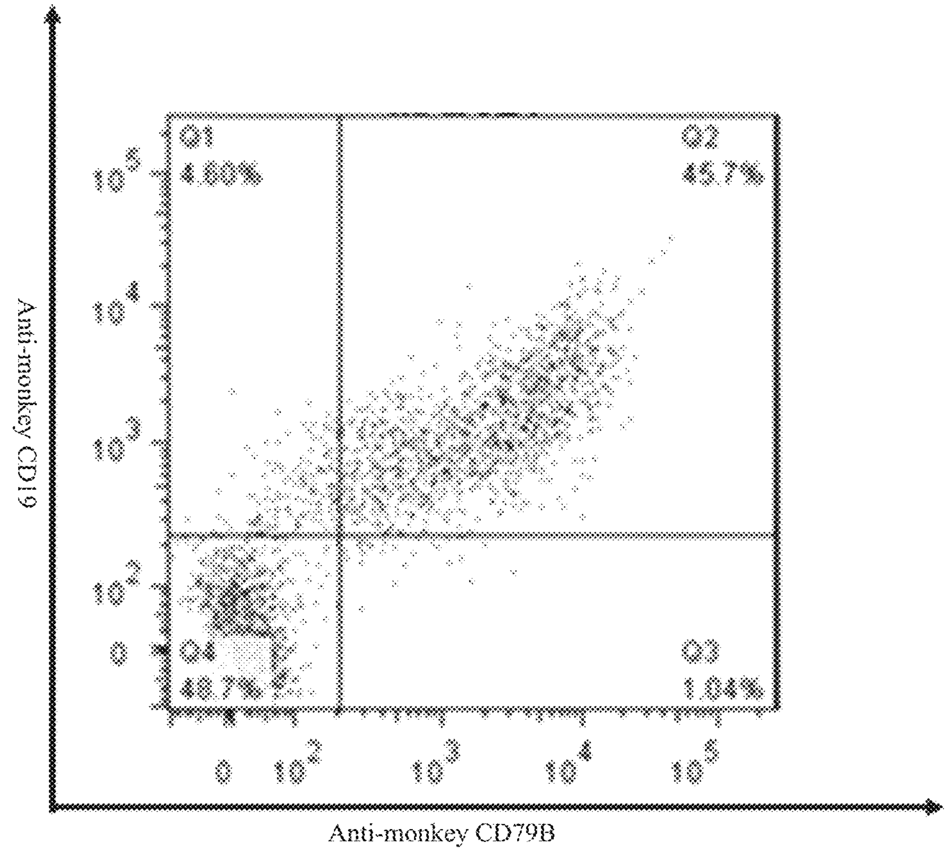
Figure 13A:
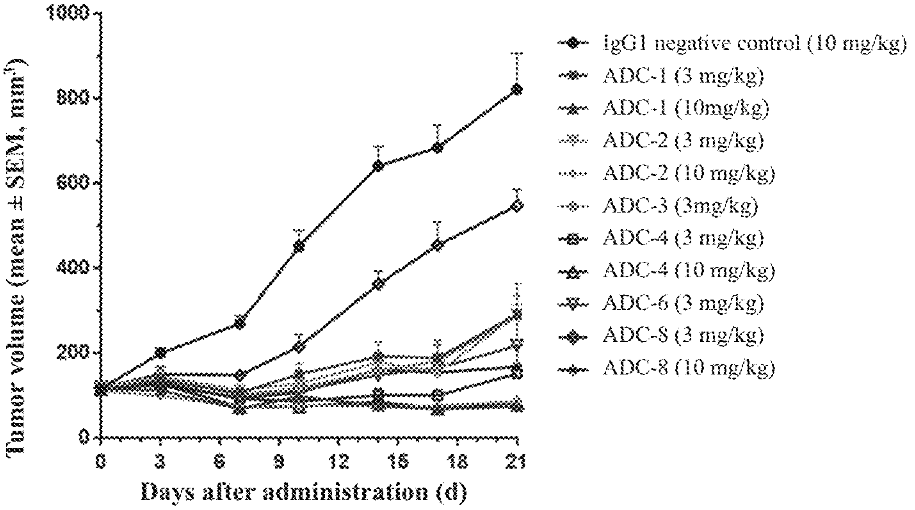
FIGS. 13A-13C show efficacy of different ADCs on human diffuse large B-cell lymphoma WSU-DLCL2-induced nude mouse subcutaneous xenograft tumor.
Figure 13B:
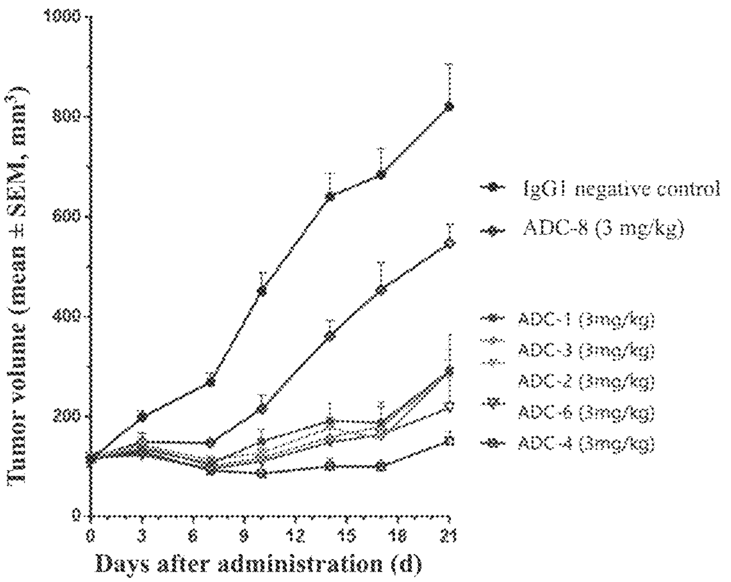
Figure 13C:
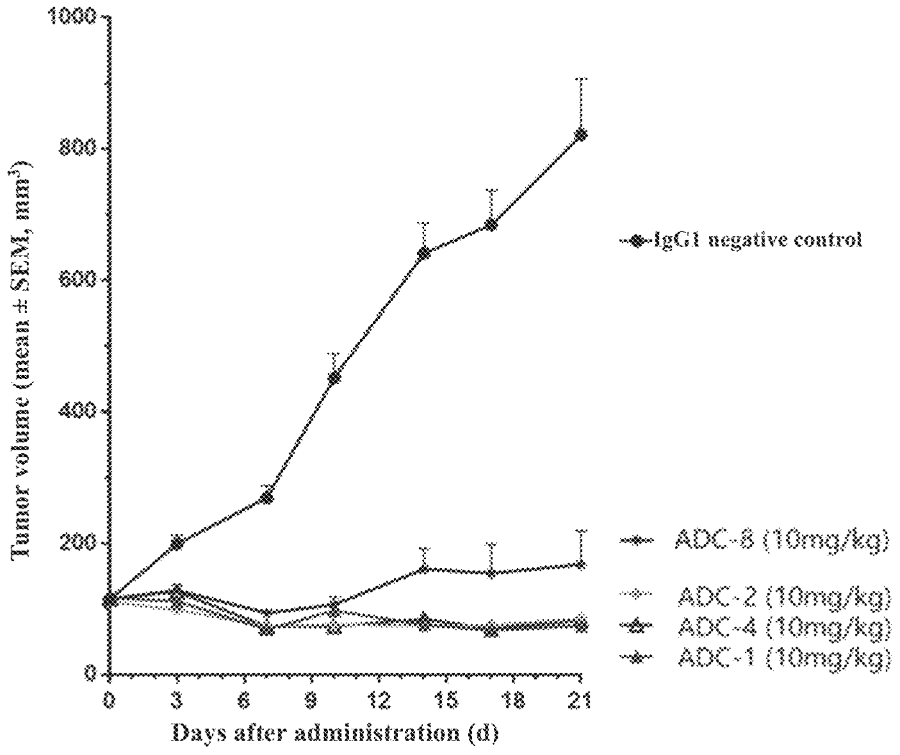
Figure 14:
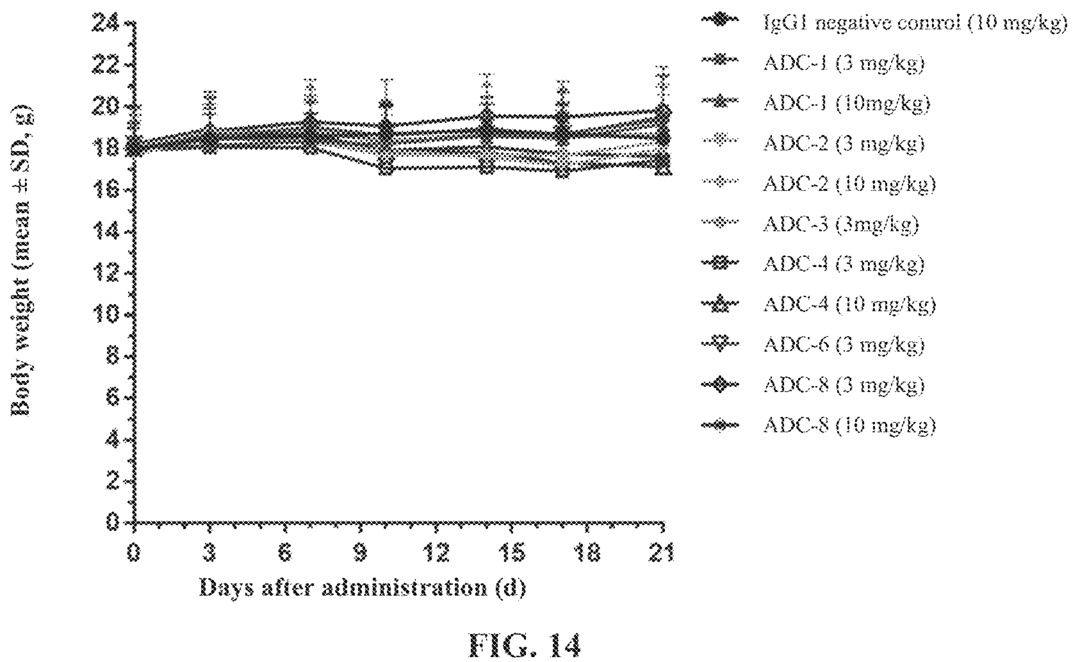
FIG. 14: effect of different ADCs on body weight of tumor-bearing nude mice.

5) Assay on anti-monkey CD79B mouse monoclonal antibodies by ELISA A plate was coated with μg/mL antigen at 50 μL/well and incubated in a refrigerator at 4° C. overnight. The next day, the coated antigen plate was washed once (washing solution: 1×PBST). After washing, the plate was blocked with 1% BSA blocking solution prepared in 1×PBST at 37° C. for 1 h. After washing the plate 3 times with 1×PBST, 50 μL of antibody diluted in a 1:10 ratio from 100 nM was added, and the plate was incubated in an incubator at 37° C. for 1 h. After washing the plate 3 times with 1×PBST, 100 μL of goat anti-mouse secondary antibody diluted in a 1:5000 ratio was added, and the plate was incubated in an incubator at 37° C. for 0.5 h. After washing the plate, TMB color development solutions A and B were mixed in a 1:1 ratio for color development. 15 min later, the color development reaction was stopped with 1 N hydrochloric acid. Fluorescence value was read at 450 nm on a Spectra Max M5 microplate reader. The results are shown in FIG. 11.

6) Assay on the binding of anti-monkey CD79B mouse monoclonal antibodies to monkey peripheral blood mononuclear cells by FACS Monkey peripheral blood mononuclear cells were extracted from fresh monkey blood. The cell suspension was centrifuged, and the cells were resuspended in PBS containing 0.1% BSA and counted. Anti-CD19 and anti-cynoCD79B antibodies were added. The cells were incubated at room temperature for 1 h and washed three times. Then Anti-Mouse IgG (Fc specific)-FITC secondary antibody was added, and the cells were incubated at room temperature for 30 min away from the light, washed three times, gently resuspended in PBS containing 0.1% BSA, and loaded on the machine for assay. The assay results of the binding of anti-monkey CD79B mouse monoclonal antibodies to monkey peripheral blood mononuclear cells by FACS are shown in FIGS. 12A to 12G. CD19 is a marker for B cells. From the results, it can be seen that 4 anti-monkey CD79B mouse monoclonal antibodies all can bind to monkey B cells.

7) Assay on anti-human CD79B mouse monoclonal antibodies by SPR The affinity of the anti-human CD79B antibody for its antigen human CD79B-His was assayed by surface plasmon resonance (SPR) technology. The antigen human CD79B-His protein was immobilized to a CM5 chip. The coupling level was set at 100 RU. The running buffer was HBS-EP+ (10 mM HEPES, 150 mM NaCl, 3 mM EDTA, 0.05% surfactant P20). The diluted antibodies were allowed to flow through the experimental and control channels at a flow rate of 30 μL/min for 3 min and dissociated for 5 min. Regeneration buffer (10 mM Glycine, pH 1.5) was then run at a flow rate of 30 μL/min for 30 s. Data were analyzed using Biacore 8K software.

Example 1-3. Amino Acid Sequencing of Variable Regions of Mouse Monoclonal Antibodies The hybridoma monoclonal cell strains with high affinity obtained in Example 1-2 were subjected to variable region amino acid sequencing and recombinantly expressed as human murine chimeric antibody (cAb) for further antibody identification. The genes encoding the heavy chain variable region and the light chain variable region were amplified by reverse transcription PCR, and connected to a vector for sequencing to obtain a light chain sequence and a heavy chain sequence. The total RNA of the single cell strains with good activity in Example 1-2 was first extracted using an RNA purification kit (Qiagen, Cat #74134). Then, a cDNA single strand was prepared using the cDNA synthesis kit (Cat #18080-051) from Invitrogen. With the single strand as a template, sequences of the light and heavy chain variable regions were synthesized by PCR, and the PCR products were cloned to TA vector pMD-18T and sent for sequencing. The obtained light and heavy chain sequences were separately cloned to expression vectors to express recombinant monoclonal antibodies. After verifying the activity, the antibodies were humanized.

The amino acid residues of VH/VL CDRs of the anti-human CD79B antibody were defined and annotated using the Chothia numbering scheme.

Sequences of monoclonal antibody mAb015 by mouse hybridoma cells:

```
Heavy chain variable region:
                                                  SEQ ID NO: 3
QVQLQQSGAELARPGASVKLSCKASGSSFTSYGINWVKQRTGQGLEWIG
EIFPRSGNTYYNEKFEGKATLTADKSSSTAYMELRSLTSEDSAVYFCAK
GDLGDFDYWGQGTTLTVSS
```

-continued

```
Light chain variable region:
                                                  SEQ ID NO: 4
DFLMTQTPLSLPVRLGDQASISCRSSQSIVHSDGNTYFEWYLQKPGQSP
KLLIYKVSNRFSGVPDRFSGSGSGTDFTLKISRVEAEDLGVYYCFQGSH
VPWTFGGGTKLEIK.
```

Sequences of monoclonal antibody mAb017 by mouse hybridoma cells:

```
Heavy chain variable region:
                                                  SEQ ID NO: 5
QVQLQQSGAELARPGASVKLSCKASGYTFTTYGINWVKQRTGQGLEWIG
EIYPRSGNIYYNEKFKGKATLTADKSSSTAYMELRSLTSEDSAVYFCAR
GSDYDGDFAYWGQGTLVTVSA

Light chain variable region:
                                                  SEQ ID NO: 6
DVLMTQTPLSLPVSLGDQASISCRSSQSIVHHDGNTYLEWYLQKPGQSP
KLLIYKVSNRFSGVPDRFSGSGSGTDFTLKISRVEAEDLGVYYCFQGSH
VPWTFGGGTQLEIK.
```

The CDR sequences of murine antibodies are shown in Table 5.

TABLE 5

CDR sequences of murine anti-human CD79B antibodies

| Antibody CDR | mAb015 | mAb017 |
|---|---|---|
| Heavy chain CDR1 | GSSFTSY (SEQ ID NO: 7) | GYTFTTY (SEQ ID NO: 13) |
| Heavy chain CDR2 | FPRSGN (SEQ ID NO: 8) | YPRSGN (SEQ ID NO: 14) |
| Heavy chain CDR3 | GDLGDFDY (SEQ ID NO: 9) | GSDYDGDFAY (SEQ ID NO: 15) |
| Light chain CDR1 | RSSQSIVHSDGNTYFE (SEQ ID NO: 10) | RSSQSIVHHDGNTYLE (SEQ ID NO: 16) |
| Light chain CDR2 | KVSNRFS (SEQ ID NO: 11) | KVSNRFS (SEQ ID NO: 17) |
| Light chain CDR3 | FQGSHVPWT (SEQ ID NO: 12) | FQGSHVPWT (SEQ ID NO: 18) |

Example 1-4. Humanization of Anti-Human CD79B Antibodies

The light and heavy chain sequences of the murine anti-CD79B monoclonal antibodies obtained in Example 1-3 were subjected to homology comparison in an antibody database, and a humanized antibody model was established. The back mutation was selected according to the model and the optimal humanized anti-CD79B monoclonal antibody was picked. A mouse Fab crystal structure model database (such as a PDB database) was searched for the crystal structures that had similar homology to the obtained murine candidate molecule, and the Fab crystal structure with high resolution (such as <2.5 Å) was selected to establish a mouse Fab model. The light and heavy chain sequences of the murine antibody were aligned to the sequences in the model, and the sequences consistent with the sequences of the murine antibody were retained to obtain a murine antibody structural model. Inconsistent amino acids were possible back-mutation sites. The murine antibody structure model was run with Swiss-pdb viewer software to optimize energy (minimize). The different amino acid sites in the model other than CDRs were back-mutated. The activity of the resulting mutant antibody (humanized) was compared with that of the antibody before the humanization. The humanized antibody with good activity was retained. The CDR regions were optimized, including avoidance of glycosylation, deamidation, oxidation sites, and the like.

The above antibodies were cloned, expressed and purified, and the humanized antibodies hAb015-10 and hAb017-10 with the best activity were selected by ELISA, FACS, SPR and other assays. The data are shown in FIG. 6. The humanized antibodies hAb015-10 and hAb017-10 retained similar affinity and related functions to the mouse monoclonal antibodies.

TABLE 6

Identification of humanized anti-CD79B antibodies

| Assay method | Protein/cell lines | hAb015-10 | hAb017-10 |
|---|---|---|---|
| ELISA assay ($EC_{50}$, nM) | Human CD79B-His protein | 0.05 | 0.06 |
| SPR assay (KD, nM) | Human CD79B-His protein | 1.5 | 4.3 |
| FACS assay ($EC_{50}$, nM) | DoHH2 cell | 0.40 | 0.55 |
| Cell killing assay ($IC_{50}$, nM) | DoHH2 cell | 0.004 | 0.002 |
| | WSU-DLCL2 cell | 0.013 | 0.049 |
| | Raji cell | >100 | >100 |
| Interspecific cross-reactivity | Human CD79B-His protein | Yes | Yes |
| | Monkey CD79B-His protein | No | No |
| | Mouse CD79B-His protein | No | No |
| Thermal stability test | DSC (Tm, ° C.) | 60 | 65 |
| | DLS (Tagg, ° C.) | 62 | 67 |

The sequences of humanized antibodies hAb015-10 and hAb017-10 are shown below.

Heavy chain variable region (VH) of hAb015-10 humanized antibody:
SEQ ID NO: 19

EVQLVQSGAEVKKPGSSVKVSCKASGSSFSSYGINWVKQAPGQGLEWIGEIFPR

SGNTYYNEKFEGRATLTADKSTSTAYMELRSLRSEDTAVYYCAKGDLGDFDYW

GQGTTVTVSS;

Light chain variable region (VL) of hAb015-10 humanized antibody:
SEQ ID NO: 20

DFVMTQTPLSLPVTPGEPASISCRSSQSIVHSDGNTYFEWYLQKPGQSPKLLIYK

VSNRFSGVPDRFSGSGSGTDFTLKISRVEAEDVGVYYCFQGSHVPWTFGGGTKV

EIK;

Heavy chain variable region (VH) of hAb017-10 humanized antibody:
SEQ ID NO: 21

EVQLVQSGAEVKKPGASVKVSCKASGYTFTTYGINWVKQAPGQGLEWIGEIYP

RSGNIYYNEKFKGKATLTADKSTSTAYMELRSLRSDDTAVYYCARGSDYDGDFA

YWGQGTLVTVSS,

Light chain variable region (VL) of hAb017-10 humanized antibody:
SEQ ID NO: 22

DVVMTQTPLSLPVTPGEPASISCRSSQSIVHHDGNTYLEWYLQKPGQSPQLLIYK

VSNRFSGVPDRFSGSGSGTDFTLKISRVEAEDVGVYYCFQGSHVPWTFGGGTKV

EIK;

Heavy chain of hAb015-10 humanized antibody:
SEQ ID NO: 28

EVQLVQSGAEVKKPGSSVKVSCKASGSSFSSYGINWVKQAPGQGLEWIGEIFPR

SGNTYYNEKFEGRATLTADKSTSTAYMELRSLRSEDTAVYYCAKGDLGDFDYW

GQGTTVTVSSASTKGPSVFPLAPSSKSTSGGTAALGCLVKDYFPEPVTVSWNSG

ALTSGVHTFPAVLQSSGLYSLSSVVTVPSSSLGTQTYICNVNHKPSNTKVDKKVE

PKSCDKTHTCPPCPAPELLGGPSVFLFPPKPKDTLMISRTPEVTCVVVDVSHEDP

-continued

EVKFNWYVDGVEVHNAKTKPREEQYNSTYRVVSVLTVLHQDWLNGKEYKCK

VSNKALPAPIEKTISKAKGQPREPQVYTLPPSREEMTKNQVSLTCLVKGFYPSDI

AVEWESNGQPENNYKTTPPVLDSDGSFFLYSKLTVDKSRWQQGNVFSCSVMHE

ALHNHYTQKSLSLSPGK;

Light chain of hAb015-10 humanized antibody:

SEQ ID NO: 29

DFVMTQTPLSLPVTPGEPASISCRSSQSIVHSDGNTYFEWYLQKPGQSPKLLIYK

VSNRFSGVPDRFSGSGSGTDFTLKISRVEAEDVGVYYCFQGSHVPWTFGGGTKV

EIKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRG

EC;

Heavy chain of hAb017-10 humanized antibody:

SEQ ID NO: 30

EVQLVQSGAEVKKPGASVKVSCKASGYTFTTYGINWVKQAPGQGLEWIGEIYP

RSGNIYYNEKFKGKATLTADKSTSTAYMELRSLRSDDTAVYYCARGSDYDGDFA

YWGQGTLVTVSSASTKGPSVFPLAPSSKSTSGGTAALGCLVKDYFPEPVTVSWN

SGALTSGVHTFPAVLQSSGLYSLSSVVTVPSSSLGTQTYICNVNHKPSNTKVDKK

VEPKSCDKTHTCPPCPAPELLGGPSVFLFPPKPKDTLMISRTPEVTCVVVDVSHE

DPEVKFNWYVDGVEVHNAKTKPREEQYNSTYRVVSVLTVLHQDWLNGKEYK

CKVSNKALPAPIEKTISKAKGQPREPQVYTLPPSREEMTKNQVSLTCLVKGFYPS

DIAVEWESNGQPENNYKTTPPVLDSDGSFFLYSKLTVDKSRWQQGNVFSCSVM

HEALHNHYTQKSLSLSPGK;

Light chain of hAb017-10 humanized antibody:

SEQ ID NO: 31

DVVMTQTPLSLPVTPGEPASISCRSSQSIVHHDGNTYLEWYLQKPGQSPQLLIYK

VSNRFSGVPDRFSGSGSGTDFTLKISRVEAEDVGVYYCFQGSHVPWTFGGGTKV

EIKRTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSFNRG

EC.

The humanized mAb015 has a T30S mutation in the HCDR1 sequence, and the mutated HCDR1 is GSSFSSY (SEQ ID NO: 23). The anti-CD79B antibodies of the present disclosure have general formulas shown in Table 7.

TABLE 7

| General formulas of CDRs | | | |
|---|---|---|---|
| Heavy chain | | Light chain | |
| HCDR1 | $GX_1X_2FX_3X_4Y$ (SEQ ID NO: 24), wherein $X_1$ is S or Y, $X_2$ is S or T, $X_3$ is T or S, and $X_4$ is S or T | LCDR1 | $RSSQSIVHX_{12}GNTYX_{13}E$ (SEQ ID NO: 27), wherein $X_{12}$ is S or H, and $X_{13}$ is F or L |
| HCDR2 | $X_5PRSGN$ (SEQ ID NO: 25), wherein $X_5$ is F or Y | LCDR2 | KVSNRFS (SEQ ID NO: 11 or 17) |
| HCDR3 | $X_6X_7X_8X_9X_{10}GDFX_{11}Y$ (SEQ ID NO: 26), wherein $X_6$ is absent or G, $X_7$ is absent or S, $X_8$ is G or D, $X_9$ is D or Y, $X_{10}$ is L or D, and $X_{11}$ is D or A | LCDR3 | FQGSHVPWT (SEQ ID NO: 12 or 18) |

Example 1-5. Endocytosis of Anti-CD79B Antibodies

In order to determine whether the CD79B antibodies of the present disclosure can be endocytosed into cells with human CD79B after binding to human CD79B, a cell endocytosis experiment was performed with DOHH-2 cells (DSMZ, ACC 47) highly expressing human CD79B protein to assess the endocytosis ability of the antibodies.

DOHH-2 cells were cultured according to a conventional method for suspending cells in a complete medium (RPMI 1640 medium (GIBCO, Cat No.: 11835-030), containing 10% (v/v) fetal bovine serum (FBS) (GIBCO, Cat No.: 10099-141) and penicillin/streptomycin (GIBCO, Cat No.: 15070-063)).

The cells were collected by low temperature centrifugation at 4° C. for 5 min at 1000 rpm during the experiment. The cells were resuspended in 10-15 mL of FACS buffer pre-cooled on ice. The FACS buffer was composed of phosphate buffered saline (PBS), pH 7.4, with 2% fetal bovine serum (FBS). Throughout the experiment, FACS buffer was pre-cooled on ice. The cells were counted and centrifuged, and added to a 96-well plate at 300,000 cells/well. After centrifugation, the supernatant was discarded, and 12.5 μg/mL Fc blocking solution (BD, Cat No.: 564220) was added at 100 μL/well. Blocking was performed at room temperature for 10 min. Then, 20 μg/mL test CD79B antibody was added to the corresponding wells, and the plate was incubated at 4° C. for 1 h away from the light. The plate was washed twice with a pre-cooled PBS buffer to remove unbound antibodies. A complete cell culture medium (RPMI 1640 medium with 10% fetal bovine serum) was added, and the plate was incubated at 37° C. with 5% $CO_2$ for 0 h, 1 h, 2 h and 4 h. After centrifugation, the supernatant was discarded, 2% PFA buffer solution was added at 100 μL/well to resuspend the cells, and the plate was left to stand for 10 min. Then, the plate was washed 3 times with an FACS buffer, and 100 μL of secondary antibody solution (fluorescent labeled goat anti-human secondary antibody: diluted in a 1:250 ratio, 2 μg/mL, Biolegend, Cat #409304) was added. The plate was incubated at 4° C. for half an hour away from the light. A pre-cooled PBS buffer was added, and the supernatant was discarded after centrifugation at 4° C., which were repeated three times. The cells were resuspended in an FACS buffer at 200 μL/well and detected using a flow cytometer (BD FACS Calibur).

The results show that all the 3 antibodies (SN8, hAb015 and hAb017) cannot be endocytosed by DOHH-2 cells during incubation at 4° C. In contrast, during incubation at 37° C., most of the antibodies are already endocytosed by DOHH-2 cells after 1 h, and antibody endocytosis reaches a maximum after 4 h. All the 3 antibodies have good endocytosis.

2. Preparation of Compounds

The structure of the compound is determined by nuclear magnetic resonance (NMR) spectroscopy and/or mass spectrometry (MS). NMR shift (δ) is given in a unit of $10^{-6}$ (ppm).

NMR spectra are determined using a Bruker AVANCE-400 nuclear magnetic resonance instrument, with deuterated dimethyl sulfoxide (DMSO-$d_6$), deuterated chloroform ($CDCl_3$) and deuterated methanol ($CD_3OD$) as determination solvents and tetramethylsilane (TMS) as an internal standard.

Mass spectra (MS) are determined using Agilent 1200/1290 DAD-6110/6120 Quadrupole MS liquid chromatography-mass spectrometry system (manufacturer: Agilent; MS model: 6110/6120 Quadrupole MS), Waters ACQuity UPLC-QD/SQD (manufacturer: waters, MS model: waters ACQuity Qda Detector/waters SQ Detector), and THERMO Ultimate 3000-Q Exactive (manufacturer: THERMO, MS model: THERMO Q Exactive).

High performance liquid chromatography (HPLC) analysis is performed using the following HPLC instruments: Agilent HPLC 1200DAD, Agilent HPLC 1200VWD and Waters HPLC e2695-2489.

Chiral HPLC analysis is performed using an Agilent 1260 DAD high performance liquid chromatograph.

High performance liquid preparative chromatography is performed using Waters 2545-2767, Waters 2767-SQ Detecor2, Shimadzu LC-20AP and Gilson GX-281 preparative chromatographs.

Chiral preparative HPLC is performed using a Shimadzu LC-20AP preparative chromatograph.

A CombiFlash rapid preparation instrument used is Combiflash Rf200 (TELEDYNE ISCO).

Huanghai HSGF254 or Qingdao GF254 silica gel plates of specifications 0.15 mm to 0.2 mm are adopted for thin layer chromatography (TLC) analysis and 0.4 mm to 0.5 mm for TLC separation and purification.

Yantai Huanghai silica gel of 200-300 mesh is generally used as a carrier in silica gel column chromatography.

Known starting materials described herein may be synthesized using or according to methods known in the art, or may be purchased from ABCR GmbH & Co. KG, Acros Organics, Aldrich Chemical Company, Accela ChemBio Inc., Chembee Chemicals, and other companies.

In the examples, the reactions can be performed in an argon atmosphere or a nitrogen atmosphere unless otherwise specified. The hydrogen atmosphere means that the reaction flask is connected to a balloon containing about 1 L of hydrogen.

Parr 3916EKX hydrogenator, Qinglan QL-500 hydrogenator or HC2-SS hydrogenator is used in the pressurized hydrogenation reactions. The hydrogenation reactions usually involve 3 cycles of vacuumization and hydrogen purge.

A CEM Discover-S 908860 microwave reactor is used in the microwave reactions.

In the examples, a solution refers to an aqueous solution unless otherwise specified.

In the examples, the reaction temperature is room temperature, i.e., 20° C. to 30° C., unless otherwise specified.

The eluent system for column chromatography purification and the developing solvent system for thin layer chromatography include: A: dichloromethane/methanol system, B: n-hexane/ethyl acetate system, and C: petroleum ether/ethyl acetate system. The volume ratio of the solvents is adjusted according to the polarity of the compound, or by adding basic or acidic reagents such as triethylamine and acetic acid.

The drug moiety of the ADCs of the present disclosure is found in WO2020063676A, U.S. Pat. Nos. 7,098,308, 6,884,869, CN202010073671.6 and CN201911390425.7, and the synthesis and tests of relevant compounds are incorporated herein by reference in their entirety. Non-limiting examples of the synthesis and tests are described below.

Example 2-1. Compound A

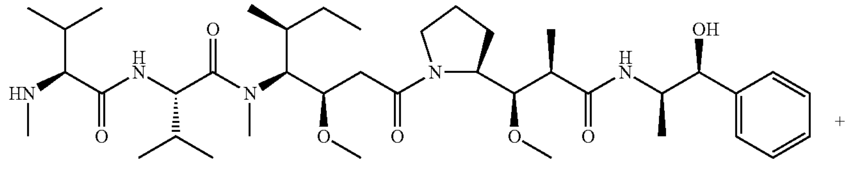

1

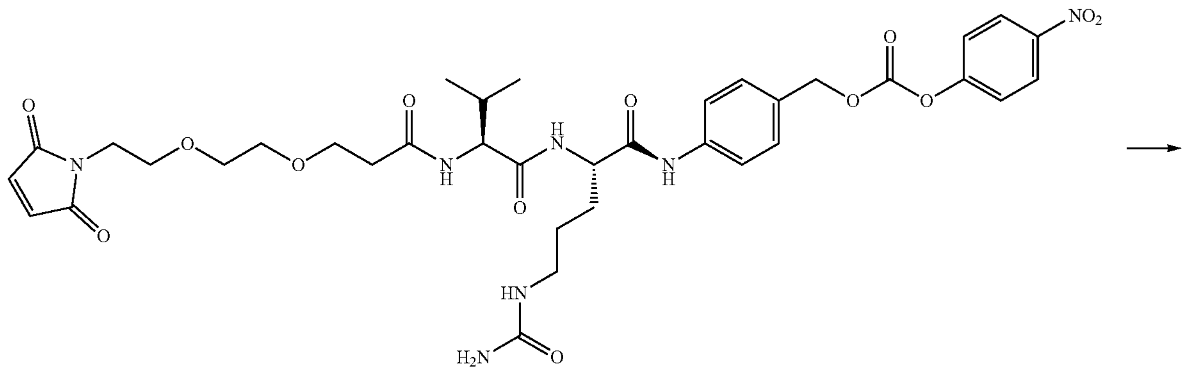

2

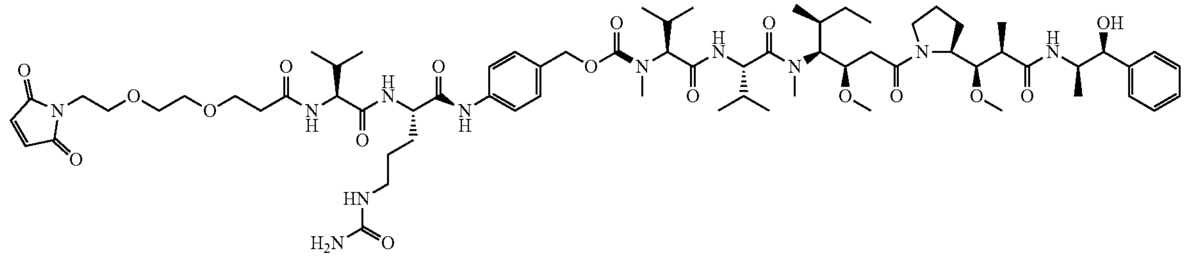

A

Malei-PEG2-vs-PAB-MMAE 1 (10 mg, 0.014 mmol, 1.0 eq) in this example, 2 (21 mg, 0.021 mmol, 1.5 eq) in this example and a catalytic amount of HOBt (0.5 mg) were dissolved in anhydrous DMF (2 mL), and the mixture was stirred under argon atmosphere. DIEA (2.71 mg) and pyridine (0.08 mL) were added, and the resulting mixture was heated to 40° C. and stirred for 2 h. The reaction solution was purified by preparative HPLC to give A (12.4 mg, 65.4% yield). LC/MS (ESI): m/z 1363.4 $[M+1]^+$.

HNMR ($CDCl_3$, 400 MHz): δ 0.63-0.95 (m, 32H), 1.05-1.36 (m, 27H), 1.60-1.98 (m, 4H), 2.1-2.55 (m, 4H), 2.78-3.02 (m, 3H), 3.17-3.79 (m, 13H), 3.93-4.20 (m, 2H), 4.60-4.96 (m, 3H), 5.14-5.36 (m, 2H), 5.67 (bs, 1H), 6.31-6.50 (m, 2H), 6.64 (s, 2H), 6.91 (d, J=14.8 Hz, 1H), 7.19-7.30 (m, 7H), 7.55 (bs, 2H), 8.96 (bs, 1H), 9.13 (bs, 1H).

Example 2-2-1. Compound B

B

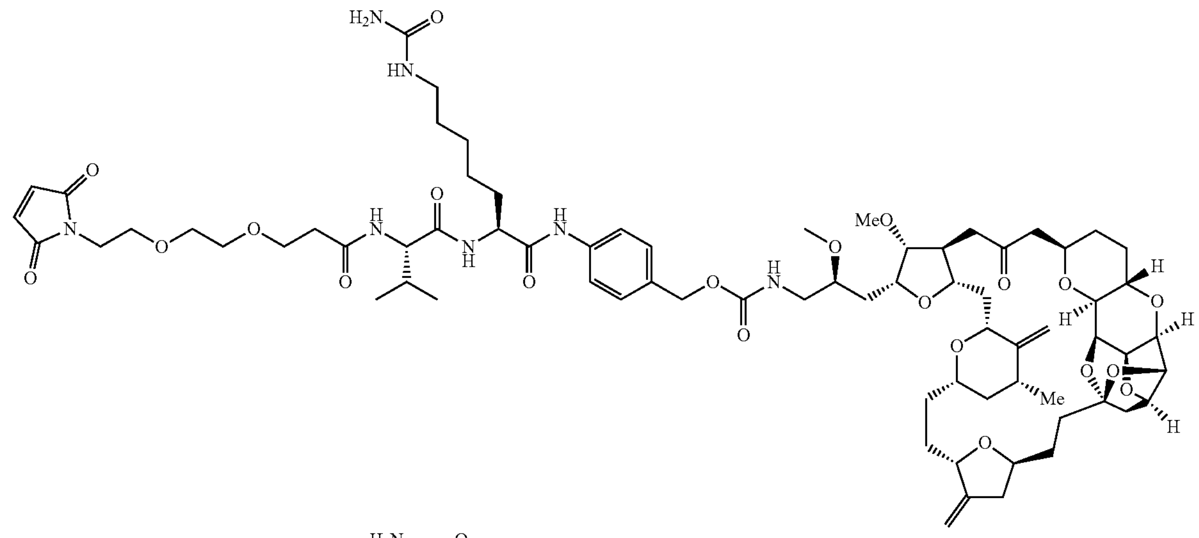

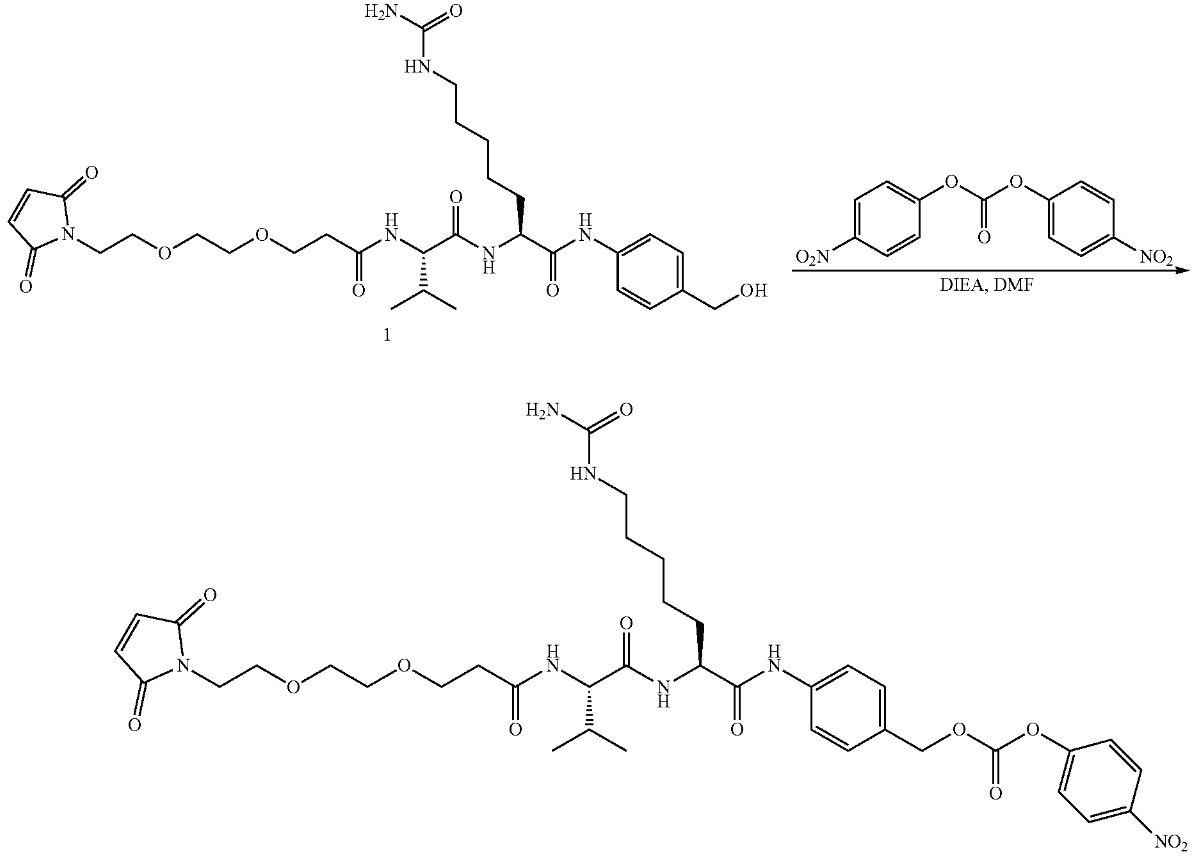

2

1 (50 mg, 0.08 mmol) in this example was dissolved in N,N-dimethylformamide (1.5 mL) under an ice-water bath, followed by the sequential addition of DIPEA (18 mg, 0.14 mmol) and bis(p-nitrophenyl) carbonate (49 mg, 0.16 mmol), and the mixture was stirred at room temperature for about 2-4 h. After the reaction was completed as monitored by HPLC, 20 mL of methyl tert-butyl ether was added, and the resulting mixture was stirred and filtered. The solid was collected and dried to give a crude product (36 mg), which was directly used in the next step. LC/MS (ESI): m/z 784.1 $[M+H]^+$.

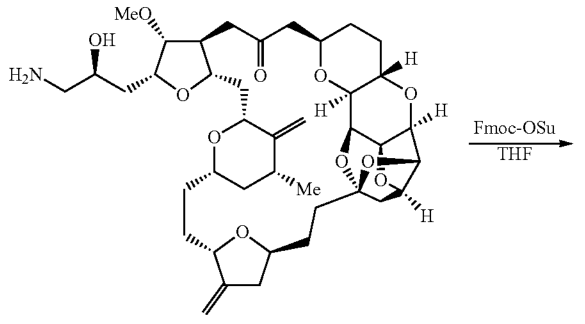

3

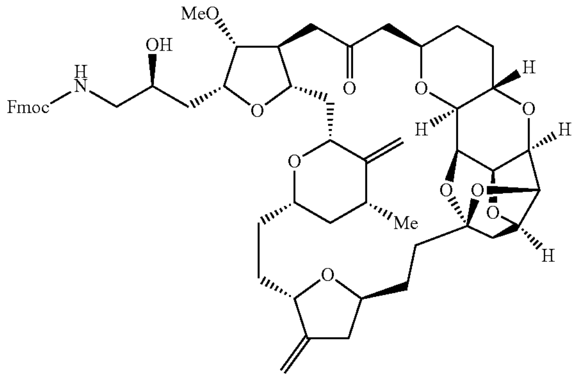

4

Compound 3 (72.91 mg, 0.1 mmol) in this example was dissolved in tetrahydrofuran (10 mL) under an ice-water bath, followed by the addition of Fmoc-OSu (41 mg, 0.12 mmol), and the mixture was stirred at room temperature for 3-5 h. After the reaction was completed as monitored by HPLC, the reaction solution was concentrated under reduced pressure to give a crude product, which was directly used in the next step.

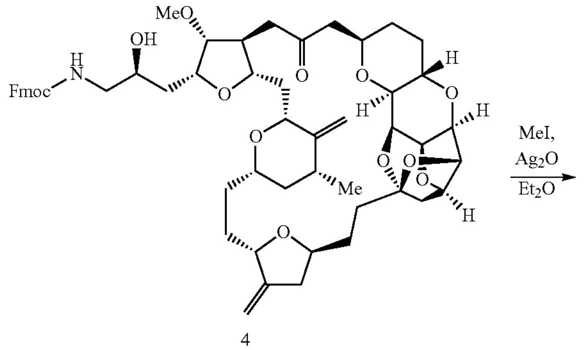

4

-continued

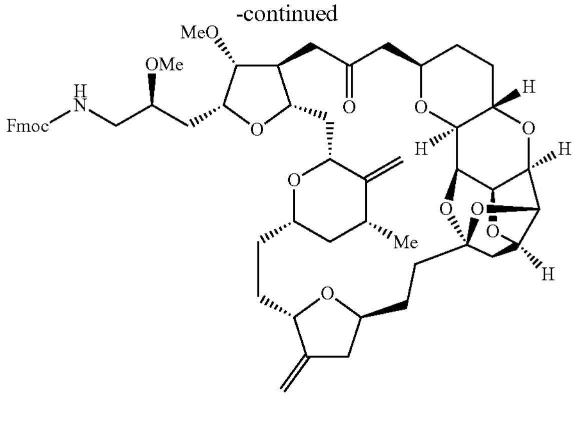

5

The above crude product of 4 in this example was dissolved in anhydrous diethyl ether (10 mL), followed by the sequential addition of silver oxide (34.8 mg, 0.15 mmol) and methyl iodide (28.4 mg, 0.2 mmol), and the mixture was reacted at room temperature for about 10-16 h. After the reaction was substantially completed as monitored, the reaction solution was filtered to remove solid, and concentrated under reduced pressure to give a crude product, which was directly used in the next step.

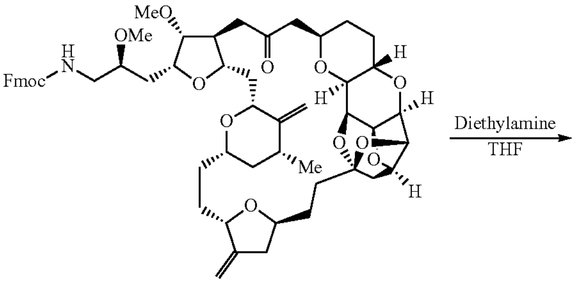

5

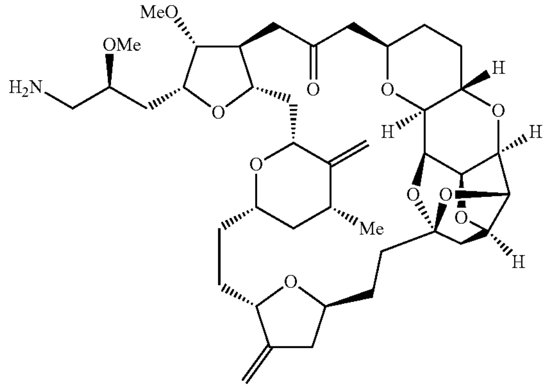

6

The above crude product of 5 in this example was dissolved in tetrahydrofuran (10 mL), followed by the addition of diethylamine (2 mL), and the mixture was stirred at room temperature for about 2-4 h. After the reaction was completed as monitored by HPLC, the reaction solution was directly concentrated under reduced pressure to give a crude product, which was then purified by silica gel column chromatography to give the product (40 mg). LC/MS (ESI): m/z 744.2 $[M+H]^+$.

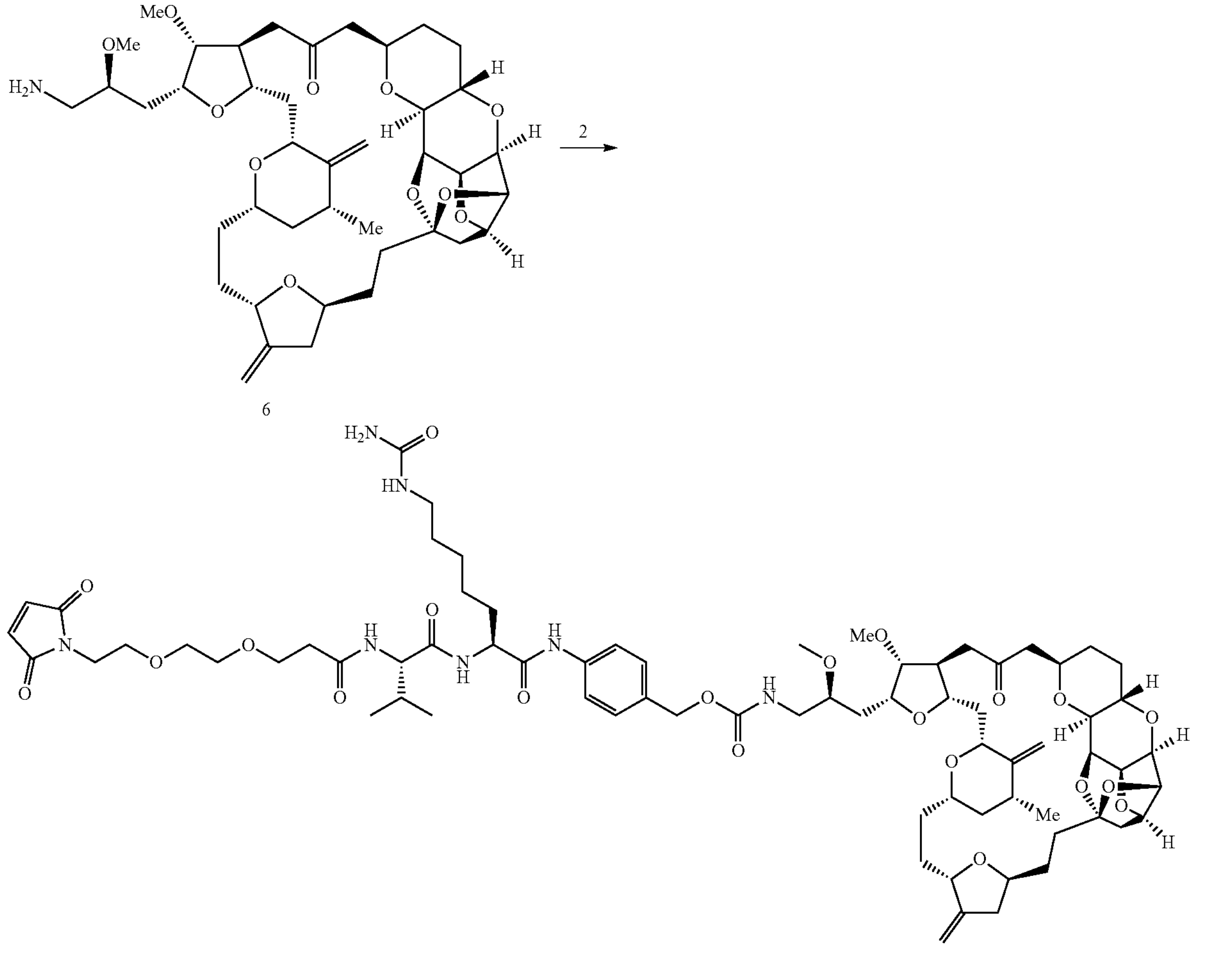

6

B

The above compound 6 (13.5 mg, 0.018 mmol) in this example was dissolved in DMF (1.5 mL), DIPEA (7 mg, 0.054 mmol) was added, followed by the addition of compound 2 (18 mg, 1.3 mmol) in portions, and the mixture was stirred for about 24-36 h. The reaction solution was concentrated under reduced pressure to give a crude product, which was separated by preparative HPLC to give compound B (12.5 mg, 96.95% purity). LC/MS (ESI): m/z 1388.3 $[M+H]^+$.

HNMR ($CDCl_3$, 400 MHz): δ 0.85-0.90 (m, 3H), 0.93-1.00 (m, 3H), 1.08-1.10 (m, 3H), 1.20-1.50 (m, 15H), 1.75-2.04 (m, 6H), 2.13-2.55 (m, 16H), 2.70-2.77 (m, 1H), 2.80-2.96 (m, 2H), 3.16-3.97 (m, 20H), 3.99-4.39 (m, 8H), 4.60-4.80 (m, 6H), 4.88-5.10 (m, 5H), 5.24-5.37 (m, 4H), 6.71 (s, 2H), 7.03 (d, J=6.8 Hz, 1H), 7.18-7.30 (m, 3H), 7.63 (d, J=8.0 Hz, 2H), 8.92 (bs, 1H).

Test Example 1. In Vitro Cytotoxic Activity Screening

1.1. Principle and Method

In this experiment, the ATP content was determined using CTG to reflect the survival condition of the tumor cells. The final culture conditions were first determined by seeding cells at different densities and culturing the cells for 3 days and 5 days based on $IC_{50}$ and the maximum inhibition rate. The killing effect of the toxin molecule was then assayed according to this condition.

1.2. Selection of Cell Strains

According to the experimental purpose, in the early stage, two disease models of breast cancer and NSCLC were selected, and three strains of SKBR3 (HER2+), MDA-MB-468 (HER2−) and A549 were picked for the screening experiment with reference to literature reports.

1.3. Determination of Cell Culture Conditions

1) Cell plating: A549 was digested with pancreatin, terminated with culture medium and counted, and $4.3\times10^5$, $7.2\times10^5$, and $11.5\times10^5$ cells were taken and allowed to reach a final volume of 26 mL. 180 μL of cell suspension was added to each well in columns 2 to 11 of a 96-well plate (3903) to obtain cell densities of 3 K/well, 5 K/well and 8 K/well. Wells in column 12 were filled with 200 μL of culture medium and the remaining wells were filled with PBS. The above operations were repeated on the SKBR3 and MDA-MB-468 cells. Each sample was run in duplicate.

2) Drug preparation: eribulin positive control was prepared in round-bottom 96-well plates (3788). 2 mM solution (10-fold dilution of stock solution in DMSO) was prepared in column 1 of the plate 1, then 10-fold gradient dilution in DMSO was performed in columns 2 to 10. The wells in column 11 were filled with DMSO. 95 μL of corresponding culture medium was added to each well of columns 2 to 11 of the plate 2, and 5 μL of solution was pipetted from columns 2 to 11 of the plate 1 and added to the plate 2. After the solution was mixed well, 20 μL of solution was pipetted and added to the plated cells, and the cells were continuously cultured for 3 days and 5 days.

3) CTG assay: the plates were taken out on day 3 and day 5, and allowed to equilibrate to room temperature. 90 μL of CTG was added to each well and reacted at room temperature for 10 min away from the light. The luminescence value was read using a microplate reader and $IC_{50}$ was calculated.

1.4. Efficacy Assay

1) Cell plating: each of A549, SKBR3 and MDA-MB-468 was digested with pancreatin, resuspended in a culture medium and counted, and $6.33 \times 10^5$ cells were added to the medium to make a final volume of 38 mL. 180 μL of the culture medium was plated in a 96-well plate (3903) to obtain a cell density of 3 K/well, and the cells were cultured at 37° C. for 24 h.

2) Drug preparation: eribulin and compound D-1 (compound 6 in Example 2-2-1) were prepared in round-bottom 96-well plates (3788). 2 mM solution (10-fold dilution of stock solution in DMSO) was prepared in column 1 of the plate 1, then 10-fold gradient dilution in DMSO was performed in columns 2 to 10. The wells in column 11 were filled with DMSO. 95 μL of corresponding culture medium was added to each well of columns 2 to 11 of the plate 2, and 5 μL of solution was pipetted from columns 2 to 11 of the plate 1 and added to the plate 2. After the solution was mixed well, 20 μL of solution was pipetted and added to the plated cells. Each sample was run in duplicate. The cells were continuously cultured for 5 days.

3) CTG assay: the plate was taken out and allowed to equilibrate to room temperature. 90 μL of CTG was added to each well and reacted at room temperature for 10 min away from the light. The luminescence value was read using a microplate reader and $IC_{50}$ was calculated.

1.5. Data Results

TABLE 8

| Compound | SKBR3 $IC_{50}$ (nM) | SKBR3 Maximum inhibition (%) | MDA-MB-468 $IC_{50}$ (nM) | MDA-MB-468 Maximum inhibition (%) | A549 $IC_{50}$ (nM) | A549 Maximum inhibition (%) |
|---|---|---|---|---|---|---|
| Eribulin | 0.7147 | 94.90 | 0.4819 | 87.47 | 0.6609 | 81.50 |
| D-1 | 0.2052 | 96.87 | 0.1827 | 88.01 | 0.5151 | 81.34 |

Conclusion: the compound D-1 has good killing effect in three tumor cell lines and is significantly superior to the positive drug eribulin.

Example 2-2-2

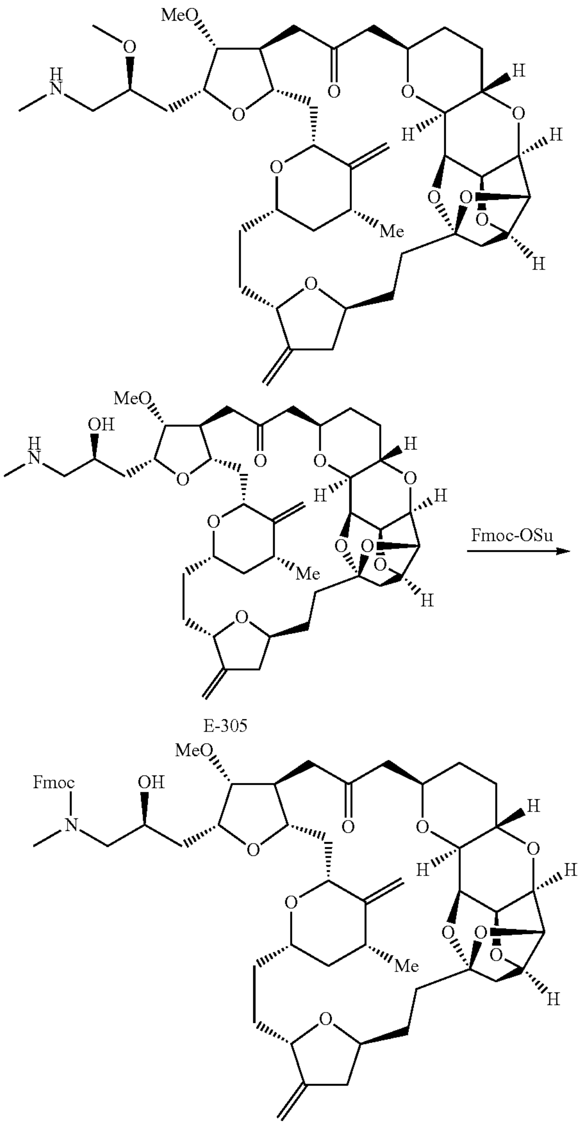

E-305

1,4-dioxane (0.3 mL) and aqueous compound E-305 (0.3 mL, 31 mg, 0.042 mmol, synthesized and obtained according to *Bioorg. Med chem. Lett.* 14 (2004) 5551-5554) were measured at room temperature, followed by the sequential addition of fluorenylmethoxycarbonylsuccinimid (17 mg, 0.050 mmol) and solid sodium carbonate (18 mg, 0.168 mmol). The mixture was stirred overnight at room temperature. After the conversion of the starting material was substantially completed as detected, the reaction was quenched with water, and the reaction solution was extracted with ethyl acetate and concentrated under reduced pressure. The residue was purified by silica gel column chromatography to give the product (15 mg). LC/MS (ESI): m/z 965.64 $[M+H]^+$.

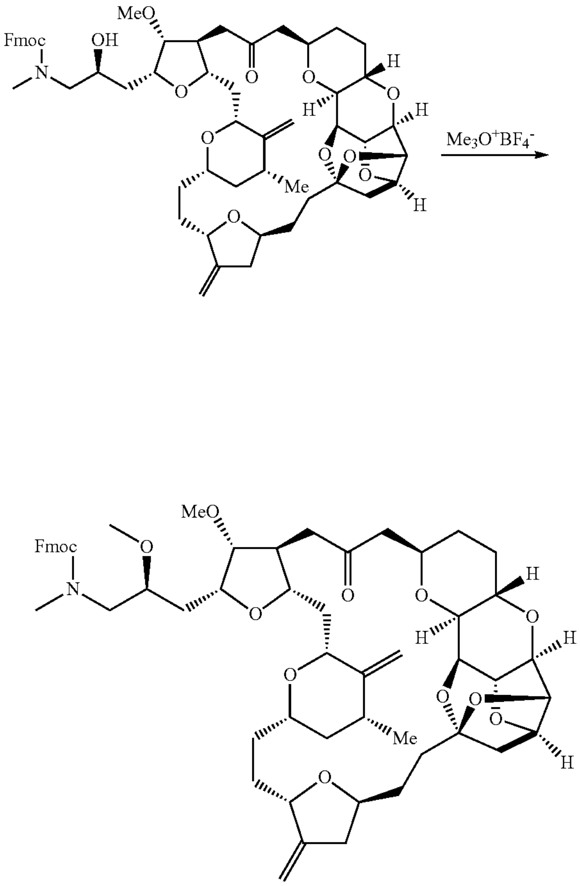

An appropriate amount of dichloromethane was measured to dissolve the product (7 mg, 0.007 mmol) obtained in the previous step at room temperature, followed by the sequential addition of 4A molecular sieves (10 mg), trimethyloxonium tetrafluoroborate (11 mg, 0.07 mmol) and proton sponge (16 mg, 0.07 mmol), and the mixture was stirred at room temperature for 1 h. After the conversion of the starting material was substantially completed as detected, the reaction was quenched with water, and the reaction solution was extracted with methyl tert-butyl ether, washed with 1 N dilute hydrochloric acid, and concentrated under reduced pressure. The residue was purified by silica gel column chromatography to give the product (7 mg). LC/MS (ESI): m/z 979.68 $[M+H]^+$.

1 mL of tetrahydrofuran was measured to dissolve the product (10 mg, 0.01 mmol) obtained in the previous step under an ice-water bath, followed by the dropwise addition of DBU (6. μL, 0.04 mmol), and the mixture was stirred until the reaction was completed. The reaction was quenched with water, and the reaction solution was extracted with dichloromethane and concentrated under reduced pressure. The residue was separated by preparative HPLC to give the product D-2 (5 mg). LC/MS (ESI): m/z 757.85 $[M+H]^+$.

Example 2-2-3

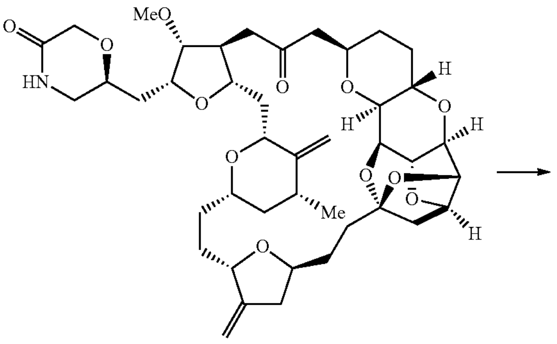

3

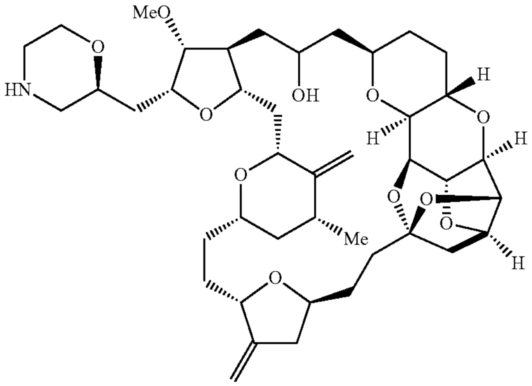

2 mL of tetrahydrofuran was measured to dissolve the compound 3 (6 mg, 0.008 mmol, synthesized according to *Bioorg. Med. Chem. Lett.*, 21 (2011) 1639-1643) in this example under an ice-water bath, followed by the dropwise addition of a lithium aluminum hydride solution (80 μL, 1 M in THF, 0.08 mmol), and the mixture was stirred and slowly heated to 40° C. After the conversion of the starting material was substantially completed as detected by LCMS, the reaction was quenched with sodium sulfate decahydrate, and the reaction solution was stirred for half an hour under an ice-water bath and filtered. The filtrate was concentrated under reduced pressure to give a crude product, which was directly used in the next step. LC/MS (ESI): m/z 758.4 [M+H]*.

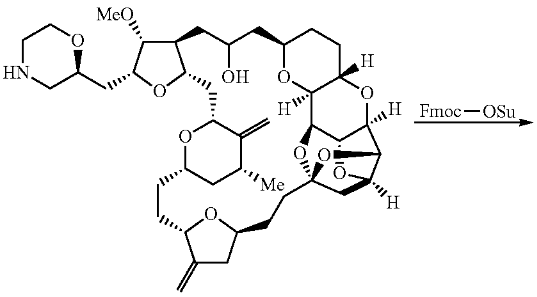

-continued

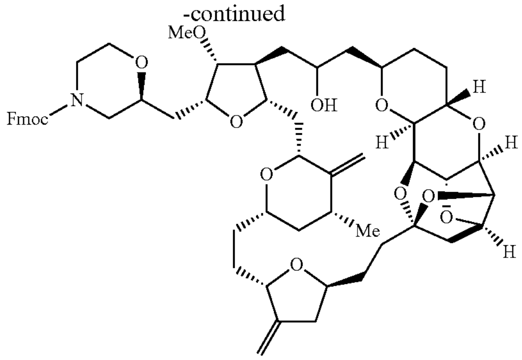

An appropriate amount of dichloromethane was measured to dissolve the product (7 mg, 0.007 mmol) obtained in the previous step at room temperature, followed by the sequential addition of 4A molecular sieves (10 mg), trimethyloxonium tetrafluoroborate (11 mg, 0.07 mmol) and proton sponge (16 mg, 0.07 mmol), and the mixture was stirred at room temperature for 1 h. After the conversion of the starting material was substantially completed as detected, the reaction was quenched with water, and the reaction solution was extracted with methyl tert-butyl ether, washed with 1 N dilute hydrochloric acid, and concentrated under reduced pressure. The residue was purified by silica gel column chromatography to give the product (7 mg). LC/MS (ESI): m/z 979.68 $[M+H]^+$.

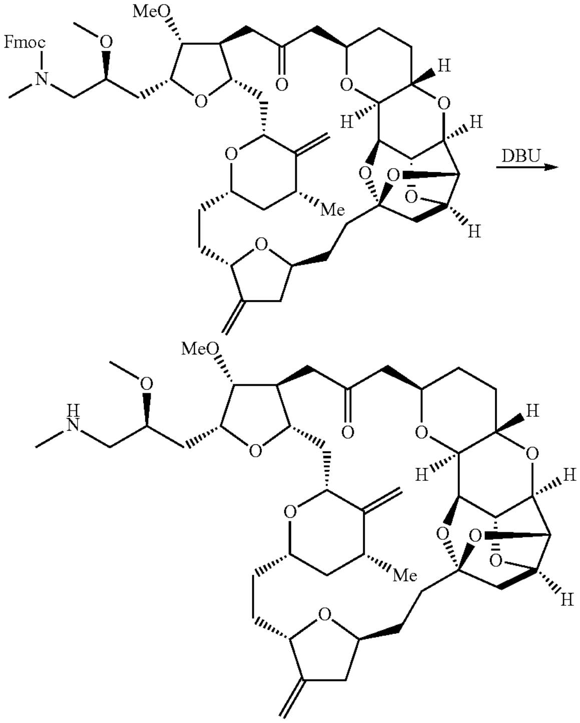

D-2

0.5 mL of 1,4-dioxane and 0.5 mL of water were measured to dissolve the product obtained in the previous steps at room temperature, followed by the sequential addition of fluorenylmethoxycarbonylsuccinimide (6.5 mg, 0.019 mmol) and sodium carbonate (6.8 mg, 0.064 mmol), and the mixture was stirred overnight at room temperature. After the conversion of the starting material was substantially completed as detected, the reaction was quenched with water, and the reaction solution was extracted with ethyl acetate and concentrated under reduced pressure. The crude product was purified by silica gel column chromatography to give the product (14 mg). LC/MS (ESI): m/z 980.4 $[M+H]^+$.

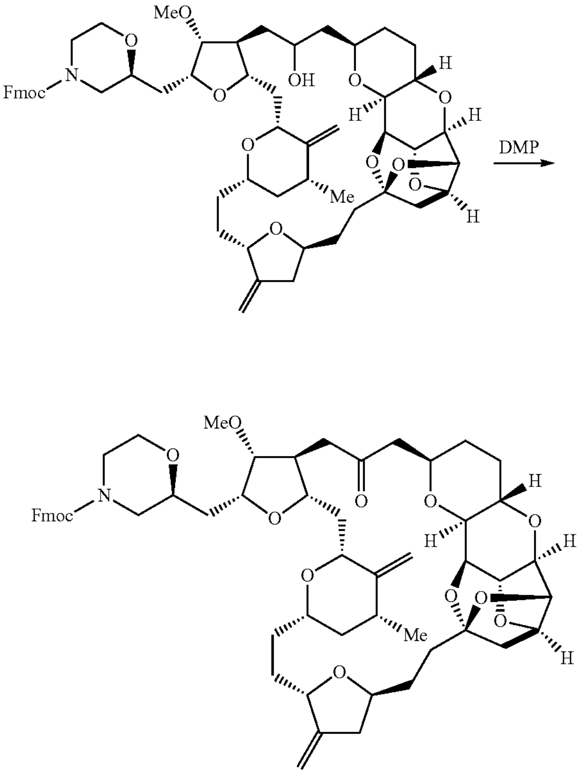

1 mL of dichloromethane was measured to dissolve the product (14 mg, 0.014 mmol) obtained in the previous steps under an ice-water bath, followed by the addition of Dess-Martin periodinane (18.2 mg, 0.042 mmol), and the mixture was stirred and slowly heated to room temperature. After the conversion of the starting material was substantially completed as detected by LCMS, the reaction was quenched with an aqueous sodium bicarbonate solution, and the mixture was extracted with dichloromethane and concentrated. The crude product was purified with silica gel column chromatography to give the product (8 mg). LC/MS (ESI): m/z 978.4 $[M+H]^+$.

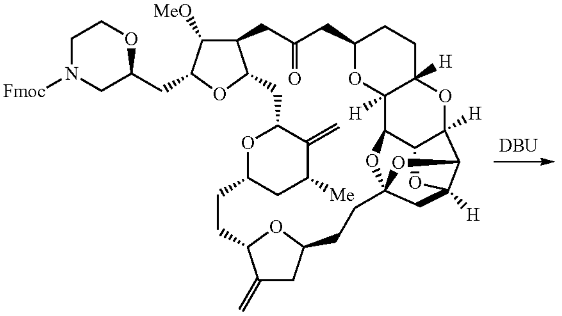

-continued

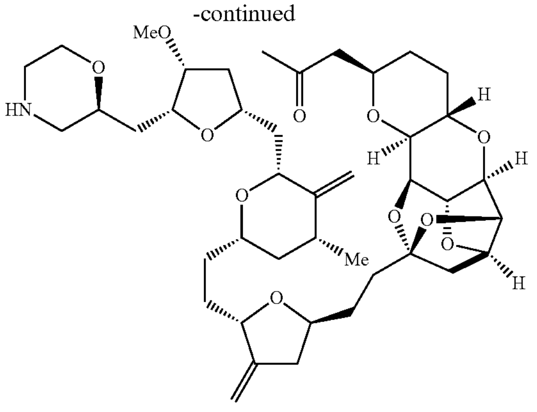

D-3

1 mL of tetrahydrofuran was measured to dissolve the product (8 mg, 0.008 mmol) obtained in the previous step under an ice-water bath, followed by the dropwise addition of DBU (6 μL, 0.032 mmol), and the mixture was stirred for 1 h. After the conversion of the starting material was substantially completed as detected by central control, the reaction was quenched with water, and the reaction solution was extracted with dichloromethane and concentrated. The crude product was separated by preparative HPLC to give the target product D-3 (1.3 mg). LC/MS (ESI): m/z 755.93 $[M+H]^+$.

Test Example 2. In Vitro Cytotoxic Activity Screening 2.1. Principle and Method In this experiment, the ATP content was determined using CTG to reflect the survival condition of the tumor cells.

2.2. Determination of Cell Culture Conditions

1) Cell Plating:

Each of A549, SKBR3 and MDA-MB-468 was digested with pancreatin, resuspended in a culture medium and counted, and the cell density was adjusted to $2.2\times10^4$ cells/mL. 135 μL of cell suspension was added to each well in columns 2 to 11 of a 96-well plate, and column 12 was set as blank control. The cells were cultured in an incubator at 37° C. with 5% $CO_2$ for 24 h.

2) Drug Preparation:

a) Stock solution preparation: the drug was dissolved in DMSO to obtain a stock solution at a concentration of 5 mM.

b) Plate 1: stock solution in column 1 was initially subjected to a 40-fold dilution, and 3-fold gradient dilutions were performed sequentially in columns 2 to 11. Column 12 was filled with DMSO.

c) Plate 2: 196 μL of the corresponding culture medium was added to columns 2 to 11, and 4 μL of culture medium was pipetted from columns 3 to 12 of the plate 1 to columns 2 to 11 of the plate 2. The culture medium was mixed well.

2.3. Cell Treatment

15 μL of culture medium was pipetted from the plate 2 and added to the cells. The cells were continuously cultured in an incubator at 37° C. with 5% $C_{02}$ for 5 days.

2.4. CTG assay: the plate was taken out and allowed to equilibrate to room temperature. 75 μL of CTG was added to each well and reacted at room temperature for 10 min away from the light. The luminescence value was read using a microplate reader and $IC_{50}$ was calculated.

2.5. Data Results

TABLE 9

| | SKBR3 | | MDA-MB-468 | | A549 | |
|---|---|---|---|---|---|---|
| Compound | $IC_{50}$ (nM) | Maximum inhibition (%) | $IC_{50}$ (nM) | Maximum inhibition (%) | $IC_{50}$ (nM) | Maximum inhibition (%) |
| D-2 | 1.086 | 96.85 | 1.881 | 89.43 | 3.076 | 62.09 |
| D-3 | 1.176 | 96.36 | 1.983 | 90.94 | 2.171 | 63.03 |
| E-305 | 0.571 | 96.42 | 1.168 | 88.53 | 2.102 | 61.27 |
| E1-30 | 0.1659 | 96.15 | 0.3596 | 90.49 | 0.7813 | 62.46 |

E-305

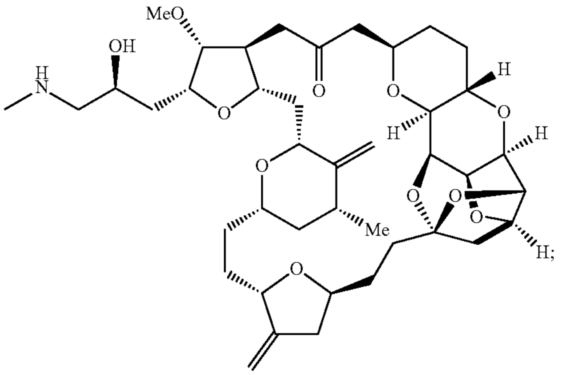

;

E1-30

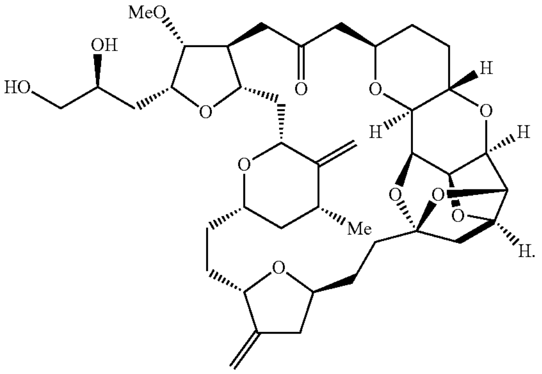

.

Example 2-2-4

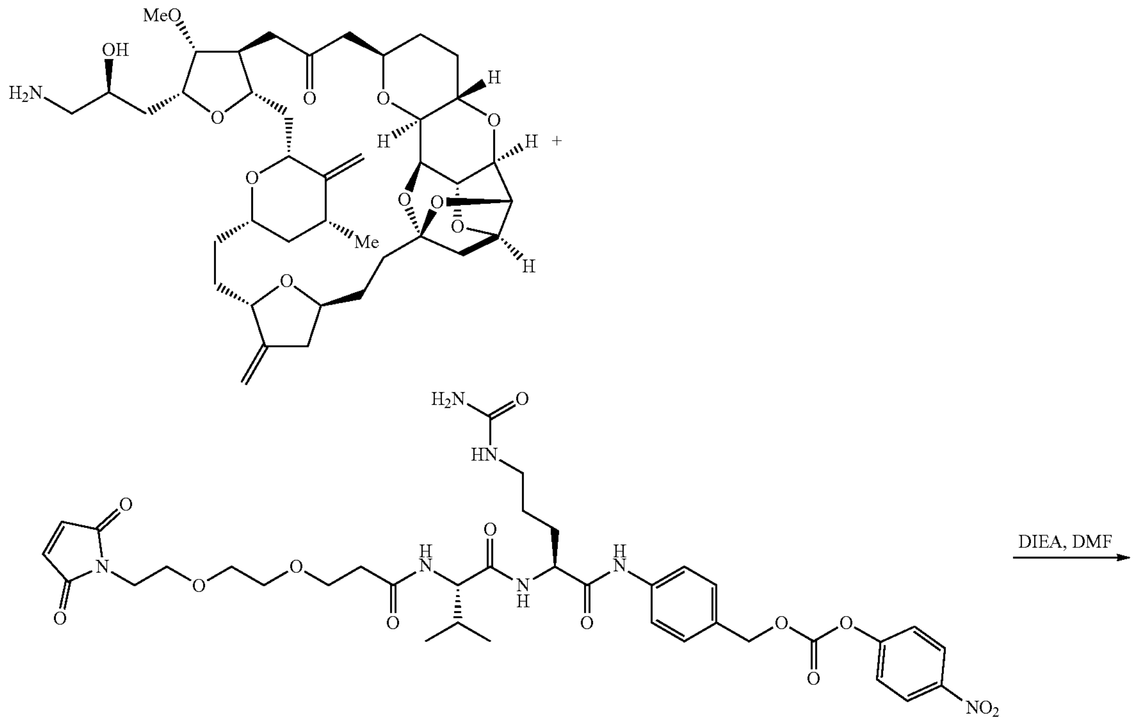

2

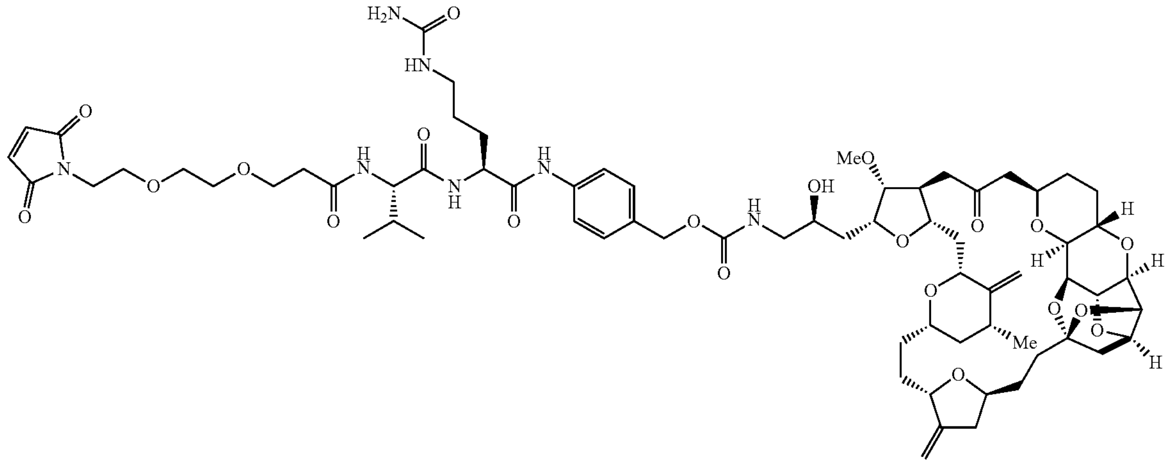

L-2

Eribulin (9 mg, 0.012 mmol) was dissolved in DMF (0.3 mL) under an ice-water bath, DIPEA (3.5 mg, 0.028 mmol) was added, followed by the addition of compound 2 (7.8 mg, 0.011 mmol) in this example in portions, and the mixture was stirred until the reaction was substantially completed. The reaction solution was concentrated under reduced pressure to give a crude product, which was then separated by preparative HPLC to give compound L-2 (4.95 mg, 97% purity). LC/MS (ESI): m/z 1374.3 $[M+H]^+$.

Example 2-2-5

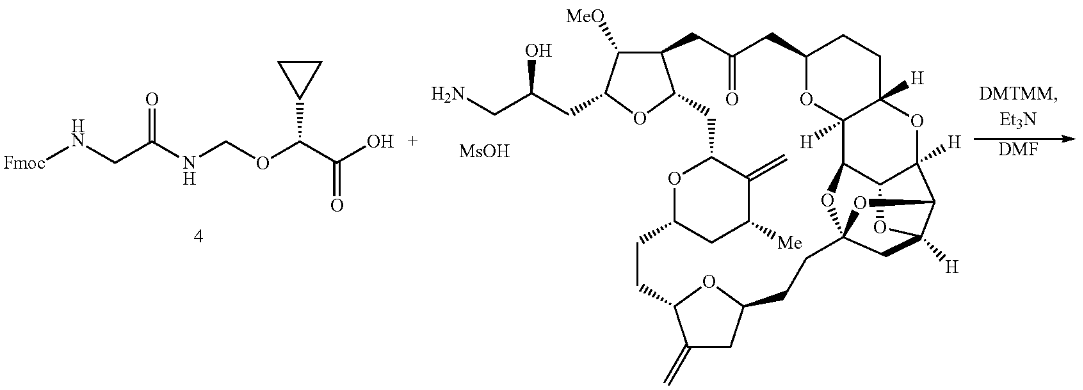

4

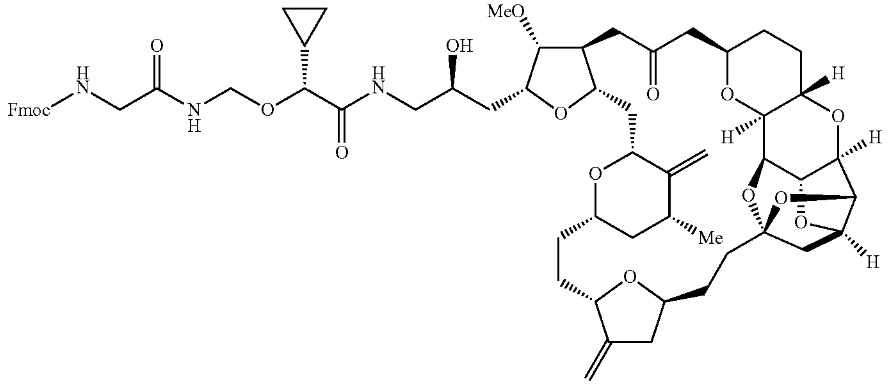

Compound 4 (13.4 mg, 0.0316 mmol, 1.7 eq) in this example and eribulin mesylate (15 mg, 0.0182 mmol, 1 eq) were weighed and dissolved in DMF (0.5 mL), followed by the addition of triethylamine (10 mg, 0.0988 mmol, 5.4 eq) and DMTMM (4-(4,6-dimethoxytriazin-2-yl)-4-methylmorpholine hydrochloride, 9.8 mg, 0.0332 mmol, 1.8 eq) under an ice bath, and the mixture was naturally warmed to room temperature and stirred until the reaction was substantially completed. Water (2 mL) and ethyl acetate (3 mL) were added for dilution and liquid separation, and the aqueous phase was extracted with ethyl acetate. The organic phases were combined, dried over anhydrous sodium sulfate and concentrated. The crude product was purified using a preparative plate to give the product (16 mg, 86.7% yield). LC/MS (ESI): m/z 1136.3 $[M+H]^+$.

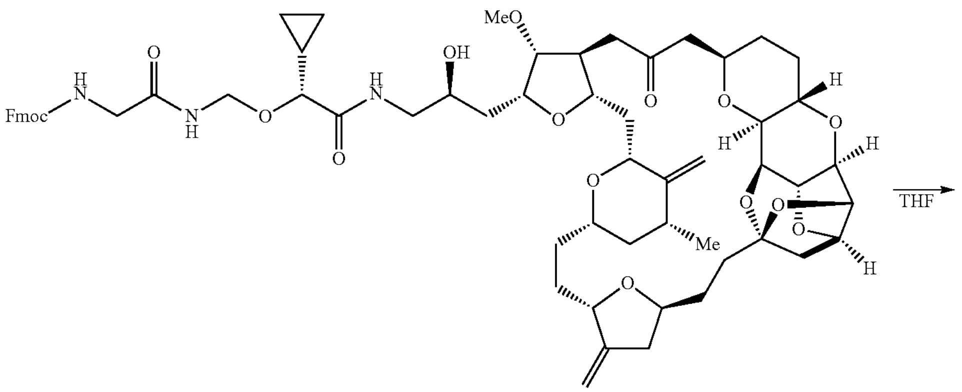

-continued

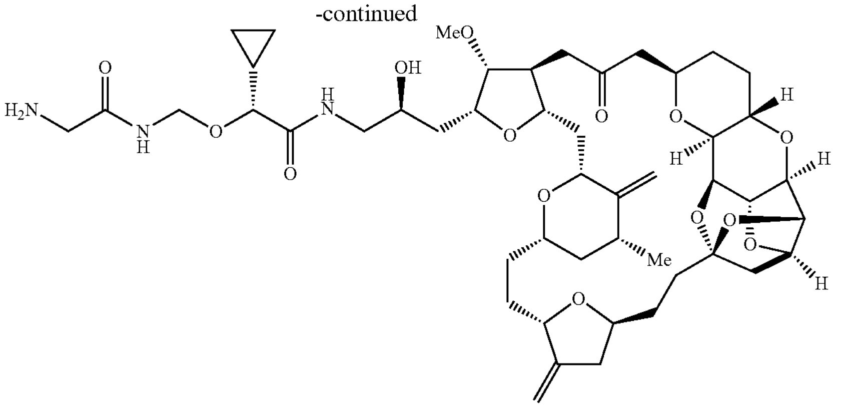

The compound (16 mg, 0.0141 mmol, 1 eq) obtained in the previous step was weighed and dissolved in THF (0.4 mL) under an ice bath, followed by the addition of triethylamine (4.2 mg, 0.057 mmol, 4 eq), and the mixture was stirred under an ice bath until the reaction was substantially completed. The reaction solution was diluted with dichloromethane (5 mL) and washed with water (2 mL×3). The organic phase was dried over anhydrous sodium sulfate and concentrated to give a crude product, which was directly used in the next step. LC/MS (ESI): m/z 914.3 $[M+H]^+$.

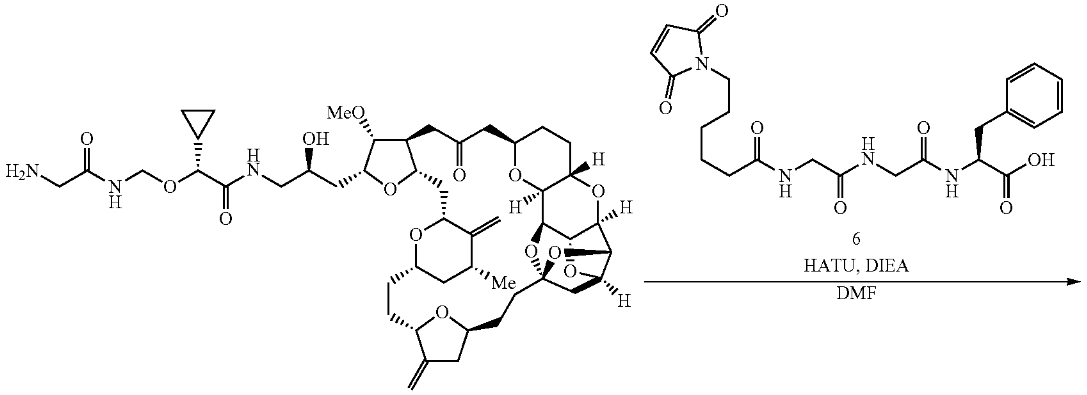

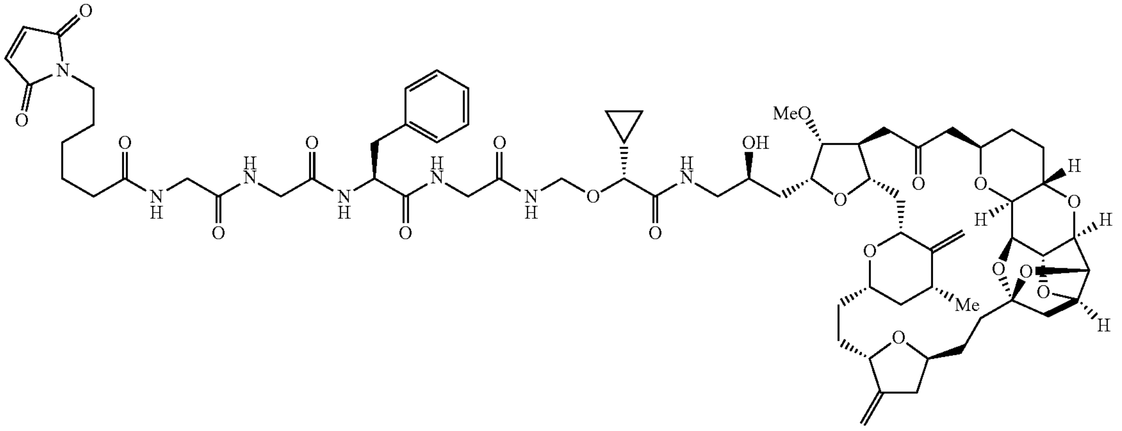

L-3

The product (16 mg, 0.0175 mmol, 1 eq) obtained in the previous step and compound 6 in this example (11.6 mg, 0.0246 mmol, 1.4 eq) were weighed and dissolved in DMF (0.5 mL), followed by the addition of o-(7-Azabenzotriazol-1-yl)-N,N,N',N'-tetramethyluronium hexafluorophosphate (9.9 mg, 0.026 mmol, 1.5 eq) and N,N-diisopropylethylamine (5.5 mg, 0.0426 mmol, 2.4 eq), and the mixture was stirred under an ice bath until the reaction was substantially completed. Water (2 mL) and ethyl acetate (3 mL) were added for dilution and liquid separation, and the aqueous phase was extracted with ethyl acetate. The organic phases were combined, dried over anhydrous sodium sulfate and concentrated. The crude product was purified by preparative HPLC to give the product L-3 (10 mg). LC/MS (ESI): m/z 1368.3 $[M+H]^+$.

Example 2-2-6

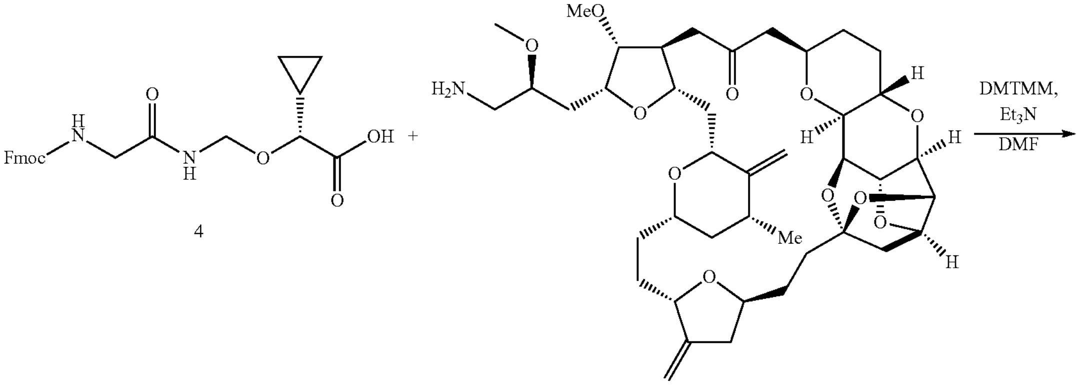

4

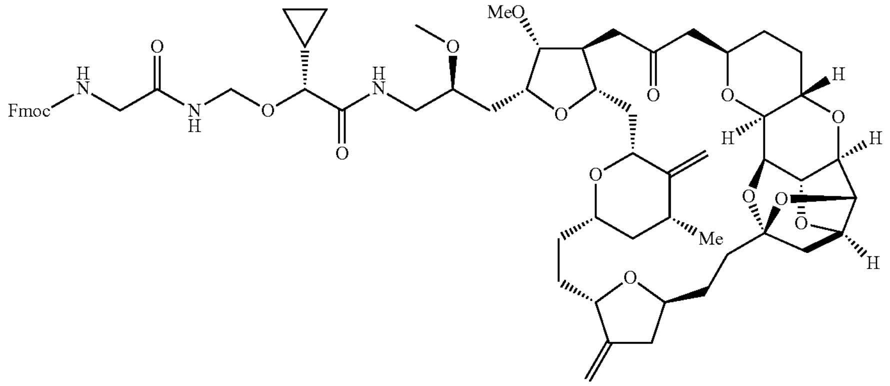

Compound 4 (11.6 mg, 0.0273 mmol, 1.5 eq) in this example and compound D-1 (eribulin derivative, 13.5 mg, 0.0181 mmol, 1 eq) in Example 2-2-1 were weighed and dissolved in N,N-dimethylformamide (0.5 mL), followed by the addition of DMTMM (10.1 mg, 0.0343 mmol, 1.3 eq) under an ice bath, and the reaction solution was reacted until the reaction was substantially completed. Water (2 mL) and ethyl acetate (3 mL) were added for quenching and dilution, followed by liquid separation, and the aqueous phase was extracted with ethyl acetate. The organic phases were combined, dried over anhydrous sodium sulfate and concentrated. The crude product was purified using a preparative plate to give the product (10 mg, 47.9% yield). LC/MS (ESI): m/z 1150.2 $[M+H]^+$.

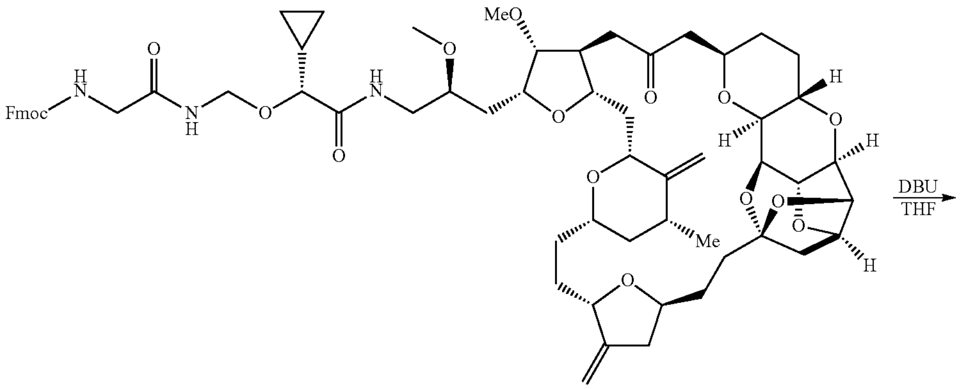

-continued

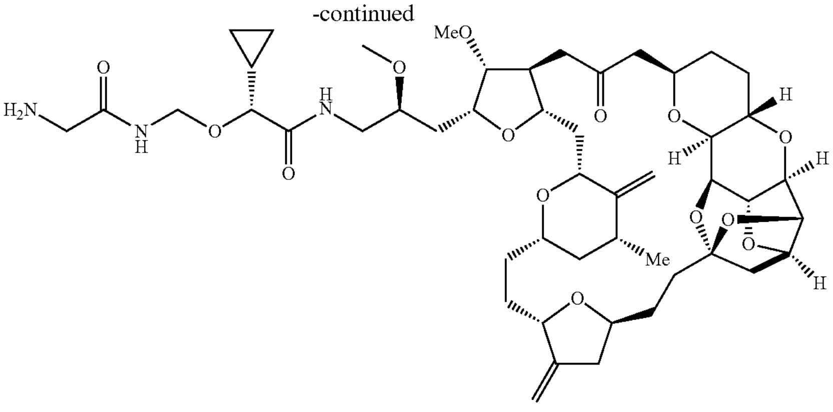

The product (10 mg, 0.0087 mmol, 1 eq) obtained in the previous step was dissolved in THF (1 mL), followed by the addition of 1,8-diazabicycloundec-7-ene (5.2 mg, 0.034 mmol, 4 eq), and the mixture was stirred under an ice bath until the reaction was substantially completed. The reaction solution was diluted with dichloromethane (5 mL) and washed with water (2 mL×3). The organic phase was dried over anhydrous sodium sulfate and concentrated to give a crude product, which was directly used in the next step. LC/MS (ESI): m/z 928.2 $[M+H]^+$.

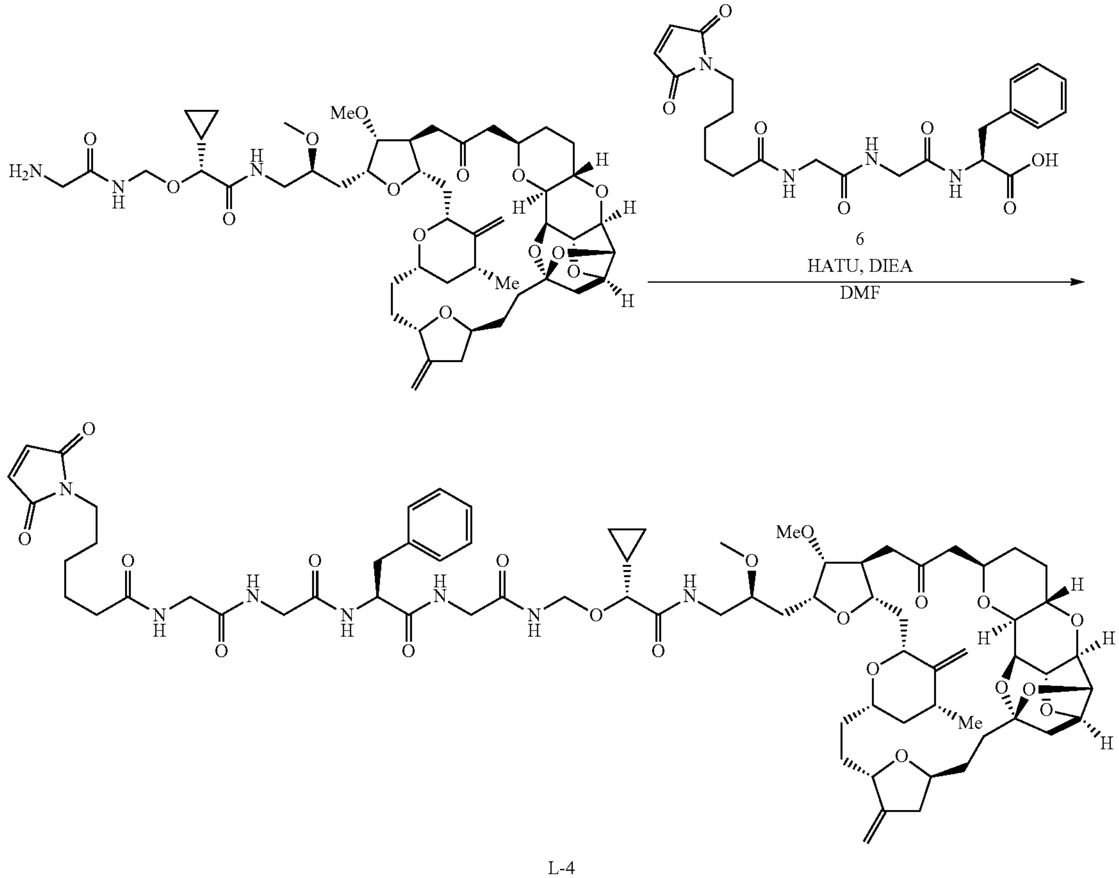

L-4

The product (16 mg, 0.0087 mmol, 1 eq) obtained in the previous step and compound 6 (7.8 mg, 0.0165 mmol, 1.9 eq) were dissolved in DMF (0.5 mL), followed by the addition of o-(7-Azabenzotriazol-1-yl)-N,N,N',N'-tetramethyluronium hexafluorophosphate (6.2 mg, 0.0163 mmol, 1.9 eq) and DIEA (5.7 mg, 0.0441 mmol, 5 eq), and the mixture was stirred under an ice bath until the reaction was substantially completed. Water (2 mL) and ethyl acetate (3 mL) were added for dilution and liquid separation, and the aqueous phase was extracted with ethyl acetate. The organic phases were combined, dried over anhydrous sodium sulfate and concentrated. The crude product was purified by preparative HPLC to give the product L-4 (3.5 mg, 29.10% yield over two steps). LC/MS (ESI): m/z 1382.2 $[M+H]^+$.

Example 2-3
(S)—N-((3R,4S,5S)-1-((1S,3S,5S)-3-((1R,2R)-3-(((1S,2R)-1-hydroxy-1-phenylpropan-2-yl)amino)-1-methoxy-2-methyl-3-oxopropyl)-2-azabicyclo[3.1.0]hexan-2-yl)-3-methoxy-5-methyl-1-oxoheptan-4-yl)-N,3-dimethyl-2-((S)-3-methyl-2-(methylamino)butanamido)butanamide Compound 1 in this example
1
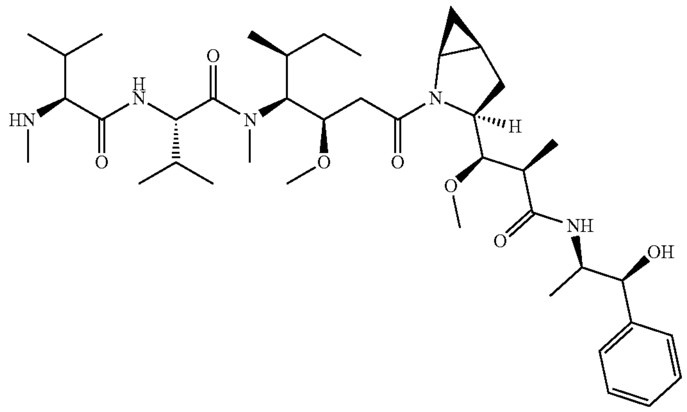
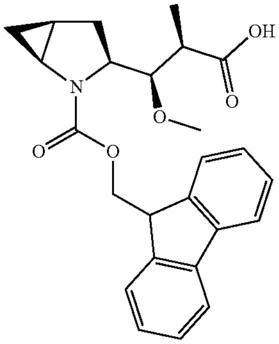
1a
+
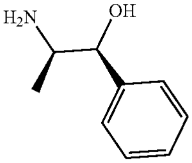
1b
Step 1
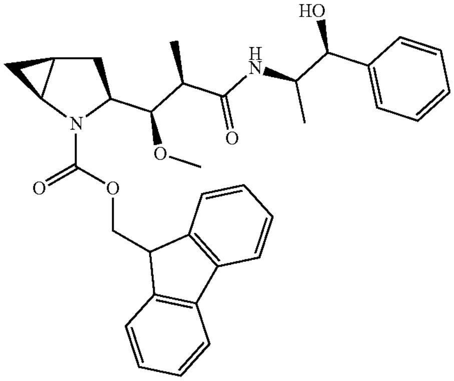
1c
Step 2
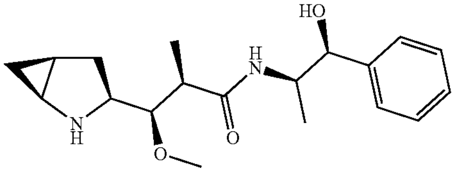
1d
+
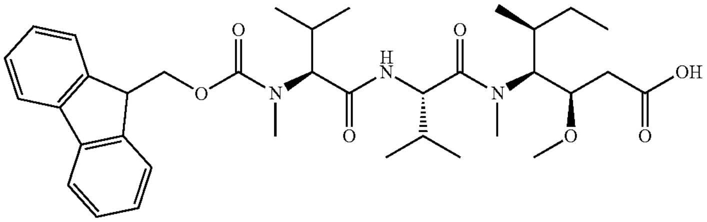
1e
Step 3

-continued

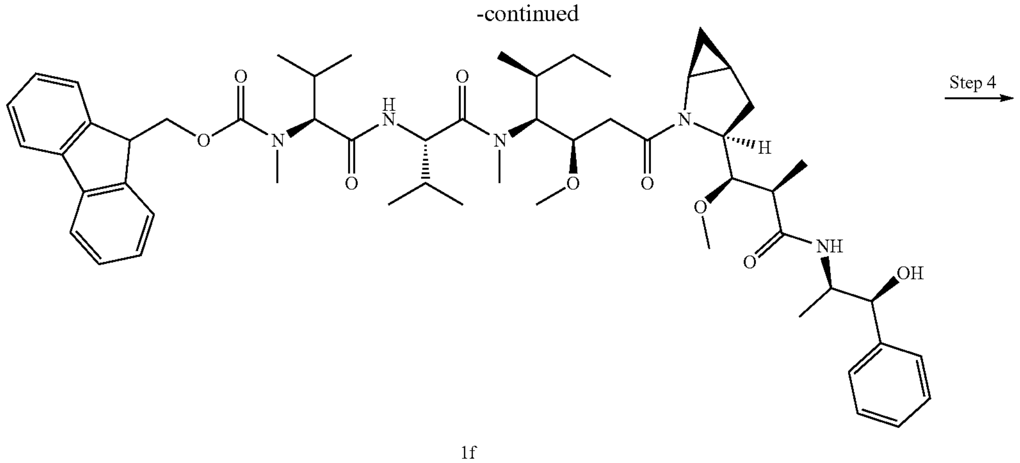

1f

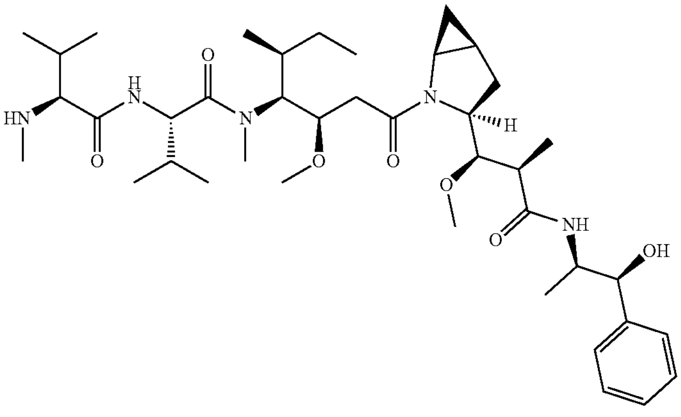

1

Step 1

(9H-fluoren-9-yl)methyl (1S,3S,5S)-3-((1R,2R)-3-(((1S,2R)-1-hydroxy-1-phenylpropan-2-yl)amino)-1-methoxy-2-methyl-3-oxopropyl)-2-azabicyclo[3.1.0]hexane-2-carboxylate Compound 1c in this example (2R,3R)-3-((1S,3S,5S)-2-(((9H-fluoren-9-yl)methoxy)carbonyl)-2-azabicyclo[3.1.0]hexan-3-yl)-3-methoxy-2-methylpropanoic acid (compound 1a in this example, 1.05 g, 2.49 mmol, prepared by the method disclosed in "step 7 on page 20 of the description of the patent application US2019/55223") and (1S,2R)-2-amino-1-phenylpropan-1-ol (compound 1b in this example, 0.42 g, 2.78 mmol, prepared by the known method "Journal of Organic Chemistry, 2012, vol. 77, #12, p. 5454-5460") were added to a reaction flask, followed by the addition of dichloromethane (10 mL) and N,N-dimethylformamide (2 mL), and the mixture was purged with argon gas three times. o-(7-Azabenzotriazol-1-yl)-N,N,N',N'-te-tramethyluronium hexafluorophosphate (1.14 g, 3.00 mmol) and N,N-diisopropylethylamine (0.97 g, 7.47 mmol) with stirring, and the resulting mixture was stirred at room temperature for 1 h. 30 mL of water was added, and the reaction solution was extracted with dichloromethane (15 mL×4). The organic phase was washed with a saturated sodium chloride solution (30 mL), dried over anhydrous sodium sulfate and filtered, and the filtrate was concentrated under reduced pressure. The resulting residue was purified by silica gel column chromatography with a developing solvent system A to give the title product, i.e., compound 1c (1.38 g, 99.8% yield) in this example.

MS m/z (ESI): 555.2 [M+1]

Step 2

(2R,3R)-3-((1S,3S,5S)-2-azabicyclo[3.1.0]hexan-3-yl)-N-((1S,2R)-1-hydroxy-1-phenylpropan-2-yl)-3-methoxy-2-methylpropanamide Compound 1d in this example Compound 1c (1.38 g, 2.49 mmol) in this example was dissolved in dichloromethane (10 mL), followed by the addition of diethylamine (20 mL), and the mixture was purged with argon three times and stirred at room temperature for 1 h. The reaction solution was concentrated. The residue was purified by silica gel column chromatography with a developing solvent system A to give the title product, i.e., compound 1d (805 mg, 97.3% yield) in this example.

MS m/z (ESI): 333.2 [M+1]

Step 3

(9H-fluoren-9-yl)methyl ((S)-1-(((S)-1-(((3R,4S,5S)-1-((1S,3S,5S)-3-((1R,2R)-3-(((1S,2R)-1-hydroxy-1-phenylpropan-2-yl)amino)-1-methoxy-2-methyl-3-oxopropyl)-2-azabicyclo[3.1.0]hexan-2-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate Compound 1f in this example (5S,8S,11S,12R)-11-((S)-sec-butyl)-1-(9H-fluoren-9-yl)-5,8-diisopropyl-12-methoxy-4,10-dimethyl-3,6,9-trioxo-2-oxa-4,7,10-triazatetradecan-14-oic acid (compound 1e in this example, 1.54 g, 2.41 mmol, supplied by Haoyuan Chemexpress) was added into a reaction flask, followed by the addition of acetonitrile (30 mL), and the mixture was purged with argon three times and cooled to 0-5° C. under an ice-water bath. o-(7-Azabenzotriazol-1-yl)-N,N,N',N'-tetramethyluronium hexafluorophosphate (1.10 g, 2.89 mmol) and N,N-diisopropylethylamine (0.94 g, 7.27 mmol) were added, and the resulting mixture was stirred for 10 min under an ice bath. A suspension of compound 1d (805 mg, 2.42 mmol) in this example in acetonitrile (10 mL) was added, and the resulting mixture was stirred for 40 min under an ice bath. 60 mL of water was added to the reaction solution, and the mixture was extracted with ethyl acetate (20 mL×4). The organic phase was washed with saturated sodium chloride solution (60 mL), dried over anhydrous sodium sulfate, and filtered. The filtrate was concentrated under reduced pressure, and the resulting residue was purified by silica gel column chromatography with a developing solvent system B to give the crude product, i.e., compound 1f (2.9 g) in this example.

MS m/z (ESI): 952.3 [M+1]

Step 4

(S)—N-((3R,4S,5S)-1-((1S,3S,5S)-3-((1R,2R)-3-(((1S,2R)-1-hydroxy-1-phenylpropan-2-yl)amino)-1-methoxy-2-methyl-3-oxopropyl)-2-azabicyclo[3.1.0]hexan-2-yl)-3-methoxy-5-methyl-1-oxoheptan-4-yl)-N,3-dimethyl-2-((S)-3-methyl-2-(methylamino)butanamido)butanamide Compound 1 in this example Compound 1f (crude, 510 mg, 0.53 mmol) in this example was dissolved in dichloromethane (2 mL), followed by the addition of diethylamine (4 mL), and the mixture was purged with argon three times and stirred at room temperature for 1 h. The reaction solution was concentrated. The residue was purified by silica gel column chromatography with a developing solvent system A to give the title product, i.e., compound 1 (266 mg, 68.0% yield) in this example.

MS m/z (ESI): 730.4 [M+1]

$^1$H NMR (400 MHz, $CD_3OD$): δ 7.36-7.40 (m, 2H), 7.31 (t, 2H), 7.24 (d, 1H), 4.69 (d, 1H), 4.56 (d, 1H), 4.17-4.28 (m, 2H), 4.06-4.14 (m, 1H), 3.91 (d, 1H), 3.78 (t, 1H), 3.27-3.44 (m, 7H), 3.15 (s, 3H), 2.84-2.93 (m, 1H), 2.60-2.67 (m, 2H), 2.30-2.37 (m, 3H), 2.02-2.10 (m, 2H), 1.79-1.95 (m, 4H), 1.38-1.53 (m, 2H), 1.25-1.36 (m, 2H), 1.21 (d, 1H), 1.13-1.17 (m, 2H), 1.07-1.11 (m, 2H), 0.93-1.05 (m, 15H), 0.83-0.89 (m, 4H), 0.70-0.79 (m, 1H).

Example 2-4

4-((S)-2-((S)-2-(6-(2,5-dioxo-2,5-dihydro-1H-pyrrol-1-yl)hexanamido)-3-methylbutanamido)-5-ureidopentanamido)benzyl ((S)-1-(((S)-1-(((3R,4S,5S)-1-((1S,3S,5S)-3-((1R,2R)-3-(((1S,2R)-1-hydroxy-1-phenylpropan-2-yl)amino)-1-methoxy-2-methyl-3-oxopropyl)-2-azabicyclo[3.1.0]hexan-2-yl)-3-methoxy-5-methyl-1-oxoheptan-4-yl)(methyl)amino)-3-methyl-1-oxobutan-2-yl)amino)-3-methyl-1-oxobutan-2-yl)(methyl)carbamate Compound 2 in this example

2

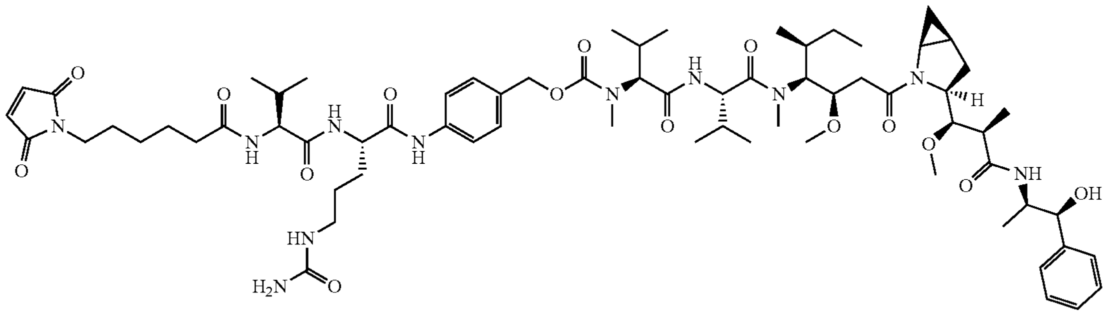

-continued

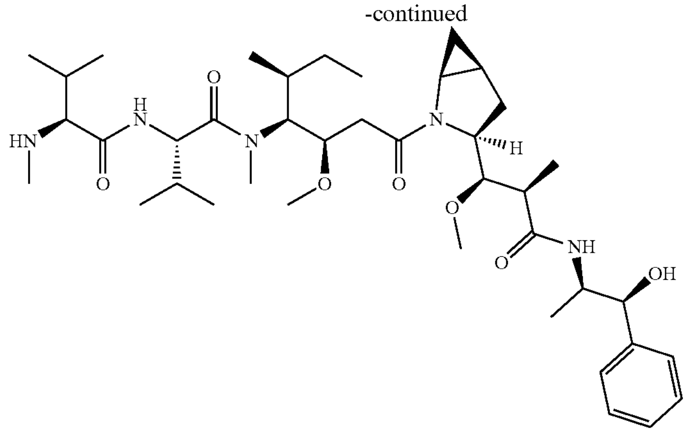

+

1

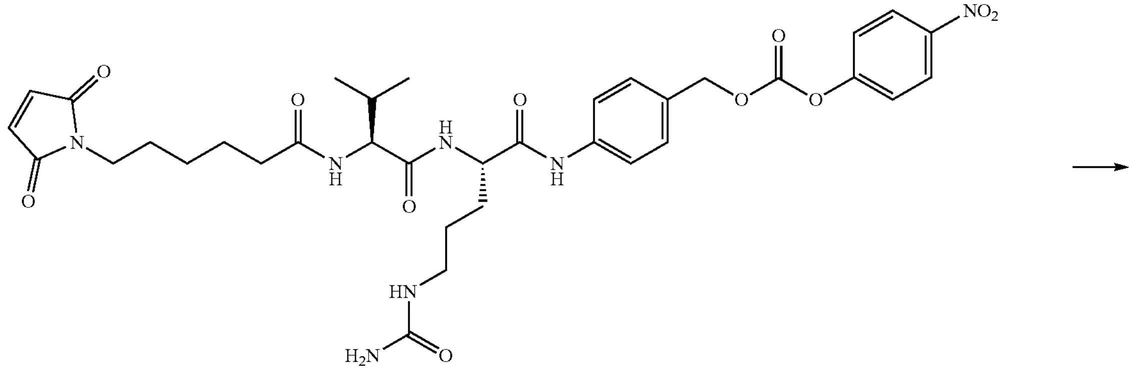

2a

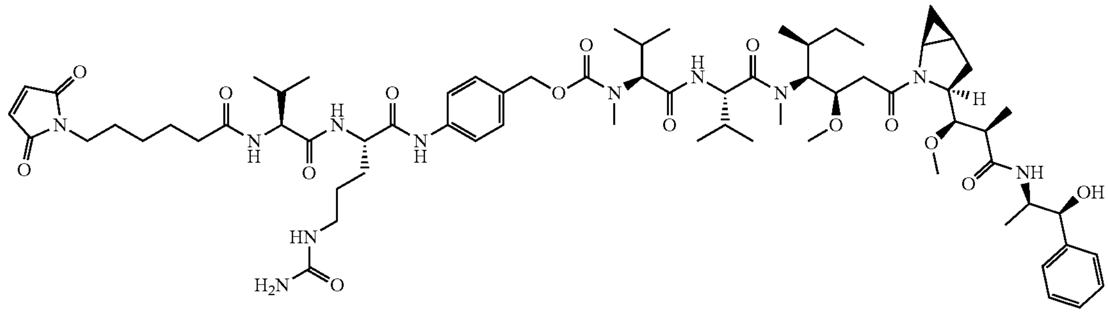

2

Compound 1 (30 mg, 0.041 mmol) in this example was added to N,N-dimethylformamide (1 mL), followed by the sequential addition of 4-((S)-2-((S)-2-(6-(2,5-dioxo-2,5-dihydro-1H-pyrrol-1-yl)hexanamide)-3-methylbutyrylamide)-5-ureidovaleramide)benzyl(4-nitrophenyl)carbonate (compound 2a in this example, 45 mg, 0.061 mmol, supplied by Ark) and pyridine (0.25 mL), and the mixture was purged with argon three times. 1-hydroxybenzotriazole (12 mg, 0.089 mmol) and N,N-diisopropylethylamine (16 mg, 0.123 mmol) were added, and the resulting mixture was stirred at room temperature for 4 h, supplemented with 2a (45 mg, 0.061 mmol), and stirred for another 16 h. The reaction solution was purified by high performance liquid chromatography (separation conditions: chromatography column: XBridge Prep C18 OBD 5 μm 19×250 mm; mobile phase: A-water (10 mmol $NH_4OAc$), B-acetonitrile, gradient elution, flow rate: 18 mL/min). The corresponding fractions were collected and concentrated under reduced pressure to give the title product, i.e., compound 2 (18 mg, 33.0% yield) in this example.

MS m/z (ESI): 1329.3 [M+1]

$^1H$ NMR (400 MHz, $CD_3OD$): δ 7.58 (d, 2H), 7.29-7.42 (m, 6H), 7.20-7.26 (m, 1H), 6.79 (s, 2H), 5.04-5.20 (m, 4H), 4.47-4.61 (m, 3H), 4.13-4.28 (m, 3H), 4.06-4.12 (m, 1H), 3.91 (d, 1H), 3.75-3.82 (m, 1H), 3.48 (t, 3H), 3.27-3.41 (m, 7H), 3.16-3.25 (m, 2H), 3.18 (s, 3H), 2.91-2.97 (m, 2H), 2.60-2.65 (m, 2H), 2.27 (t, 2H), 2.20 (t, 1H), 2.01-2.10 (m, 3H), 1.69-1.94 (m, 6H), 1.63-1.68 (m, 6H), 1.46-1.51 (m, 1H), 1.27-1.37 (m, 5H), 1.12-1.21 (m, 3H), 1.09 (d, 2H), 0.93-1.04 (m, 11H), 0.80-0.92 (m, 11H), 0.70-0.77 (m, 2H).

3. Preparation of Anti-CD79B Antibody-Drug Conjugate

Experimental Purpose and Principle of ADC Drug-Loading Analysis:

The ADC loading was determined by ultraviolet spectrophotometry (UV-Vis) (Thermo nanodrop2000 ultraviolet spectrophotometer). The principle is that the total absorbance value of the ADC at a certain wavelength is equal to the sum of the absorbance values of the drug and the antibody at that wavelength.

Experimental Procedures

Cuvettes containing a sodium succinate buffer were separately placed into the reference cell and sample cell, and the absorbance value of the solvent blank was subtracted. Then, a cuvette containing the test solution was placed into the sample cell, and the absorbance values at 280 nm and 370 nm were determined.

Calculation for Results:

$$A280_{nm}=\varepsilon_{mab\text{-}280}bC_{mab}+\varepsilon_{Drug\text{-}280}bC_{Drug} \qquad \text{Equation (1)}$$

$\varepsilon_{Drug\text{-}280}$: the mean molar extinction coefficient of the drug at 280 nm of 5100;

$C_{Drug}$: the concentration of the drug;

$\varepsilon_{mab\text{-}280}$: the mean molar extinction coefficient of the monoclonal antibody at 280 nm of 214,600;

$C_{mab}$: the concentration of the monoclonal antibody;

b: the optical path length of 1 cm.

Similarly, an equation for the total absorbance value of the sample at 370 nm can be given as:

$$A370\ \text{nm}=\varepsilon mab\text{-}370bCmab+\varepsilon\text{Drug-}370bC\text{Drug} \qquad \text{Equation (2)}$$

$\varepsilon_{Drug\text{-}370}$: the mean molar extinction coefficient of the drug at 370 nm of 19,000;

$C_{Drug}$: the concentration of the drug;

$\varepsilon_{mab\text{-}370}$: the extinction coefficient of the monoclonal antibody at 370 nm of 0;

$C_{mab}$: the concentration of the monoclonal antibody;

b: the optical path length of 1 cm.

The drug loading of ADC can be calculated using both equations (1) and (2) as well as the extinction coefficients of the monoclonal antibody and the drug at both wavelengths and their concentrations: drug loading=$C_{Drug}/C_{mab}$.

Example 3-1. ADC-1

ADC-1

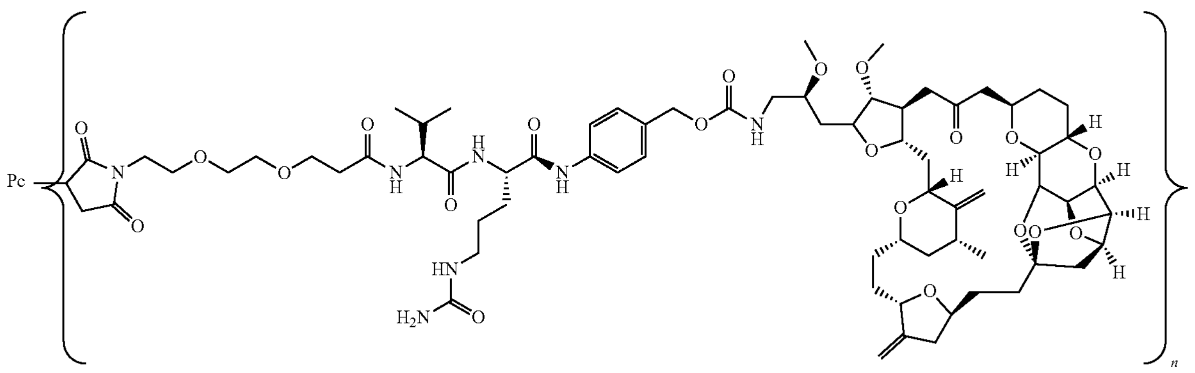

To antibody hAb015-10 in aqueous PBS buffer (0.05 M aqueous PBS buffer at pH 6.5, 10.0 mg/mL, 1.5 mL, 0.101 μmol) was added a prepared aqueous tris(2-carboxyethyl) phosphine (TCEP) solution (10 mM, 25.3 μL, 0.253 μmol) at 37° C. The mixture was shaken on a water bath shaker at 37° C. for 3 h before the reaction was stopped. The reaction solution was cooled to 25° C. under a water bath.

Compound B (1.41 mg, 1.015 μmol) in Example 2-2-1 was dissolved in dimethylsulfoxide (50 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5, containing 0.001 M EDTA) to give the title product ADC-1 (i.e., hAb015-10-cys-B) in PBS buffer (0.84 mg/mL, 13.5 mL) in this example, which was frozen and stored at 4° C.

Calculation of mean value by HIC: n=3.06.

Example 3-2. ADC-2

ADC-2

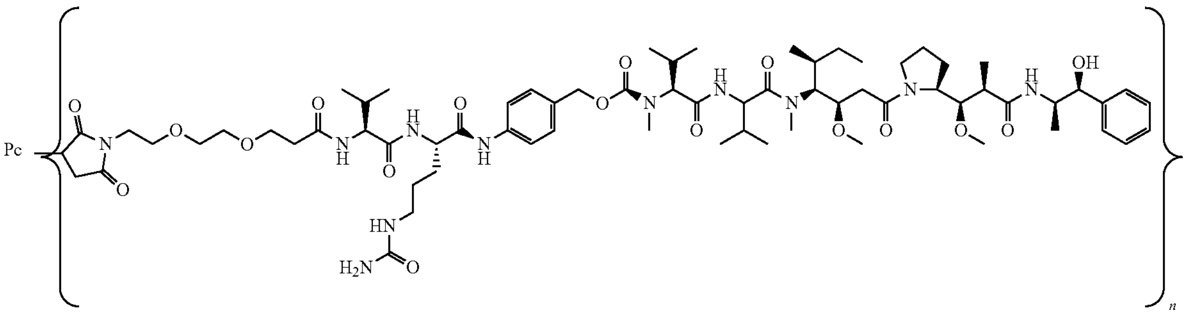

To antibody hAb015-10 in aqueous PBS buffer (0.05 M aqueous PBS buffer at pH 6.5, 10.0 mg/mL, 3.5 mL, 0.236 μmol) was added a prepared aqueous tris(2-carboxyethyl) phosphine (TCEP) solution (10 mM, 59.1 μL, 0.591 μmol) at 37° C. The mixture was shaken on a water bath shaker at 37° C. for 3 h before the reaction was stopped. The reaction solution was cooled to 25° C. under a water bath.

Compound A (3.2 mg, 2.348 μmol) was dissolved in dimethylsulfoxide (150 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 M PBS buffer at pH 6.5, containing 0.001 M EDTA) to give the title product ADC-2 (i.e., hAb015-10-cys-Malei-PEG2-vc-PAB-MMAE) in PBS buffer (2.17 mg/mL, 16.4 mL) in this example, which was frozen and stored at 4° C.

Mean calculated by RP-HPLC: n=3.68.

Example 3-3. ADC-3

To antibody hAb015-10 in aqueous PBS buffer (0.05 M aqueous PBS buffer at pH 6.5, 10.0 mg/mL, 5.0 mL, 0.338 μmol) was added a prepared aqueous tris(2-carboxyethyl) phosphine (TCEP) solution (10 mM, 85.0 μL, 0.850 μmol) at 37° C. The mixture was shaken on a water bath shaker at 37° C. for 3 h before the reaction was stopped. The reaction solution was cooled to 25° C. under a water bath.

Compound MC-vc-PAB-MMAE (4.45 mg, 3.380 μmol) was dissolved in dimethylsulfoxide (250 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5, containing 0.001 M EDTA) to give the title product ADC-3 (i.e., hAb015-10-cys-MC-vc-PAB-MMAE) in PBS buffer (2.79 mg/mL, 17.4 mL) in this example, which was frozen and stored at 4° C.

Calculation of mean value by CE-SDS: n=3.09.

ADC-3

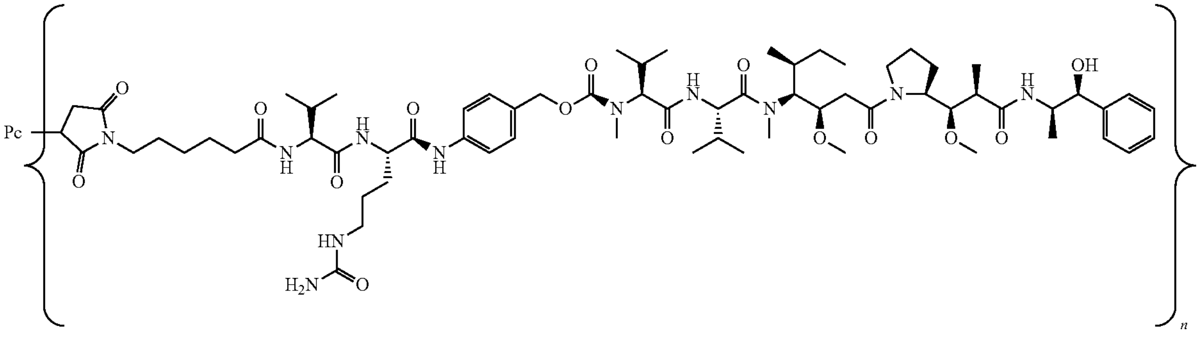

Example 3-4. ADC-4

ADC-4

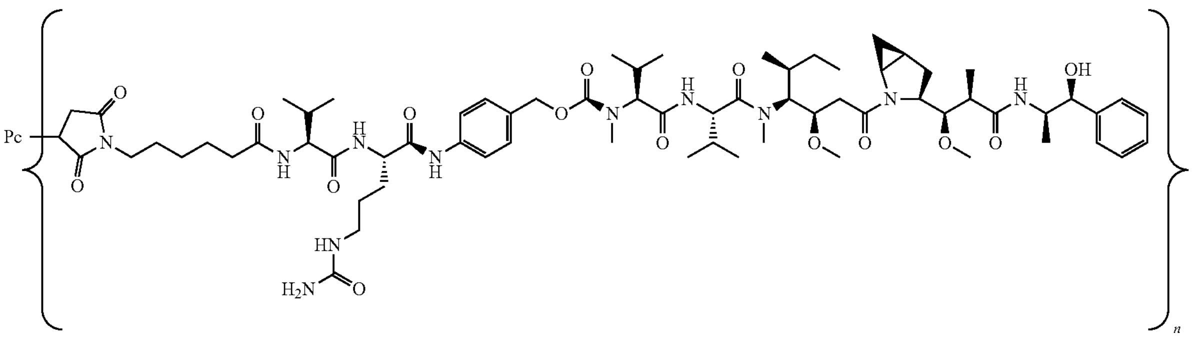

To antibody hAb015-10 in aqueous PBS buffer (0.05 M aqueous PBS buffer at pH 6.5, 10.0 mg/mL, 1.8 mL, 0.122 μmol) was added a prepared aqueous tris(2-carboxyethyl) phosphine (TCEP) solution (10 mM, 30.4 μL, 0.304 μmol) at 37° C. The mixture was shaken on a water bath shaker at 37° C. for 3 h before the reaction was stopped. The reaction solution was cooled to 25° C. under a water bath.

C

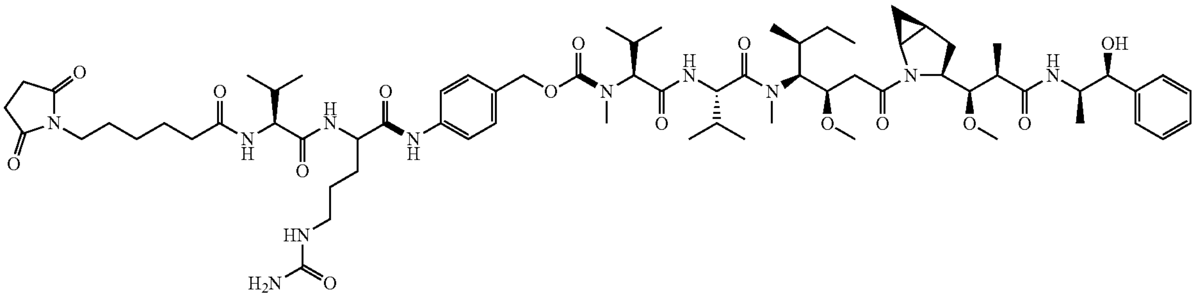

Compound C (1.62 mg, 1.220 μmol) in this example was dissolved in dimethylsulfoxide (90 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5, containing 0.001 M EDTA) to give the title product ADC-4 (i.e., hAb015-10-cys-C) in PBS buffer (1.37 mg/mL, 12.0 mL) in this example, which was frozen and stored at 4° C.

Calculation of mean value by RP-HPLC: n=4.52.

Example 3-5. ADC-5

ADC-5

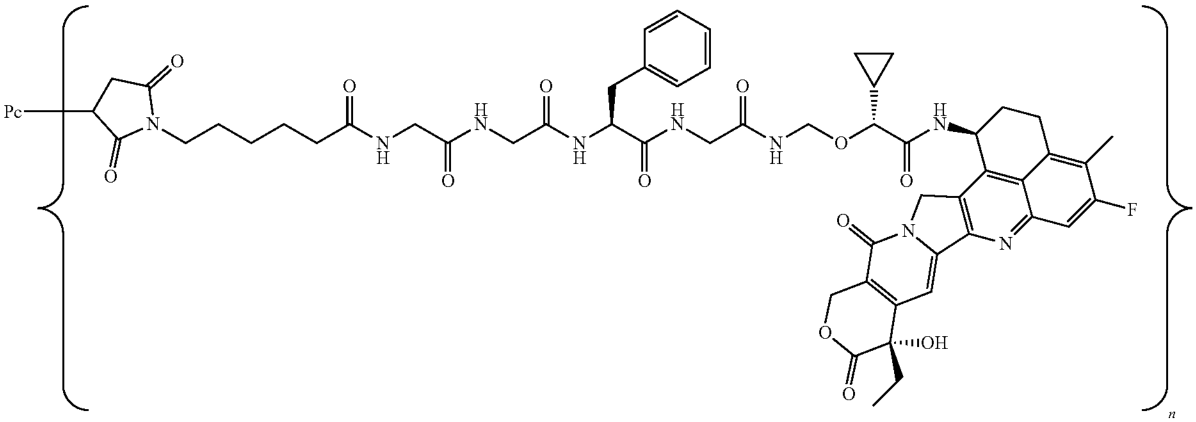

To antibody hAb015-10 in aqueous PBS buffer (0.05 M aqueous PBS buffer at pH 6.5, 10.0 mg/mL, 1.5 mL, 0.101 μmol) was added a prepared aqueous tris(2-carboxyethyl) phosphine (TCEP) solution (10 mM, 16.2 μL, 0.162 μmol) at 37° C. The mixture was shaken on a water bath shaker at 37° C. for 3 h before the reaction was stopped. The reaction solution was cooled to 25° C. under a water bath.

D

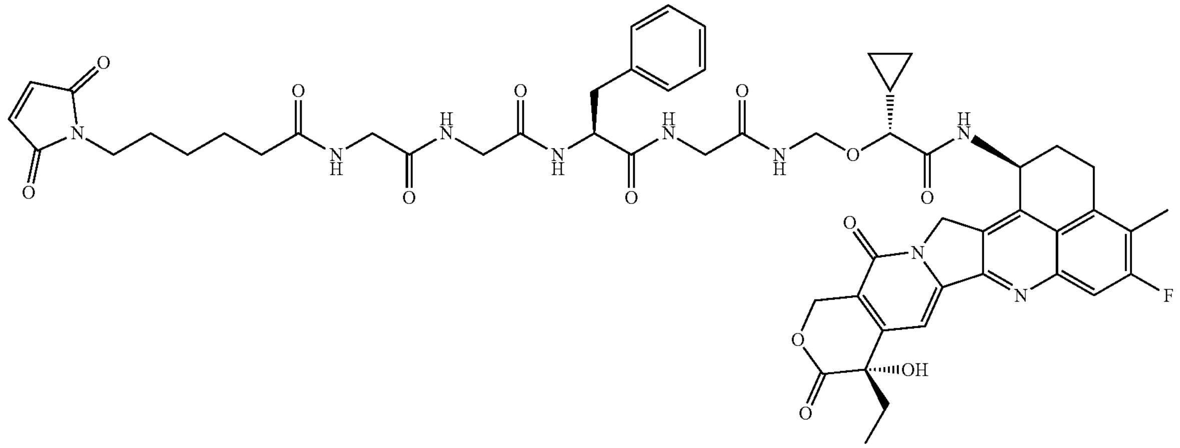

Compound D (0.87 mg, 0.810 μmol) in this example was dissolved in dimethylsulfoxide (37 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5 containing 0.001 M EDTA) to give the title product ADC-5 (i.e., HAB015-10-cys-D, with a DAR value of about 2) in PBS buffer (0.90 mg/mL, 14.0 mL) in this example, which was frozen and stored at 4° C. Compound D was prepared with reference to the method described in WO2020063676 Å, e.g., Example 9 therein.

Calculation of mean value by RP-HPLC: n=1.81.

Example 3-6. ADC-6

ADC-6

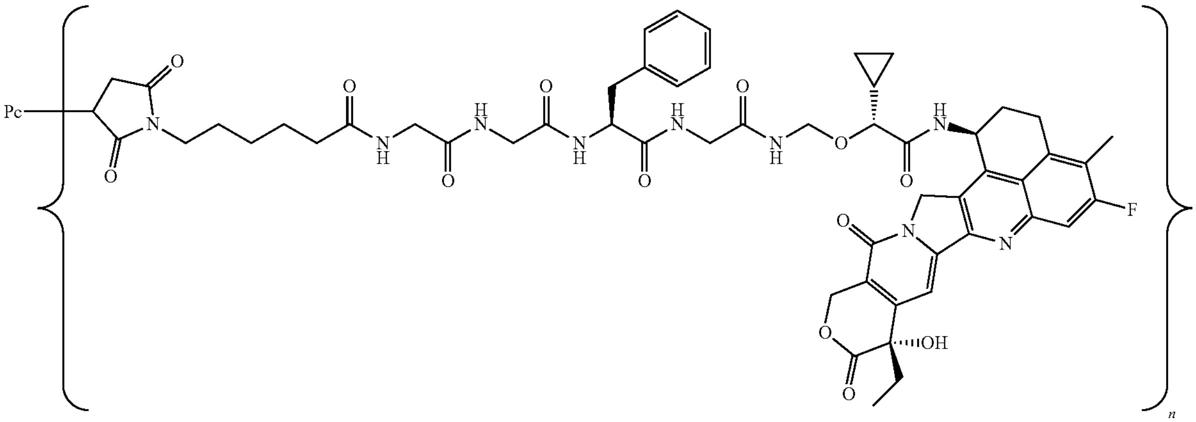

To antibody hAb015-10 in aqueous PBS buffer (0.05 M aqueous PBS buffer at pH 6.5, 10.0 mg/mL, 1.5 mL, 0.101 μmol) was added a prepared aqueous tris(2-carboxyethyl) phosphine (TCEP) solution (10 mM, 25.3 μL, 0.253 μmol) at 37° C. The mixture was shaken on a water bath shaker at 37° C. for 3 h before the reaction was stopped. The reaction solution was cooled to 25° C. under a water bath.

Compound D (1.09 mg, 1.015 μmol) in Example 3-5 was dissolved in dimethylsulfoxide (45 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5, containing 0.001 M EDTA) to give the title product ADC-6 (i.e., hAb015-10-cys-D, with a target DAR value of about 4) in PBS buffer (0.71 mg/mL, 14.0 mL) in this example, which was frozen and stored at 4° C.

Calculation of mean value by RP-HPLC: n=3.46.

Example 3-7. ADC-7

To antibody hAb015-10 in aqueous PBS buffer (0.05 M aqueous PBS buffer at pH 6.5, 10.0 mg/mL, 1.5 mL, 0.101 μmol) was added a prepared aqueous tris(2-carboxyethyl) phosphine (TCEP) solution (10 mM, 50.7 μL, 0.507 μmol) at 37° C. The mixture was shaken on a water bath shaker at 37° C. for 3 h before the reaction was stopped. The reaction solution was cooled to 25° C. under a water bath.

Compound D (1.63 mg, 1.518 μmol) in Example 3-5 was dissolved in dimethylsulfoxide (68 μL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5, containing 0.001 M EDTA) to give the title product ADC-7 (i.e., hAb015-10-cys-D, with a DAR value of about 6) in PBS buffer (0.81 mg/mL, 13.5 mL) in this example, which was frozen and stored at 4° C. Calculation of mean value by RP-HPLC: n=5.84.

ADC-7

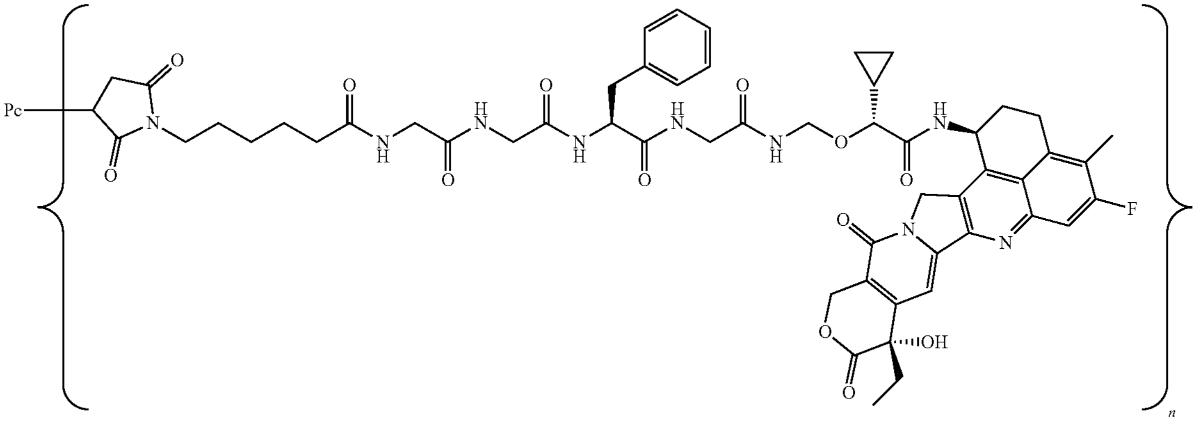

Example 3-8. ADC-8

ADC-8

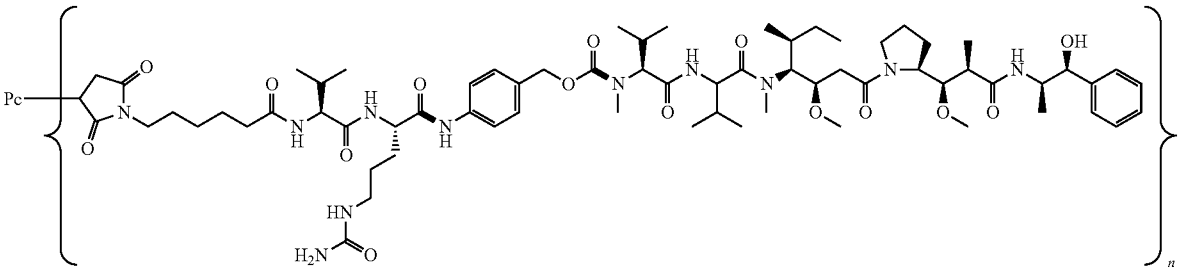

To antibody SN8 in aqueous PBS buffer (0.05 M aqueous PBS buffer at pH 6.5, 10.0 mg/mL, 79 mL, 5.338 μmol) was added a prepared aqueous tris(2-carboxyethyl)phosphine (TCEP) solution (10 mM, 1.388 mL, 13.88 μmol) at 37° C. The mixture was shaken on a water bath shaker at 37° C. for 3 h before the reaction was stopped. The reaction solution was cooled to 25° C. under a water bath.

Compound MC-VC-PAB-MMAE (70.3 mg, 53.40 μmol) was dissolved in dimethylsulfoxide (3.5 mL), and the solution was added to the above reaction solution. The resulting mixture was shaken on a water bath shaker at 25° C. for 3 h before the reaction was stopped. The reaction mixture was desalted and purified through a Sephadex G25 gel column (elution phase: 0.05 MPBS buffer at pH 6.5, containing 0.001 M EDTA) to give the title product ADC-8 (i.e., SN8-cys-MC-PAB-MMAE, with a DAR value of about 4) in PBS buffer (5.83 mg/mL, 132 mL) in this example, which was frozen and stored at 4° C.

Calculation of mean value by CE-SDS: n=3.59.

4. Biological Evaluation

Example 4-1. Biacore Affinity Assay

This example was performed to determine the affinity of CD79B antibodies (hAb015-10 and SN8) and ADC for CD79B protein using Biacore.

Experimental instruments, materials and reagents: Biacore T200 (GE); biosensor chip CM5 (Cat. #BR-1005-30, GE); amino coupling kit (Cat. #BR-1000-50, GE); human antibody capture kit (Cat. #BR-1008-39, GE); human CD79B-His protein (Cat. #29750-$H_{08}$H, Sino Biological); HBS-EP+10× buffer (Cat. #BR-1006-69, GE) diluted to 1× (pH 7.4) with D. I. Water.

Experimental procedures: human antibody capture antibodies were covalently coupled to a CM5 biochip according to the method described instructions of the human antibody capture kit for affinity capture of a certain amount of CD79B antibody.

Statistics and analysis of data: data were fitted by BIAevaluation version 4.1, GE software using a (1:1) Langmuir model to obtain affinity values.

Experimental results and conclusion: the assay results of the affinity for the binding of CD79B antibodies and ADC to CD79B protein are shown in Table 10. The naked antibodies and different ADCs have similar binding force to human CD79B protein, which is higher than that of the positive drug Polivy.

Sequences of SN8 (i.e., the antibody in Polivy):

```
>Heavy chain amino acid sequence of SN8
                                               SEQ ID NO: 32
EVQLVESGGGLVQPGGSLRLSCAASGYTFSSYWIEWVRQAPGKGLEWIG

EILPGGGDTNYNEIFKGRATFSADTSKNTAYLQMNSLRAEDTAVYYCTR

RVPIRLDYWGQGTLVTVSSASTKGPSVFPLAPSSKSTSGGTAALGCLVK

DYFPEPVTVSWNSGALTSGVHTFPAVLQSSGLYSLSSVVTVPSSSLGTQ

TYICNVNHKPSNTKVDKKVEPKSCDKTHTCPPCPAPELLGGPSVFLFPP

KPKDTLMISRTPEVTCVVVDVSHEDPEVKFNWYVDGVEVHNAKTKPREE

QYNSTYRVVSVLTVLHQDWLNGKEYKCKVSNKALPAPIEKTISKAKGQP

REPQVYTLPPSREEMTKNQVSLTCLVKGFYPSDIAVEWESNGQPENNYK

TTPPVLDSDGSFFLYSKLTVDKSRWQQGNVFSCSVMHEALHNHYTQKSL

SLSPGK

>Light chain amino acid sequence of SN8
                                               SEQ ID NO: 33
DIQLTQSPSSLSASVGDRVTITCKASQSVDYEGDSFLNWYQQKPGKAPK

LLIYAASNLESGVPSRFSGSGSGTDFTLTISSLQPEDFATYYCQQSNED

PLTFGQGTKVEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC.
```

TABLE 10

Binding force of antibodies and different ADCs to human CD79B protein

| ADC/antibodies | Human CD79B $EC_{50}$ (nM) |
|---|---|
| hAb015-10 | 0.38 |
| ADC-1 | 0.51 |
| ADC-2 | 0.48 |
| ADC-3 | 0.40 |
| ADC-4 | 0.32 |
| ADC-5 | 0.80 |
| ADC-6 | 0.43 |
| ADC-7 | 0.53 |
| ADC-8 | 5.98 |

Example 4-2. In Vitro Endocytosis Assay

A cell endocytosis experiment was performed with DOHH-2 cells (DSMZ, ACC 47) highly expressing human CD79B protein to assess the endocytosis ability of ADCs.

DOHH-2 cells were cultured according to a conventional method for suspending cells in a complete medium (RPMI 1640 medium (GIBCO, Cat No.: 11835-030), containing 10% (v/v) fetal bovine serum (FBS) (GIBCO, Cat No.: 10099-141) and penicillin/streptomycin (GIBCO, Cat No.: 15070-063)). The cells were collected by low temperature centrifugation at 4° C. for 5 min at 1000 rpm during the experiment. The cells were resuspended in 10-15 mL of FACS buffer pre-cooled on ice. The FACS buffer was composed of phosphate buffered saline (PBS), pH 7.4, with 2% fetal bovine serum (FBS). Throughout the experiment, FACS buffer was pre-cooled on ice. The cells were counted and centrifuged, and added to a 96-well plate at 300,000 cells/well. After centrifugation, the supernatant was discarded, and 12.5 μg/mL Fc blocking solution (BD, Cat No.: 564220) was added at 100 μL/well. Blocking was performed at room temperature for 10 min. Then, 20 μg/mL test ADC was added to the corresponding wells, and the plate was incubated at 4° C. for 1 h away from the light. The plate was washed twice with a pre-cooled PBS buffer to remove unbound ADCs. A complete cell culture medium (RPMI 1640 medium with 10% fetal bovine serum) was added, and the plate was incubated at 37° C. with 5% $CO_2$ for 0 h and 4 h. After centrifugation, the supernatant was discarded, 2% PFA buffer solution was added at 100 μL/well to resuspend the cells, and the plate was left to stand for 10 min. Then, the plate was washed 3 times with an FACS buffer, and 100 μL of secondary antibody solution (fluorescent labeled goat anti-human secondary antibody: diluted in a 1:250 ratio, 2 μg/mL, Biolegend, Cat #409304) was added. The plate was incubated at 4° C. for half an hour away from the light. A pre-cooled PBS buffer was added, and the supernatant was discarded after centrifugation at 4° C., which were repeated three times. The cells were resuspended in an FACS buffer at 200 μL/well and detected using a flow cytometer (BD FACS Calibur).

The results are shown in Table 11. Different ADCs have an endocytosis rate of more than 65% after incubation with DoHH2 cells for 4 h, and thus have good endocytosis ability. The endocytosis rate of each ADC was comparable to that of the positive drug Polivy.

TABLE 11

Endocytosis of different ADCs in DoHH2 cells

| $EC_{50}$ | Endocytosis rate (4 h) |
|---|---|
| ADC-1 | 73% |
| ADC-2 | 66% |
| ADC-3 | 70% |
| ADC-4 | 81% |
| ADC-5 | 76% |
| ADC-6 | 75% |
| ADC-7 | 68% |
| ADC-8 | 76% |

Example 4-3. Cell Proliferation Assay

This example was performed to evaluate the effect of different ADCs on the proliferation of DoHH2, WSU-DLCL2 and Raji cells cultured in vitro. According to literature reports (Leukemia. 2015 July; 29(7): 1578-1586; Blood. 2007 Jul. 15; 110(2): 616-623), DoHH2 is a CD79B high-expression cell, WSU-DLCL2 is a CD79B low-expression cell, and Raji is a CD79B negative-expression cell.

Experimental Materials:

ADC-1: colorless and clear liquid, at the concentration of 0.84 mg/mL and the purity of 99.17%;

ADC-2: colorless and clear liquid, at the concentration of 2.17 mg/mL and the purity of 97.93%;

ADC-3: colorless and clear liquid, at the concentration of 2.79 mg/mL and the purity of 98.28%;

ADC-4: colorless and clear liquid, at the concentration of 1.36 mg/mL and the purity of 98.48%;

ADC-5: colorless and clear liquid, at the concentration of 0.9 mg/mL and the purity of 98.49%;

ADC-6: colorless and clear liquid, at the concentration of 0.71 mg/mL and the purity of 98.71%;

ADC-7: colorless and clear liquid, at the concentration of 0.81 mg/mL and the purity of 98.27%;

ADC-8: colorless and clear liquid, at the concentration of 5.83 mg/mL and the purity of 97.07%.

Upon actual detection, DAR=3.06 for ADC-1, DAR=3.68 for ADC-2; DAR=3.09 for ADC-3; DAR=4.52 for ADC-4; DAR=1.81 for ADC-5; DAR=3.46 for ADC-6; DAR=5.84 for ADC-7; and DAR=3.59 for ADC-8.

The above drugs were all stored under sealed and shaded conditions at 4° C.

Cell strain: DoHH2 cells were purchased from DSMZ, WSU-DLCL-2 cells were purchased from American Type Culture Collection (ATCC), and Raji cells were purchased from American Type Culture Collection (ATCC).

Cells were cultured in an RPMI 1640 medium containing 10% fetal bovine serum (FBS).

Reagents and instruments: RPMI 1640 and FBS were purchased from Gibco; tetramethylazozole salt (3-(4,5-dimethyltriazol-2-yl)-2,5-diphenyltetrazolium bromide, MTT) was purchased from Sangon Biotech. Microplate reader was purchased from BioTek.

Experimental Procedures:

A certain number of cells in logarithmic growth phase were seeded into a 96-well culture plate, and drugs at different concentrations were added to the culture plate for reaction for 72 h. After the reaction was completed, an MTT working solution was added for reaction for 4 h, then blue-purple crystalline formazan was dissolved with a triplex solution. OD values at the wavelength of 570 nm and 690 nm were read using a microplate reader, and the cell growth inhibition rate was calculated by the following formula:

$$\text{Inhibition rate} = (\text{control well}_{OD570\ nm-OD690\ nm} - \text{dosing well}_{OD570\ nm-OD690\ nm}) / \text{control well}_{OD570\ nm-OD690\ nm} \times 100\%$$

From the inhibition rate at each concentration, the half maximal inhibitory concentration $IC_{50}$ was calculated using PrismGraph 8.

The results are shown in Table 12.

TABLE 12

Inhibitory activity of different ADCs to in vitro proliferation

| | | $IC_{50}$ (ng/ml) | | |
|---|---|---|---|---|
| Compound | Toxin | DoHH2 | WSU-DLCL2 | Raji |
| ADC-1 | tubulin | 2.1 | 3.2 | >10000 |
| ADC-2 | polymerization | 1.1 | 1.3 | >10000 |

TABLE 12-continued

Inhibitory activity of different ADCs to in vitro proliferation

| | | $IC_{50}$ (ng/ml) | | |
|---|---|---|---|---|
| Compound | Toxin | DoHH2 | WSU-DLCL2 | Raji |
| ADC-3 | inhibitor | 3.3 | 5.9 | >10000 |
| ADC-4 | | 1.7 | 3.7 | >10000 |
| ADC-5 | Topo I | 8.5 | 68.3 | >10000 |
| ADC-6 | inhibitor | 3.3 | 54.2 | >10000 |
| ADC-7 | | 2.0 | 53.4 | ~10000 |
| ADC-8 | tubulin polymerization inhibitor | 80.6 | 116.9 | >10000 |

Example 4-4. Efficacy of ADCs on Human Diffuse Large B-Cell Lymphoma WSU-DLCL2-Induced Nude Mouse Subcutaneous Xenograft Tumor This example was performed to evaluate and compare the efficacy of ADC drugs on nude mouse subcutaneous xenograft tumor.

hIgG1(HRP00252): colorless and clear liquid, at the concentration of 22.77 mg/mL and the purity of 99.03%, produced on Jul. 24, 2018 and expired by Jan. 24, 2020 (18 months tentatively); cryopreserved at −70° C.

1. Drugs: ADC-1, ADC-2, ADC-3, ADC-4, ADC-6 and ADC-8 were the same as those in Example 4-3.

2. Cells and mice: human diffuse large B-cell lymphoma WSU-DLCL2 cells were purchased from American Type Culture Collection. WSU-DLCL2 cells were cultured in a 10 cm petri dish with an RPMI 1640 culture medium (Gibco) containing 10% fetal bovine serum, penicillin and streptomycin and incubated in an incubator at 37° C. with 5% $CO_2$. Subculturing was performed 2-3 times a week, and cells were collected, counted and seeded when they were in exponential growth phase.

Nude mice, BALB/c-nu, 35 days of age, female, were purchased from Beijing Huafukang Biotechnology Co., Ltd, with production license number of SCXK (Beijing) 2019-0008, and animal certification number of 1103222011004014. Housing environment: SPF grade.

3. Experimental steps: each nude mouse was subcutaneously inoculated with $2.1\times10^7$ WSU-DLCL2 cells, and after the tumor volume reached 100-150 $mm^3$, the animals were grouped according to tumor volume (D0). The mice were administrated by intravenous injection (IV) at an administration volume of 10 mL/kg. Specific doses and administration regimen are shown in Table X. The tumor volumes and body weights were measured twice a week and the results were recorded.

4. Experimental index and statistical analysis:

The experimental index is to study the effect of the drug on the tumor growth, and the specific index is T/C % or tumor growth inhibition TGI (%).

Tumor diameters were measured twice a week with a vernier caliper and tumor volume (V) was calculated according to the following formula:

$V=\frac{1}{2}\times a\times b^2$, where $a$ and $b$ represent length and width, respectively.

T/C (%)=$(T-T_0)/(C-C_0)\times100$, where T and C represent the tumor volume of animals at the end of the experiment in the treatment group and control group, respectively; $T_0$ and $C_0$ represent the tumor volume of animals at the beginning of the experiment in the treatment group and control group, respectively; where T is the tumor volume of the ADC administered and C is the tumor volume of IgG1 administered as a control group.

Tumor growth inhibition % (TGI %)=100−$T/C$(%);

When tumor started to regress, tumor growth inhibition % (TGI %)=100−$(T-T_0)/T_0\times100$;

if the tumor had reduced volume compared with the initial volume, i.e., $T<T_0$ or $C<C_0$, it was defined as partial regression (PR) of tumor; if the tumor completely disappeared, it was defined as complete regression (CR) of tumor.

At the end of the experiment, at the experiment endpoint, or when the mean tumor volume in the solvent group reached 1500 $mm^3$, the animals were sacrificed by $CO_2$ anesthesia and dissected to give the tumors. The tumors were photographed. Unless otherwise indicated, comparison between tumor volumes of the two groups was made by two-way ANOVA test, with $P<0.05$ defined as statistically significant difference.

5. Results

ADC-1 (3 mg/kg and 10 mg/kg, IV, D0) inhibited the growth of WSU-DLCL2-induced nude mice subcutaneous xenograft tumor in a dose-dependent manner, with tumor growth inhibition rates of 75% and 137%, respectively, and with partial regression occurred in all tumors in the 10 mg/kg dose group;

the tumor growth inhibition rates of ADC-2 (3 mg/kg and 10 mg/kg, IV, D0) on WSU-DLCL2 were 76% and 123%, respectively, with partial regression occurred in all tumors in the 10 mg/kg dose group;

the tumor growth inhibition rate of ADC-3 (3 mg/kg, IV, D0) on WSU-DLCL2 was 76%, with partial regression occurred in 1/6 of the tumors;

the tumor growth inhibition rates of ADC-4 (3 mg/kg and 10 mg/kg, IV, D0) on WSU-DLCL2 were 95% and 129%, respectively, with partial regression occurred in 1/6 of tumors in the 3 mg/kg dose group and in 6/6 of tumors in 10 mg/kg dose group;

the tumor growth inhibition rate of ADC-6 (3 mg/kg, IV, D0) on WSU-DLCL2 was 86%, with partial regression occurred in 2/6 of the tumors;

the tumor growth inhibition rates of ADC-8 (3 mg/kg and 10 mg/kg, IV, D0) on WSU-DLCL2 were 39% and 93%, respectively, with partial regression occurred in 4/6 of tumors in the 10 mg/kg dose group.

The tumor-bearing mice were able to well tolerate all of the above drugs, and no symptoms such as significant weight loss were observed. IgG1 was used as negative control. The results are shown in Table 13 and FIGS. 13A-13C and 14.

TABLE 13

Efficacy of ADCs on WSU-DLCL2-induced nude mouse subcutaneous xenograft tumor

| Group | Route Time | Route of administration | Mean tumor volume ($mm^3$ ± SEM) D0 | D21 | T/C (%) D21 | Tumor growth inhibition (%) D21 | P value D21 | Partial regression | Number of animals at the beginning/end of experiment |
|---|---|---|---|---|---|---|---|---|---|
| IgG1 (10 mg/kg) | D0 | IV | 115.3 ± 2.8 | 821.3 ± 85.1 | — | — | — | — | 10/10 |
| ADC-1 (3 mg/kg) | D0 | IV | 113.6 ± 3.8 | 291.8 ± 71.6 | 25 | 75 | <0.0001 | 0 | 6/6 |
| ADC-1 (10 mg/kg) | D0 | IV | 116.7 ± 4.6 | 74.0 ± 3.3 | −37 | 137 | <0.0001 | 6 | 6/6 |
| ADC-2 (3 mg/kg) | D0 | IV | 119.4 ± 3.2 | 289.2 ± 24.5 | 24 | 76 | <0.0001 | 0 | 6/6 |
| ADC-2 (10 mg/kg) | D0 | IV | 110.8 ± 1.8 | 85.2 ± 4.2 | −23 | 123 | <0.0001 | 6 | 6/6 |
| ADC-3 (3 mg/kg) | D0 | IV | 114.4 ± 2.9 | 284.8 ± 50.0 | 24 | 76 | <0.0001 | 1 | 6/6 |
| ADC-4 (3 mg/kg) | D0 | IV | 114.8 ± 3.8 | 151.5 ± 18.7 | 5 | 95 | <0.0001 | 1 | 6/6 |
| ADC-4 (10 mg/kg) | D0 | IV | 115.4 ± 4.9 | 82.5 ± 3.0 | −29 | 129 | <0.0001 | 6 | 6/6 |
| ADC-6 (3 mg/kg) | D0 | IV | 118.1 ± 4.5 | 217.4 ± 80.3 | 14 | 86 | <0.0001 | 2 | 6/6 |
| ADC-8 (3 mg/kg) | D0 | IV | 117.6 ± 3.0 | 547.2 ± 38.1 | 61 | 39 | <0.0001 | 0 | 6/6 |
| ADC-8 (10 mg/kg) | D0 | IV | 115.0 ± 3.7 | 167.8 ± 50.3 | 7 | 93 | <0.0001 | 4 | 6/6 |

D0: time of the first administration; P value: obtained by comparison to the solvent; IV: intravenous injection; partial regression: tumor volume on D21 was less than that on D0.

6. Conclusion

ADC-1, ADC-2, ADC-3, ADC-4, ADC-6 and ADC-8 (3 mg/kg or 10 mg/kg, single intravenous injection) all have significant efficacy on WSU-DLCL2-induced nude mouse subcutaneous xenograft tumor, and cause partial regression in tumors; the drugs have significant dose dependence, and the efficacy of each ADC is better than that of the positive drug ADC-8 (namely Polivy) at an equal dose. The tumor-bearing mice can well tolerate all of the above drugs.

Example 4-5. Efficacy of ADCs on Human Diffuse Large B-Cell Lymphoma WSU-DLCL2-Induced Nude Mouse Subcutaneous Xenograft Tumor This example was performed to further evaluate and compare the efficacy of ADC drugs on WSU-DLCL2-induced nude mouse subcutaneous xenograft tumor.

1. Drugs: ADC-5, ADC-6, ADC-7, ADC-1 and ADC-8 drugs were diluted with normal saline to the concentrations described in Example 4-3, respectively.

2. Cells and mice: same as those in Example 4-4.

3. Experimental steps: each nude mouse was subcutaneously inoculated with $2\times10^7$ WSU-DLCL2 cells, and after the tumor volume reached 100-150 $mm^3$, the animals were grouped according to tumor volume (D0). The mice were administrated by intravenous injection (IV) at an administration volume of 10 mL/kg. Specific doses and administration regimen are shown in Table 12. The tumor volumes and body weights were measured twice a week and the results were recorded.

4. The experimental index was the same as that in Example 4-4, and the statistical analysis was as follows:

Unless otherwise indicated, comparison between tumor volumes of the two groups was made by two-tailed Student's t-test, with $P<0.05$ defined as statistically significant difference.

5. Results

The tumor growth inhibition rates of ADC-5 (3 mg/kg, 6 mg/kg, and 12 mg/kg, IV, D0) on WSU-DLCL2-induced nude mouse subcutaneous xenograft tumor were 69%, 86% and 88%, respectively, with partial regression occurred in 1/6 of tumors in the 6 mg/kg dose group and in 1/6 of tumors in 12 mg/kg dose group; the tumor growth inhibition rates of ADC-6 (1.5 mg/kg, 3 mg/kg, and 6 mg/kg, IV, D0) on WSU-DLCL2-induced subcutaneous xenograft tumor were 66%, 108% and 125%, respectively, with partial regression occurred in 5/6 of tumors in the 3 mg/kg dose group and 6/6 of tumors in the 6 mg/kg dose group;

the tumor growth inhibition rate of ADC-7 (1 mg/kg, IV, D0) on WSU-DLCL2-induced subcutaneous xenograft tumor was 910%, with partial regression occurred in 1/6 of tumors; the tumor growth inhibition rate of ADC-1 (3 mg/kg, IV, D0) on WSU-DLCL2-induced subcutaneous xenograft tumor was 44%;

the tumor growth inhibition rate of ADC-8 (3 mg/kg, IV, D0) on WSU-DLCL2-induced subcutaneous xenograft tumor was 10%.

The tumor-bearing mice were able to well tolerate all of the above drugs, and no symptoms such as weight loss were observed.

Figure 15:
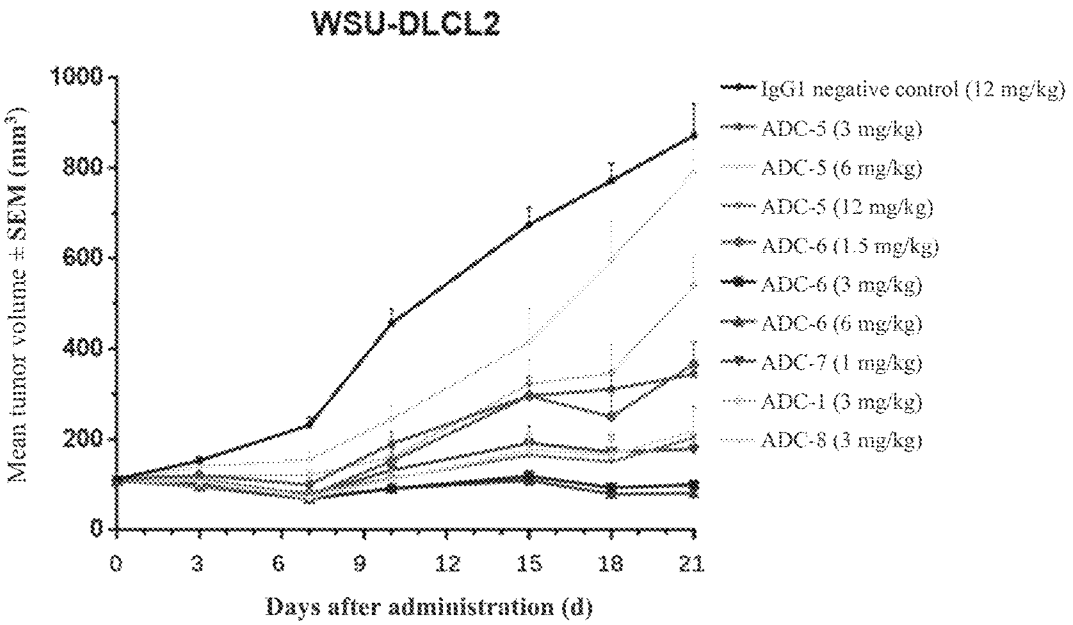
FIG. 15: efficacy of different ADCs on human diffuse large B-cell lymphoma WSU-DLCL2-induced nude mouse subcutaneous xenograft tumor.
Figure 16:
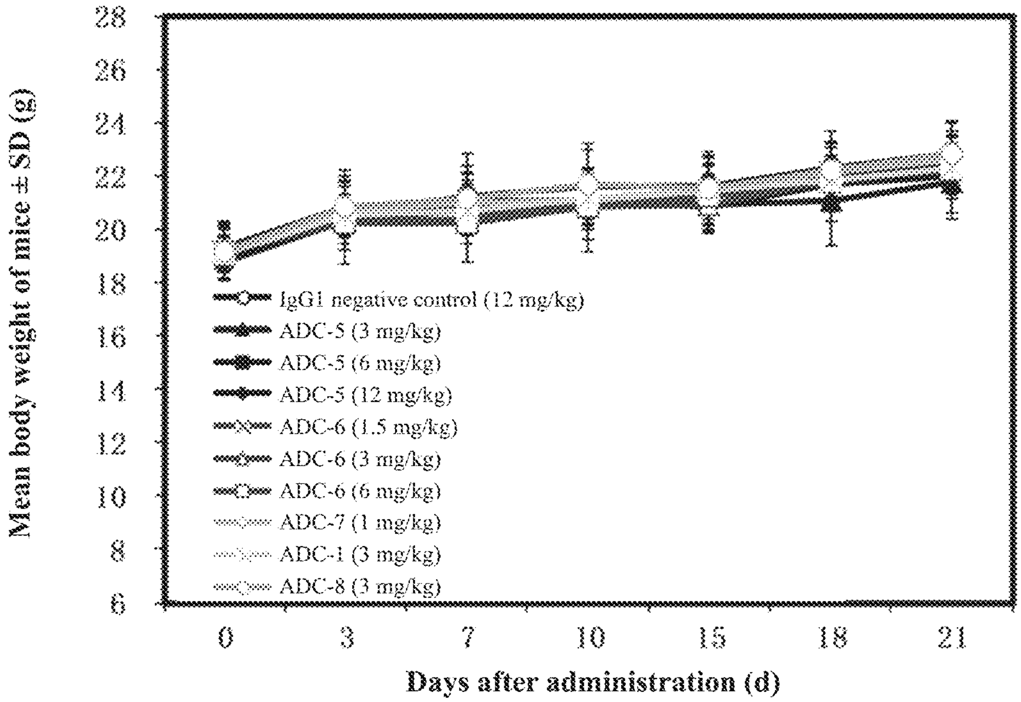
FIG. 16: effect of different ADCs on body weight of WSU-DLCL2 tumor-bearing nude mice.
Figure 17:
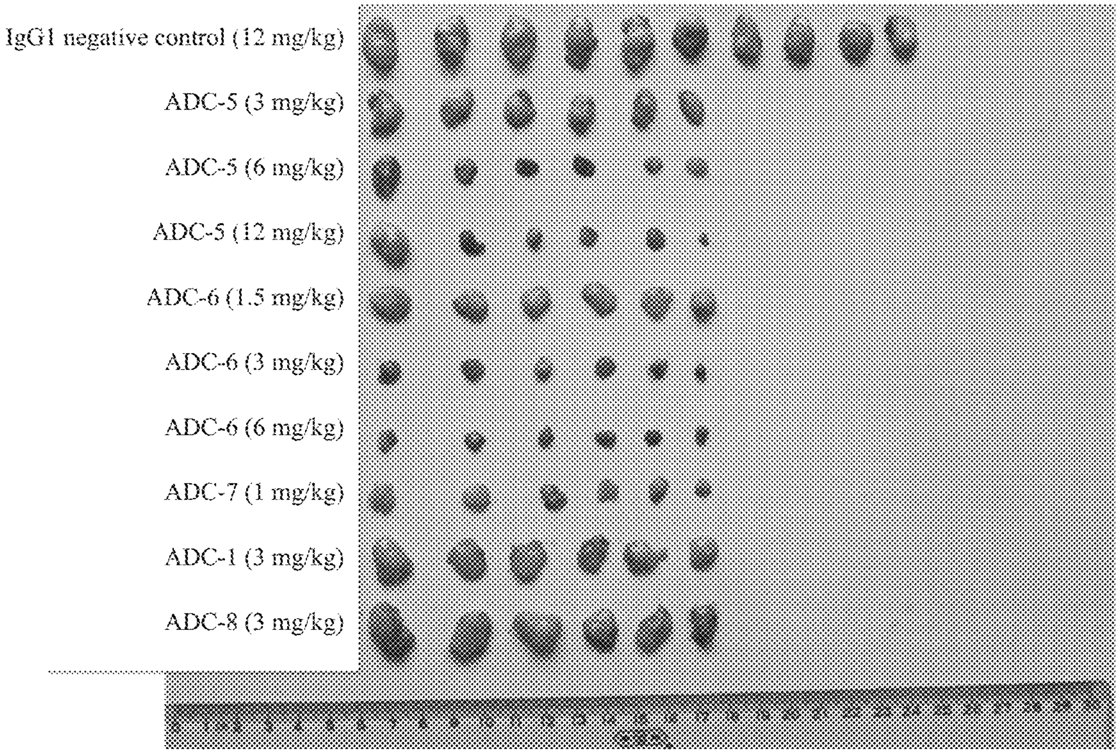
FIG. 17: tumor photographs showing efficacy of different ADCs on human diffuse large B-cell lymphoma WSU-DLCL2-induced nude mice subcutaneous xenograft tumor.

The specific results are shown in Table 14 and FIGS. 15-17.

TABLE 14

Administration regimen and results

| Group | Time point of administration | Route of administration | Mean tumor volume ($mm^3$) D0 | Mean volume tumor ($mm^3$) SEM | D21 | SEM | % T/C D21 | % Tumor growth inhibition D21 | P value D21 | Partial regression | Number of animals in each group at the beginning of experiment | Number of animals in each group at the end of experiment |
|---|---|---|---|---|---|---|---|---|---|---|---|---|
| IgG1 negative control (12 mg/kg) | D0 | IV | 111.9 | ±2.2 | 872.1 | ±70.0 | — | — | — | 0 | 10 | 10 |
| ADC-5 (3 mg/kg) | D0 | IV | 111.0 | ±20 | 343.7 | ±31.4 | 31 | 69 | 0.000 | 0 | 6 | 6 |
| ADC-5 (6 mg/kg) | D0 | IV | 110.8 | ±17 | 218.5 | ±43.7 | 14 | 86 | 0.000 | 1 | 6 | 6 |
| ADC-5 (12 mg/kg) | D0 | IV | 111.3 | ±3.0 | 203.6 | ±68.3 | 12 | 88 | 0.000 | 1 | 6 | 6 |
| ADC-6 (1.5 mg/kg) | D0 | IV | 109.7 | ±0.9 | 366.3 | ±49.9 | 34 | 66 | 0.000 | 0 | 6 | 6 |
| ADC-6 (3 mg/kg) | D0 | IV | 108.6 | ±2.5 | 99.4 | ±9.3 | −8 | 108 | 0.000 | 5 | 6 | 6 |
| ADC-6 (6 mg/kg) | D0 | IV | 108.7 | ±1.5 | 81.2 | ±3.4 | −25 | 125 | 0.000 | 6 | 6 | 6 |
| ADC-7 (1 mg/kg) | D0 | IV | 107.0 | ±0.8 | 178.1 | ±25.7 | 9 | 91 | 0.000 | 1 | 6 | 6 |
| ADC-1 (3 mg/kg) | D0 | IV | 113.0 | ±2.6 | 541.8 | ±68.8 | 56 | 44 | 0.007 | 0 | 6 | 6 |
| ADC-8 (3 mg/kg) | D0 | IV | 105.0 | ±1.4 | 792.6 | ±75.9 | 90 | 10 | 0.505 | 0 | 6 | 6 |

D0: time of the first administration; P value: obtained by comparison to the solvent; IV: intravenous injection.

Example 4-6. Efficacy of ADCs on Human B-Cell Lymphoma DoHH2-Induced Nude Mouse Subcutaneous Xenograft Tumor This example was performed to further evaluate and compare the efficacy of ADC drugs on DoHH2-induced nude mouse subcutaneous xenograft tumor.

1. Drugs: ADC-1, ADC-6 and ADC-8 drugs were diluted with normal saline to the concentrations described in Example 4-3, respectively.

2. Cells and mice: DOHH-2 cells were purchased from DSMZ, Germany. DOHH-2 cells were cultured in a 10 cm petri dish with an RPMI 1640 culture medium (Gibco) containing 10% fetal bovine serum, penicillin and streptomycin and incubated in an incubator at 37° C. with 5% $CO_2$. Subculturing was performed 2-3 times a week, and cells were collected, counted and seeded when they were in exponential growth phase.

Nude mice, BALB/c-nu, 4-5 weeks of age, female, were purchased from Shanghai Lingchang Biotechnology Co., Ltd, with production license number of SCXK (Shanghai) 2018-0003, and animal certification number of 20180003010222. Housing environment: SPF grade.

3. Experimental steps: each nude mouse was subcutaneously inoculated with $3\times10^7$ DOHH-2 cells, and after the tumor volume reached 100-150 $mm^3$, the animals were grouped according to tumor volume (D0). The mice were administrated by intravenous injection (IV) at an administration volume of 10 mL/kg. Specific doses and administration regimen are shown in Table 15. The tumor volumes and body weights were measured twice a week and the results were recorded.

4. Experimental index and statistical analysis:

The experimental index is to study the effect of the drug on the tumor growth, and the specific index is T/C % or tumor growth inhibition TGI (%).

Tumor diameters were measured twice a week with a vernier caliper and tumor volume (V) was calculated according to the following formula:

$V=\frac{1}{2}\times a\times b^2$ where $a$ and $b$ represent length and width, respectively.

T/C (%)=(T−$T_0$)/(C−$C_0$)×100 where T and C represent the tumor volume of animals at the end of the experiment in the treatment group and control group, respectively; $T_0$ and $C_0$ represent the tumor volume of animals at the beginning of the experiment in the treatment group and control group, respectively; where T is the tumor volume of the ADC administered and C is the tumor volume of IgG1 administered as a control group.

Tumor growth inhibition % (TGI %)=100−$T/C$(%);

when tumor started to regress, tumor growth inhibition % (TGI %)=100−(T−$T_0$)/$T_0$×100;

if the tumor had reduced volume compared with the initial volume, i.e., $T<T_0$ or $C<C_0$, it was defined as partial regression (PR) of tumor; if the tumor completely disappeared, it was defined as complete regression (CR) of tumor.

At the end of the experiment, at the experiment endpoint, or when the mean tumor volume in the solvent group reached 1500 $mm^3$, the animals were sacrificed by $CO_2$ anesthesia and dissected to give the tumors. The tumors were photographed.

Unless otherwise indicated, comparison between tumor volumes of the two groups was made by two-way ANOVA test, with $P<0.05$ defined as statistically significant difference.

5. Results

The tumor growth inhibition rates of ADC-1, ADC-6 and ADC-8 (1 mg/kg, IV, D0) on DOHH-2-induced nude mouse subcutaneous xenograft tumor were 82% (1/6 PR), 127% (5/6 PR) and 41%, respectively; the tumor-bearing mice were able to well tolerate the above drugs, and no symptoms such as significant weight loss were observed.

Figure 18:
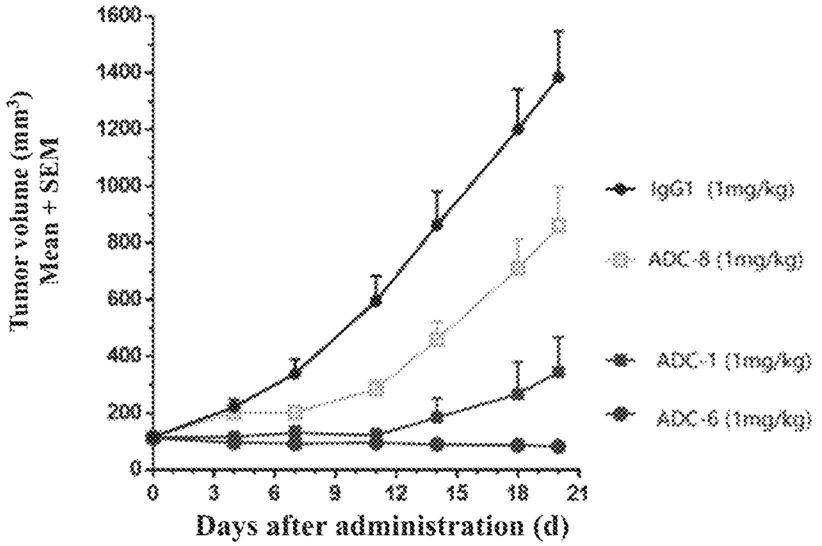
FIG. 18: efficacy of different ADCs on human follicular lymphoma DOHH-2-induced nude mouse subcutaneous xenograft tumor.
Figure 19:
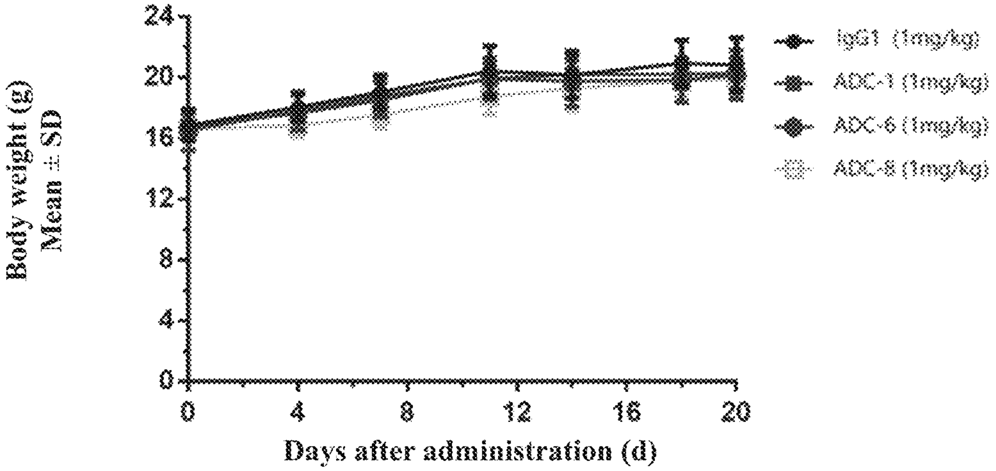
FIG. 19: effect of different ADCs on body weight of DOHH-2 tumor-bearing nude mice.

The results are shown in Table 15 and FIGS. 18 and 19.

TABLE 15

Efficacy of different ADCs on human follicular lymphoma DOHH-2-induced nude mouse subcutaneous xenograft tumor

| Group | Time point of administration | Route of administration | Mean tumor volume ($mm^3$) D0 | SEM | Mean tumor volume ($mm^3$) D20 | SEM | T/C (%) D20 | Tumor growth inhibition (%) D20 | P value D20 | Partial regression | Number of animals in each group at the beginning/ end of experiment |
|---|---|---|---|---|---|---|---|---|---|---|---|
| IgG1 (1 mg/kg) | D0 | IV | 115.7 | ±2.7 | 1385.4 | ±162.1 | — | — | — | 0 | 10/10 |
| ADC-1 (1 mg/kg) | D0 | IV | 113.7 | ±3.3 | 345.0 | ±122.5 | 18 | 82 | 0.000 | 1 | 6/6 |
| ADC-6 (1 mg/kg) | D0 | IV | 112.9 | ±3.5 | 82.4 | ±6.3 | −27 | 127 | 0.000 | 5 | 6/6 |
| ADC-8 (1 mg/kg) | D0 | IV | 117.1 | ±3.5 | 862.1 | ±136.6 | 59 | 41 | 0.042 | 0 | 6/6 |

D0: time of the first administration; P value: obtained by comparison to the solvent; IV: intravenous injection; partial regression: tumor volume on D21 was less than that on D0.

6. Conclusion

ADC-1 and ADC-6 (1 mg/kg, single intravenous injection) have significant efficacy on human follicular lymphoma DoHH2-induced nude mouse subcutaneous xenograft tumor, and cause partial regression in tumors; the efficacy of both drugs is better than that of positive drug ADC-8 (namely Polivy). The tumor-bearing mice can well tolerate all of the above drugs.

The use and welfare of the laboratory animals in the present disclosure were carried out in compliance with the provisions of Association for Assessment and Accreditation of Laboratory Animal Care, International (AAALAC). The health and death of the animals were monitored daily, and routine examinations included observation of the effects of the test substance and drug on the daily performance of the animals, such as behavioral activities, weight changes and appearance.

The invention claimed is:

1. A ligand-drug conjugate or a pharmaceutically acceptable salt or solvate thereof, wherein:

the drug is selected from the group consisting of a tubulin polymerization inhibitor, a Topo I inhibitor, and MMAE or a derivative thereof; and the ligand is an anti-CD79B antibody or an antigen-binding fragment thereof comprising:

a heavy chain HCDR1 comprising a sequence set forth in SEQ ID NO: 24;

a heavy chain HCDR2 comprising a sequence set forth in SEQ ID NO: 25;

a heavy chain HCDR3 comprising a sequence set forth in SEQ ID NO: 26;

a light chain LCDR1 comprising a sequence set forth in SEQ ID NO: 27;

a light chain LCDR2 comprising a sequence set forth in SEQ ID NO: 11 or SEQ ID NO: 17; and a light chain LCDR3 comprising a sequence set forth in SEQ ID NO: 12 or SEQ ID NO: 18.

2. The ligand-drug conjugate or the pharmaceutically acceptable salt or solvate thereof according to claim 1, wherein the anti-CD79B antibody or the antigen-binding fragment thereof comprises:

a) a HCDR1, a HCDR2 and a HCDR3 set forth in SEQ ID NOs: 23, 8 and 9, respectively, and a LCDR1, a LCDR2 and a LCDR3 set forth in SEQ ID NOs: 10, 11 and 12, respectively;

b) a HCDR1, a HCDR2 and a HCDR3 set forth in SEQ ID NOs: 7, 8 and 9, respectively, and a LCDR1, a LCDR2 and a LCDR3 set forth in SEQ ID NOs: 10, 11 and 12, respectively; or c) a HCDR1, a HCDR2 and a HCDR3 set forth in SEQ ID NOs: 13, 14 and 15, respectively, and a LCDR1, a LCDR2 and a LCDR3 set forth in SEQ ID NOs: 16, 17 and 18, respectively.

3. The ligand-drug conjugate or the pharmaceutically acceptable salt or solvate thereof according to claim 1, wherein the anti-CD79B antibody or the antigen-binding fragment thereof is a murine antibody, a chimeric antibody, a humanized antibody, or a fragment thereof.

4. The ligand-drug conjugate or the pharmaceutically acceptable salt or solvate thereof according to claim 1, wherein the anti-CD79B antibody or the antigen-binding fragment thereof comprises:

a heavy chain variable region set forth in SEQ ID NO: 3 or having at least 90% identity thereto, and a light chain variable region set forth in SEQ ID NO: 4 or having at least 90% identity thereto;

or, a heavy chain variable region set forth in SEQ ID NO: 5 or having at least 90% identity thereto, and a light chain variable region set forth in SEQ ID NO: 6 or having at least 90% identity thereto;

or, a heavy chain variable region set forth in SEQ ID NO: 19 or having at least 90% identity thereto, and a light chain variable region set forth in SEQ ID NO: 20 or having at least 90% identity thereto;

or, a heavy chain variable region set forth in SEQ ID NO: 21 or having at least 90% identity thereto, and a light chain variable region set forth in SEQ ID NO: 22 or having at least 90% identity thereto.

5. The ligand-drug conjugate or the pharmaceutically acceptable salt or solvate thereof according to claim 1, wherein the anti-CD79B antibody or the antigen-binding fragment thereof is an scFv, Fv, Fab or Fab' fragment.

6. The ligand-drug conjugate or the pharmaceutically acceptable salt or solvate thereof according to claim 1, wherein the anti-CD79B antibody or the antigen-binding fragment thereof comprises:

a heavy chain set forth in SEQ ID NO: 28 or having at least 90% identity thereto, and a light chain set forth in SEQ ID NO: 29 or having at least 90% identity thereto;

or a heavy chain set forth in SEQ ID NO: 30 or having at least 90% identity thereto, and a light chain set forth in SEQ ID NO: 31 or having at least 90% identity thereto.

7. The ligand-drug conjugate or the pharmaceutically acceptable salt or solvate thereof according to claim 1, wherein the ligand-drug conjugate or the pharmaceutically acceptable salt or solvate thereof comprises formula (I) or a pharmaceutically acceptable salt or solvate thereof:

wherein:

W is selected from the group consisting of $C_{1-8}$ alkyl, $C_{1-8}$ alkyl-cycloalkyl and linear heteroalkyl of 1 to 8 atoms, the heteroalkyl comprising 1 to 3 heteroatoms selected from the group consisting of N, O and S, wherein the $C_{1-8}$ alkyl, cycloalkyl and linear heteroalkyl are each independently and optionally further substituted with one or more substituents selected from the group consisting of halogen, hydroxy, cyano, amino, alkyl, chloroalkyl, deuterated alkyl, alkoxy and cycloalkyl;

$L^2$ is selected from the group consisting of $-NR^4(CH_2CH_2O)p^1CH_2CH_2C(O)-$, $—NR^4(CH_2CH_2O)p^1CH_2C(O)-$, $-S(CH_2)p^1C(O)-$ and a chemical bond, wherein p1 is an integer from 1 to 20;

$L^3$ is a peptide residue consisting of 2 to 7 amino acids, wherein the amino acids are optionally substituted with one or more substituents selected from the group consisting of halogen, hydroxy, cyano, amino, alkyl, chloroalkyl, deuterated alkyl, alkoxy and cycloalkyl;

$R^1$ is selected from the group consisting of hydrogen atom, halogen, cycloalkylalkyl, deuterated alkyl, cycloalkyl, heterocyclyl, aryl and heteroaryl;

$R^2$ is selected from the group consisting of hydrogen atom, halogen, haloalkyl, deuterated alkyl, cycloalkyl, heterocyclyl, aryl and heteroaryl;

or, $R^1$ and $R^2$, together with the carbon atom to which they are attached, form cycloalkyl or heterocyclyl;

$R^4$ and $R^5$ are identical or different and are each independently selected from the group consisting of hydrogen atom, alkyl, haloalkyl, deuterated alkyl and hydroxyalkyl;

$R^6$ and $R^7$ are identical or different and are each independently selected from the group consisting of hydrogen atom, halogen, alkyl, haloalkyl, deuterated alkyl and hydroxyalkyl;

m is an integer from 0 to 4;

n is 1 to 10 and can be an integer or a decimal; and

Pc is the anti-CD79B antibody or the antigen-binding fragment thereof as defined in claim 1.

8. The ligand-drug conjugate or the pharmaceutically acceptable salt or solvate thereof according to claim 1, wherein the ligand-drug conjugate or the pharmaceutically acceptable salt or solvate thereof comprises a structural formula selected from the group consisting of:

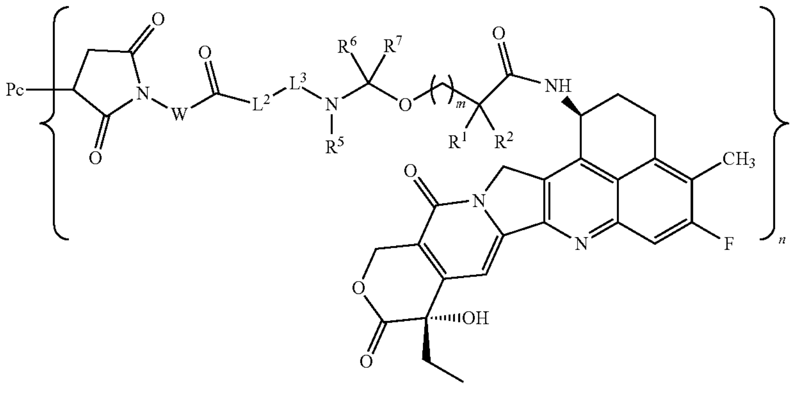

formula (I)

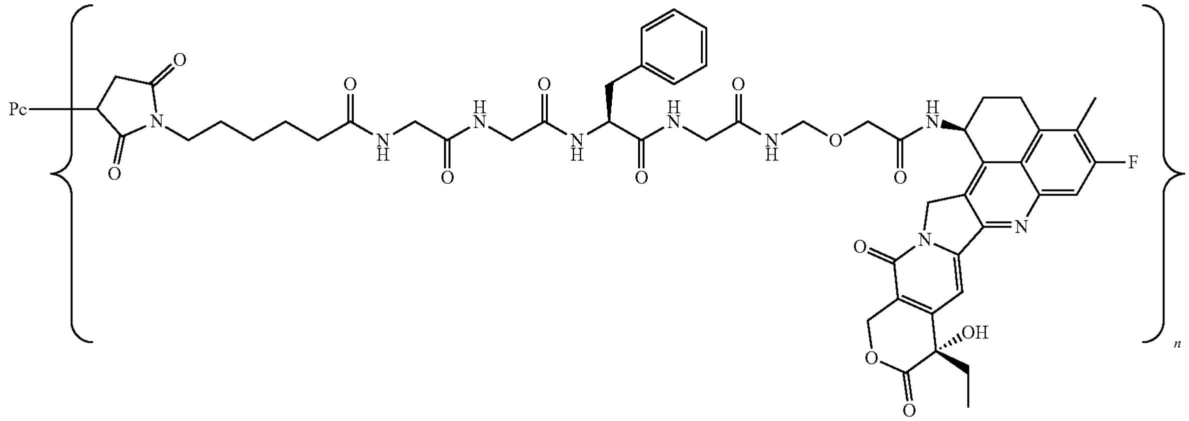
,
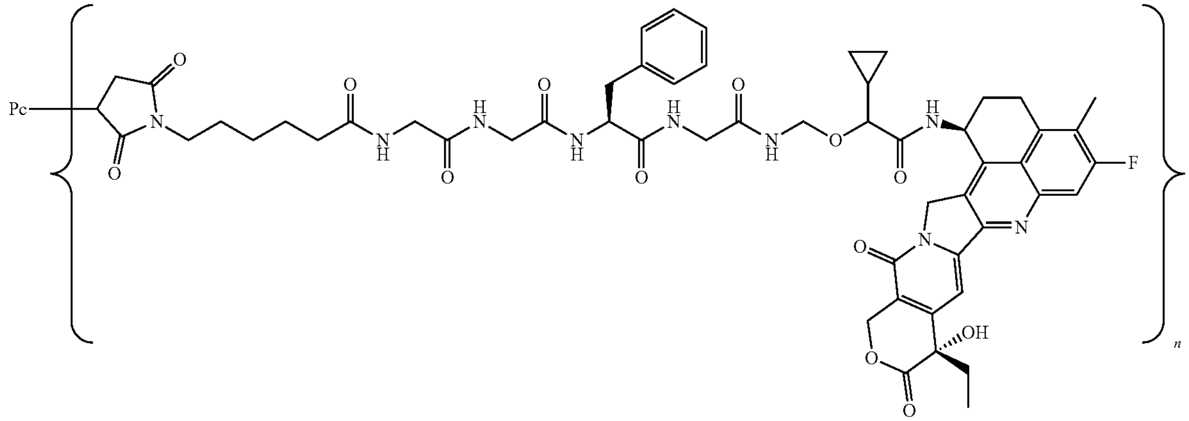
,
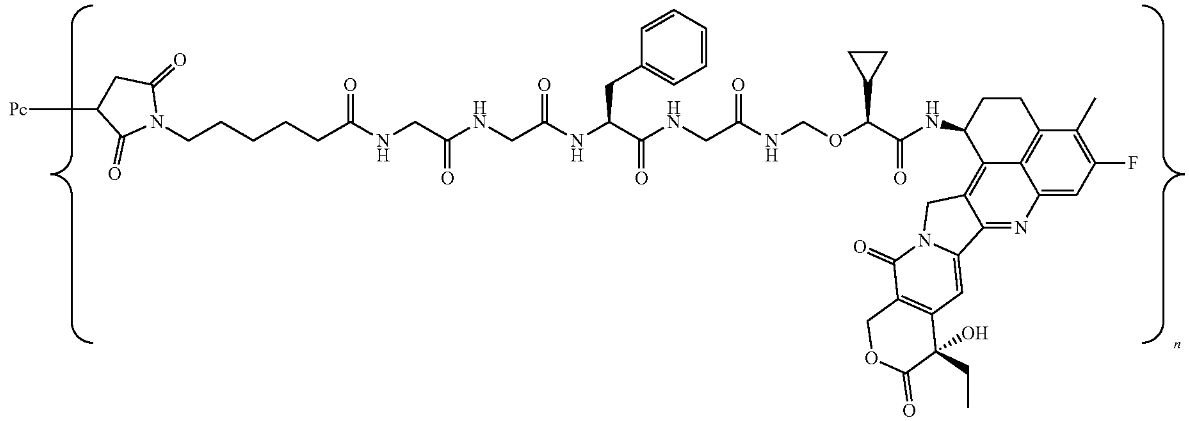
,
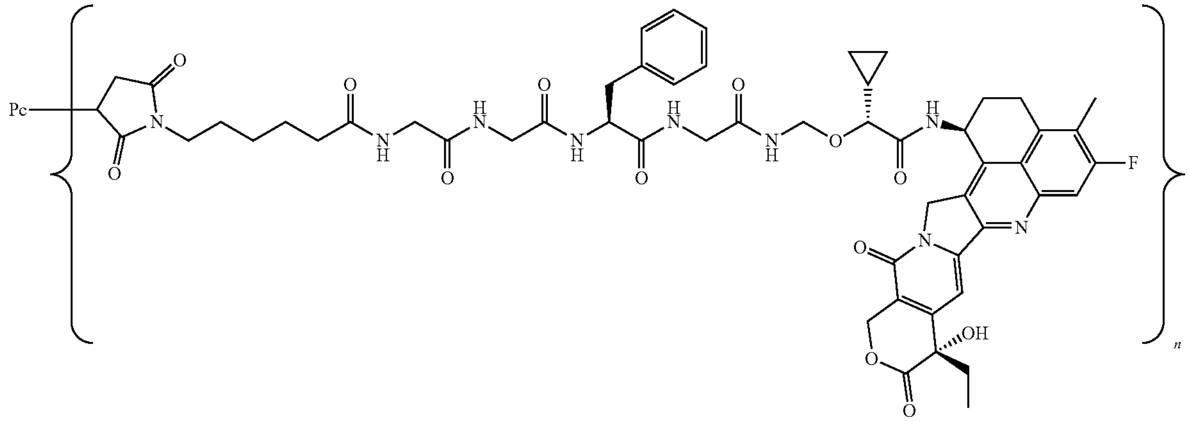
, wherein:

n is 1 to 10 and can be an integer or a decimal; and

Pc is the anti-CD79B antibody or the antigen-binding fragment thereof as defined in claim 1.

9. A method for preparing the ligand-drug conjugate or the pharmaceutically acceptable salt or solvate thereof according to claim 1, comprising: step:

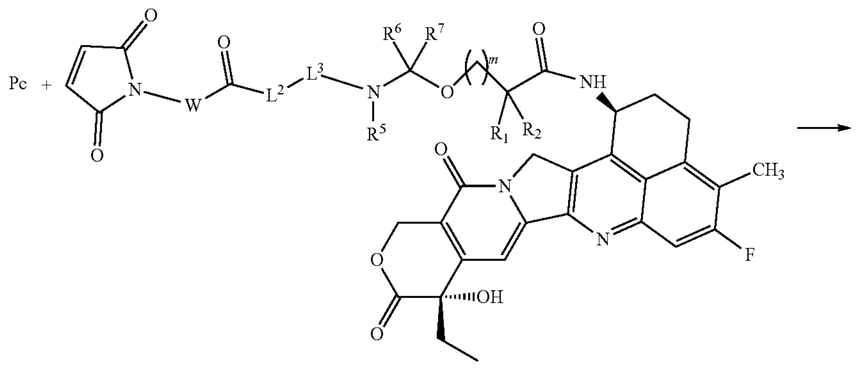

formula (VIII)

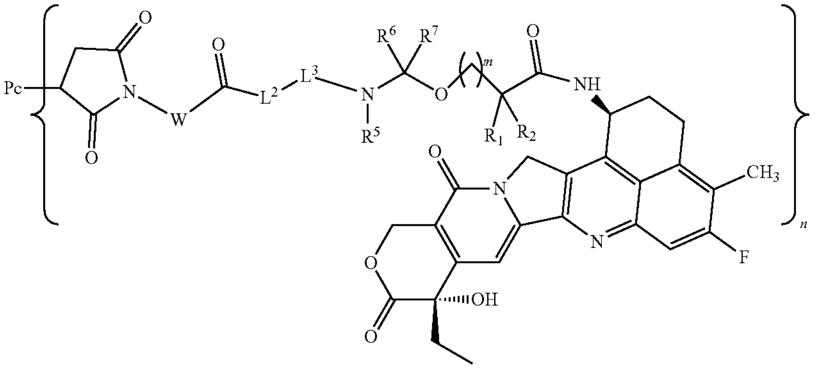

formula (I)

subjecting reduced Pc to a coupling reaction with a compound of general formula to give a ligand-drug conjugate of general formula;

wherein:

Pc is the anti-CD79B antibody or the antigen-binding fragment thereof as defined in claim 1; and W, $L^2$, $L^3$, $R^1$, $R^2$, $R^5$, $R^6$, $R^7$, m and n are as defined in claim 7.

10. The ligand-drug conjugate or the pharmaceutically acceptable salt or solvate thereof according to claim 1, comprising a structure as shown in general formula Pc-(L-D)$_k$, wherein:

Pc is the anti-CD79B antibody or the antigen-binding fragment thereof as defined in claim 1;

L is a linker;

k is an integer or a decimal from 1 to 20; and

D is as shown in formula (III):

formula (III)

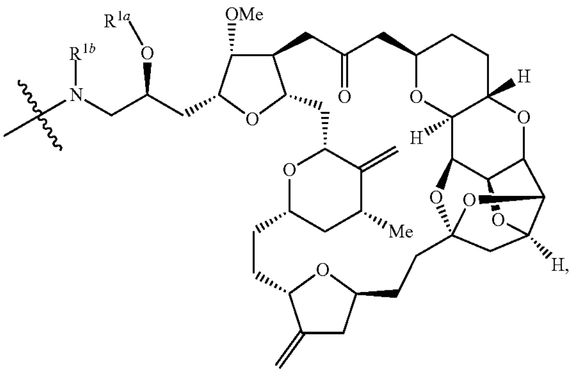

wherein, $R^{1a}$ is selected from the group consisting of hydrogen, alkyl, cycloalkyl, aryl and heteroaryl, wherein the alkyl, cycloalkyl, aryl and heteroaryl are each independently and optionally substituted with one or more substituents selected from the group consisting of alkyl, alkoxy, halogen, deuterium, amino, cyano, nitro, hydroxy, hydroxyalkyl, cycloalkyl, heterocyclyl, aryl and heteroaryl; preferably, $R^{1a}$ is methyl;

$R^{1b}$ is selected from the group consisting of hydrogen, alkyl, alkoxy, cycloalkyl, aryl and heteroaryl, wherein the alkyl, cycloalkyl, aryl and heteroaryl are each independently and optionally substituted with one or more substituents selected from the group consisting of alkyl, alkoxy, halogen, deuterium, amino, cyano, nitro, hydroxy, hydroxyalkyl, cycloalkyl, heterocyclyl, aryl and heteroaryl; preferably, $R^{1b}$ is hydrogen; or $R^{1a}$ and $R^{1b}$, together with the atom to which they are attached, form $C_{5-8}$ heterocycloalkyl, wherein the heterocycloalkyl is optionally substituted with one or more substituents of alkyl, alkoxy, halogen, deuterium, amino, cyano, nitro, hydroxy, hydroxyalkyl, cycloalkyl, heterocyclyl, aryl and heteroaryl; and $R^{1a}$ and $R^{1b}$ are not both hydrogen.

11. The ligand-drug conjugate or the pharmaceutically acceptable salt or solvate thereof according to claim 10, comprising any one of structures selected from the group consisting of the followings:

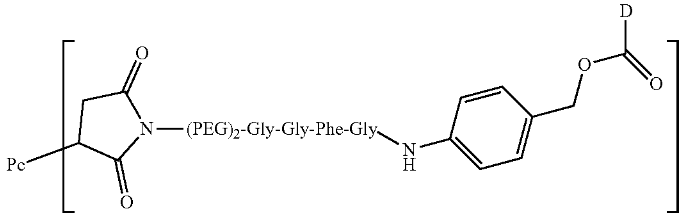
k,

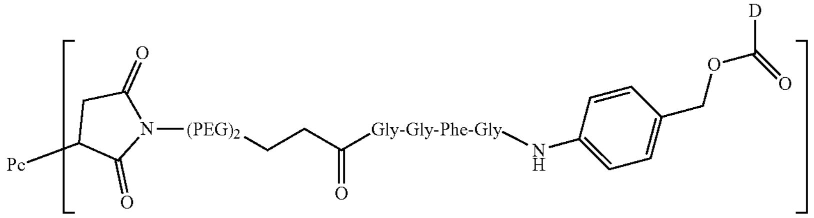
k,

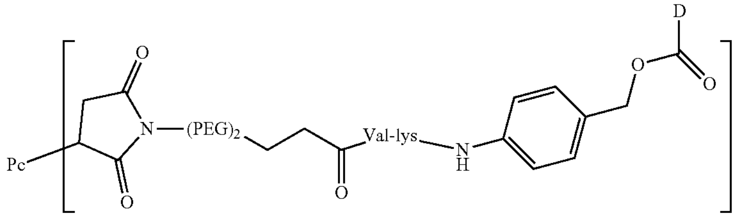
k,

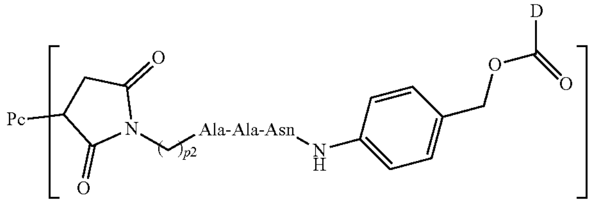
k, wherein k is selected from the group consisting of 1 to 10, and can be an integer or a decimal;

in D, $R^{1a}$ is methyl and $R^{1b}$ is hydrogen; and Pc is the anti-CD79B antibody or the antigen-binding fragment thereof as defined in claim 1.

12. The ligand-drug conjugate or the pharmaceutically acceptable salt or solvate thereof according to claim 1, as shown in formula (IV):

formula (IV)

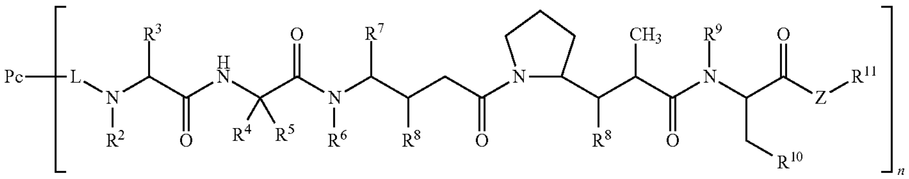

wherein, $R^2$ is $C_1$-$C_8$ alkyl;

$R^3$ is $C_1$-$C_8$ alkyl;

$R^4$ is $C_1$-$C_8$ alkyl;

$R^5$ is H;

$R^6$ is $C_1$-$C_8$ alkyl;

$R^7$ is $C_1$-$C_8$ alkyl;

$R^8$ are each independently O-($C_1$-$C_8$alkyl);

$R^9$ is H;

$R^{10}$ is phenyl;

Z is O or NH;

$R^{11}$ is selected from the group consisting of H, $C_1$-$C_{20}$ alkyl and —($R^{13}O)_3$-$R^{14}$;

$R^{13}$ is $C_2$-$C_8$ alkyl;

$R^{14}$ is $C_1$-$C_8$ alkyl;

Pc is the anti-CD79B antibody or the antigen-binding fragment thereof as defined in claim 1;

L is a linker; and n is 1 to 10 and can be an integer or a decimal.

13. The ligand-drug conjugate or the pharmaceutically acceptable salt or solvate thereof according to claim 12, comprising a structure as shown below:

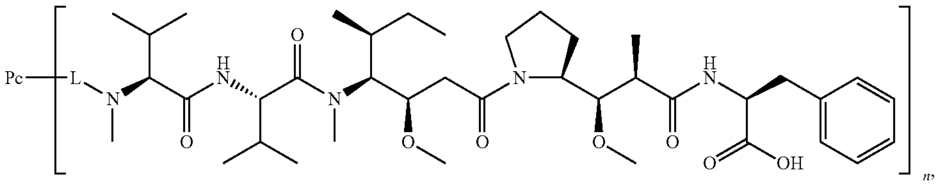

wherein,

Pc is the anti-CD79B antibody or the antigen-binding fragment thereof as defined in claim 1;

n is 1 to 10 and can be an integer or a decimal; and the linker is selected from the group consisting of:

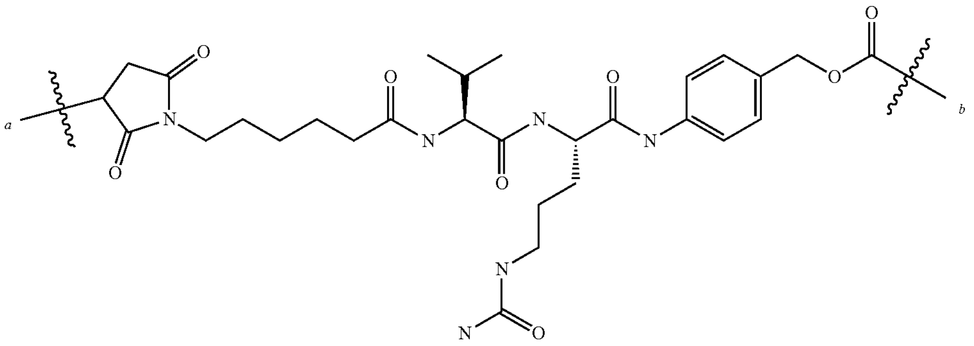

and

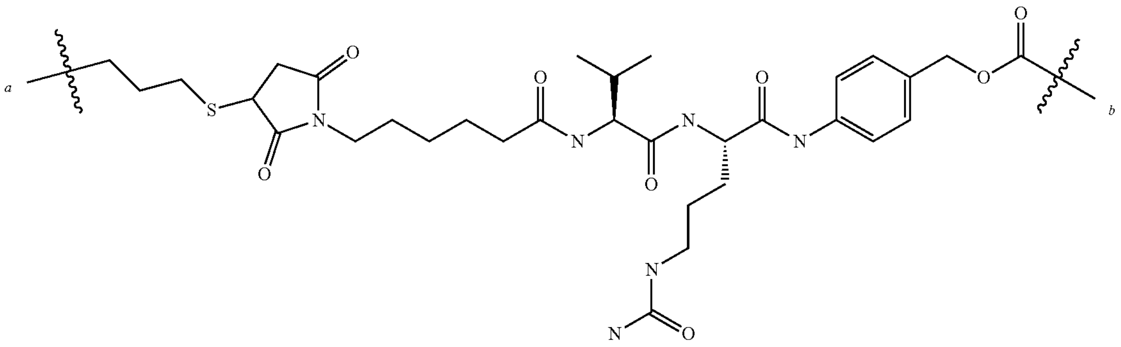

wherein the end a is linked to the Pc, and the end b is linked to the drug.

14. The ligand-drug conjugate or the pharmaceutically acceptable salt or solvate thereof according to claim 1, comprising a structure as shown in formula (V):

formula (V)

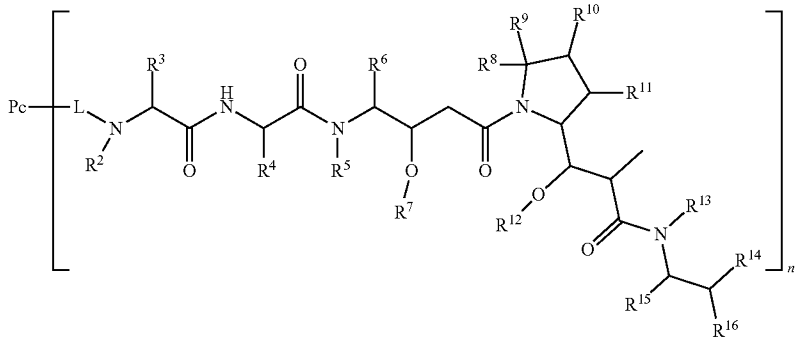

wherein $R^2$-$R^6$ are selected from the group consisting of hydrogen atom, halogen, hydroxy, cyano, alkyl, alkoxy and cycloalkyl;

$R^7$ is selected from the group consisting of hydrogen, alkyl, alkoxy and cycloalkyl;

any two of $R^8$-$R^{11}$ form cycloalkyl, and the remaining two groups are selected from the group consisting of hydrogen atom, alkyl and cycloalkyl;

$R^{12}$ is selected from the group consisting of hydrogen atom and alkyl;

$R^{13}$-$R^{15}$ are selected from the group consisting of hydrogen atom, hydroxy, alkyl, alkoxy and halogen;

$R^{16}$ is selected from the group consisting of aryl and heteroaryl, wherein the aryl and heteroaryl are optionally substituted with a substituent selected from the group consisting of hydrogen atom, halogen, hydroxy, alkyl, alkoxy and cycloalkyl;

n is 1 to 10 and can be an integer or a decimal;

Pc is the anti-CD79B antibody or the antigen-binding fragment thereof as defined in claim 1; and L is a linker.

15. The ligand-drug conjugate or the pharmaceutically acceptable salt or solvate thereof according to claim 14, comprising a structure selected from the group consisting of following structural formulas:

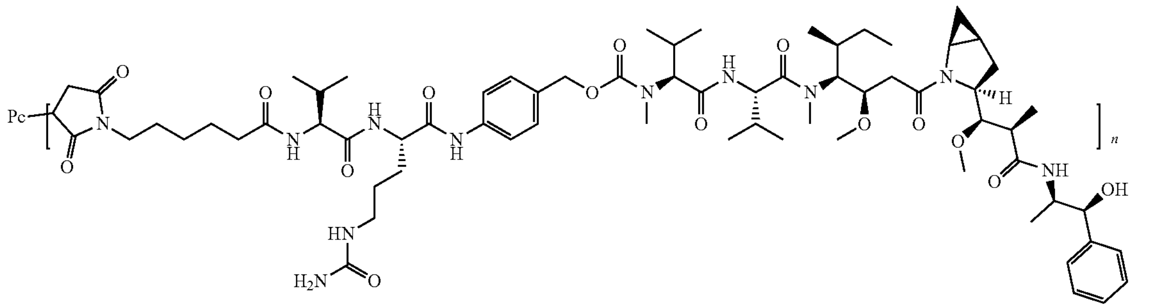

and

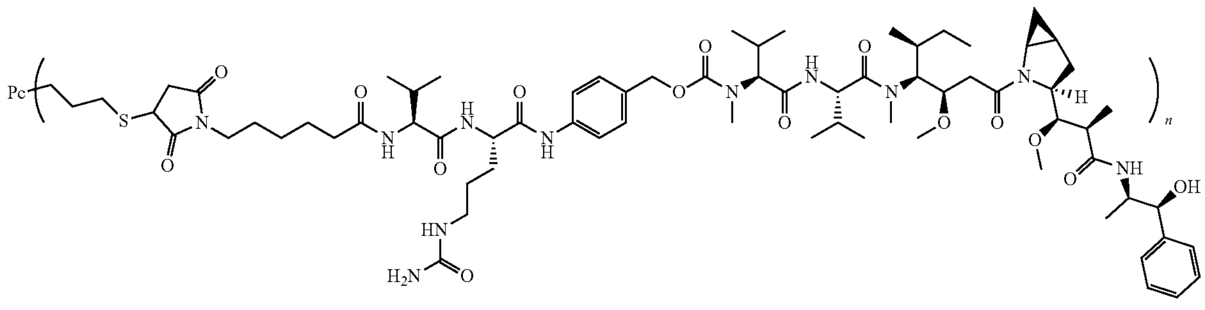

wherein:

n is 1 to 10 and can be an integer or a decimal; and

Pc is the anti-CD79B antibody or the antigen-binding fragment thereof as defined in claim 1.

16. A ligand-drug conjugate or a pharmaceutically acceptable salt or solvate thereof, as shown in any one of structures selected from the group consisting of:

ADC-1
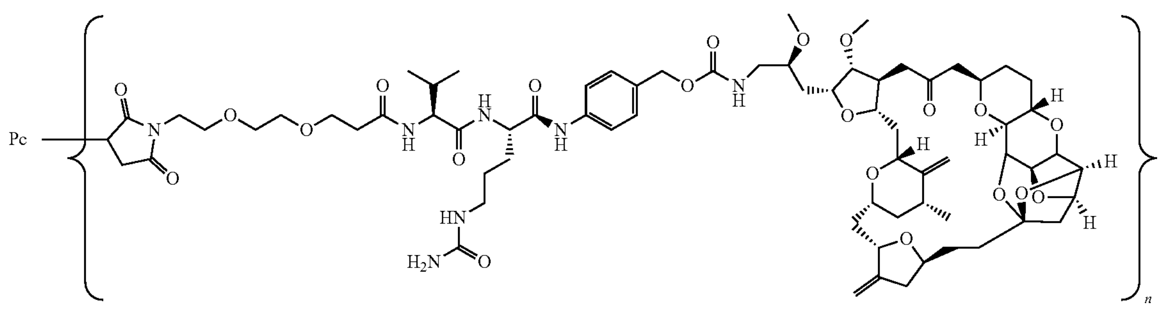
ADC-2
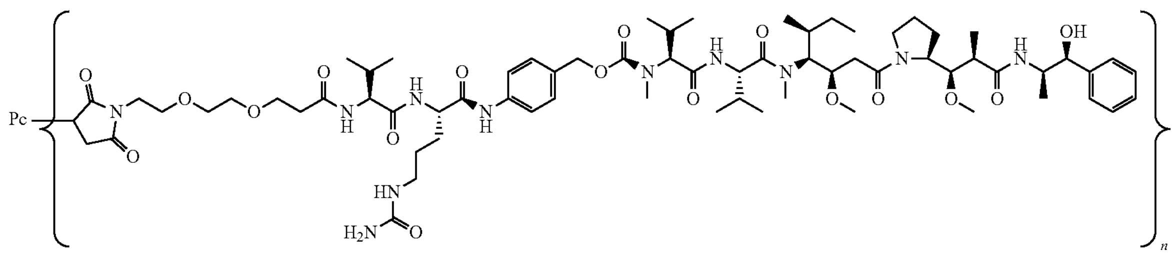
ADC-3
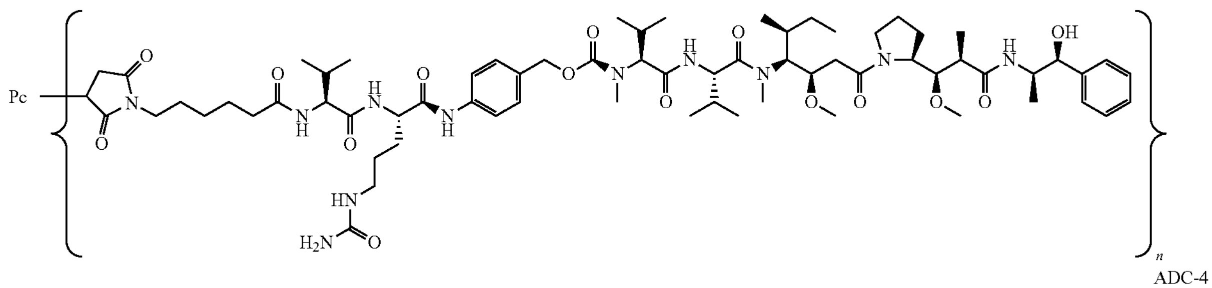
ADC-4
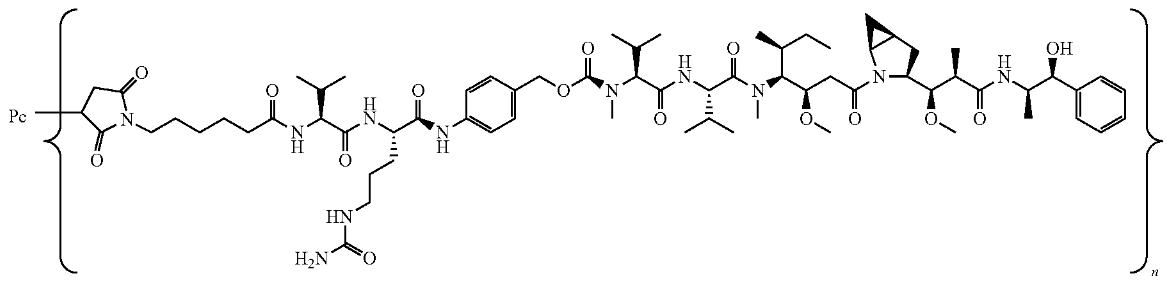
and
ADC-5
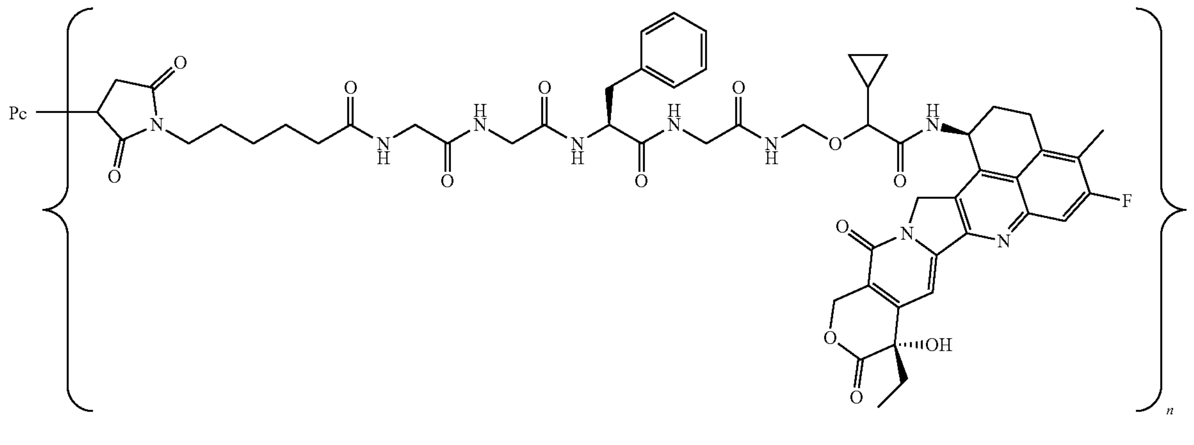

wherein Pc is the anti-CD79B antibody or the antigen-binding fragment thereof as defined in claim 1, and n is 1 to 10 and can be an integer or a decimal.

17. A ligand-drug conjugate or a pharmaceutically acceptable salt or solvate thereof, wherein the ligand-drug conjugate or a pharmaceutically acceptable salt or solvate thereof is a deuteride or a mixture thereof of the ligand-drug conjugate according to claim 1.

18. A pharmaceutical composition comprising:

a pharmaceutically acceptable carrier, diluent or excipient; and a therapeutically effective amount of the ligand-drug conjugate or the pharmaceutically acceptable salt or solvate thereof according to claim 1.

19. A method for treating a proliferative disease or delaying the progression of the proliferative disease in a subject in need thereof, the method comprising:

administering an effective amount of the ligand-drug conjugate or the pharmaceutically acceptable salt or solvate thereof according to claim 1 to the subject, wherein the proliferative disorder is a cancer or a tumor selected from the group consisting of lymphoma, B-cell lymphoma, diffuse large B-cell lymphoma, non-Hodgkin's lymphoma (NHL), aggressive NHL, relapsed and aggressive NHL, relapsed and indolent NHL, refractory NHL, refractory and indolent NHL, chronic lymphocytic leukemia (CLL), small lymphocytic lymphoma, leukemia, hairy cell leukemia (HCL), acute lymphocytic leukemia (ALL), and mantle cell lymphoma.

20. A method for enhancing immune function in a subject having a B-cell proliferative disorder or an autoimmune disorder, comprising:

administering to a subject the ligand-drug conjugate or the pharmaceutically acceptable salt or solvate thereof according to claim 1, wherein the B-cell proliferative disorder is a cancer or a tumor selected from the group consisting of lymphoma, B-cell lymphoma, diffuse large B-cell lymphoma, non-Hodgkin's lymphoma (NHL), aggressive NHL, relapsed and aggressive NHL, relapsed and indolent NHL, refractory NHL, refractory and indolent NHL, chronic lymphocytic leukemia (CLL), small lymphocytic lymphoma, leukemia, hairy cell leukemia (HCL), acute lymphocytic leukemia (ALL), and mantle cell lymphoma.

* * * * *